US011965016B2

(12) United States Patent
Elsharkawy et al.

(10) Patent No.: US 11,965,016 B2
(45) Date of Patent: Apr. 23, 2024

(54) CRYSTAL STRUCTURES COMPRISING ELASTIN-LIKE PEPTIDES

(71) Applicant: Mintech-V, LLC, Wilmington, DE (US)

(72) Inventors: Sherif Ahmed Abdelsalam Elsharkawy, London (GB); Maisoon Al-Jawad, London (GB); Alvaro Mata Chavarria, London (GB); Esther Tejeda-Montes, London (GB)

(73) Assignee: Mintech-V, LLC, Wilmington, DE (US)

( * ) Notice: Subject to any disclaimer, the term of this patent is extended or adjusted under 35 U.S.C. 154(b) by 0 days.

(21) Appl. No.: 17/588,579

(22) Filed: Jan. 31, 2022

(65) Prior Publication Data
US 2022/0363734 A1 Nov. 17, 2022

Related U.S. Application Data

(63) Continuation of application No. 16/089,492, filed as application No. PCT/GB2017/050937 on Apr. 3, 2017, now abandoned.

(30) Foreign Application Priority Data

Apr. 1, 2016 (GB) ...................... 1605629

(51) Int. Cl.
| | |
|---|---|
| *C30B 29/14* | (2006.01) |
| *C07K 14/78* | (2006.01) |
| *C30B 7/04* | (2006.01) |
| *C30B 29/58* | (2006.01) |
| *A61K 38/00* | (2006.01) |

(52) U.S. Cl.
CPC ............... *C07K 14/78* (2013.01); *C30B 7/04* (2013.01); *C30B 29/58* (2013.01); *A61K 38/00* (2013.01)

(58) Field of Classification Search
None
See application file for complete search history.

(56) References Cited

U.S. PATENT DOCUMENTS

2019/0135897 A1  5/2019  Elsharkawy et al.

OTHER PUBLICATIONS

Final Office Action received for U.S. Appl. No. 16/089,492, dated Sep. 1, 2021, 13 pages.
Non-Final Office Action received for U.S. Appl. No. 16/089,492, dated Jan. 22, 2021, 10 pages.
Requirement for Restriction/Election received for U.S. Appl. No. 16/089,492, dated Jun. 26, 2020, 6 pages.
A. Girotti et al., "Design and bioproduction of a recombinant multi(bio)functional elastin-like protein polymer containing Cell adherion sequences for tissue engineering purposes", Journal of Materials Science: Materials in Medicine, 2004, 15:479-484.
A.C. Larson and R.B. Von Dreele, R.B. General Structure Analysis System (GSAS), Los Alamos National Laboratory Report LAUR, 2004, 86-748.
Addadi, L., et al., "Interactions between acidic proteins and crystals: Stereochemical requirements in biomineralization," Proceedings of the National Academy of Sciences of the United States of America, vol. 82, 1985, pp. 4110-4114.
Addadi, L., et al., "On how proteins interact with crystals and their effect on crystal formation," Zeitschrift fur Kardiologie, vol. 90, 2001, pp. 92-98.
Baddiel, C.B., et al., "Spectra structure correlations in hydroxy and fluorapatite," Spectrochimica Acta, vol. 22, 1966, pp. 1407-1416.
Bauer, John et al.; "Ritonavir: an extraordinary example of conformational polymorphism." Pharm. Res. (2001) 18(6) p. 859-866.
Beniash, E., et al., "Transient amorphous calcium phosphate in forming enamel," Journal of Structural Biology, vol. 166, May 2009, pp. 133-143.
Bertazzo, S., et al., "Nano-analytical electron microscopy reveals fundamental insights into human cardiovascular tissue calcification," Nature Materials, vol. 12, No. 6, Jun. 2013, pp. 576-583.
Boyde, A., "Microstructure of enamel," CIBA, Foundation Symposia, 1997, pp. 18-31.
Busch, S., "Regeneration of human tooth enameL," Angewandte Chemie—International Edition, vol. 43, 2004, pp. 1428-1431.
Bushby et al., 2011, Nat. Protocol (2011) 6(6) p. 845-858
C. Sanchez et al., "Biomimetism and bioinspiration as tools for the design of innovative materials and systems", Nature Materials, 2005, 4:277-288.
Chaussain-Miller, C., et al., "The role of matrix metalloproteinases (MMPs) in human caries," Journal of Dental Research, vol. 85, 2006, pp. 22-32.
Chen, H., et al., Aceilular synthesis of a human enamel-like microstructure. Advanced Materials, vol. 18, 2006, pp. 1846-1851.
Chen, H., et al., "Synthesis of Fluorapatite Nanorods and Nanowires by Direct Precipitation from Solution," Cryst Grovvth Des, vol. 6, No. 6, Jun. 1, 2006, pp. 1504-1508.

(Continued)

*Primary Examiner* — Fred H Reynolds
(74) *Attorney, Agent, or Firm* — SMITH, GAMBRELL & RUSSELL, LLP; Michael J. Riesen

(57) ABSTRACT

The present invention relates to new biomimetic mineralized apatite structures. The present invention also relates to processes for the production of new biomimetic mineralized apatite structures based on natural and synthetic protein scaffolds. In particular, the invention provides synthetic crystal having a hierarchical structure formed on an elastin-like polypeptide membrane or hydrogel. The invention also provides methods of making such crystals, both in vivo and in vitro, as well as kits comprising membranes or hydrogels with cross-linking agents and/or mineralization solutions. The invention also provides the use of such structures in methods of treatment.

7 Claims, 61 Drawing Sheets
Specification includes a Sequence Listing.

(56) References Cited

OTHER PUBLICATIONS

CM Bellingham et al.: "Recombinant human elastin polypeptides self-assemble into biomaterials with elastin-like properties", Biopolymers, vol. 70, No. 4, 2003, pp. 445-455, XP2567426.

Cruz-Cabeza, Aurora etal; "Open questions in organic crystal polymorphism." Comm. Chem. (2020) 3(142).

D.L. Nettles, "Applications of elastin-like polypeptides in tissue engineering", Advanced Drug Delivery Reviews, 2010, 62:1479-1485.

Dickinson, M.E., et al., "Probing more than the surface," Materials Today, vol. 12, 2009, pp. 46-50.

Elliot, J.C., "Structure, crystal chemistry and density of enamel apatites," CIBA Foundation Symposia, 1997, pp. 54-72.

Fincham, A.G., et al., "Evidence for Amelogenin "Nanospheres" as Functional Components of Secretory-Stage Enamel Matrix," Journal of Structural Biology, vol. 115, Issue 1, Jul. 1995, pp. 50-59.

Fujisawa, R.., et al., "Conformation of dentin phosphophoryn adsorbed on hydroxyapatite crystals," European Journal of Oral Sciences, vol. 106, 1998, pp. 249-253.

Galler, K.M., et al., "Biomaterials and their potential applications for dental tissue engineering," Journal of Materials Chemistry, vol. 20, 2010, pp. 8730-8746.

Gillam, D.G., "Dentine hypersensitivity : advances in diagnosis, management, and treatment," 2016.

Greenfield, E.M., et al., Ionotropic nucleation of calcium carbonate by molluscan matrix, Integrative and Comparative Biology, vol. 24, 1984, pp. 925-932.

Greenwald, S.E., et al., "Experimental investigation of the distribution of residual strains in the artery wall," Journal of Biomechanical Engineering, vol. 119, No. 4, Nov. 1997, pp. 438-444.

Hsu, P.W., et al., "Evaluation of porcine dermal collagen (Permacol) used in abdominal wall reconstruction," J Plastic Reconst Aesthetic Surg, vol. 62, No. 11, Nov. 2009, pp. 1484-14899.

Huang, Z., et al., "Bioactive nanofibers instruct cells to proliferate and differentiate during enamel regeneration," Journal of Bone and Mineral Research, vol. 23, No. 12, Dec. 2008, pp. 1995-2006.

J. F. Almine et al., "Elastin-based materials", Chemical Society Reviews, 2010, 39:3371-3379.

J. Xu et al., "FT-Raman and high-pressure infrared spectroscopic studies of dicalcium phosphate dihydrate (CaHPO4—2H2O) and anhydrous dicalcium phosphate (CaHPO4)", Spectrochimica Acta—Part A: Molecular and Biomolecular Spectroscopy, 1999, 55:2801-2809.

Kato, T., et al., "Macromolecular templating for the formation of inorganic-organic hybrid structures," MRS Bulletin, vol. 35, 2010, pp. 127-132.

KIDD.E.A.M., "Essentials of dental caries," 3rd edn, Oxford University Press, 2005.

Kirkham, J., et al., "Self-assembling peptide scaffolds promote enamel remineralization," J Dent Res., vol. 86. No. 5, May 2007, pp. 426-430.

Kowalczyk, Tomasz et al; "Elastin-like polypeptides as a promising family of genetically engineered protein based polymers." World J. Microbial. Biotechnol (2014) 30 p. 2141-2152.

Mohammed, N.R., et al., "Effects of fluoride on in vitro enamel demineralization analyzed by 19F MASNMR," Caries Research, vol. 47, 2013, pp. 421-428.

Mohammed, N.R., et al., "Inhibitory Effects of Zinc Ions on Enamel Demineralisation Kinetics in vitro," Caries Research, vol. 49, 2015, pp. 600-605.

Mukherjee, K., et al., "Repairing human tooth enamei with leucine-rich amelogenin peptide-chitosan hydrogel," Journal of Materials Research, vol. 31, 2016, pp. 556-563.

Naval Warfare Center, "Heteroepitaxy with large lattice mismatch." Photonics Tech Briefs Magazine (1998).

Nicol, A., et al., "Elastic protein-based polymers as cell attachment matrices," Journal of Vascular Surgery, vol. 13, Issue 5, May 1991, pp. 746-748.

Oaki, Y., et al., "Experimental demonstration for the morphological evolution of crystals grown in gel media," Crystal Grm.-vth and Design, vol. 3, 2003, pp. 711-716.

Orchardson, R., "Managing dentin hypersensitivity," Journal of the American Dental Association, vol. 137, 2006, pp. 990-998.

Panitch, A., et al., "Design and Biosynthesis of Elastin-like Artificial Extracellular Matrix Proteins Containing Periodically Spaced Fibronectin CS5 Domains," Macromolecules, vol. 32, No. 5, 1999, pp. 1701-1703.

Pashley, D.H., et al., "Collagen degradation by host-derived enzymes during aging," Journal of Dental Research, vol. 83, 2004, pp. 216-221.

Peck, Donald and Ostrander, Alfred; "Crystallography: the monoclinic system." https://www.mindat.org/article.php/2787/Crystallography%3A+The+Monoclinic+System, last modified Apr. 21, 2020.

Raj, P.A., et al., "Salivary statherin. Dependence on sequence, charge, hydrogen bonding potency, and helical conformation for adsorption to hydroxyapatite and inhibition of mineralization," J Bioi Chem, vol. 267, No. 9, Mar. 25, 1992, pp. 5968-5976.

Robinson, C., et al.., "Variation in Composition of Dental Enamel Within Thin Ground Tooth Sections," Caries Research, 1971, pp. 44-57.

Ruan, Q., et al., "An amelogenin-chitosan matrix promotes assembly of an enamel-like layer with a dense interface," Acta Biomaterialia, vol. 9, No. 7, Jul. 2013, pp. 7289-7297.

Ruan, Q., et al., "Development of amelogenin-chitosan hydrogel for In Vitro enamel regrowth with a dense interface," Journal of Visualized Experiments, No. 89, Jul. 10, 2014, 51606.

S Prieto et al.: "Biomimetic calcium phosphate mineralization with multifunctional ekasin-like recombinamers", Biomacromolecules, vol. 12, Mar. 25, 2011 (Mar. 25, 2011), pp. 1480-1486.

Sakamoto, T., et al., "Three-dimensional relief structures of CaCO3 crystal assemblies formed by spontaneous two-step crystal growth on a polymer thin film," Crystal Growth and Design, Vo. 9, 2009, pp. 622-625.

Shtukenberg, A.G., et al., "Spherulites," Chemical Reviews, vol. 112, 2012, pp. 1805-1838.

Simmer, J.P., et al., "Molecular mechanisms of dental enamel formation," Critical Reviews in Oral Biology and Medicine, vol. 6, 1995, pp. 84-108.

Simmons, L.M., et al., "Mapping the spatial and temporal progression of human dental enamel biomineraiization using synchrotron X-ray diffraction," Arch Oral Bil, vol. 58, 2013, pp. 1726-1734.

Simon, P., et al., "Hierarchical architecture and real structure in a biomimetic nano-composite of fluorapatite with gelatine: A model system for steps in dentino—and osteogenesis?," Journal of Materials Chemistry, vol. 15, 205, pp. 4992-4996, 2005.

Srivastava, G.K., et al., "Elastin-like recombinamers as substrates for retinal pigment epithelial cell growth," J Biomed Mater Res A, vol. 97, No. 3, Jun. 1, 2011, pp. 243-250.

Sudarsanan, K., et al., "Comparison of synthetic and mineral fluorapatite, Ca5 (PO4)3F, in crystallographic detail. Materials Research Bulletin," vol. 7, 1972, pp. 1331-1337.

Teaford, M.F., et al., "Nanoindentation mapping of the mechanical properties of human moiar tooth enamel," Archives of Oral Biology, vol. 47, 2002, pp. 281-291.

Tejeda-Montes, E., et al., "Bioactive membranes for bone regeneration applications: effect of physical and biomolecular signals on mesenchymal stem cell behavior," Acta Biomaterialia, vol. 10, Jan. 2014, pp. 134-141.

Tejeda-Montes, E., et al., "Engineering membrane scaffolds with both physical and biomolecular signaling," Acta Biomaterialia vol. 8, No. 3, Mar. 2012, pp. 998-1009.

Tejeda-Montes, E., et al., "Mineralization and bone regeneration using a bioactive elastin-like recombinamer membrane," Biomateriais, vol. 35, Sep. 2014, pp. 8339-8347.

U. Wegst et al., "Bioinspired structural materials", Nature Materials, 2014, 23-36.

Urry, D.W., What sustains life?: Consilient mechanisms for protein-based machines and materials, 2006.

Van De Locht, R., et al., "Microstructural evolution and nanoscale crystallography in scleractinian coral spherulites," Journal of Structural Biology, vol. 183, 2013, pp. 57-65.

(56) References Cited

OTHER PUBLICATIONS

Weiner, S., "Organization of organic matrix components in mineralized tissues," Integrative and Comparative Biology, vol. 24, 1984, pp. 945-951.
Weiner, S., et al., "Strategies in mineralized biological materials," Journal of Materials Chemistry, vol. 7, 1997, pp. 689-702.
White, S.N., et al., "Biological organization of hydroxyapatite crystallites into a fibrous continuum toughens and controls anisotropy in human enamel," Journal of Dental Research, vol. 80, No. 1, Jan. 2001, pp. 321-326.
Wu., D., et al., "Hydroxyapatite-anchored dendrimer for in situ remineralization of human tooth enamel," Biomaterials, vol. 34, No. 21, Jul. 2013, pp. 5036-5047.
Y Li et al.: "Hybrid nanotopographical surfaces obtained by biomimetic mineralization of statherin-inspired elastin-like recombinamers", Advanced Healthcare Materials, vol. 3, 2014, pp. 1638-1647, XP002771746.
Y Li et al.: "Intrafibrillar mineralization of self-assembled elastin-like recombinamer fibrils", ACS Applied Materials and Interfaces, vol. 9, Jan. 27, 2017 (Jan. 27, 2017), pp. 5838-5846, XP002771747.
Yang, X., et al., "How amelogenin orchestrates the organization of hierarchical elongated microstructures of apatite," Journal of Physical Chemistry B, vol. 114, No. 6, Feb. 18, 2020, pp. 2293-2300.
Young, R.A., et al. Atomic-scale bases for several properties of apatites, Archives of Oral Biology, vol. 11, Issue 7, Jul. 1966, pp. 699-707.

f g

| Type of ELP | Sequence (bioactive sequence is bolded) | Isoelectric point (pI) | Molecular weight | Inverse transition temperature (DW) | | |
|---|---|---|---|---|---|---|
| | | | | pH | $T_t$ (°C) | |
| IK | MESLLP-(VPGIG VPGKG VPGIG VPGIG VPGIG)$_{24}$ (SEQ ID NO:40) | 11 | 51.9 kDa | pH | $T_t$ (°C) | |
| | | | | 3.5 | 39-41 | |
| | | | | 7.2 | 32-34 | |
| | | | | 10.5 | 24-26 | |
| SN | MESLLP-[[(VPGIG)$_2$(VPGKG)(VPGIG)$_2$]$_2$ DDDEEKFLRRIGRFG[(VPGIG)$_2$(VPGKG)(VPGIG)$_2$]$_3$ (SEQ ID NO:41) | 9.9 | 31.9 kDa | pH | $T_t$ (°C) | |
| | | | | 3.5 | >60 | |
| | | | | 7.2 | 23 | |
| | | | | 10.5 | 25 | |
| RGDS | MGSSHHHHHHSSGLVPRGSHMESLLP-[[(VPGIG)$_2$(VPGKG)(VPGIG)$_2$]$_2$AVTGRGDSPASS[(VPGIG)$_2$(VPGKG)(VPGIG)$_2$]$_2$]$_6$ (SEQ ID NO:39) | 11.1 | 60.6 kDa | pH | $T_t$ (°C) | |
| | | | | 3.5 | 39-41 | |
| | | | | 7.2 | 35-37 | |
| | | | | 10.5 | 26-28 | |
| SN-RGDS | MESLLP-[[(VPGIG)$_2$(VPGKG)(VPGIG)$_2$]$_2$ DDDEEKFLRRIGRFG[(VPGIG)$_2$(VPGKG)(VPGIG)$_2$]$_4$[[(VPGIG)$_2$(VPGKG)(VPGIG)$_2$]$_2$AVTGRGDSPASS[(VPGIG)$_2$(VPGKG)(VPGIG)$_2$]$_2$]$_4$ (SEQ ID NO:42) | 10.8 | 80.7 kDa | pH | $T_t$ (°C) | |
| | | | | 3.5 | >60 | |
| | | | | 7.2 | 33 | |
| | | | | 10.5 | 25 | |

Figure 2

TEM liftout sample preparation

TEM liftout sample preparation

Diffusion coefficients at different crosslinking ratios

| Crosslinker to Lysine ratio | Equilibrium radius squared ($r^2$) (mm) | Characteristic time ($\tau$) of swelling (minutes) | Diffusion coefficient ($r^2/\tau$) (mm$^2$/minute) |
|---|---|---|---|
| 0.5 | 2994.2784 | 50 | 59.885568 |
| 1 | 2829.1761 | 120 | 23.5764675 |
| 3 | 2702.9601 | 240 | 11.26233375 |
| 6 | 2642.9881 | 300 | 8.80996033 |
| 12 | 2611.21 | 420 | 6.217166667 |

Figure 24 a b

SEQUENCE LISTING

```
<160> NUMBER OF SEQ ID NOS: 43

<210> SEQ ID NO 1
<211> LENGTH: 4
<212> TYPE: PRT
<213> ORGANISM: Artificial Sequence
<220> FEATURE:
<223> OTHER INFORMATION: Bioactive epitope

<400> SEQUENCE: 1

Arg Gly Asp Ser
1

<210> SEQ ID NO 2
<211> LENGTH: 15
<212> TYPE: PRT
<213> ORGANISM: Artificial Sequence
<220> FEATURE:
<223> OTHER INFORMATION: statherin-derived peptide

<400> SEQUENCE: 2

Asp Asp Asp Glu Glu Lys Phe Leu Arg Arg Ile Gly Arg Phe Gly
```

```
1               5               10              15
```

<210> SEQ ID NO 3
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (2)..(5)
<223> OTHER INFORMATION: X is any amino acid

<400> SEQUENCE: 3

Gly Xaa Xaa Xaa Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(5)
<223> OTHER INFORMATION: X is any amino acid

<400> SEQUENCE: 4

Xaa Gly Xaa Xaa Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(5)
<223> OTHER INFORMATION: X is any amino acid

<400> SEQUENCE: 5

Xaa Xaa Gly Xaa Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(5)
<223> OTHER INFORMATION: X is any amino acid

<400> SEQUENCE: 6

Xaa Xaa Xaa Gly Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X

```
<222> LOCATION: (1)..(5)
<223> OTHER INFORMATION: X is any amino acid

<400> SEQUENCE: 7

Xaa Xaa Xaa Xaa Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (2)..(5)
<223> OTHER INFORMATION: X is an amino acid selected from the group
      consisting of V, P, G, S, F and I.

<400> SEQUENCE: 8

Gly Xaa Xaa Xaa Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(5)
<223> OTHER INFORMATION: X is an amino acid selected from the group
      consisting of V, P, G, S, F and I.

<400> SEQUENCE: 9

Xaa Gly Xaa Xaa Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(5)
<223> OTHER INFORMATION: X is an amino acid selected from the group
      consisting of V, P, G, S, F and I.

<400> SEQUENCE: 10

Xaa Xaa Gly Xaa Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(5)
<223> OTHER INFORMATION: X is an amino acid selected from the group
      consisting of V, P, G, S, F and I.

<400> SEQUENCE: 11

Xaa Xaa Xaa Gly Xaa
1               5
```

```
<210> SEQ ID NO 12
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(4)
<223> OTHER INFORMATION: X is an amino acid selected from the group
      consisting of V, P, G, S, F and I.

<400> SEQUENCE: 12

Xaa Xaa Xaa Xaa Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: repeat_unit
<222> LOCATION: (1)..(5)
<223> OTHER INFORMATION: Pentapeptide is repeated any number of times
<220> FEATURE:
<221> NAME/KEY: X
<222> LOCATION: (2)..(5)
<223> OTHER INFORMATION: X is any amino acid

<400> SEQUENCE: 13

Gly Xaa Xaa Xaa Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(5)
<223> OTHER INFORMATION: X is any amino acid
<220> FEATURE:
<221> NAME/KEY: repeat_unit
<222> LOCATION: (1)..(5)
<223> OTHER INFORMATION: Pentapeptide is repeated any number of times

<400> SEQUENCE: 14

Xaa Gly Xaa Xaa Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(5)
<223> OTHER INFORMATION: X is any amino acid
<220> FEATURE:
<221> NAME/KEY: repeat_unit
<222> LOCATION: (1)..(5)
<223> OTHER INFORMATION: Pentapeptide is repeated any number of times

<400> SEQUENCE: 15
```

-continued

Xaa Xaa Gly Xaa Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(5)
<223> OTHER INFORMATION: X is any amino acid
<220> FEATURE:
<221> NAME/KEY: repeat_unit
<222> LOCATION: (1)..(5)
<223> OTHER INFORMATION: Pentapeptide is repeated any number of times

<400> SEQUENCE: 16

Xaa Xaa Xaa Gly Xaa
1               5

<210> SEQ ID NO 17
<211> LENGTH: 5
<212> TYPE: PRT
<213> ORGANISM: Artificial Sequence
<220> FEATURE:
<223> OTHER INFORMATION: Pentapeptide
<220> FEATURE:
<221> NAME/KEY: X
<222> LOCATION: (1)..(4)
<223> OTHER INFORMATION: X is any amino acid
<220> FEATURE:
<221> NAME/KEY: repeat_unit
<222> LOCATION: (1)..(5)
<223> OTHER INFORMATION: Pentapeptide is repeated any number of times

<400> SEQUENCE: 17

Xaa Xaa Xaa Xaa Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Tropoelastin recurrent motif
<220> FEATURE:
<221> NAME/KEY: X
<222> LOCATION: (4)..(4)
<223> OTHER INFORMATION: X is an amino acid selected from the group
      consisting of V, P, G, S, F and I

<400> SEQUENCE: 18

Val Pro Gly Xaa Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Tropoelastin recurrent motif
<220> FEATURE:
<221> NAME/KEY: X
<222> LOCATION: (4)..(4)
<223> OTHER INFORMATION: X is any amino acid apart from Proline

<400> SEQUENCE: 19

Val Pro Gly Xaa Gly
1               5

```
<210> SEQ ID NO 20
<211> LENGTH: 5
<212> TYPE: PRT
<213> ORGANISM: Artificial Sequence
<220> FEATURE:
<223> OTHER INFORMATION: Tropoelastin recurrent motif
<220> FEATURE:
<221> NAME/KEY: repeat_unit
<222> LOCATION: (1)..(5)
<223> OTHER INFORMATION: Motif is to be repeated any number of times
<220> FEATURE:
<221> NAME/KEY: X
<222> LOCATION: (4)..(4)
<223> OTHER INFORMATION: X is any amino acid apart from Proline

<400> SEQUENCE: 20

Val Pro Gly Xaa Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Tropoelastin recurrent motif

<400> SEQUENCE: 21

Pro Gly Ile Pro Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Tropoelastin recurrent motif
<220> FEATURE:
<221> NAME/KEY: repeat_unit
<222> LOCATION: (1)..(5)
<223> OTHER INFORMATION: Motif is to be repeated any number of times

<400> SEQUENCE: 22

Pro Gly Ile Pro Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Tropoelastin recurrent motif

<400> SEQUENCE: 23

Pro Val Gly Ser Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Tropoelastin recurrent motif
<220> FEATURE:
<221> NAME/KEY: repeat_unit
<222> LOCATION: (1)..(5)
<223> OTHER INFORMATION: Motif is to be repeated any number of times

<400> SEQUENCE: 24
```

```
Pro Val Gly Ser Gly
1               5
```

<210> SEQ ID NO 25
<211> LENGTH: 5
<212> TYPE: PRT
<213> ORGANISM: Artificial Sequence
<220> FEATURE:
<223> OTHER INFORMATION: Tropoelastin recurrent motif

<400> SEQUENCE: 25

```
Val Gly Phe Pro Gly
1               5
```

<210> SEQ ID NO 26
<211> LENGTH: 5
<212> TYPE: PRT
<213> ORGANISM: Artificial Sequence
<220> FEATURE:
<223> OTHER INFORMATION: Tropoelastin recurrent motif
<220> FEATURE:
<221> NAME/KEY: repeat_unit
<222> LOCATION: (1)..(5)
<223> OTHER INFORMATION: Motif is to be repeated any number of times

<400> SEQUENCE: 26

```
Val Gly Phe Pro Gly
1               5
```

<210> SEQ ID NO 27
<211> LENGTH: 699
<212> TYPE: PRT
<213> ORGANISM: Artificial Sequence
<220> FEATURE:
<223> OTHER INFORMATION: Peptide sequence

<400> SEQUENCE: 27

```
Met Gly Ser Ser His His His His His Ser Ser Gly Leu Val Pro
1               5                   10                  15

Arg Gly Ser His Met Glu Ser Leu Leu Pro Val Pro Gly Ile Gly Val
                20                  25                  30

Pro Gly Ile Gly Val Pro Gly Lys Gly Val Pro Gly Ile Gly Val Pro
            35                  40                  45

Gly Ile Gly Val Pro Gly Ile Gly Val Pro Gly Ile Gly Val Pro Gly
        50                  55                  60

Lys Gly Val Pro Gly Ile Gly Val Pro Gly Ile Gly Ala Val Thr Gly
65                  70                  75                  80

Arg Gly Asp Ser Pro Ala Ser Ser Val Pro Gly Ile Gly Val Pro Gly
                85                  90                  95

Ile Gly Val Pro Gly Lys Gly Val Pro Gly Ile Gly Val Pro Gly Ile
            100                 105                 110

Gly Val Pro Gly Ile Gly Val Pro Gly Ile Gly Val Pro Gly Lys Gly
        115                 120                 125

Val Pro Gly Ile Gly Val Pro Gly Ile Gly Val Pro Gly Ile Gly Val
    130                 135                 140

Pro Gly Ile Gly Val Pro Gly Lys Gly Val Pro Gly Ile Gly Val Pro
145                 150                 155                 160

Gly Ile Gly Val Pro Gly Ile Gly Val Pro Gly Ile Gly Val Pro Gly
                165                 170                 175

Lys Gly Val Pro Gly Ile Gly Val Pro Gly Ile Gly Ala Val Thr Gly
            180                 185                 190
```

```
Arg Gly Asp Ser Pro Ala Ser Ser Val Pro Gly Ile Gly Val Pro Gly
            195                 200                 205
Ile Gly Val Pro Gly Lys Gly Val Pro Gly Ile Gly Val Pro Gly Ile
        210                 215                 220
Gly Val Pro Gly Ile Gly Val Pro Gly Ile Gly Val Pro Gly Lys Gly
225                 230                 235                 240
Val Pro Gly Ile Gly Val Pro Gly Ile Gly Val Pro Gly Ile Gly Val
                245                 250                 255
Pro Gly Ile Gly Val Pro Gly Lys Gly Val Pro Gly Ile Gly Val Pro
            260                 265                 270
Gly Ile Gly Val Pro Gly Ile Gly Val Pro Gly Ile Gly Val Pro Gly
        275                 280                 285
Lys Gly Val Pro Gly Ile Gly Val Pro Gly Ile Gly Ala Val Thr Gly
    290                 295                 300
Arg Gly Asp Ser Pro Ala Ser Ser Val Pro Gly Ile Gly Val Pro Gly
305                 310                 315                 320
Ile Gly Val Pro Gly Lys Gly Val Pro Gly Ile Gly Val Pro Gly Ile
                325                 330                 335
Gly Val Pro Gly Ile Gly Val Pro Gly Ile Gly Val Pro Gly Lys Gly
            340                 345                 350
Val Pro Gly Ile Gly Val Pro Gly Ile Gly Val Pro Gly Ile Gly Val
        355                 360                 365
Pro Gly Ile Gly Val Pro Gly Lys Gly Val Pro Gly Ile Gly Val Pro
    370                 375                 380
Gly Ile Gly Val Pro Gly Ile Gly Val Pro Gly Ile Gly Val Pro Gly
385                 390                 395                 400
Lys Gly Val Pro Gly Ile Gly Val Pro Gly Ile Gly Ala Val Thr Gly
                405                 410                 415
Arg Gly Asp Ser Pro Ala Ser Ser Val Pro Gly Ile Gly Val Pro Gly
            420                 425                 430
Ile Gly Val Pro Gly Lys Gly Val Pro Gly Ile Gly Val Pro Gly Ile
        435                 440                 445
Gly Val Pro Gly Ile Gly Val Pro Gly Ile Gly Val Pro Gly Lys Gly
450                 455                 460
Val Pro Gly Ile Gly Val Pro Gly Ile Gly Val Pro Gly Ile Gly Val
465                 470                 475                 480
Pro Gly Ile Gly Val Pro Gly Lys Gly Val Pro Gly Ile Gly Val Pro
                485                 490                 495
Gly Ile Gly Val Pro Gly Ile Gly Val Pro Gly Ile Gly Val Pro Gly
            500                 505                 510
Lys Gly Val Pro Gly Ile Gly Val Pro Gly Ile Gly Ala Val Thr Gly
        515                 520                 525
Arg Gly Asp Ser Pro Ala Ser Ser Val Pro Gly Ile Gly Val Pro Gly
    530                 535                 540
Ile Gly Val Pro Gly Lys Gly Val Pro Gly Ile Gly Val Pro Gly Ile
545                 550                 555                 560
Gly Val Pro Gly Ile Gly Val Pro Gly Ile Gly Val Pro Gly Lys Gly
                565                 570                 575
Val Pro Gly Ile Gly Val Pro Gly Ile Gly Val Pro Gly Ile Gly Val
            580                 585                 590
Pro Gly Ile Gly Val Pro Gly Lys Gly Val Pro Gly Ile Gly Val Pro
        595                 600                 605
Gly Ile Gly Val Pro Gly Ile Gly Val Pro Gly Ile Gly Val Pro Gly
```

```
                    610                 615                 620
Lys Gly Val Pro Gly Ile Gly Val Pro Gly Ile Gly Ala Val Thr Gly
625                 630                 635                 640

Arg Gly Asp Ser Pro Ala Ser Ser Val Pro Gly Ile Gly Val Pro Gly
                    645                 650                 655

Ile Gly Val Pro Gly Lys Gly Val Pro Gly Ile Gly Val Pro Gly Ile
                660                 665                 670

Gly Val Pro Gly Ile Gly Val Pro Gly Ile Gly Val Pro Gly Lys Gly
            675                 680                 685

Val Pro Gly Ile Gly Val Pro Gly Ile Gly Val
            690                 695

<210> SEQ ID NO 28
<211> LENGTH: 877
<212> TYPE: PRT
<213> ORGANISM: Artificial Sequence
<220> FEATURE:
<223> OTHER INFORMATION: Peptide sequence

<400> SEQUENCE: 28

Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly Glu
                20                  25                  30

Glu Ile Gln Ile Gly His Ile Pro Arg Glu Asp Val Asp Tyr His Leu
            35                  40                  45

Tyr Pro Val Pro Gly Ile Gly Val Pro Gly Ile Gly Val Pro Gly Lys
        50                  55                  60

Gly Val Pro Gly Ile Gly Val Pro Gly Ile Gly Val Gly Val Ala Pro
65                  70                  75                  80

Gly Val Gly Val Ala Pro Gly Val Gly Val Ala Pro Gly Val Pro Gly
                85                  90                  95

Ile Gly Val Pro Gly Ile Gly Val Pro Gly Lys Gly Val Pro Gly Ile
                100                 105                 110

Gly Val Pro Gly Ile Gly Glu Glu Ile Gln Ile Gly His Ile Pro Arg
            115                 120                 125

Glu Asp Val Asp Tyr His Leu Tyr Pro Val Pro Gly Ile Gly Val Pro
        130                 135                 140

Gly Ile Gly Val Pro Gly Lys Gly Val Pro Gly Ile Gly Val Pro Gly
145                 150                 155                 160

Ile Gly Val Gly Val Ala Pro Gly Val Gly Val Ala Pro Gly Val Gly
                165                 170                 175

Val Ala Pro Gly Val Pro Gly Ile Gly Val Pro Gly Ile Gly Val Pro
                180                 185                 190

Gly Lys Gly Val Pro Gly Ile Gly Val Pro Gly Ile Gly Glu Glu Ile
            195                 200                 205

Gln Ile Gly His Ile Pro Arg Glu Asp Val Asp Tyr His Leu Tyr Pro
        210                 215                 220

Val Pro Gly Ile Gly Val Pro Gly Ile Gly Val Pro Gly Lys Gly Val
225                 230                 235                 240

Pro Gly Ile Gly Val Pro Gly Ile Gly Val Gly Val Ala Pro Gly Val
                245                 250                 255

Gly Val Ala Pro Gly Val Gly Val Ala Pro Gly Val Pro Gly Ile Gly
                260                 265                 270

Val Pro Gly Ile Gly Val Pro Gly Lys Gly Val Pro Gly Ile Gly Val
```

```
            275                 280                 285
Pro Gly Ile Gly Glu Glu Ile Gln Ile Gly His Ile Pro Arg Glu Asp
    290                 295                 300

Val Asp Tyr His Leu Tyr Pro Val Pro Gly Ile Gly Val Pro Gly Ile
305                 310                 315                 320

Gly Val Pro Gly Lys Gly Val Pro Gly Ile Gly Val Pro Gly Ile Gly
                325                 330                 335

Val Gly Val Ala Pro Gly Val Gly Val Ala Pro Gly Val Gly Val Ala
            340                 345                 350

Pro Gly Val Pro Gly Ile Gly Val Pro Gly Ile Gly Val Pro Gly Lys
        355                 360                 365

Gly Val Pro Gly Ile Gly Val Pro Gly Ile Gly Glu Glu Ile Gln Ile
    370                 375                 380

Gly His Ile Pro Arg Glu Asp Val Asp Tyr His Leu Tyr Pro Val Pro
385                 390                 395                 400

Gly Ile Gly Val Pro Gly Ile Gly Val Pro Gly Lys Gly Val Pro Gly
                405                 410                 415

Ile Gly Val Pro Gly Ile Gly Val Gly Val Ala Pro Gly Val Gly Val
            420                 425                 430

Ala Pro Gly Val Gly Val Ala Pro Gly Val Pro Gly Ile Gly Val Pro
        435                 440                 445

Gly Ile Gly Val Pro Gly Lys Gly Val Pro Gly Ile Gly Val Pro Gly
    450                 455                 460

Ile Gly Glu Glu Ile Gln Ile Gly His Ile Pro Arg Glu Asp Val Asp
465                 470                 475                 480

Tyr His Leu Tyr Pro Val Pro Gly Ile Gly Val Pro Gly Ile Gly Val
                485                 490                 495

Pro Gly Lys Gly Val Pro Gly Ile Gly Val Pro Gly Ile Gly Val Gly
            500                 505                 510

Val Ala Pro Gly Val Gly Val Ala Pro Gly Val Gly Val Ala Pro Gly
        515                 520                 525

Val Pro Gly Ile Gly Val Pro Gly Ile Gly Val Pro Gly Lys Gly Val
    530                 535                 540

Pro Gly Ile Gly Val Pro Gly Ile Gly Glu Glu Ile Gln Ile Gly His
545                 550                 555                 560

Ile Pro Arg Glu Asp Val Asp Tyr His Leu Tyr Pro Val Pro Gly Ile
                565                 570                 575

Gly Val Pro Gly Ile Gly Val Pro Gly Lys Gly Val Pro Gly Ile Gly
            580                 585                 590

Val Pro Gly Ile Gly Val Gly Val Ala Pro Gly Val Gly Val Ala Pro
        595                 600                 605

Gly Val Gly Val Ala Pro Gly Val Pro Gly Ile Gly Val Pro Gly Ile
    610                 615                 620

Gly Val Pro Gly Lys Gly Val Pro Gly Ile Gly Val Pro Gly Ile Gly
625                 630                 635                 640

Glu Glu Ile Gln Ile Gly His Ile Pro Arg Glu Asp Val Asp Tyr His
                645                 650                 655

Leu Tyr Pro Val Pro Gly Ile Gly Val Pro Gly Ile Gly Val Pro Gly
            660                 665                 670

Lys Gly Val Pro Gly Ile Gly Val Pro Gly Ile Gly Val Gly Val Ala
        675                 680                 685

Pro Gly Val Gly Val Ala Pro Gly Val Gly Val Ala Pro Gly Val Pro
    690                 695                 700
```

```
Gly Ile Gly Val Pro Gly Ile Gly Val Pro Gly Lys Gly Val Pro Gly
705                 710                 715                 720

Ile Gly Val Pro Gly Ile Gly Glu Glu Ile Gln Ile Gly His Ile Pro
                725                 730                 735

Arg Glu Asp Val Asp Tyr His Leu Tyr Pro Val Pro Gly Ile Gly Val
            740                 745                 750

Pro Gly Ile Gly Val Pro Gly Lys Gly Val Pro Gly Ile Gly Val Pro
        755                 760                 765

Gly Ile Gly Val Gly Val Ala Pro Gly Val Gly Val Ala Pro Gly Val
770                 775                 780

Gly Val Ala Pro Gly Pro Gly Ile Gly Val Pro Gly Ile Gly Val
785                 790                 795                 800

Pro Gly Lys Gly Val Pro Gly Ile Gly Val Pro Gly Ile Gly Glu Glu
        805                 810                 815

Ile Gln Ile Gly His Ile Pro Arg Glu Asp Val Asp Tyr His Leu Tyr
        820                 825                 830

Pro Val Pro Gly Ile Gly Val Pro Gly Ile Gly Val Pro Gly Lys Gly
        835                 840                 845

Val Pro Gly Ile Gly Val Pro Gly Ile Gly Val Gly Val Ala Pro Gly
    850                 855                 860

Val Gly Val Ala Pro Gly Val Gly Val Ala Pro Gly Val
865                 870                 875

<210> SEQ ID NO 29
<211> LENGTH: 1107
<212> TYPE: PRT
<213> ORGANISM: Artificial Sequence
<220> FEATURE:
<223> OTHER INFORMATION: Peptide sequence

<400> SEQUENCE: 29

Met Glu Ser Leu Leu Pro Val Pro Gly Val Gly Val Pro Gly Val Gly
1               5                   10                  15

Val Pro Gly Glu Gly Val Pro Gly Val Gly Val Pro Gly Val Gly Val
                20                  25                  30

Pro Gly Val Gly Val Pro Gly Val Gly Val Pro Gly Glu Gly Val Pro
            35                  40                  45

Gly Val Gly Val Pro Gly Val Gly Val Pro Gly Val Gly Val Pro Gly
        50                  55                  60

Val Gly Val Pro Gly Glu Gly Val Pro Gly Val Gly Val Pro Gly Val
65                  70                  75                  80

Gly Val Pro Gly Val Gly Val Pro Gly Val Gly Val Pro Gly Glu Gly
                85                  90                  95

Val Pro Gly Val Gly Val Pro Gly Val Gly Val Pro Gly Val Gly Val
            100                 105                 110

Pro Gly Val Gly Val Pro Gly Glu Gly Val Pro Gly Val Gly Val Pro
        115                 120                 125

Gly Val Gly Val Pro Gly Val Gly Val Pro Gly Val Gly Val Pro Gly
    130                 135                 140

Glu Gly Val Pro Gly Val Gly Val Pro Gly Val Gly Val Pro Gly Val
145                 150                 155                 160

Gly Val Pro Gly Val Gly Val Pro Gly Glu Gly Val Pro Gly Val Gly
                165                 170                 175

Val Pro Gly Val Gly Val Pro Gly Val Gly Val Pro Gly Val Gly Val
            180                 185                 190
```

-continued

Pro Gly Glu Gly Val Pro Gly Val Gly Val Pro Gly Val Gly Val Pro
        195                 200                 205

Gly Val Gly Val Pro Gly Val Gly Val Pro Gly Glu Gly Val Pro Gly
        210                 215                 220

Val Gly Val Pro Gly Val Gly Val Pro Gly Val Gly Val Pro Gly Val
225                 230                 235                 240

Gly Val Pro Gly Glu Gly Val Pro Gly Val Gly Val Pro Gly Val Gly
                245                 250                 255

Val Gly Ile Pro Gly Val Gly Ile Pro Gly Val Gly Ile Pro Gly Val
            260                 265                 270

Gly Ile Pro Gly Val Gly Ile Pro Gly Val Gly Ile Pro Gly Val Gly
        275                 280                 285

Ile Pro Gly Val Gly Ile Pro Gly Val Gly Ile Pro Gly Val Gly Ile
    290                 295                 300

Pro Gly Val Gly Ile Pro Gly Val Gly Ile Pro Gly Val Gly Ile Pro
305                 310                 315                 320

Gly Val Gly Ile Pro Gly Val Gly Ile Pro Gly Val Gly Ile Pro Gly
                325                 330                 335

Val Gly Ile Pro Gly Val Gly Ile Pro Gly Val Gly Ile Pro Gly Val
            340                 345                 350

Gly Ile Pro Gly Val Gly Ile Pro Gly Val Gly Ile Pro Gly Val Gly
        355                 360                 365

Ile Pro Gly Val Gly Ile Pro Gly Val Gly Ile Pro Gly Val Gly Ile
    370                 375                 380

Pro Gly Val Gly Ile Pro Gly Val Gly Ile Pro Gly Val Gly Ile Pro
385                 390                 395                 400

Gly Val Gly Ile Pro Gly Val Gly Ile Pro Gly Val Gly Ile Pro Gly
                405                 410                 415

Val Gly Ile Pro Gly Val Gly Ile Pro Gly Val Gly Ile Pro Gly Val
            420                 425                 430

Gly Ile Pro Gly Val Gly Ile Pro Gly Val Gly Ile Pro Gly Val Gly
        435                 440                 445

Ile Pro Gly Val Gly Ile Pro Gly Val Gly Ile Pro Gly Val Gly Ile
    450                 455                 460

Pro Gly Val Gly Ile Pro Gly Val Gly Ile Pro Gly Val Gly Ile Pro
465                 470                 475                 480

Gly Val Gly Ile Pro Gly Val Gly Ile Pro Gly Val Gly Ile Pro Gly
                485                 490                 495

Val Gly Ile Pro Gly Val Gly Ile Pro Gly Val Gly Ile Pro Gly Val
            500                 505                 510

Gly Ile Pro Gly Val Gly Ile Pro Gly Val Gly Ile Pro Gly Val Gly
        515                 520                 525

Ile Pro Gly Val Gly Ile Pro Gly Val Gly Ile Pro Gly Val Gly Ile
    530                 535                 540

Pro Gly Val Gly Ile Pro Gly Val Gly Ile Pro Gly Val Pro Gly Val
545                 550                 555                 560

Gly Val Pro Gly Val Gly Val Pro Gly Glu Gly Val Pro Gly Val Gly
                565                 570                 575

Val Pro Gly Val Gly Val Pro Gly Val Gly Val Pro Gly Val Gly Val
            580                 585                 590

Pro Gly Glu Gly Val Pro Gly Val Gly Val Pro Gly Val Gly Val Pro
        595                 600                 605

-continued

Gly Val Gly Val Pro Gly Val Gly Val Pro Gly Glu Gly Val Pro Gly
    610                 615                 620

Val Gly Val Pro Gly Val Gly Val Pro Gly Val Gly Val Pro Gly Val
625                 630                 635                 640

Gly Val Pro Gly Glu Gly Val Pro Gly Val Gly Val Pro Gly Val Gly
            645                 650                 655

Val Pro Gly Val Gly Val Pro Gly Val Gly Val Pro Gly Glu Gly Val
            660                 665                 670

Pro Gly Val Gly Val Pro Gly Val Gly Val Pro Gly Val Gly Val Pro
            675                 680                 685

Gly Val Gly Val Pro Gly Glu Gly Val Pro Gly Val Gly Val Pro Gly
    690                 695                 700

Val Gly Val Pro Gly Val Gly Val Pro Gly Val Gly Val Pro Gly Glu
705                 710                 715                 720

Gly Val Pro Gly Val Gly Val Pro Gly Val Gly Val Pro Gly Val Gly
            725                 730                 735

Val Pro Gly Val Gly Val Pro Gly Glu Gly Val Pro Gly Val Gly Val
            740                 745                 750

Pro Gly Val Gly Val Pro Gly Val Gly Val Pro Gly Val Gly Val Pro
            755                 760                 765

Gly Glu Gly Val Pro Gly Val Gly Val Pro Gly Val Gly Val Pro Gly
    770                 775                 780

Val Gly Val Pro Gly Val Gly Val Pro Gly Glu Gly Val Pro Gly Val
785                 790                 795                 800

Gly Val Pro Gly Val Gly Val Gly Ile Pro Gly Val Gly Ile Pro Gly
            805                 810                 815

Val Gly Ile Pro Gly Val Gly Ile Pro Gly Val Gly Ile Pro Gly Val
            820                 825                 830

Gly Ile Pro Gly Val Gly Ile Pro Gly Val Gly Ile Pro Gly Val Gly
    835                 840                 845

Ile Pro Gly Val Gly Ile Pro Gly Val Gly Ile Pro Gly Val Gly Ile
    850                 855                 860

Pro Gly Val Gly Ile Pro Gly Val Gly Ile Pro Gly Val Gly Ile Pro
865                 870                 875                 880

Gly Val Gly Ile Pro Gly Val Gly Ile Pro Gly Val Gly Ile Pro Gly
            885                 890                 895

Val Gly Ile Pro Gly Val Gly Ile Pro Gly Val Gly Ile Pro Gly Val
            900                 905                 910

Gly Ile Pro Gly Val Gly Ile Pro Gly Val Gly Ile Pro Gly Val Gly
    915                 920                 925

Ile Pro Gly Val Gly Ile Pro Gly Val Gly Ile Pro Gly Val Gly Ile
    930                 935                 940

Pro Gly Val Gly Ile Pro Gly Val Gly Ile Pro Gly Val Gly Ile Pro
945                 950                 955                 960

Gly Val Gly Ile Pro Gly Val Gly Ile Pro Gly Val Gly Ile Pro Gly
            965                 970                 975

Val Gly Ile Pro Gly Val Gly Ile Pro Gly Val Gly Ile Pro Gly Val
            980                 985                 990

Gly Ile Pro Gly Val Gly Ile Pro  Gly Val Gly Ile Pro  Gly Val Gly
    995                 1000                1005

Ile Pro  Gly Val Gly Ile Pro  Gly Val Gly Ile Pro  Gly Val Gly
    1010                1015                1020

Ile Pro  Gly Val Gly Ile Pro  Gly Val Gly Ile Pro  Gly Val Gly

```
                1025                1030                1035

Ile Pro Gly Val Gly Ile Pro Gly Val Gly Ile Pro Gly Val Gly
            1040                1045                1050

Ile Pro Gly Val Gly Ile Pro Gly Val Gly Ile Pro Gly Val Gly
            1055                1060                1065

Ile Pro Gly Val Gly Ile Pro Gly Val Gly Ile Pro Gly Val Gly
            1070                1075                1080

Ile Pro Gly Val Gly Ile Pro Gly Val Gly Ile Pro Gly Val Gly
            1085                1090                1095

Ile Pro Gly Val Gly Ile Pro Gly Val
            1100                1105

<210> SEQ ID NO 30
<211> LENGTH: 607
<212> TYPE: PRT
<213> ORGANISM: Artificial Sequence
<220> FEATURE:
<223> OTHER INFORMATION: Peptide sequence

<400> SEQUENCE: 30

Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly Val
                20                  25                  30

Pro Gly Ile Gly Val Pro Gly Ile Gly Val Pro Gly Lys Gly Val Pro
            35                  40                  45

Gly Ile Gly Val Pro Gly Ile Gly Val Pro Gly Ile Gly Val Pro Gly
        50                  55                  60

Ile Gly Val Pro Gly Lys Gly Val Pro Gly Ile Gly Val Pro Gly Ile
65                  70                  75                  80

Gly Val Pro Gly Ile Gly Val Pro Gly Ile Gly Val Pro Gly Lys Gly
                85                  90                  95

Val Pro Gly Ile Gly Val Pro Gly Ile Gly Val Pro Gly Ile Gly Val
                100                 105                 110

Pro Gly Ile Gly Val Pro Gly Lys Gly Val Pro Gly Ile Gly Val Pro
            115                 120                 125

Gly Ile Gly Val Pro Gly Ile Gly Val Pro Gly Ile Gly Val Pro Gly
        130                 135                 140

Lys Gly Val Pro Gly Ile Gly Val Pro Gly Ile Gly Val Pro Gly Ile
145                 150                 155                 160

Gly Val Pro Gly Ile Gly Val Pro Gly Lys Gly Val Pro Gly Ile Gly
                165                 170                 175

Val Pro Gly Ile Gly Val Pro Gly Ile Gly Val Pro Gly Ile Gly Val
                180                 185                 190

Pro Gly Lys Gly Val Pro Gly Ile Gly Val Pro Gly Ile Gly Val Pro
            195                 200                 205

Gly Ile Gly Val Pro Gly Ile Gly Val Pro Gly Lys Gly Val Pro Gly
        210                 215                 220

Ile Gly Val Pro Gly Ile Gly Val Pro Gly Ile Gly Val Pro Gly Ile
225                 230                 235                 240

Gly Val Pro Gly Lys Gly Val Pro Gly Ile Gly Val Pro Gly Ile Gly
                245                 250                 255

Val Pro Gly Ile Gly Val Pro Gly Ile Gly Val Pro Gly Lys Gly Val
                260                 265                 270

Pro Gly Ile Gly Val Pro Gly Ile Gly Val Pro Gly Ile Gly Val Pro
```

```
            275                 280                 285
Gly Ile Gly Val Pro Gly Lys Gly Val Pro Gly Ile Gly Val Pro Gly
        290                 295                 300
Ile Gly Val Pro Gly Ile Gly Val Pro Gly Ile Gly Val Pro Gly Lys
305                 310                 315                 320
Gly Val Pro Gly Ile Gly Val Pro Gly Ile Gly Val Pro Gly Ile Gly
                325                 330                 335
Val Pro Gly Ile Gly Val Pro Gly Lys Gly Val Pro Gly Ile Gly Val
            340                 345                 350
Pro Gly Ile Gly Val Pro Gly Ile Gly Val Pro Gly Ile Gly Val Pro
        355                 360                 365
Gly Lys Gly Val Pro Gly Ile Gly Val Pro Gly Ile Gly Val Pro Gly
    370                 375                 380
Ile Gly Val Pro Gly Ile Gly Val Pro Gly Lys Gly Val Pro Gly Ile
385                 390                 395                 400
Gly Val Pro Gly Ile Gly Val Pro Gly Ile Gly Val Pro Gly Ile Gly
                405                 410                 415
Val Pro Gly Lys Gly Val Pro Gly Ile Gly Val Pro Gly Ile Gly Val
            420                 425                 430
Pro Gly Ile Gly Val Pro Gly Ile Gly Val Pro Gly Lys Gly Val Pro
        435                 440                 445
Gly Ile Gly Val Pro Gly Ile Gly Val Pro Gly Ile Gly Val Pro Gly
    450                 455                 460
Ile Gly Val Pro Gly Lys Gly Val Pro Gly Ile Gly Val Pro Gly Ile
465                 470                 475                 480
Gly Val Pro Gly Ile Gly Val Pro Gly Ile Gly Val Pro Gly Lys Gly
                485                 490                 495
Val Pro Gly Ile Gly Val Pro Gly Ile Gly Val Pro Gly Ile Gly Val
            500                 505                 510
Pro Gly Ile Gly Val Pro Gly Lys Gly Val Pro Gly Ile Gly Val Pro
        515                 520                 525
Gly Ile Gly Val Pro Gly Ile Gly Val Pro Gly Ile Gly Val Pro Gly
    530                 535                 540
Lys Gly Val Pro Gly Ile Gly Val Pro Gly Ile Gly Val Pro Gly Ile
545                 550                 555                 560
Gly Val Pro Gly Ile Gly Val Pro Gly Lys Gly Val Pro Gly Ile Gly
                565                 570                 575
Val Pro Gly Ile Gly Val Pro Gly Ile Gly Val Pro Gly Ile Gly Val
            580                 585                 590
Pro Gly Lys Gly Val Pro Gly Ile Gly Val Pro Gly Ile Gly Val
        595                 600                 605

<210> SEQ ID NO 31
<211> LENGTH: 376
<212> TYPE: PRT
<213> ORGANISM: Artificial Sequence
<220> FEATURE:
<223> OTHER INFORMATION: Protein sequence

<400> SEQUENCE: 31

Val Pro Gly Val Gly Val Pro Gly Val Gly Val Pro Gly Glu Gly Val
1               5                   10                  15
Pro Gly Val Gly Val Pro Gly Val Gly Val Pro Gly Val Gly Val Pro
            20                  25                  30
Gly Val Gly Val Pro Gly Glu Gly Val Pro Gly Val Gly Val Pro Gly
```

```
                35                  40                  45
Val Gly Val Pro Gly Val Gly Val Pro Gly Val Gly Val Pro Gly Glu
 50                  55                  60

Gly Val Pro Gly Val Gly Val Pro Gly Val Gly Val Pro Gly Val Gly
 65                  70                  75                  80

Val Pro Gly Val Gly Val Pro Gly Glu Gly Val Pro Gly Val Gly Val
                 85                  90                  95

Pro Gly Val Gly Val Pro Gly Val Gly Val Pro Gly Val Gly Val Pro
            100                 105                 110

Gly Glu Gly Val Pro Gly Val Gly Val Pro Gly Val Gly Val Pro Gly
        115                 120                 125

Val Gly Val Pro Gly Val Gly Val Pro Gly Glu Gly Val Pro Gly Val
    130                 135                 140

Gly Val Pro Gly Val Gly Val Pro Gly Val Gly Val Pro Gly Val Gly
145                 150                 155                 160

Val Pro Gly Glu Gly Val Pro Gly Val Gly Val Pro Gly Val Gly Val
                165                 170                 175

Pro Gly Val Gly Val Pro Gly Val Gly Val Pro Gly Glu Gly Val Pro
            180                 185                 190

Gly Val Gly Val Pro Gly Val Gly Val Pro Gly Val Gly Val Pro Gly
        195                 200                 205

Val Gly Val Pro Gly Glu Gly Val Pro Gly Val Gly Val Pro Gly Val
    210                 215                 220

Gly Val Pro Gly Val Gly Val Pro Gly Val Gly Val Pro Gly Glu Gly
225                 230                 235                 240

Val Pro Gly Val Gly Val Pro Gly Val Gly Val Pro Gly Val Gly Val
                245                 250                 255

Pro Gly Val Gly Val Pro Gly Glu Gly Val Pro Gly Val Gly Val Pro
            260                 265                 270

Gly Val Gly Val Pro Gly Val Gly Val Pro Gly Val Gly Val Pro Gly
        275                 280                 285

Glu Gly Val Pro Gly Val Gly Val Pro Gly Val Gly Val Pro Gly Val
    290                 295                 300

Gly Val Pro Gly Val Gly Val Pro Gly Glu Gly Val Pro Gly Val Gly
305                 310                 315                 320

Val Pro Gly Val Gly Val Pro Gly Val Gly Val Pro Gly Val Gly Val
                325                 330                 335

Pro Gly Glu Gly Val Pro Gly Val Gly Val Pro Gly Val Gly Val Pro
            340                 345                 350

Gly Val Gly Val Pro Gly Val Gly Val Pro Gly Glu Gly Val Pro Gly
        355                 360                 365

Val Gly Val Pro Gly Val Gly Val
    370                 375

<210> SEQ ID NO 32
<211> LENGTH: 352
<212> TYPE: PRT
<213> ORGANISM: Artificial Sequence
<220> FEATURE:
<223> OTHER INFORMATION: Peptide sequence

<400> SEQUENCE: 32

Met Glu Ser Leu Leu Pro Val Pro Gly Ile Gly Val Pro Gly Ile Gly
 1               5                  10                  15

Val Pro Gly Lys Gly Val Pro Gly Ile Gly Val Pro Gly Ile Gly Val
```

```
              20                  25                  30

Pro Gly Ile Gly Val Pro Gly Ile Gly Val Pro Gly Lys Gly Val Pro
            35                  40                  45

Gly Ile Gly Val Pro Gly Ile Gly Asp Asp Asp Glu Glu Lys Phe Leu
            50                  55                  60

Arg Arg Ile Gly Arg Phe Gly Val Pro Gly Ile Gly Val Pro Gly Ile
 65                  70                  75                  80

Gly Val Pro Gly Lys Gly Val Pro Gly Ile Gly Val Pro Gly Ile Gly
                85                  90                  95

Val Pro Gly Ile Gly Val Pro Gly Ile Gly Val Pro Gly Lys Gly Val
                100                 105                 110

Pro Gly Ile Gly Val Pro Gly Ile Gly Val Pro Gly Ile Gly Val Pro
            115                 120                 125

Gly Ile Gly Val Pro Gly Lys Gly Val Pro Gly Ile Gly Val Pro Gly
            130                 135                 140

Ile Gly Val Pro Gly Ile Gly Val Pro Gly Ile Gly Val Pro Gly Lys
145                 150                 155                 160

Gly Val Pro Gly Ile Gly Val Pro Gly Ile Gly Asp Asp Asp Glu Glu
                165                 170                 175

Lys Phe Leu Arg Arg Ile Gly Arg Phe Gly Val Pro Gly Ile Gly Val
                180                 185                 190

Pro Gly Ile Gly Val Pro Gly Lys Gly Val Pro Gly Ile Gly Val Pro
            195                 200                 205

Gly Ile Gly Val Pro Gly Ile Gly Val Pro Gly Ile Gly Val Pro Gly
            210                 215                 220

Lys Gly Val Pro Gly Ile Gly Val Pro Gly Ile Gly Val Pro Gly Ile
225                 230                 235                 240

Gly Val Pro Gly Ile Gly Val Pro Gly Lys Gly Val Pro Gly Ile Gly
                245                 250                 255

Val Pro Gly Ile Gly Val Pro Gly Ile Gly Val Pro Gly Ile Gly Val
                260                 265                 270

Pro Gly Lys Gly Val Pro Gly Ile Gly Val Pro Gly Ile Gly Asp Asp
            275                 280                 285

Asp Glu Glu Lys Phe Leu Arg Arg Ile Gly Arg Phe Gly Val Pro Gly
            290                 295                 300

Ile Gly Val Pro Gly Ile Gly Val Pro Gly Lys Gly Val Pro Gly Ile
305                 310                 315                 320

Gly Val Pro Gly Ile Gly Val Pro Gly Ile Gly Val Pro Gly Ile Gly
                325                 330                 335

Val Pro Gly Lys Gly Val Pro Gly Ile Gly Val Pro Gly Ile Gly Val
            340                 345                 350

<210> SEQ ID NO 33
<211> LENGTH: 452
<212> TYPE: PRT
<213> ORGANISM: Artificial Sequence
<220> FEATURE:
<223> OTHER INFORMATION: Peptide sequence

<400> SEQUENCE: 33

Met Glu Ser Leu Leu Pro Val Pro Gly Ile Gly Val Pro Gly Ile Gly
 1               5                  10                  15

Val Pro Gly Lys Gly Val Pro Gly Ile Gly Val Pro Gly Ile Gly Val
            20                  25                  30

Pro Gly Ile Gly Val Pro Gly Ile Gly Val Pro Gly Lys Gly Val Pro
```

```
                35                  40                  45
Gly Ile Gly Val Pro Gly Ile Gly Asp Asp Glu Glu Lys Phe Leu
         50                  55                  60
Arg Arg Ile Gly Arg Phe Gly Val Pro Gly Ile Gly Val Pro Gly Ile
 65                  70                  75                  80
Gly Val Pro Gly Lys Gly Val Pro Gly Ile Gly Val Pro Gly Ile Gly
                 85                  90                  95
Val Pro Gly Ile Gly Val Pro Gly Ile Gly Val Pro Gly Lys Gly Val
             100                 105                 110
Pro Gly Ile Gly Val Pro Gly Ile Gly Val Pro Gly Ile Gly Val Pro
         115                 120                 125
Gly Ile Gly Val Pro Gly Lys Gly Val Pro Gly Ile Gly Val Pro Gly
     130                 135                 140
Ile Gly Val Pro Gly Ile Gly Val Pro Gly Ile Gly Val Pro Gly Lys
145                 150                 155                 160
Gly Val Pro Gly Ile Gly Val Pro Gly Ile Gly Asp Asp Glu Glu
                165                 170                 175
Lys Phe Leu Arg Arg Ile Gly Arg Phe Gly Val Pro Gly Ile Gly Val
             180                 185                 190
Pro Gly Ile Gly Val Pro Gly Lys Gly Val Pro Gly Ile Gly Val Pro
         195                 200                 205
Gly Ile Gly Val Pro Gly Ile Gly Val Pro Gly Ile Gly Val Pro Gly
     210                 215                 220
Lys Gly Val Pro Gly Ile Gly Val Pro Gly Ile Gly Val Pro Gly Ile
225                 230                 235                 240
Gly Val Pro Gly Ile Gly Val Pro Gly Lys Gly Val Pro Gly Ile Gly
                245                 250                 255
Val Pro Gly Ile Gly Val Pro Gly Ile Gly Val Pro Gly Ile Gly Val
             260                 265                 270
Pro Gly Lys Gly Val Pro Gly Ile Gly Val Pro Gly Ile Gly Asp Asp
         275                 280                 285
Asp Glu Glu Lys Phe Leu Arg Arg Ile Gly Arg Phe Gly Val Pro Gly
     290                 295                 300
Ile Gly Val Pro Gly Ile Gly Val Pro Gly Lys Gly Val Pro Gly Ile
305                 310                 315                 320
Gly Val Pro Gly Ile Gly Val Pro Gly Ile Gly Val Pro Gly Ile Gly
                325                 330                 335
Val Pro Gly Lys Gly Val Pro Gly Ile Gly Val Pro Gly Ile Gly Val
             340                 345                 350
Pro Ala Val Gly Val Pro Ala Val Gly Val Pro Ala Val Gly Val Pro
         355                 360                 365
Ala Val Gly Val Pro Ala Val Gly Val Pro Ala Val Gly Val Pro Ala
     370                 375                 380
Val Gly Val Pro Ala Val Gly Val Pro Ala Val Gly Val Pro Ala Val
385                 390                 395                 400
Gly Val Pro Ala Val Gly Val Pro Ala Val Gly Val Pro Ala Val Gly
                405                 410                 415
Val Pro Ala Val Gly Val Pro Ala Val Gly Val Pro Ala Val Gly Val
             420                 425                 430
Pro Ala Val Gly Val Pro Ala Val Gly Val Pro Ala Val Gly Val Pro
         435                 440                 445
Ala Val Gly Val
         450
```

<210> SEQ ID NO 34
<211> LENGTH: 797
<212> TYPE: PRT
<213> ORGANISM: Artificial Sequence
<220> FEATURE:
<223> OTHER INFORMATION: Peptide sequence

<400> SEQUENCE: 34

```
Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly Val
                20                  25                  30

Pro Gly Ile Gly Val Pro Gly Ile Gly Val Pro Gly Lys Gly Val Pro
            35                  40                  45

Gly Ile Gly Val Pro Gly Ile Gly Asp Asp Asp Glu Glu Lys Phe Leu
        50                  55                  60

Arg Arg Ile Gly Arg Phe Gly Val Pro Gly Ile Gly Val Pro Gly Ile
65                  70                  75                  80

Gly Val Pro Gly Lys Gly Val Pro Gly Ile Gly Val Pro Gly Ile Gly
                85                  90                  95

Val Pro Gly Ile Gly Val Pro Gly Ile Gly Val Pro Gly Lys Gly Val
                100                 105                 110

Pro Gly Ile Gly Val Pro Gly Ile Gly Val Pro Gly Ile Gly Val Pro
            115                 120                 125

Gly Ile Gly Val Pro Gly Lys Gly Val Pro Gly Ile Gly Val Pro Gly
        130                 135                 140

Ile Gly Val Pro Gly Ile Gly Val Pro Gly Ile Gly Val Pro Gly Lys
145                 150                 155                 160

Gly Val Pro Gly Ile Gly Val Pro Gly Ile Gly Asp Asp Asp Glu Glu
                165                 170                 175

Lys Phe Leu Arg Arg Ile Gly Arg Phe Gly Val Pro Gly Ile Gly Val
                180                 185                 190

Pro Gly Ile Gly Val Pro Gly Lys Gly Val Pro Gly Ile Gly Val Pro
            195                 200                 205

Gly Ile Gly Val Pro Gly Ile Gly Val Pro Gly Ile Gly Val Pro Gly
        210                 215                 220

Lys Gly Val Pro Gly Ile Gly Val Pro Gly Ile Gly Val Pro Gly Ile
225                 230                 235                 240

Gly Val Pro Gly Ile Gly Val Pro Gly Lys Gly Val Pro Gly Ile Gly
                245                 250                 255

Val Pro Gly Ile Gly Val Pro Gly Ile Gly Val Pro Gly Ile Gly Val
                260                 265                 270

Pro Gly Lys Gly Val Pro Gly Ile Gly Val Pro Gly Ile Gly Asp Asp
            275                 280                 285

Asp Glu Glu Lys Phe Leu Arg Arg Ile Gly Arg Phe Gly Val Pro Gly
        290                 295                 300

Ile Gly Val Pro Gly Ile Gly Val Pro Gly Lys Gly Val Pro Gly Ile
305                 310                 315                 320

Gly Val Pro Gly Ile Gly Val Pro Gly Ile Gly Val Pro Gly Ile Gly
                325                 330                 335

Val Pro Gly Lys Gly Val Pro Gly Ile Gly Val Pro Gly Ile Gly Val
                340                 345                 350

Pro Ala Val Gly Val Pro Ala Val Gly Val Pro Ala Val Gly Val Pro
            355                 360                 365
```

```
Ala Val Gly Val Pro Ala Val Gly Val Pro Ala Val Gly Val Pro Ala
    370                 375                 380

Val Gly Val Pro Ala Val Gly Val Pro Ala Val Gly Val Pro Ala Val
385                 390                 395                 400

Gly Val Pro Ala Val Gly Val Pro Ala Val Gly Val Pro Ala Val Gly
                405                 410                 415

Val Pro Ala Val Gly Val Pro Ala Val Gly Val Pro Ala Val Gly Val
            420                 425                 430

Pro Ala Val Gly Val Pro Ala Val Gly Val Pro Ala Val Gly Val Pro
        435                 440                 445

Ala Val Gly Val Pro Gly Ile Gly Val Pro Gly Ile Gly Val Pro Gly
    450                 455                 460

Lys Gly Val Pro Gly Ile Gly Val Pro Gly Ile Gly Val Pro Gly Ile
465                 470                 475                 480

Gly Val Pro Gly Ile Gly Val Pro Gly Lys Gly Val Pro Gly Ile Gly
                485                 490                 495

Val Pro Gly Ile Gly Asp Asp Asp Glu Glu Lys Phe Leu Arg Arg Ile
            500                 505                 510

Gly Arg Phe Gly Val Pro Gly Ile Gly Val Pro Gly Ile Gly Val Pro
        515                 520                 525

Gly Lys Gly Val Pro Gly Ile Gly Val Pro Gly Ile Gly Val Pro Gly
    530                 535                 540

Ile Gly Val Pro Gly Ile Gly Val Pro Gly Lys Gly Val Pro Gly Ile
545                 550                 555                 560

Gly Val Pro Gly Ile Gly Val Pro Gly Ile Gly Val Pro Gly Ile Gly
                565                 570                 575

Val Pro Gly Lys Gly Val Pro Gly Ile Gly Val Pro Gly Ile Gly Val
            580                 585                 590

Pro Gly Ile Gly Val Pro Gly Ile Gly Val Pro Gly Lys Gly Val Pro
        595                 600                 605

Gly Ile Gly Val Pro Gly Ile Gly Asp Asp Asp Glu Glu Lys Phe Leu
    610                 615                 620

Arg Arg Ile Gly Arg Phe Gly Val Pro Gly Ile Gly Val Pro Gly Ile
625                 630                 635                 640

Gly Val Pro Gly Lys Gly Val Pro Gly Ile Gly Val Pro Gly Ile Gly
                645                 650                 655

Val Pro Gly Ile Gly Val Pro Gly Ile Gly Val Pro Gly Lys Gly Val
            660                 665                 670

Pro Gly Ile Gly Val Pro Gly Ile Gly Val Pro Gly Ile Gly Val Pro
        675                 680                 685

Gly Ile Gly Val Pro Gly Lys Gly Val Pro Gly Ile Gly Val Pro Gly
    690                 695                 700

Ile Gly Val Pro Gly Ile Gly Val Pro Gly Ile Gly Val Pro Gly Lys
705                 710                 715                 720

Gly Val Pro Gly Ile Gly Val Pro Gly Ile Gly Asp Asp Asp Glu Glu
                725                 730                 735

Lys Phe Leu Arg Arg Ile Gly Arg Phe Gly Val Pro Gly Ile Gly Val
            740                 745                 750

Pro Gly Ile Gly Val Pro Gly Lys Gly Val Pro Gly Ile Gly Val Pro
        755                 760                 765

Gly Ile Gly Val Pro Gly Ile Gly Val Pro Gly Ile Gly Val Pro Gly
    770                 775                 780
```

-continued

Lys Gly Val Pro Gly Ile Gly Val Pro Gly Ile Gly Val
785                 790                 795

<210> SEQ ID NO 35
<211> LENGTH: 457
<212> TYPE: PRT
<213> ORGANISM: Artificial Sequence
<220> FEATURE:
<223> OTHER INFORMATION: Peptide sequence

<400> SEQUENCE: 35

Met Glu Ser Leu Leu Pro Val Pro Gly Val Gly Val Pro Gly Val Gly
1               5                   10                  15

Val Pro Gly Glu Gly Val Pro Gly Val Gly Val Pro Gly Val Gly Val
                20                  25                  30

Pro Gly Val Gly Val Pro Gly Val Gly Val Pro Gly Glu Gly Val Pro
            35                  40                  45

Gly Val Gly Val Pro Gly Val Gly Val Pro Gly Val Gly Val Pro Gly
        50                  55                  60

Val Gly Val Pro Gly Glu Gly Val Pro Gly Val Gly Val Pro Gly Val
65                  70                  75                  80

Gly Val Pro Gly Val Gly Val Pro Gly Val Gly Val Pro Gly Glu Gly
                85                  90                  95

Val Pro Gly Val Gly Val Pro Gly Val Gly Val Pro Gly Val Gly Val
                100                 105                 110

Pro Gly Val Gly Val Pro Gly Glu Gly Val Pro Gly Val Gly Val Pro
            115                 120                 125

Gly Val Gly Val Pro Gly Val Gly Val Pro Gly Val Gly Val Pro Gly
        130                 135                 140

Glu Gly Val Pro Gly Val Gly Val Pro Gly Val Gly Val Pro Gly Val
145                 150                 155                 160

Gly Val Pro Gly Val Gly Val Pro Gly Glu Gly Val Pro Gly Val Gly
                165                 170                 175

Val Pro Gly Val Gly Val Pro Gly Val Gly Val Pro Gly Val Gly Val
                180                 185                 190

Pro Gly Glu Gly Val Pro Gly Val Gly Val Pro Gly Val Gly Val Pro
            195                 200                 205

Gly Val Gly Val Pro Gly Val Gly Val Pro Gly Glu Gly Val Pro Gly
        210                 215                 220

Val Gly Val Pro Gly Val Gly Val Pro Gly Val Gly Val Pro Gly Val
225                 230                 235                 240

Gly Val Pro Gly Glu Gly Val Pro Gly Val Gly Val Pro Gly Val Gly
                245                 250                 255

Val Pro Ala Val Gly Val Pro Ala Val Gly Val Pro Ala Val Gly Val
                260                 265                 270

Pro Ala Val Gly Val Pro Ala Val Gly Val Pro Ala Val Gly Val Pro
            275                 280                 285

Ala Val Gly Val Pro Ala Val Gly Val Pro Ala Val Gly Val Pro Ala
        290                 295                 300

Val Gly Val Pro Ala Val Gly Val Pro Ala Val Gly Val Pro Ala Val
305                 310                 315                 320

Gly Val Pro Ala Val Gly Val Pro Ala Val Gly Val Pro Ala Val Gly
                325                 330                 335

Val Pro Ala Val Gly Val Pro Ala Val Gly Val Pro Ala Val Gly Val
                340                 345                 350

```
Pro Ala Val Gly Val Pro Ala Val Gly Val Pro Ala Val Gly Val Pro
            355                 360                 365

Ala Val Gly Val Pro Ala Val Gly Val Pro Ala Val Gly Val Pro Ala
            370                 375                 380

Val Gly Val Pro Ala Val Gly Val Pro Ala Val Gly Val Pro Ala Val
385                 390                 395                 400

Gly Val Pro Ala Val Gly Val Pro Ala Val Gly Val Pro Ala Val Gly
                405                 410                 415

Val Pro Ala Val Gly Val Pro Ala Val Gly Val Pro Ala Val Gly Val
            420                 425                 430

Pro Ala Val Gly Val Pro Ala Val Gly Val Pro Ala Val Gly Val Pro
            435                 440                 445

Ala Val Gly Val Pro Ala Val Gly Val
            450                 455

<210> SEQ ID NO 36
<211> LENGTH: 557
<212> TYPE: PRT
<213> ORGANISM: Artificial Sequence
<220> FEATURE:
<223> OTHER INFORMATION: Peptide sequence

<400> SEQUENCE: 36

Met Glu Ser Leu Leu Pro Val Pro Gly Val Gly Val Pro Gly Val Gly
1               5                   10                  15

Val Pro Gly Glu Gly Val Pro Gly Val Gly Val Pro Gly Val Gly Val
            20                  25                  30

Pro Gly Val Gly Val Pro Gly Val Gly Val Pro Gly Glu Gly Val Pro
            35                  40                  45

Gly Val Gly Val Pro Gly Val Gly Val Pro Gly Val Gly Val Pro Gly
        50                  55                  60

Val Gly Val Pro Gly Glu Gly Val Pro Gly Val Gly Val Pro Gly Val
65                  70                  75                  80

Gly Val Pro Gly Val Gly Val Pro Gly Val Gly Val Pro Gly Glu Gly
                85                  90                  95

Val Pro Gly Val Gly Val Pro Gly Val Gly Val Pro Gly Val Gly Val
            100                 105                 110

Pro Gly Val Gly Val Pro Gly Glu Gly Val Pro Gly Val Gly Val Pro
            115                 120                 125

Gly Val Gly Val Pro Gly Val Gly Val Pro Gly Val Gly Val Pro Gly
        130                 135                 140

Glu Gly Val Pro Gly Val Gly Val Pro Gly Val Gly Val Pro Gly Val
145                 150                 155                 160

Gly Val Pro Gly Val Gly Val Pro Gly Glu Gly Val Pro Gly Val Gly
                165                 170                 175

Val Pro Gly Val Gly Val Pro Gly Val Gly Val Pro Gly Val Gly Val
            180                 185                 190

Pro Gly Glu Gly Val Pro Gly Val Gly Val Pro Gly Val Gly Val Pro
            195                 200                 205

Gly Val Gly Val Pro Gly Val Gly Val Pro Gly Glu Gly Val Pro Gly
        210                 215                 220

Val Gly Val Pro Gly Val Gly Val Pro Gly Val Gly Val Pro Gly Val
225                 230                 235                 240

Gly Val Pro Gly Glu Gly Val Pro Gly Val Gly Val Pro Gly Val Gly
                245                 250                 255
```

Val Pro Ala Val Gly Val Pro Ala Val Gly Val Pro Ala Val Gly Val
            260                 265                 270

Pro Ala Val Gly Val Pro Ala Val Gly Val Pro Ala Val Gly Val Pro
            275                 280                 285

Ala Val Gly Val Pro Ala Val Gly Val Pro Ala Val Gly Val Pro Ala
            290                 295                 300

Val Gly Val Pro Ala Val Gly Val Pro Ala Val Gly Val Pro Ala Val
305                 310                 315                 320

Gly Val Pro Ala Val Gly Val Pro Ala Val Gly Val Pro Ala Val Gly
            325                 330                 335

Val Pro Ala Val Gly Val Pro Ala Val Gly Val Pro Ala Val Gly Val
            340                 345                 350

Pro Ala Val Gly Val Pro Ala Val Gly Val Pro Ala Val Gly Val Pro
            355                 360                 365

Ala Val Gly Val Pro Ala Val Gly Val Pro Ala Val Gly Val Pro Ala
            370                 375                 380

Val Gly Val Pro Ala Val Gly Val Pro Ala Val Gly Val Pro Ala Val
385                 390                 395                 400

Gly Val Pro Ala Val Gly Val Pro Ala Val Gly Val Pro Ala Val Gly
            405                 410                 415

Val Pro Ala Val Gly Val Pro Ala Val Gly Val Pro Ala Val Gly Val
            420                 425                 430

Pro Ala Val Gly Val Pro Ala Val Gly Val Pro Ala Val Gly Val Pro
            435                 440                 445

Ala Val Gly Val Pro Ala Val Gly Val Pro Ala Val Gly Val Pro Ala
            450                 455                 460

Val Gly Val Pro Ala Val Gly Val Pro Ala Val Gly Val Pro Ala Val
465                 470                 475                 480

Gly Val Pro Ala Val Gly Val Pro Ala Val Gly Val Pro Ala Val Gly
            485                 490                 495

Val Pro Ala Val Gly Val Pro Ala Val Gly Val Pro Ala Val Gly Val
            500                 505                 510

Pro Ala Val Gly Val Pro Ala Val Gly Val Pro Ala Val Gly Val Pro
            515                 520                 525

Ala Val Gly Val Pro Ala Val Gly Val Pro Ala Val Gly Val Pro Ala
            530                 535                 540

Val Gly Val Pro Ala Val Gly Val Pro Ala Val Gly Val
545                 550                 555

<210> SEQ ID NO 37
<211> LENGTH: 707
<212> TYPE: PRT
<213> ORGANISM: Artificial Sequence
<220> FEATURE:
<223> OTHER INFORMATION: Peptide sequence

<400> SEQUENCE: 37

Met Glu Ser Leu Leu Pro Val Pro Gly Val Gly Val Pro Gly Val Gly
1               5                   10                  15

Val Pro Gly Glu Gly Val Pro Gly Val Gly Val Pro Gly Val Gly Val
            20                  25                  30

Pro Gly Val Gly Val Pro Gly Val Gly Val Pro Gly Glu Gly Val Pro
            35                  40                  45

Gly Val Gly Val Pro Gly Val Gly Val Pro Gly Val Gly Val Pro Gly
            50                  55                  60

```
Val Gly Val Pro Gly Glu Gly Val Pro Gly Val Gly Val Pro Gly Val
 65                  70                  75                  80

Gly Val Pro Gly Val Gly Val Pro Gly Val Gly Val Pro Gly Glu Gly
                 85                  90                  95

Val Pro Gly Val Gly Val Pro Gly Val Gly Val Pro Gly Val Gly Val
            100                 105                 110

Pro Gly Val Gly Val Pro Gly Glu Gly Val Pro Gly Val Gly Val Pro
        115                 120                 125

Gly Val Gly Val Pro Gly Val Gly Val Pro Gly Val Gly Val Pro Gly
    130                 135                 140

Glu Gly Val Pro Gly Val Gly Val Pro Gly Val Gly Val Pro Gly Val
145                 150                 155                 160

Gly Val Pro Gly Val Gly Val Pro Gly Glu Gly Val Pro Gly Val Gly
                165                 170                 175

Val Pro Gly Val Gly Val Pro Gly Val Gly Val Pro Gly Val Gly Val
            180                 185                 190

Pro Gly Glu Gly Val Pro Gly Val Gly Val Pro Gly Val Gly Val Pro
        195                 200                 205

Gly Val Gly Val Pro Gly Val Gly Val Pro Gly Glu Gly Val Pro Gly
    210                 215                 220

Val Gly Val Pro Gly Val Gly Val Pro Gly Val Gly Val Pro Gly Val
225                 230                 235                 240

Gly Val Pro Gly Glu Gly Val Pro Gly Val Gly Val Pro Gly Val Gly
                245                 250                 255

Val Pro Gly Val Gly Val Pro Gly Val Gly Val Pro Gly Glu Gly Val
            260                 265                 270

Pro Gly Val Gly Val Pro Gly Val Gly Val Pro Gly Val Gly Val Pro
        275                 280                 285

Gly Val Gly Val Pro Gly Glu Gly Val Pro Gly Val Gly Val Pro Gly
    290                 295                 300

Val Gly Val Pro Gly Val Gly Val Pro Gly Val Gly Val Pro Gly Glu
305                 310                 315                 320

Gly Val Pro Gly Val Gly Val Pro Gly Val Gly Val Pro Gly Val Gly
                325                 330                 335

Val Pro Gly Val Gly Val Pro Gly Glu Gly Val Pro Gly Val Gly Val
            340                 345                 350

Pro Gly Val Gly Val Pro Gly Val Gly Val Pro Gly Val Gly Val Pro
        355                 360                 365

Gly Glu Gly Val Pro Gly Val Gly Val Pro Gly Val Gly Val Pro Gly
    370                 375                 380

Val Gly Val Pro Gly Val Gly Val Pro Gly Glu Gly Val Pro Gly Val
385                 390                 395                 400

Gly Val Pro Gly Val Gly Val Pro Gly Val Gly Val Pro Gly Val Gly
                405                 410                 415

Val Pro Gly Glu Gly Val Pro Gly Val Gly Val Pro Gly Val Gly Val
            420                 425                 430

Pro Gly Val Gly Val Pro Gly Val Gly Val Pro Gly Glu Gly Val Pro
        435                 440                 445

Gly Val Gly Val Pro Gly Val Gly Val Pro Gly Val Gly Val Pro Gly
    450                 455                 460

Val Gly Val Pro Gly Glu Gly Val Pro Gly Val Gly Val Pro Gly Val
465                 470                 475                 480

Gly Val Pro Gly Val Gly Val Pro Gly Val Gly Val Pro Gly Glu Gly
```

485                 490                 495
Val Pro Gly Val Gly Val Pro Gly Val Gly Val Pro Ala Val Gly Val
                500                 505                 510
Pro Ala Val Gly Val Pro Ala Val Gly Val Pro Ala Val Gly Val Pro
            515                 520                 525
Ala Val Gly Val Pro Ala Val Gly Val Pro Ala Val Gly Val Pro Ala
        530                 535                 540
Val Gly Val Pro Ala Val Gly Val Pro Ala Val Gly Val Pro Ala Val
545                 550                 555                 560
Gly Val Pro Ala Val Gly Val Pro Ala Val Gly Val Pro Ala Val Gly
                565                 570                 575
Val Pro Ala Val Gly Val Pro Ala Val Gly Val Pro Ala Val Gly Val
                580                 585                 590
Pro Ala Val Gly Val Pro Ala Val Gly Val Pro Ala Val Gly Val Pro
            595                 600                 605
Ala Val Gly Val Pro Ala Val Gly Val Pro Ala Val Gly Val Pro Ala
        610                 615                 620
Val Gly Val Pro Ala Val Gly Val Pro Ala Val Gly Val Pro Ala Val
625                 630                 635                 640
Gly Val Pro Ala Val Gly Val Pro Ala Val Gly Val Pro Ala Val Gly
                645                 650                 655
Val Pro Ala Val Gly Val Pro Ala Val Gly Val Pro Ala Val Gly Val
                660                 665                 670
Pro Ala Val Gly Val Pro Ala Val Gly Val Pro Ala Val Gly Val Pro
            675                 680                 685
Ala Val Gly Val Pro Ala Val Gly Val Pro Ala Val Gly Val Pro Ala
        690                 695                 700
Val Gly Val
705

<210> SEQ ID NO 38
<211> LENGTH: 707
<212> TYPE: PRT
<213> ORGANISM: Artificial Sequence
<220> FEATURE:
<223> OTHER INFORMATION: Peptide sequence

<400> SEQUENCE: 38

Met Glu Ser Leu Leu Pro Val Pro Gly Val Gly Val Pro Gly Val Gly
1               5                   10                  15
Val Pro Gly Glu Gly Val Pro Gly Val Gly Val Pro Gly Val Gly Val
                20                  25                  30
Pro Gly Val Gly Val Pro Gly Val Gly Val Pro Gly Glu Gly Val Pro
            35                  40                  45
Gly Val Gly Val Pro Gly Val Gly Val Pro Gly Val Gly Val Pro Gly
        50                  55                  60
Val Gly Val Pro Gly Glu Gly Val Pro Gly Val Gly Val Pro Gly Val
65                  70                  75                  80
Gly Val Pro Gly Val Gly Val Pro Gly Val Gly Val Pro Gly Glu Gly
                85                  90                  95
Val Pro Gly Val Gly Val Pro Gly Val Gly Val Pro Gly Val Gly Val
                100                 105                 110
Pro Gly Val Gly Val Pro Gly Glu Gly Val Pro Gly Val Gly Val Pro
            115                 120                 125
Gly Val Gly Val Pro Gly Val Gly Val Pro Gly Val Gly Val Pro Gly

-continued

```
                130                 135                 140
Glu Gly Val Pro Gly Val Gly Val Pro Gly Val Gly Val Pro Gly Val
145                 150                 155                 160

Gly Val Pro Gly Val Gly Val Pro Gly Glu Gly Val Pro Gly Val Gly
                165                 170                 175

Val Pro Gly Val Gly Val Pro Gly Val Gly Val Pro Gly Val Gly Val
            180                 185                 190

Pro Gly Glu Gly Val Pro Gly Val Gly Val Pro Gly Val Gly Val Pro
            195                 200                 205

Gly Val Gly Val Pro Gly Val Gly Val Pro Gly Glu Gly Val Pro Gly
        210                 215                 220

Val Gly Val Pro Gly Val Gly Val Pro Gly Val Gly Val Pro Gly Val
225                 230                 235                 240

Gly Val Pro Gly Glu Gly Val Pro Gly Val Gly Val Pro Gly Val Gly
            245                 250                 255

Val Pro Ala Val Gly Val Pro Ala Val Gly Val Pro Ala Val Gly Val
        260                 265                 270

Pro Ala Val Gly Val Pro Ala Val Gly Val Pro Ala Val Gly Val Pro
        275                 280                 285

Ala Val Gly Val Pro Ala Val Gly Val Pro Ala Val Gly Val Pro Ala
    290                 295                 300

Val Gly Val Pro Ala Val Gly Val Pro Ala Val Gly Val Pro Ala Val
305                 310                 315                 320

Gly Val Pro Ala Val Gly Val Pro Ala Val Gly Val Pro Ala Val Gly
            325                 330                 335

Val Pro Ala Val Gly Val Pro Ala Val Gly Val Pro Ala Val Gly Val
        340                 345                 350

Pro Ala Val Gly Val Pro Ala Val Gly Val Pro Ala Val Gly Val Pro
        355                 360                 365

Ala Val Gly Val Pro Ala Val Gly Val Pro Ala Val Gly Val Pro Ala
    370                 375                 380

Val Gly Val Pro Ala Val Gly Val Pro Ala Val Gly Val Pro Ala Val
385                 390                 395                 400

Gly Val Pro Ala Val Gly Val Pro Ala Val Gly Val Pro Ala Val Gly
            405                 410                 415

Val Pro Ala Val Gly Val Pro Ala Val Gly Val Pro Ala Val Gly Val
        420                 425                 430

Pro Ala Val Gly Val Pro Ala Val Gly Val Pro Ala Val Gly Val Pro
        435                 440                 445

Ala Val Gly Val Pro Ala Val Gly Val Pro Gly Val Gly Val Pro Gly
    450                 455                 460

Val Gly Val Pro Gly Glu Gly Val Pro Gly Val Gly Val Pro Gly Val
465                 470                 475                 480

Gly Val Pro Gly Val Gly Val Pro Gly Val Gly Val Pro Gly Glu Gly
            485                 490                 495

Val Pro Gly Val Gly Val Pro Gly Val Gly Val Pro Gly Val Gly Val
        500                 505                 510

Pro Gly Val Gly Val Pro Gly Glu Gly Val Pro Gly Val Gly Val Pro
        515                 520                 525

Gly Val Gly Val Pro Gly Val Gly Val Pro Gly Val Gly Val Pro Gly
    530                 535                 540

Glu Gly Val Pro Gly Val Gly Val Pro Gly Val Gly Val Pro Gly Val
545                 550                 555                 560
```

```
Gly Val Pro Gly Val Gly Val Pro Gly Glu Gly Val Pro Gly Val
                565                 570                 575
Val Pro Gly Val Gly Val Pro Gly Val Gly Val Pro Gly Val Gly Val
                580                 585                 590
Pro Gly Glu Gly Val Pro Gly Val Gly Val Pro Gly Val Gly Val Pro
                595                 600                 605
Gly Val Gly Val Pro Gly Val Gly Val Pro Gly Glu Gly Val Pro Gly
                610                 615                 620
Val Gly Val Pro Gly Val Gly Val Pro Gly Val Gly Val Pro Gly Val
625                 630                 635                 640
Gly Val Pro Gly Glu Gly Val Pro Gly Val Gly Val Pro Gly Val Gly
                645                 650                 655
Val Pro Gly Val Gly Val Pro Gly Val Gly Val Pro Gly Glu Gly Val
                660                 665                 670
Pro Gly Val Gly Val Pro Gly Val Gly Val Pro Gly Val Gly Val Pro
                675                 680                 685
Gly Val Gly Val Pro Gly Glu Gly Val Pro Gly Val Gly Val Pro Gly
                690                 695                 700
Val Gly Val
705

<210> SEQ ID NO 39
<211> LENGTH: 698
<212> TYPE: PRT
<213> ORGANISM: Artificial Sequence
<220> FEATURE:
<223> OTHER INFORMATION: Bioactive sequence

<400> SEQUENCE: 39

Met Gly Ser Ser His His His His His Ser Ser Gly Leu Val Pro
1               5                   10                  15
Arg Gly Ser His Met Glu Ser Leu Leu Pro Val Pro Gly Ile Gly Val
                20                  25                  30
Pro Gly Ile Gly Val Pro Gly Lys Gly Val Pro Gly Ile Gly Val Pro
                35                  40                  45
Gly Ile Gly Val Pro Gly Ile Gly Val Pro Gly Ile Gly Val Pro Gly
                50                  55                  60
Lys Gly Val Pro Gly Ile Gly Val Pro Gly Ile Gly Ala Val Thr Gly
65                  70                  75                  80
Arg Gly Asp Ser Pro Ala Ser Ser Val Pro Gly Ile Gly Val Pro Gly
                85                  90                  95
Ile Gly Val Pro Gly Lys Gly Val Pro Gly Ile Gly Val Pro Gly Ile
                100                 105                 110
Gly Val Pro Gly Ile Gly Val Pro Gly Ile Gly Val Pro Gly Lys Gly
                115                 120                 125
Val Pro Gly Ile Gly Val Pro Gly Ile Gly Val Pro Gly Ile Gly Val
                130                 135                 140
Pro Gly Ile Gly Val Pro Gly Lys Gly Val Pro Gly Ile Gly Val Pro
145                 150                 155                 160
Gly Ile Gly Val Pro Gly Ile Gly Val Pro Gly Ile Gly Val Pro Gly
                165                 170                 175
Lys Gly Val Pro Gly Ile Gly Val Pro Gly Ile Gly Ala Val Thr Gly
                180                 185                 190
Arg Gly Asp Ser Pro Ala Ser Ser Val Pro Gly Ile Gly Val Pro Gly
                195                 200                 205
```

```
Ile Gly Val Pro Gly Lys Val Pro Gly Ile Val Pro Gly Ile
    210                 215                 220

Gly Val Pro Gly Ile Gly Val Pro Gly Ile Gly Val Pro Gly Lys Gly
225                 230                 235                 240

Val Pro Gly Ile Gly Val Pro Gly Ile Gly Val Pro Gly Ile Gly Val
                245                 250                 255

Pro Gly Ile Gly Val Pro Gly Lys Gly Val Pro Gly Ile Gly Val Pro
            260                 265                 270

Gly Ile Gly Val Pro Gly Ile Gly Val Pro Gly Ile Gly Val Pro Gly
        275                 280                 285

Lys Gly Val Pro Gly Ile Gly Val Pro Gly Ile Gly Ala Val Thr Gly
    290                 295                 300

Arg Gly Asp Ser Pro Ala Ser Ser Val Pro Gly Ile Gly Val Pro Gly
305                 310                 315                 320

Ile Gly Val Pro Gly Lys Gly Val Pro Gly Ile Gly Val Pro Gly Ile
                325                 330                 335

Gly Val Pro Gly Ile Gly Val Pro Gly Ile Gly Val Pro Gly Lys Gly
                340                 345                 350

Val Pro Gly Ile Gly Val Pro Gly Ile Gly Val Pro Gly Ile Gly Val
                355                 360                 365

Pro Gly Ile Gly Val Pro Gly Lys Gly Val Pro Gly Ile Gly Val Pro
            370                 375                 380

Gly Ile Gly Val Pro Gly Ile Gly Val Pro Gly Ile Gly Val Pro Gly
385                 390                 395                 400

Lys Gly Val Pro Gly Ile Gly Val Pro Gly Ile Gly Ala Val Thr Gly
                405                 410                 415

Arg Gly Asp Ser Pro Ala Ser Ser Val Pro Gly Ile Gly Val Pro Gly
                420                 425                 430

Ile Gly Val Pro Gly Lys Gly Val Pro Gly Ile Gly Val Pro Gly Ile
                435                 440                 445

Gly Val Pro Gly Ile Gly Val Pro Gly Ile Gly Val Pro Gly Lys Gly
                450                 455                 460

Val Pro Gly Ile Gly Val Pro Gly Ile Gly Val Pro Gly Ile Gly Val
465                 470                 475                 480

Pro Gly Ile Gly Val Pro Gly Lys Gly Val Pro Gly Ile Gly Val Pro
            485                 490                 495

Gly Ile Gly Val Pro Gly Ile Gly Val Pro Gly Ile Gly Val Pro Gly
        500                 505                 510

Lys Gly Val Pro Gly Ile Gly Val Pro Gly Ile Gly Ala Val Thr Gly
    515                 520                 525

Arg Gly Asp Ser Pro Ala Ser Ser Val Pro Gly Ile Gly Val Pro Gly
    530                 535                 540

Ile Gly Val Pro Gly Lys Gly Val Pro Gly Ile Gly Val Pro Gly Ile
545                 550                 555                 560

Gly Val Pro Gly Ile Gly Val Pro Gly Ile Gly Val Pro Gly Lys Gly
                565                 570                 575

Val Pro Gly Ile Gly Val Pro Gly Ile Gly Val Pro Gly Ile Gly Val
                580                 585                 590

Pro Gly Ile Gly Val Pro Gly Lys Gly Val Pro Gly Ile Gly Val Pro
            595                 600                 605

Gly Ile Gly Val Pro Gly Ile Gly Val Pro Gly Ile Gly Val Pro Gly
        610                 615                 620
```

-continued

```
Lys Gly Val Pro Gly Ile Gly Val Pro Gly Ile Gly Val Thr Gly
625                 630                 635                 640

Arg Gly Asp Ser Pro Ala Ser Ser Val Pro Gly Ile Gly Val Pro Gly
            645                 650                 655

Ile Gly Val Pro Gly Lys Gly Val Pro Gly Ile Gly Val Pro Gly Ile
            660                 665                 670

Gly Val Pro Gly Ile Gly Val Pro Gly Ile Gly Val Pro Gly Lys Gly
            675                 680                 685

Val Pro Gly Ile Gly Val Pro Gly Ile Gly
            690                 695

<210> SEQ ID NO 40
<211> LENGTH: 606
<212> TYPE: PRT
<213> ORGANISM: Artificial Sequence
<220> FEATURE:
<223> OTHER INFORMATION: ELP membrane sequence

<400> SEQUENCE: 40

Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly Val
            20                  25                  30

Pro Gly Ile Gly Val Pro Gly Ile Gly Val Pro Gly Lys Gly Val Pro
        35                  40                  45

Gly Ile Gly Val Pro Gly Ile Gly Val Pro Gly Ile Gly Val Pro Gly
    50                  55                  60

Ile Gly Val Pro Gly Lys Gly Val Pro Gly Ile Gly Val Pro Gly Ile
65                  70                  75                  80

Gly Val Pro Gly Ile Gly Val Pro Gly Ile Gly Val Pro Gly Lys Gly
                85                  90                  95

Val Pro Gly Ile Gly Val Pro Gly Ile Gly Val Pro Gly Ile Gly Val
            100                 105                 110

Pro Gly Ile Gly Val Pro Gly Lys Gly Val Pro Gly Ile Gly Val Pro
        115                 120                 125

Gly Ile Gly Val Pro Gly Ile Gly Val Pro Gly Ile Gly Val Pro Gly
    130                 135                 140

Lys Gly Val Pro Gly Ile Gly Val Pro Gly Ile Gly Val Pro Gly Ile
145                 150                 155                 160

Gly Val Pro Gly Ile Gly Val Pro Gly Lys Gly Val Pro Gly Ile Gly
                165                 170                 175

Val Pro Gly Ile Gly Val Pro Gly Ile Gly Val Pro Gly Ile Gly Val
            180                 185                 190

Pro Gly Lys Gly Val Pro Gly Ile Gly Val Pro Gly Ile Gly Val Pro
        195                 200                 205

Gly Ile Gly Val Pro Gly Ile Gly Val Pro Gly Lys Gly Val Pro Gly
    210                 215                 220

Ile Gly Val Pro Gly Ile Gly Val Pro Gly Ile Gly Val Pro Gly Ile
225                 230                 235                 240

Gly Val Pro Gly Lys Gly Val Pro Gly Ile Gly Val Pro Gly Ile Gly
                245                 250                 255

Val Pro Gly Ile Gly Val Pro Gly Ile Gly Val Pro Gly Lys Gly Val
            260                 265                 270

Pro Gly Ile Gly Val Pro Gly Ile Gly Val Pro Gly Ile Gly Val Pro
        275                 280                 285
```

Gly Ile Gly Val Pro Gly Lys Gly Val Pro Gly Ile Gly Val Pro Gly
            290                 295                 300

Ile Gly Val Pro Gly Ile Gly Val Pro Gly Ile Gly Val Pro Gly Lys
305                 310                 315                 320

Gly Val Pro Gly Ile Gly Val Pro Gly Ile Gly Val Pro Gly Ile Gly
                325                 330                 335

Val Pro Gly Ile Gly Val Pro Gly Lys Gly Val Pro Gly Ile Gly Val
            340                 345                 350

Pro Gly Ile Gly Val Pro Gly Ile Gly Val Pro Gly Ile Gly Val Pro
            355                 360                 365

Gly Lys Gly Val Pro Gly Ile Gly Val Pro Gly Ile Gly Val Pro Gly
        370                 375                 380

Ile Gly Val Pro Gly Ile Gly Val Pro Gly Lys Gly Val Pro Gly Ile
385                 390                 395                 400

Gly Val Pro Gly Ile Gly Val Pro Gly Ile Gly Val Pro Gly Ile Gly
                405                 410                 415

Val Pro Gly Lys Gly Val Pro Gly Ile Gly Val Pro Gly Ile Gly Val
            420                 425                 430

Pro Gly Ile Gly Val Pro Gly Ile Gly Val Pro Gly Lys Gly Val Pro
            435                 440                 445

Gly Ile Gly Val Pro Gly Ile Gly Val Pro Gly Ile Gly Val Pro Gly
        450                 455                 460

Ile Gly Val Pro Gly Lys Gly Val Pro Gly Ile Gly Val Pro Gly Ile
465                 470                 475                 480

Gly Val Pro Gly Ile Gly Val Pro Gly Ile Gly Val Pro Gly Lys Gly
                485                 490                 495

Val Pro Gly Ile Gly Val Pro Gly Ile Gly Val Pro Gly Ile Gly Val
            500                 505                 510

Pro Gly Ile Gly Val Pro Gly Lys Gly Val Pro Gly Ile Gly Val Pro
            515                 520                 525

Gly Ile Gly Val Pro Gly Ile Gly Val Pro Gly Ile Gly Val Pro Gly
        530                 535                 540

Lys Gly Val Pro Gly Ile Gly Val Pro Gly Ile Gly Val Pro Gly Ile
545                 550                 555                 560

Gly Val Pro Gly Ile Gly Val Pro Gly Lys Gly Val Pro Gly Ile Gly
                565                 570                 575

Val Pro Gly Ile Gly Val Pro Gly Ile Gly Val Pro Gly Ile Gly Val
            580                 585                 590

Pro Gly Lys Gly Val Pro Gly Ile Gly Val Pro Gly Ile Gly
            595                 600                 605

<210> SEQ ID NO 41
<211> LENGTH: 351
<212> TYPE: PRT
<213> ORGANISM: Artificial Sequence
<220> FEATURE:
<223> OTHER INFORMATION: ELP membrane sequence

<400> SEQUENCE: 41

Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly Val
            20                  25                  30

Pro Gly Ile Gly Val Pro Gly Ile Gly Val Pro Gly Lys Gly Val Pro
        35                  40                  45

Gly Ile Gly Val Pro Gly Ile Gly Asp Asp Asp Glu Glu Lys Phe Leu
            50                  55                  60

Arg Arg Ile Gly Arg Phe Gly Val Pro Gly Ile Gly Val Pro Gly Ile
65                  70                  75                  80

Gly Val Pro Gly Lys Gly Val Pro Gly Ile Gly Val Pro Gly Ile Gly
                85                  90                  95

Val Pro Gly Ile Gly Val Pro Gly Ile Gly Val Pro Gly Lys Gly Val
            100                 105                 110

Pro Gly Ile Gly Val Pro Gly Ile Gly Val Pro Gly Ile Gly Val Pro
            115                 120                 125

Gly Ile Gly Val Pro Gly Lys Gly Val Pro Gly Ile Gly Val Pro Gly
            130                 135                 140

Ile Gly Val Pro Gly Ile Gly Val Pro Gly Ile Gly Val Pro Gly Lys
145                 150                 155                 160

Gly Val Pro Gly Ile Gly Val Pro Gly Ile Gly Asp Asp Asp Glu Glu
                165                 170                 175

Lys Phe Leu Arg Arg Ile Gly Arg Phe Gly Val Pro Gly Ile Gly Val
            180                 185                 190

Pro Gly Ile Gly Val Pro Gly Lys Gly Val Pro Gly Ile Gly Val Pro
            195                 200                 205

Gly Ile Gly Val Pro Gly Ile Gly Val Pro Gly Ile Gly Val Pro Gly
            210                 215                 220

Lys Gly Val Pro Gly Ile Gly Val Pro Gly Ile Gly Val Pro Gly Ile
225                 230                 235                 240

Gly Val Pro Gly Ile Gly Val Pro Gly Lys Gly Val Pro Gly Ile Gly
                245                 250                 255

Val Pro Gly Ile Gly Val Pro Gly Ile Gly Val Pro Gly Ile Gly Val
            260                 265                 270

Pro Gly Lys Gly Val Pro Gly Ile Gly Val Pro Gly Ile Gly Asp Asp
            275                 280                 285

Asp Glu Glu Lys Phe Leu Arg Arg Ile Gly Arg Phe Gly Val Pro Gly
            290                 295                 300

Ile Gly Val Pro Gly Ile Gly Val Pro Gly Lys Gly Val Pro Gly Ile
305                 310                 315                 320

Gly Val Pro Gly Ile Gly Val Pro Gly Ile Gly Val Pro Gly Ile Gly
                325                 330                 335

Val Pro Gly Lys Gly Val Pro Gly Ile Gly Val Pro Gly Ile Gly
            340                 345                 350

<210> SEQ ID NO 42
<211> LENGTH: 914
<212> TYPE: PRT
<213> ORGANISM: Artificial Sequence
<220> FEATURE:
<223> OTHER INFORMATION: ELP membrane sequence

<400> SEQUENCE: 42

Met Glu Ser Leu Leu Pro Val Pro Gly Ile Gly Val Pro Gly Ile Gly
1               5                   10                  15

Val Pro Gly Lys Gly Val Pro Gly Ile Gly Val Pro Gly Ile Gly Val
            20                  25                  30

Pro Gly Ile Gly Val Pro Gly Ile Gly Val Pro Gly Lys Gly Val Pro
            35                  40                  45

Gly Ile Gly Val Pro Gly Ile Gly Asp Asp Asp Glu Glu Lys Phe Leu
            50                  55                  60

```
Arg Arg Ile Gly Arg Phe Gly Val Pro Gly Ile Gly Val Pro Gly Ile
 65                  70                  75                  80
Gly Val Pro Gly Lys Gly Val Pro Gly Ile Gly Val Pro Gly Ile Gly
                 85                  90                  95
Val Pro Gly Ile Gly Val Pro Gly Ile Gly Val Pro Gly Lys Gly Val
            100                 105                 110
Pro Gly Ile Gly Val Pro Gly Ile Gly Val Pro Gly Ile Gly Val Pro
        115                 120                 125
Gly Ile Gly Val Pro Gly Lys Gly Val Pro Gly Ile Gly Val Pro Gly
    130                 135                 140
Ile Gly Val Pro Gly Ile Gly Val Pro Gly Ile Gly Val Pro Gly Lys
145                 150                 155                 160
Gly Val Pro Gly Ile Gly Val Pro Gly Ile Gly Asp Asp Asp Glu Glu
                165                 170                 175
Lys Phe Leu Arg Arg Ile Gly Arg Phe Gly Val Pro Gly Ile Gly Val
            180                 185                 190
Pro Gly Ile Gly Val Pro Gly Lys Gly Val Pro Gly Ile Gly Val Pro
        195                 200                 205
Gly Ile Gly Val Pro Gly Ile Gly Val Pro Gly Ile Gly Val Pro Gly
    210                 215                 220
Lys Gly Val Pro Gly Ile Gly Val Pro Gly Ile Gly Val Pro Gly Ile
225                 230                 235                 240
Gly Val Pro Gly Ile Gly Val Pro Gly Lys Gly Val Pro Gly Ile Gly
                245                 250                 255
Val Pro Gly Ile Gly Val Pro Gly Ile Gly Val Pro Gly Ile Gly Val
            260                 265                 270
Pro Gly Lys Gly Val Pro Gly Ile Gly Val Pro Gly Ile Gly Asp Asp
        275                 280                 285
Asp Glu Glu Lys Phe Leu Arg Arg Ile Gly Arg Phe Gly Val Pro Gly
    290                 295                 300
Ile Gly Val Pro Gly Ile Gly Val Pro Gly Lys Gly Val Pro Gly Ile
305                 310                 315                 320
Gly Val Pro Gly Ile Gly Val Pro Gly Ile Gly Val Pro Gly Ile Gly
                325                 330                 335
Val Pro Gly Lys Gly Val Pro Gly Ile Gly Val Pro Gly Ile Gly Val
            340                 345                 350
Pro Gly Ile Gly Val Pro Gly Ile Gly Val Pro Gly Lys Gly Val Pro
        355                 360                 365
Gly Ile Gly Val Pro Gly Ile Gly Val Pro Gly Ile Gly Val Pro Gly
    370                 375                 380
Ile Gly Val Pro Gly Lys Gly Val Pro Gly Ile Gly Val Pro Gly Ile
385                 390                 395                 400
Gly Asp Asp Asp Glu Glu Lys Phe Leu Arg Arg Ile Gly Arg Phe Gly
                405                 410                 415
Val Pro Gly Ile Gly Val Pro Gly Ile Gly Val Pro Gly Lys Gly Val
            420                 425                 430
Pro Gly Ile Gly Val Pro Gly Ile Gly Val Pro Gly Ile Gly Val Pro
        435                 440                 445
Gly Ile Gly Val Pro Gly Lys Gly Val Pro Gly Ile Gly Val Pro Gly
    450                 455                 460
Ile Gly Val Pro Gly Ile Gly Val Pro Gly Ile Gly Val Pro Gly Lys
465                 470                 475                 480
Gly Val Pro Gly Ile Gly Val Pro Gly Ile Gly Val Pro Gly Ile Gly
```

-continued

```
                485                 490                 495
Val Pro Gly Ile Gly Val Pro Gly Lys Gly Val Pro Gly Ile Gly Val
                500                 505                 510
Pro Gly Ile Gly Ala Val Thr Gly Arg Gly Asp Ser Pro Ala Ser Ser
                515                 520                 525
Val Pro Gly Ile Gly Val Pro Gly Ile Gly Val Pro Gly Lys Gly Val
                530                 535                 540
Pro Gly Ile Gly Val Pro Gly Ile Gly Val Pro Gly Ile Gly Val Pro
545                 550                 555                 560
Gly Ile Gly Val Pro Gly Lys Gly Val Pro Gly Ile Gly Val Pro Gly
                565                 570                 575
Ile Gly Val Pro Gly Ile Gly Val Pro Gly Ile Gly Val Pro Gly Lys
                580                 585                 590
Gly Val Pro Gly Ile Gly Val Pro Gly Ile Gly Val Pro Gly Ile Gly
                595                 600                 605
Val Pro Gly Ile Gly Val Pro Gly Lys Gly Val Pro Gly Ile Gly Val
                610                 615                 620
Pro Gly Ile Gly Ala Val Thr Gly Arg Gly Asp Ser Pro Ala Ser Ser
625                 630                 635                 640
Val Pro Gly Ile Gly Val Pro Gly Ile Gly Val Pro Gly Lys Gly Val
                645                 650                 655
Pro Gly Ile Gly Val Pro Gly Ile Gly Val Pro Gly Ile Gly Val Pro
                660                 665                 670
Gly Ile Gly Val Pro Gly Lys Gly Val Pro Gly Ile Gly Val Pro Gly
                675                 680                 685
Ile Gly Val Pro Gly Ile Gly Val Pro Gly Ile Gly Val Pro Gly Lys
                690                 695                 700
Gly Val Pro Gly Ile Gly Val Pro Gly Ile Gly Val Pro Gly Ile Gly
705                 710                 715                 720
Val Pro Gly Ile Gly Val Pro Gly Lys Gly Val Pro Gly Ile Gly Val
                725                 730                 735
Pro Gly Ile Gly Ala Val Thr Gly Arg Gly Asp Ser Pro Ala Ser Ser
                740                 745                 750
Val Pro Gly Ile Gly Val Pro Gly Ile Gly Val Pro Gly Lys Gly Val
                755                 760                 765
Pro Gly Ile Gly Val Pro Gly Ile Gly Val Pro Gly Ile Gly Val Pro
                770                 775                 780
Gly Ile Gly Val Pro Gly Lys Gly Val Pro Gly Ile Gly Val Pro Gly
785                 790                 795                 800
Ile Gly Val Pro Gly Ile Gly Val Pro Gly Ile Gly Val Pro Gly Lys
                805                 810                 815
Gly Val Pro Gly Ile Gly Val Pro Gly Ile Gly Val Pro Gly Ile Gly
                820                 825                 830
Val Pro Gly Ile Gly Val Pro Gly Lys Gly Val Pro Gly Ile Gly Val
                835                 840                 845
Pro Gly Ile Gly Ala Val Thr Gly Arg Gly Asp Ser Pro Ala Ser Ser
850                 855                 860
Val Pro Gly Ile Gly Val Pro Gly Ile Gly Val Pro Gly Lys Gly Val
865                 870                 875                 880
Pro Gly Ile Gly Val Pro Gly Ile Gly Val Pro Gly Ile Gly Val Pro
                885                 890                 895
Gly Ile Gly Val Pro Gly Lys Gly Val Pro Gly Ile Gly Val Pro Gly
                900                 905                 910
```

```
Ile Gly

<210> SEQ ID NO 43
<211> LENGTH: 5
<212> TYPE: PRT
<213> ORGANISM: Artificial Sequence
<220> FEATURE:
<223> OTHER INFORMATION: Tropoelastin recurrent motif

<400> SEQUENCE: 43

Val Pro Gly Ile Gly
1               5
```

CRYSTAL STRUCTURES COMPRISING ELASTIN-LIKE PEPTIDES

SEQUENCE LISTING

The application contains a Sequence Listing which has been submitted electronically in .TXT format and is hereby incorporated by reference in its entirety. Said .TXT copy, created on Aug. 9, 2022, is named "18832610311SEQ.TXT" and is 95,036 bytes in size. The sequence listing contained in this .TXT file is part of the specification and is hereby incorporated by reference herein in its entirety.

FIELD OF THE INVENTION

The present invention relates to new biomimetic mineralized apatite structures. The present invention also relates to processes for the production of new biomimetic mineralized apatite structures based on natural and synthetic protein scaffolds.

BACKGROUND TO THE INVENTION

Nature is rich with examples of sophisticated materials displaying outstanding properties that emerge from their specific hierarchical structure. Dental enamel has a distinctive hierarchical organization that generates its remarkable toughness, wear resistance, and critical role in tooth function (Boyde, A. Microstructure of enamel. CIBA Foundation Symposia, 18-31 (1997). At the molecular level, enamel is 97% by weight carbonated hydroxyapatite (HAp) (the rest being organic matrix and water) (Elliott, J. C. Structure, crystal chemistry and density of enamel apatites. CIBA Foundation Symposia, 54-72 (1997)) with different ionic substitutions in the lattice according to location (Robinson, C., Weatherell, J. A. & Hallsworth, A. S. Variation in composition of dental enamel within thin ground tooth sections. Caries Research 5, 44-57 (1971). At the nanoscale, HAp forms well-defined and aligned crystals that are about 70 nm wide, 25 nm thick, and might extend across the full width of enamel (Boyde, A. Microstructure of enamel. CIBA Foundation Symposia, 18-31 (1997). Groups of about 1000 of these crystallites come together to create well-organized microscopic prisms of about 5 µm in diameter (Elliott, J. C. Structure, crystal chemistry and density of enamel apatites. *CIBA Foundation Symposia*, 54-72 (1997)).

Unlike dentine and bone, mature enamel has no regenerative capacity or appropriate alternatives due to the complexity to create materials that mimic its unique structure (White, S. N. et al. Biological organization of hydroxyapatite crystallites into a fibrous continuum toughens and controls anisotropy in human enamel. *Journal of Dental Research* 80, 321-326 (2001). Approaches that enable the development of restorative materials that mimic tooth structures would have a major influence to both biomedical and dental fields.

Organic matrices control the biomineralization of dental hard tissues. For example, in dental enamel, self-assembling nanospheres of amelogenin act as a structural framework that is thought to precisely guide crystal growth in specific directions (Fincham, A. G. et al. Evidence for amelogenin 'nanospheres' as functional components of secretory-stage enamel matrix. *Journal of Structural Biology* 115, 50-59 (1995)). Given the precision of supramolecular chemistry and its potential in biomineralization, self-assembling methodologies based on recombinant amelogenin to mimic biomineralization (Ruan, Q., Zhang, Y., Yang, X., Nutt, S. & Moradian-Oldak, J. An amelogenin-chitosan matrix promotes assembly of an enamel-like layer with a dense interface. *Acta Biomaterialia* 9, 7289-7297 (2013)), poly(amido amine)-type (PAMAM) dendrimers as analogues to amelogenin (Wu, D. et al. Hydroxyapatite-anchored dendrimer for in situ remineralization of human tooth enamel. *Biomaterials* 34, 5036-5047 (2013)), peptide amphiphile nanofibres to stimulate cell-based therapies (Huang, Z. et al. Bioactive nanofibers instruct cells to proliferate and differentiate during enamel regeneration. *Journal of Bone and Mineral Research* 23, 1995-2006 (2008)), or commercially available peptide-based scaffolds (Curodont™) (Kirkham, J. et al. Self-assembling peptide scaffolds promote enamel remineralization. *J Dent Res* 86, 426-430 (2007)) have been developed. Nevertheless, none of these previous attempts have successfully recreated the highly organized mineralized apatite structure across multiple length-scales found in natural enamel, which evidences the current absence of a functional highly organized material for dental applications.

Elastin-like polypeptides (ELPs) have been used as bioactive building-blocks of materials and can easily incorporate bioactive epitopes to provide specific functionality (Panitch, A., Yamaoka, T., Fournier, M. J., Mason, T. L. & Tirrell, D. A. Design and Biosynthesis of Elastin-like Artificial Extracellular Matrix Proteins Containing Periodically Spaced Fibronectin CS5 Domains. *Macromolecules* 32, 1701-1703 (1999)) such as RGDS (SEQ ID NO:1) to promote cell adhesion (Nicol, A., Gowda, C. & Urry, D. W. Elastic protein-based polymers as cell attachment matrices. *Journal of Vascular Surgery* 13, 746-748 (1991)) or the statherin-derived peptide DDDEEKFLRRIGRFG (SEQ ID NO:2) to promote mineralisation (Tejeda-Montes, E. et al. Bioactive membranes for bone regeneration applications: Effect of physical and biomolecular signals on mesenchymal stem cell behavior. *Acta Biomaterialia* 10, 134-141 (2014), Tejeda-Montes, E. et al. Mineralization and bone regeneration using a bioactive elastin-like recombinamer membrane. *Biomaterials* 35, 8339-8347 (2014)). Statherin is a salivary protein that naturally acts as a chelating agent for calcium ions in order to enhance enamel remineralisation during acid attacks (Raj, P. A., Johnsson, M., Levine, M. J. & Nancollas, G. H. Salivary statherin. Dependence on sequence, charge, hydrogen bonding potency, and helical conformation for adsorption to hydroxyapatite and inhibition of mineralization. *J Biol Chem* 267, 5968-5976 (1992)). While ELPs containing this statherin-derived peptide have been used in fabricating membranes for periosteal regeneration (Tejeda-Montes, E. et al. Mineralization and bone regeneration using a bioactive elastin-like recombinamer membrane. *Biomaterials* 35, 8339-8347 (2014)) and implant coatings (Li, Y. et al. Hybrid Nanotopographical Surfaces Obtained by Biomimetic Mineralization of Statherin-Inspired Elastin-Like Recombinamers. *Advanced Healthcare Materials* 3, 1638-1647 in order to enhance mineralisation, they have generated amorphous calcium phosphate (ACP) with no hierarchical organisation. Since recent studies suggest that at the early stage of formation, enamel ribbons are ACP (Beniash, E., Metzler, R. A., Lam, R. S. K. & Gilbert, P. U. P. A. Transient amorphous calcium phosphate in forming enamel. *Journal of Structural Biology* 166, 133-143 (2009), Yang, X. et al. How amelogenin orchestrates the organization of hierarchical elongated microstructures of apatite. *Journal of Physical Chemistry B* 114, 2293-2300 (2010)), it may be that these previous attempts have achieved the early stage of biomineralisation, but not the complete process concluding in the mineral crystallising into hydroxyapatite.

SUMMARY OF THE INVENTION

The present inventors have surprisingly found a novel hybrid organic-inorganic system based on protein scaffold membranes that is able to grow hierarchically-ordered apatite crystalline structures that resemble those found in natural dental enamel, in both hierarchical organization and chemical composition.

In a first aspect of the invention there is provided a synthetic crystal having a hierarchical structure formed on a protein scaffold membrane.

In a second aspect of the invention there is provided a process for producing hierarchically ordered crystal structures comprising the step of contacting a protein scaffold membrane with a solution of mineralizing ions. The contacting step may be performed at physiological pH and temperature. The invention also extends to synthetic crystals obtainable by such methods.

In a third aspect of the invention there is provided a process for tuning or controlling the directionality of crystal growth.

In a fourth aspect of the invention there is provided a synthetic crystal of the invention for use in medicine, such as for use in the prevention and/or treatment of demineralisation of teeth or dental disease or dental hypersensitivity.

In a further aspect of the invention there is provided a synthetic crystal of the invention for use in the prevention and/or treatment of bone demineralisation, low bone density and/or osteoporosis.

In a further aspect of the invention, there is provided a synthetic crystal of the invention for use in the prevention and/or treatment of bone disease.

In a further aspect of the invention, there is provided a synthetic crystal of the invention for use in the prevention and/or treatment of a bone defect.

In a further aspect of the invention there is provided the use of a synthetic crystal of the invention in the preparation of a medicament for the treatment and/or prevention of demineralisation of teeth or dental disease or tooth hypersensitivity.

In a further aspect of the invention, there is provided the use of a synthetic crystal of the invention in the preparation of a medicament for the treatment and/or prevention of bone demineralisation, low bone density and/or osteoporosis.

In a further aspect of the invention, there is provided the use of a synthetic crystal of the invention in the preparation of a medicament for the treatment and/or prevention of bone disease.

In a further aspect of the invention, there is provided the use of a synthetic crystal of the invention in the preparation of a medicament for the treatment and/or prevention of bone defect.

In a further embodiment there is provided a method of treatment of or prevention of demineralisation of teeth or dental disease or tooth hypersensitivity in a subject, comprising administration to the subject a synthetic crystal of the invention.

In a further embodiment there is provided a method of treatment of or prevention of bone demineralisation, low bone density or osteoporosis in a subject, comprising administration to the subject a synthetic crystal of the invention.

In a further embodiment there is provided a method of treatment of or prevention of bone disease in a subject, comprising administration to the subject a synthetic crystal of the invention.

In a further embodiment there is provided a method of treatment of or prevention of bone defect, comprising administration to the subject a synthetic crystal of the invention.

In a further aspect of the invention, there is provided a medical implant, such as a dental implant, comprising the synthetic crystal of the invention, and methods for implantation of such devices.

In a still further aspect of the invention, there is provided a bone implant comprising the synthetic crystal of the invention, and methods for implantation of such devices.

BRIEF DESCRIPTION OF FIGURES

FIG. 24. Diffusion coefficients at different crosslinking ratios.

DETAILED DESCRIPTION

Figure 1:
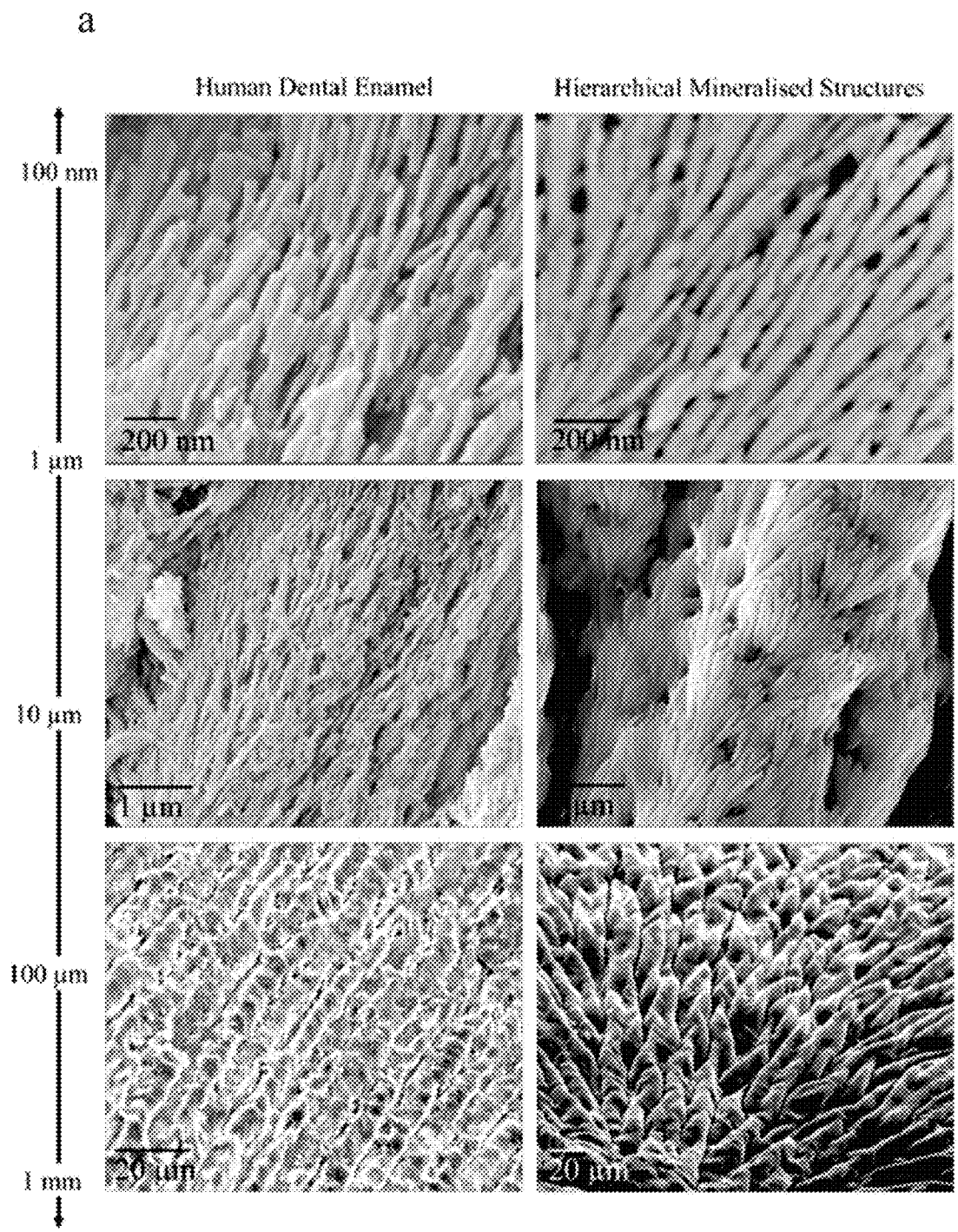
FIG. 1. Morphological, mechanical and chemical description of hierarchically-ordered mineralized structures on the surface of the membranes.
  a) SEM images showing the close resemblance of human of dental enamel (left) to the hierarchically-ordered mineralized structures (right) grown on a RGDS-ELP membrane at multiple lengthscales; at nano-, micro-, and macro-scale. b) A photograph showing the transparent, robust and flexible ELP membranes before mineralization. c) AFM nanoindentation of the different materials (sapphire, mineralized structures, human dental enamel, and unmineralized membrane) showing the significant difference between the mineralized structures and human dental enamel, while no significant difference exists between sapphire and the mineralized structures. d) SEM image showing the circular morphology of the hierarchical mineralized structures on RGDS-ELP membrane, e) their capacity to grow until adjacently assembling into a coating-like macrostructure on the surface of the statherin-ELP membrane, and f) populating whole thicknesses. g) The aligned nanocrystals organized in enamel prism-like structures parallel to the surface of the membrane and exhibiting incremental growth lines and an interlocking interface between mineralized structures. h) Rietveld modelling of XRD pattern of mineralized membranes showing the fluorapatite nature of the crystalline phase with the typical Bragg peaks of apatite. i) 19F solid-state MAS-NMR spectra confirm the presence of fluorapatite and CaF2 (fluorite) phase at −103 and −108 ppm, respectively, with increasing FAp peak intensity on the mineralized membrane (green) compared to without the ELP membrane (red) at the same conditions.
Figure 1:
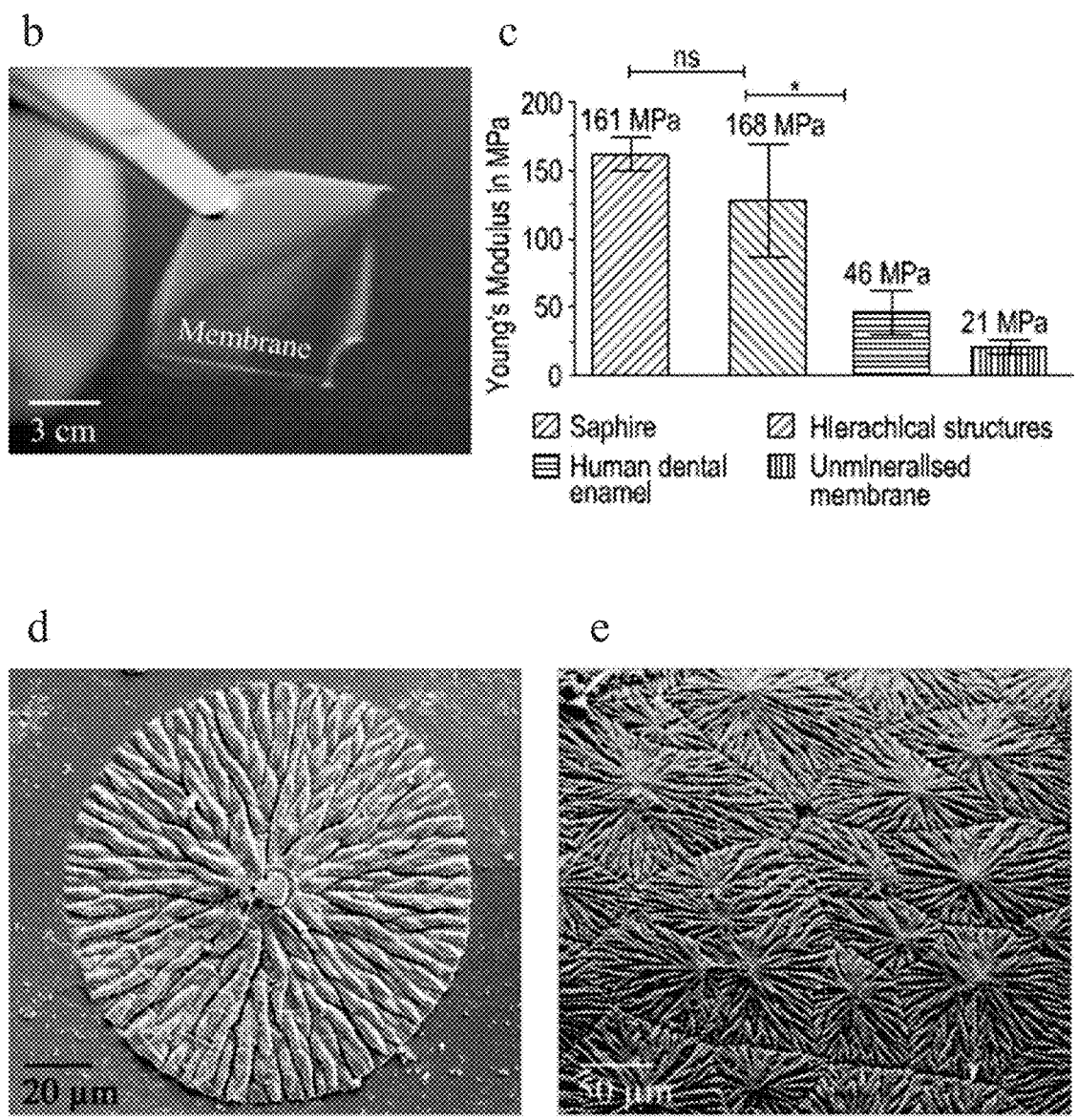
Figure 1:
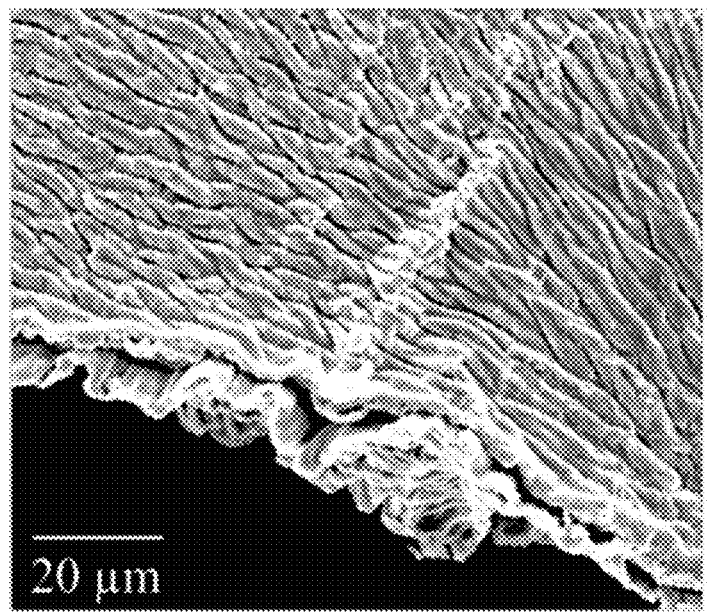
Figure 1:
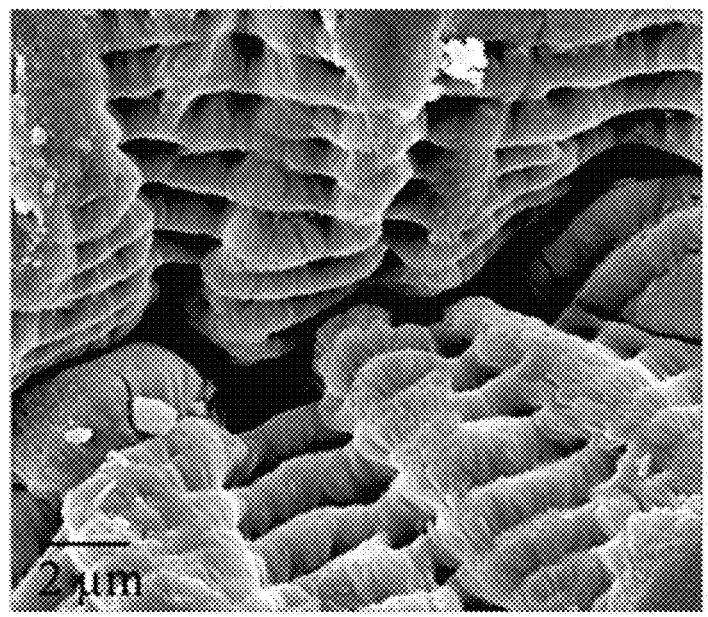
Figure 1:
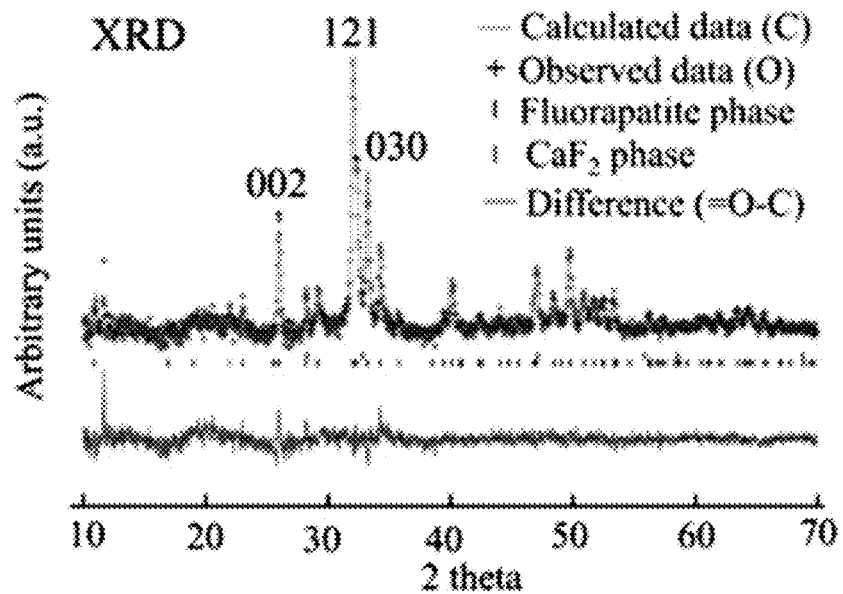
Figure 1:
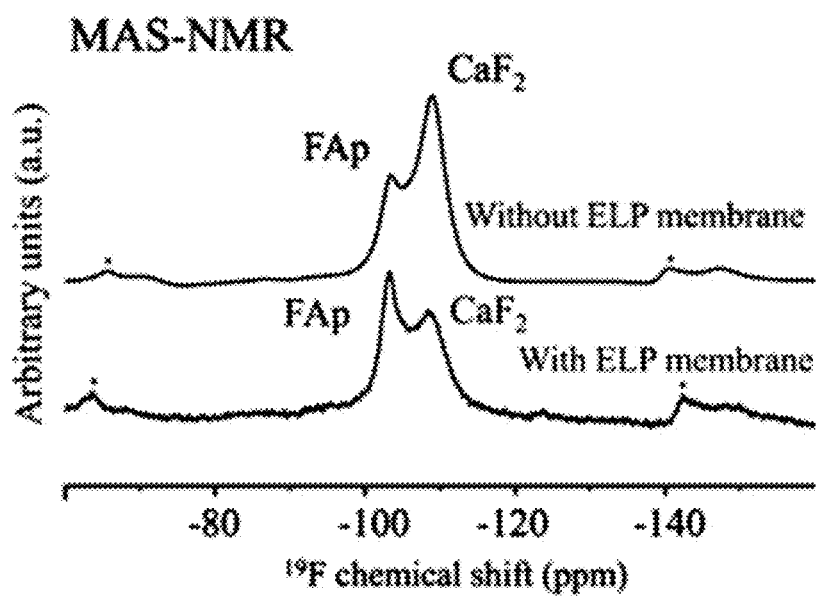

In one embodiment of the invention there is provided a synthetic crystal having a hierarchal structure wherein the structure is formed on a protein scaffold membrane. The synthetic crystals can also be referred to as artificial or synthetic dental enamel or artificial or synthetic bone.

A crystal is a homogeneous solid substance having a natural geometrically regular form with symmetrically arranged plane faces.

In one embodiment, the synthetic crystal having a hierarchal structure is apatite. Apatite refers to a phosphate mineral. Apatites are flexible structures with wide range of optional substitutions that can happen in their lattice at both cation and anion positions; therefore have the general formula $A_{10}(BO_n)_6X_2$ (alternatively $A_5(BO_n)_3X$). In one embodiment A is a divalent cation selected from the group comprising $Ca^{2+}$, $Sr^{2+}$, $Ba^{2+}$ and $Pb^{2+}$. In one embodiment BOn is an anionic complex, such as an anionic complex selected from the group comprising $PO_4^{3-}$, $AsO_4^{3-}$, $VO_4^{3-}$ or $CO_3^{2}$. X is generally an anion. In one embodiment X is selected from the group comprising OH, F and Cl.

In particular embodiments of the invention, the apatite has the formula $Ca_5(PO_4)_3F$.

Apatites have hexagonal crystallographic symmetry. The space group of apatites is usually ($P6_3/m$) where the 6-fold c-axis is perpendicular to 3 a-axes at 120° to one another with some lower symmetry analogues.

In one embodiment of the invention, the apatite is selected from the group comprising fluroapatite, hydroxyapatite and chlorapatite.

In one embodiment, the apatite is fluorapatite. Fluroapatite is a phosphate mineral with the general formula $Ca_5(PO_4)_3F$. Fluroapatite is alternatively referred to as $Ca_{10}(PO_4)F_2$ or FAp. FAp is hexagonal with space group P63/m and lattice parameters a=9.367(1) and c (the hexagonal axis)=6.884(1) Angstroms with one formula unit of $Ca_{10}(PO_4)_6F_2$ per unit cell.

In one embodiment, the apatite is hydroxyapatite. Hydroxyapatite is a phosphate mineral with the general formula $Ca_5(PO_4)_3(OH)$.

In one embodiment, the apatite is chlorapatite. Chlorapatite is a phosphate mineral with the general formula $Ca_5(PO_4)_3Cl$.

In one embodiment, the apatite is flurohydroxyapatite.

In a preferred embodiment, the apatite is fluorapatite.

In one embodiment the scaffold membrane is formed from a material with high mineralizing properties, i.e. the material is able to convert the components of a solution into a mineral. In one embodiment, the scaffold membrane is selected from the group consisting of a chitin, gelatine, polyacrylamide, alginate, poly-lactic acid, poly-glycolic acid, poly-lysine polymer, collagen, amelogenin, silk, chitosan, elastin or elastin-like membrane.

In one embodiment the membrane is formed of natural elastin. In one embodiment, the natural elastin comprises a pentapeptide selected from the group consisting of Gly-X-X-X-X, X-Gly-X-X-X, X-X-Gly-X-X, X-X-X-Gly-X and X-X-X-X-Gly, (GXXXX (SEQ ID NO:3), XGXXX (SEQ ID NO:4), XXGXX (SEQ ID NO:5), XXXGX (SEQ ID NO:6), XXXXG (SEQ ID NO:7)), wherein X is any amino acid. In one embodiment, the natural elastin comprises at least one pentapeptide selected from the group consisting of Gly-X-X-X-X, X-Gly-X-X-X, X-X-Gly-X-X, X-X-X-Gly-X and X-X-X-X-Gly, (GXXXX (SEQ ID NO:3), XGXXX (SEQ ID NO:4), XXGXX (SEQ ID NO:5), XXXGX (SEQ ID NO:6), XXXXG (SEQ ID NO:7)), wherein X is any amino acid. In one embodiment, the natural elastin comprises at least two, at least three, at least four, at least five, at least six, at least seven, at least eight or at least ten pentapepetides selected from the group consisting of Gly-X-X-X-X, X-Gly-X-X-X, X-X-Gly-X-X, X-X-X-Gly-X and X-X-X-X-Gly, (GXXXX (SEQ ID NO:3), XGXXX (SEQ ID NO:4), XXGXX (SEQ ID NO:5), XXXGX (SEQ ID NO:6), XXXXG (SEQ ID NO:7)), wherein X is any amino acid. In some embodiments, the natural elastin comprises at least two, at least three, at least four, at least five, at least six, at least seven, at least eight or at least ten pentapepetides selected from the group consisting of Gly-X-X-X-X, X-Gly-X-X-X, X-X-Gly-X-X, X-X-X-Gly-X and X-X-X-X-Gly, (GXXXX (SEQ ID NO:8), XGXXX (SEQ ID NO:9), XXGXX (SEQ ID NO:10), XXXGX (SEQ ID NO:11), XXXXG (SEQ ID NO:12)), wherein X is an amino acid selected from the group consisting of V, P, G, S, F and I. In one embodiment, the natural elastin comprises a pentapeptide selected from the group consisting of (Gly-X-X-X-X)y (SEQ ID NO:13), (X-Gly-X-X-X)y (SEQ ID NO:14), (X-X-Gly-X-X)y (SEQ ID NO:15), (X-X-X-Gly-X)y (SEQ ID NO:16) and (X-X-X-X-Gly)y (SEQ ID NO:17), wherein X is any amino acid and wherein y is the number of repeats. For example, y may be at least 5 or at least 10. In one embodiment, the natural elastin comprises the tropoelastin recurrent motif Val-Pro-Gly-X-Gly (VPGXG (SEQ ID NO:19)), where X is any amino acid apart from proline. In one embodiment, the natural elastin comprises at least one tropoelastin recurrent motif Val-Pro-Gly-X-Gly (VPGXG (SEQ ID NO:19)), where X is any amino acid apart from proline. In one embodiment, the natural elastin comprises at least two, at least three, at least four, at least five, at least six, at least seven, at least eight or at least ten tropoelastin recurrent motifs Val-Pro-Gly-X-Gly (VPGXG (SEQ ID NO:19)), where X is any amino acid apart from proline. In some embodiments, X is an amino acid selected from the group consisting of V, P, G, S, F and I (SEQ ID NO:18) In one embodiment, the natural elastin comprises the tropoelastin recurrent motif Val-Pro-Gly-X-Gly (VPGXG)y (SEQ ID NO:20), where X is any amino acid apart from proline and wherein y is the number of repeats. For example, y may be at least 5 or at least 10. In some embodiments, y is 1 or more, in particular when the peptide is cross-linked.

In one embodiment, the natural elastin comprises the tropoelastin recurrent motif Pro-Gly-Ile-Pro-Gly (PGIPG (SEQ ID NO:21)). In one embodiment, the natural elastin comprises at least one tropoelastin recurrent motif Pro-Gly-Ile-Pro-Gly (PGIPG (SEQ ID NO:21)). In one embodiment, the natural elastin comprises at least two, at least three, at least four, at least five, at least six, at least seven, at least eight or at least ten tropoelastin recurrent motifs Pro-Gly-Ile-Pro-Gly (PGIPG (SEQ ID NO:21)). In one embodiment, the natural elastin comprises the tropoelastin recurrent motif Pro-Gly-Ile-Pro-Gly (PGIPG)y (SEQ ID NO:22), wherein y is the number of repeats. For example, y may be at least 5 or at least 10. In some embodiments, y is 1 or more, in particular when the peptide is cross-linked.

In one embodiment, the natural elastin comprises the tropoelastin recurrent motif Pro-Val-Gly-Ser-Gly (PVGSG (SEQ ID NO:23)). In one embodiment, the natural elastin comprises at least one tropoelastin recurrent motif Pro-Val-Gly-Ser-Gly (PVGSG (SEQ ID NO:23)). In one embodiment, the natural elastin comprises at least two, at least three, at least four, at least five, at least six, at least seven, at least eight or at least ten tropoelastin recurrent motifs Pro-Val-Gly-Ser-Gly (PVGSG (SEQ ID NO:23)). In one embodiment, the natural elastin comprises the tropoelastin recurrent motif Pro-Val-Gly-Ser-Gly (PVGSG)y (SEQ ID NO:24), wherein y is the number of repeats. For example, y may be at least 5 or at least 10. In some embodiments, y is 1 or more, in particular when the peptide is cross-linked.

In one embodiment, the natural elastin comprises the tropoelastin recurrent motif Val-Gly-Phe-Pro-Gly (VGFPG (SEQ ID NO:25)). In one embodiment, the natural elastin comprises at least one tropoelastin recurrent motif Val-Gly-Phe-Pro-Gly (VGFPG (SEQ ID NO:25)). In one embodiment, the natural elastin comprises at least two, at least three, at least four, at least five, at least six, at least seven, at least eight or at least ten tropoelastin recurrent motifs Val-Gly-Phe-Pro-Gly (VGFPG (SEQ ID NO:25)). In one embodiment, the natural elastin comprises the tropoelastin recurrent motif Val-Gly-Phe-Pro-Gly (VGFPG)y (SEQ ID NO:26), wherein y is the number of repeats. For example, y may be at least 5 or at least 10. In some embodiments, y is 1 or more, in particular when the peptide is cross-linked.

The skilled person would understand that natural elastin membrane is tuneable and can include numerous modifications based on the pentapeptide containing glycine or the pentapeptides (VPGXG (SEQ ID NO:19)), (PGIPG (SEQ ID NO:21)), (PVGSG (SEQ ID NO:23)) and (VGFPG (SEQ ID NO:25)).

In a preferred embodiment, the membrane is an Elastin-like protein membrane or Elastin-like protein hydrogel. The skilled person would understand that an Elastin-like protein membrane can also be a hydrogel. Elastin-like proteins (ELP) are recombinant polymers that exhibit comparable biological and mechanical properties to natural elastin. These polymers have generated great interest due to their modular structure, biocompatibility, biodegradability, ease of design and production, and capacity to be synthesised with a high level of molecular control and tuneability. ELPs allow for tuneable molecular design. The term elastin-like protein is interchangeable with the term elastin-like polypeptide, elastin-like polymer and elastin-like recombinamers.

In one embodiment the membrane is formed of Elastin-like protein membrane or Elastin-like protein hydrogel. In one embodiment, the ELP membrane or hydrogel comprises a pentapeptide selected from the group consisting of Gly-X-X-X-X, X-Gly-X-X-X, X-X-Gly-X-X, X-X-X-Gly-X and X-X-X-X-Gly, (GXXXX (SEQ ID NO:3), XGXXX (SEQ ID NO:4), XXGXX (SEQ ID NO:5), XXXGX (SEQ ID NO:6), XXXXG (SEQ ID NO:7)), wherein X is any amino acid. In one embodiment, the ELP membrane or hydrogel comprises at least one pentapeptide selected from the group consisting of Gly-X-X-X-X, X-Gly-X-X-X, X-X-Gly-X-X, X-X-X-Gly-X and X-X-X-X-Gly, (GXXXX (SEQ ID NO:3), XGXXX (SEQ ID NO:4), XXGXX (SEQ ID NO:5), XXXGX (SEQ ID NO:6), XXXXG (SEQ ID NO:7)), wherein X is any amino acid. In some embodiments, X is an amino acid selected from the group consisting of V, P, G, S, F and I. In one embodiment, the ELP membrane or hydrogel comprises at least two, at least three, at least four, at least five, at least six, at least seven, at least eight or at least ten pentapepetides selected from the group consisting of Gly-X-X-X-X, X-Gly-X-X-X, X-X-Gly-X-X, X-X-X-Gly-X and X-X-X-X-Gly, (GXXXX (SEQ ID NO:3), XGXXX (SEQ ID NO:4), XXGXX (SEQ ID NO:5), XXXGX (SEQ ID NO:6), XXXXG (SEQ ID NO:7)), wherein X is any amino acid. In one embodiment, the ELP membrane or hydrogel comprises a pentapeptide selected from the group consisting of (Gly-X-X-X-X)y, (X-Gly-X-X-X)y, (X-X-Gly-X-X)y, (X-X-X-Gly-X)y and (X-X-X-X-Gly)y, wherein X is any amino acid and wherein y is the number of repeats. In one embodiment, the ELP membrane or hydrogel comprises the tropoelastin recurrent motif Val-Pro-Gly-X-Gly (VPGXG (SEQ ID NO:19)), where X is any amino acid apart from proline. In one embodiment, the ELP membrane or hydrogel comprises at least one tropoelastin recurrent motif Val-Pro-Gly-X-Gly (VPGXG (SEQ ID NO:19)), where X is any amino acid apart from proline. In one embodiment, the ELP membrane or hydrogel comprises at least two, at least three, at least four, at least five, at least six, at least seven, at least eight or at least ten tropoelastin recurrent motifs Val-Pro-Gly-X-Gly (VPGXG (SEQ ID NO:19)), where X is any amino acid apart from proline. In one embodiment, the ELP membrane or hydrogel comprises the tropoelastin recurrent motif Val-Pro-Gly-X-Gly (VPGXG)y (SEQ ID NO:20), where X is any amino acid apart from proline and wherein y is the number of repeats. For example, y may be at least 5 or at least 10. In some embodiments, y is 1 or more, in particular when the peptide is cross-linked.

In one embodiment, the ELP membrane or hydrogel comprises the tropoelastin recurrent motif Pro-Gly-Ile-Pro-Gly (PGIPG (SEQ ID NO:21)). In one embodiment, the ELP membrane or hydrogel comprises at least one tropoelastin recurrent motif Pro-Gly-Ile-Pro-Gly (PGIPG (SEQ ID NO:21)). In one embodiment, the ELP membrane or hydrogel comprises at least two, at least three, at least four, at least five, at least six, at least seven, at least eight or at least ten tropoelastin recurrent motifs Pro-Gly-Ile-Pro-Gly (PGIPG (SEQ ID NO:21)). In one embodiment, the ELP membrane or hydrogel comprises the tropoelastin recurrent motif Pro-Gly-Ile-Pro-Gly (PGIPG)y (SEQ ID NO:22), wherein y is the number of repeats. For example, y may be at least 5 or at least 10. In some embodiments, y is 1 or more, in particular when the peptide is cross-linked.

In one embodiment, the ELP membrane or hydrogel comprises the tropoelastin recurrent motif Pro-Val-Gly-Ser-Gly (PVGSG (SEQ ID NO:23)). In one embodiment, the ELP membrane or hydrogel comprises at least one tropoelastin recurrent motif Pro-Val-Gly-Ser-Gly (PVGSG (SEQ ID NO:23)). In one embodiment, the ELP membrane or hydrogel comprises at least two, at least three, at least four, at least five, at least six, at least seven, at least eight or at least ten tropoelastin recurrent motifs Pro-Val-Gly-Ser-Gly (PVGSG (SEQ ID NO:23)). In one embodiment, the ELP membrane or hydrogel comprises the tropoelastin recurrent motif Pro-Val-Gly-Ser-Gly (PVGSG)y (SEQ ID NO:24), wherein y is the number of repeats. For example, y may be at least 5 or at least 10. In some embodiments, y is 1 or more, in particular when the peptide is cross-linked.

In one embodiment, the ELP membrane or hydrogel comprises the tropoelastin recurrent motif Val-Gly-Phe-Pro-Gly (VGFPG (SEQ ID NO:25)). In one embodiment, the ELP membrane or hydrogel comprises at least one tropoelastin recurrent motif Val-Gly-Phe-Pro-Gly (VGFPG (SEQ ID NO:25)). In one embodiment, the ELP membrane or hydrogel comprises at least two, at least three, at least four, at least five, at least six, at least seven, at least eight or at least ten tropoelastin recurrent motifs Val-Gly-Phe-Pro-Gly (VGFPG (SEQ ID NO:25)). In one embodiment, the ELP membrane or hydrogel comprises the tropoelastin recurrent motif Val-Gly-Phe-Pro-Gly (VGFPG)y (SEQ ID NO:26), wherein y is the number of repeats. For example, y may be at least 5 or at least 10. In some embodiments, y is 1 or more, in particular when the peptide is cross-linked.

The skilled person would understand that an ELP membrane or hydrogel is tuneable and can include numerous modifications based on the pentapeptide containing glycine or the pentapeptides (VPGXG (SEQ ID NO:19)), (PGIPG (SEQ ID NO:21)), (PVGSG (SEQ ID NO:23)) and (VGFPG (SEQ ID NO:25)).

ELP membranes are membranes formed of ELPs. ELP membranes can be generated using standard methods, for example as described in Tejeda-Montes et al., 2012.

In one embodiment, the ELP membrane or hydrogel is cross-linked by a cross-linker. A cross-linker is an inorganic or organic reagent that reacts with either a carboxylic group or an amine group of an ELP membrane or hydrogel, protein, polymer, peptide or amino acid through covalent bonds, or non-covalent bonds such as electrostatic, hydrogen bonds, or Van der Waals. The degree of cross-linking can determine the stiffness of the ELP membrane and can be used to tune the morphology or organisation of the hierarchal structures. By increasing the degree of cross-linking in an ELP membrane, and therefore the stiffness of the ELP membrane, the ELP membranes will exhibit a higher degree of hierarchally organized structures. In one embodiment, the ELP membrane or hydrogel can be cross-linked by chemical cross-linking, enzymatic cross-linking by tissue transglutaminase, photoinitiated and/or γ-irradiation cross-linking In one embodiment, the ELP membrane or hydrogel has a cross linker ratio of greater than about 0.1, about 0.2, or about 0.25. In some embodiments, the cross linker ratio is up to about 50, or up to about 30 or up to about 25, or up to about 20. In one embodiment, the ELP membrane or hydrogel has a cross linker ratio of between about 0.25 to 24. In one embodiment, the ELP membrane or hydrogel has a cross linker ratio of between about 0.25 to 20. In a preferred embodiment, the ELP membrane or hydrogel has a cross linker ratio of about 0.5 to about 12. In one embodiment, the ELP membrane or hydrogel has a cross linker ratio of about 6 to 12. In one embodiment, the ELP membrane or hydrogel has a cross linker ratio of about 12. In one embodiment, the ELP membrane or hydrogel has a cross linker to lysine ratio of greater than about 0.25. In one embodiment, the ELP membrane or hydrogel has a cross linker to lysine ratio of between about 0.25 to 24. The cross-linker ratio is the ratio of the molar concentration of cross-linker to the molar concentration of amine or carboxylic groups of the ELP membrane or hydrogel, protein, polymer, peptide or amino acid. In one embodiment, the ELP membrane or hydrogel has a cross linker to lysine ratio of between about 0.25 to 20. In a preferred embodiment, the ELP membrane or hydrogel has a cross linker to lysine ratio of about 0.5 to about 12. In one embodiment, the ELP membrane or hydrogel has a cross linker to lysine ratio of about 6 to 12. In one embodiment, the ELP membrane or hydrogel has a cross linker to lysine ratio of about 12. In one embodiment the cross-linker is hexamethyl diisocyanate.

Young's modulus (or Elastic modulus) values can provide a measure of the stiffness of a solid material. The synthetic crystals of the invention have been found to have higher stiffness, in particular higher Young's modulus values. compared to enamel. For example, the synthetic crystals of the invention have a stiffness, in particular Young's modulus values. that are comparable to sapphire. Young's modulus values can be measured using nanoindentation or atomic force microscopy (AFM) nanoindentation. In some embodiments, the synthetic crystal has a Young's modulus value of at least about 30, at least about 40, at least about 50, in particular at least about 60, or at least about 70, or at least about 80, or at least about 90, or at least about 100 MPa. In some embodiments, the synthetic crystal has a Young's modulus value of up to about 300, up to about 250 or up to about 200 MPa. In one embodiment, the synthetic crystal has a Young's modulus value of from 70 to 190 MPa. In one embodiment, the synthetic crystal has a Young's modulus value of from 90 to 170 MPa. In one embodiment, the synthetic crystal has a Young's modulus value of from 110 to 180 MPa. In one embodiment, the synthetic crystal has a Young's modulus value of from 120 to 140 MPa. In one embodiment, the Young's modulus value is measured using AFM nanoindentation. For comparison, the Young's modulus value for enamel is approximately 40 to 50 MPa when using AFM nanoindentation.

In one embodiment, the synthetic crystal develops a hierarchical structure as a function of time. In one embodiment, the synthetic crystal has a Young's modulus value of between 70 and 190 MPa following 6 to 10 days mineralization. In one embodiment, the synthetic crystal has a Young's modulus value of between 90 and 170 MPa following 6 to 10 days mineralization. In one embodiment, the synthetic crystal has a Young's modulus value of between 110 and 180 MPa following 6 to 10 days mineralization. In one embodiment, the synthetic crystal has a Young's modulus value of between 120 and 140 MPa following 6 to 10 days mineralization.

In one embodiment, the ELP membrane or hydrogel comprises a negatively charged or a neutral charge molecule.

In one embodiment, the ELP membrane or hydrogel is substantially non-porous. In one embodiment, the ELP membrane or hydrogel comprises pores or micropores. In one embodiment, the ELP membrane of hydrogel comprises pores less than about 30 microns in diameter.

The scaffold membrane, in particular the ELP membrane or hydrogel, can include various peptide sequences. In one embodiment the peptide sequence is selected from the group consisting of

```
                                            (SEQ ID NO: 27)
(a) MGSSHHHHHHSSGLVPRGSHMESLLP-

[VPGIGVPGIGVPGKGVPGIGVPGIGVPGIGVPGIGVPGKGVPGIGVPG

IGAVTGRGDSPASSVPGIGVPGIGVPGKGVPGIGVPGIGVPGIGVPGIG

VPGKGVPGIGVPGIG]6-V (SEQ ID NO: 28)
(b) MESLLP-

VPGIGVPGIGVPGKGVPGIGVPGIGEEIQIGHIPREDVDYHLYPVPGIGV

PGIGVPGKGVPGIGVPGIGVGVAPGVGVAPGVGVAPG]10-V (SEQ ID NO: 29)
(c) MESLLP-[(VPGVG VPGVG VPGEG VPGVG VPGVG)10-

(VGIPG)60]2-V (SEQ ID NO: 30)
(d) MESLLP-VPGIG VPGIG VPGKG VPGIG VPGIG VPGIG VPG

GI VPGKG VPGIG VPGIG]12-V (SEQ ID NO: 31)
(e) [VPGVGVPGVGVPGEGVPGVGVPGVG]15-V (SEQ ID NO: 32)
(f) MESLLP-[((VPGIG)2VPGKG(VPGIG)2)2-DDDEEKFLRRIGR

F(G-VPGIG)2VPGKG(VPGIG)2)2]3-V (SEQ ID NO: 33)
(g) MESLLP-[((VPGIG)2VPGKG(VPGIG)2)2-DDDEEKFLRRIGR

F(G-(VPGIG)2VPGKG(VPGIG)2)2]3-(VPAVG)20-V (SEQ ID NO: 34)
(h) MESLLP-[((VPGIG)2VPGKG(VPGIG)2)2-DDDEEKFLRRIGR

FG-((VPGIG)2VPGKG(VPGIG)2)2]3-(VPAVG)20-[((VPGIG)2

VPGKG(VPGIG)2)2-DDDEEKFLRRIGRFG-((VPGIG)2VPGKG(VPG

IG)2)2]3-V
```

-continued (i) MESLLP-(VPGVG VPGVG VPGEG VPGVG VPGVG)10-(VPAV
G)40-V
(SEQ ID NO: 35)

(j) MESLLP-(VPGVG VPGVG VPGEG VPGVG VPGVG)10-(VPAV
G)60-V
(SEQ ID NO: 36)

(k) MESLLP-(VPGVG VPGVG VPGEG VPGVG VPGVG)20-(VPAV
G)40-V
(SEQ ID NO: 37)
and (l) MESLLP-(VPGVG VPGVG VPGEG VPGVG VPGVG)10-(VPAV
G)40-(VPGVG VPGVG VPGEG VPGVGVPGVG)10-V.
(SEQ ID NO: 38)

In one embodiment, the peptide sequence is MGSSHHHHHHSSGLVPRGSHMESLLP-[VPGIGVP-GIGVPGKGVPGIGVPGIGVPGIGVPGIGVPGKGVP-GIGVPGIGAVTGRGDSPASSVPGIGVPGIG VPGKGVP-GIGVPGIGVPGIGVPGIGVPGKGVPGIGVPGIG]6-V (SEQ ID NO:27).

In one embodiment, the peptide sequence is MESLLP-VPGIGVPGIGVPGKGVPGIGVPGIGEEIQI-GHIPREDVDYHLYPVPGIGVPGIGVPGKGVPGIGVP-GIGVGVA PGVGVAPGVGVAPG]10-V (SEQ ID NO:28). In one embodiment, the peptide sequence is MESLLP-[(VPGVG VPGVG VPGEG VPGVG VPGVG)10-(VGIPG)60]2-V (SEQ ID NO:29). In one embodiment, the peptide sequence is MESLLP-[VPGIG VPGIG VPGKG VPGIG VPGIG VPGIG VPGIG VPGKG VPGIG VPGIG]12-V (SEQ ID NO:30). In one embodiment, the peptide sequence is MESLLP-[((VPGIG)2VPGKG(VPGIG)2)2-DD-DEEKFLRRIGRFG-(VPGIG)2VPGKG(VPGIG)2)2]3-V (SEQ ID NO: 32). In one embodiment, the peptide sequence is MESLLP-[((VPGIG)2VPGKG(VPGIG)2)2-DD-DEEKFLRRIGRFG-((VPGIG)2VPGKG(VPGIG)2)2]3-V. In one embodiment, the peptide sequence is MESLLP-[((VPGIG)2VPGKG(VPGIG)2)2-DDDEEKFLRRIGRFG-((VPGIG)2VPGKG(VPGIG)2)2]3-(VPAVG)20-V (SEQ ID NO:33). In one embodiment, the peptide sequence is MESLLP-[((VPGIG)2VPGKG(VPGIG)2)2-DD-DEEKFLRRIGRFG-((VPGIG)2VPGKG(VPGIG)2)2]3-(VPAVG)20-[((VPGIG)2VPGKG(VPGIG)2)2-DD-DEEKFLRRIGRFG-((VPGIG)2VPGKG(VPGIG)2)2]3-V (SEQ ID NO:34) In one embodiment, the peptide sequence is MESLLP-(VPGVG VPGVG VPGEG VPGVG VPGVG)10-(VPAVG)40-V (SEQ ID NO:35). In one embodiment, the peptide sequence is MESLLP-(VPGVG VPGVG VPGEG VPGVG VPGVG)10-(VPAVG)60-V (SEQ ID NO:36). In one embodiment, the peptide sequence is MESLLP-(VPGVG VPGVG VPGEG VPGVG VPGVG)20-(VPAVG)40-V (SEQ ID NO:37). In one embodiment, the peptide sequence is MESLLP-(VPGVG VPGVG VPGEG VPGVG VPGVG)10-(VPAVG)40-(VPGVG VPGVG VPGEG VPGVG VPGVG)10-V (SEQ ID NO:38).

The scaffold membrane, in particular the ELP membrane or hydrogel, can include bioactive sequences. In one embodiment the bioactive sequence is MGSSHHHHHHSSGLVPRGSHMESLLP-[[(VPGIG)2(VPGKG)(VPGIG)2]2AVTGRGDSPASS[(VPGIG)2(VPGKG)(VPGIG)2]2]6 (SEQ ID NO:39). In one embodiment the bioactive sequence is RGDS (SEQ ID NO:1). RGDS (SEQ ID NO:1) promotes cell adhesion. In a preferred embodiment the bioactive sequence is statherin-derived peptide DDDEEKFLRRIGRFG (SEQ ID NO:2). Statherin is a salivary protein that naturally acts as a chelating agent for calcium ions in order to enhance enamel remineralization during acid attacks.

Figure 2:
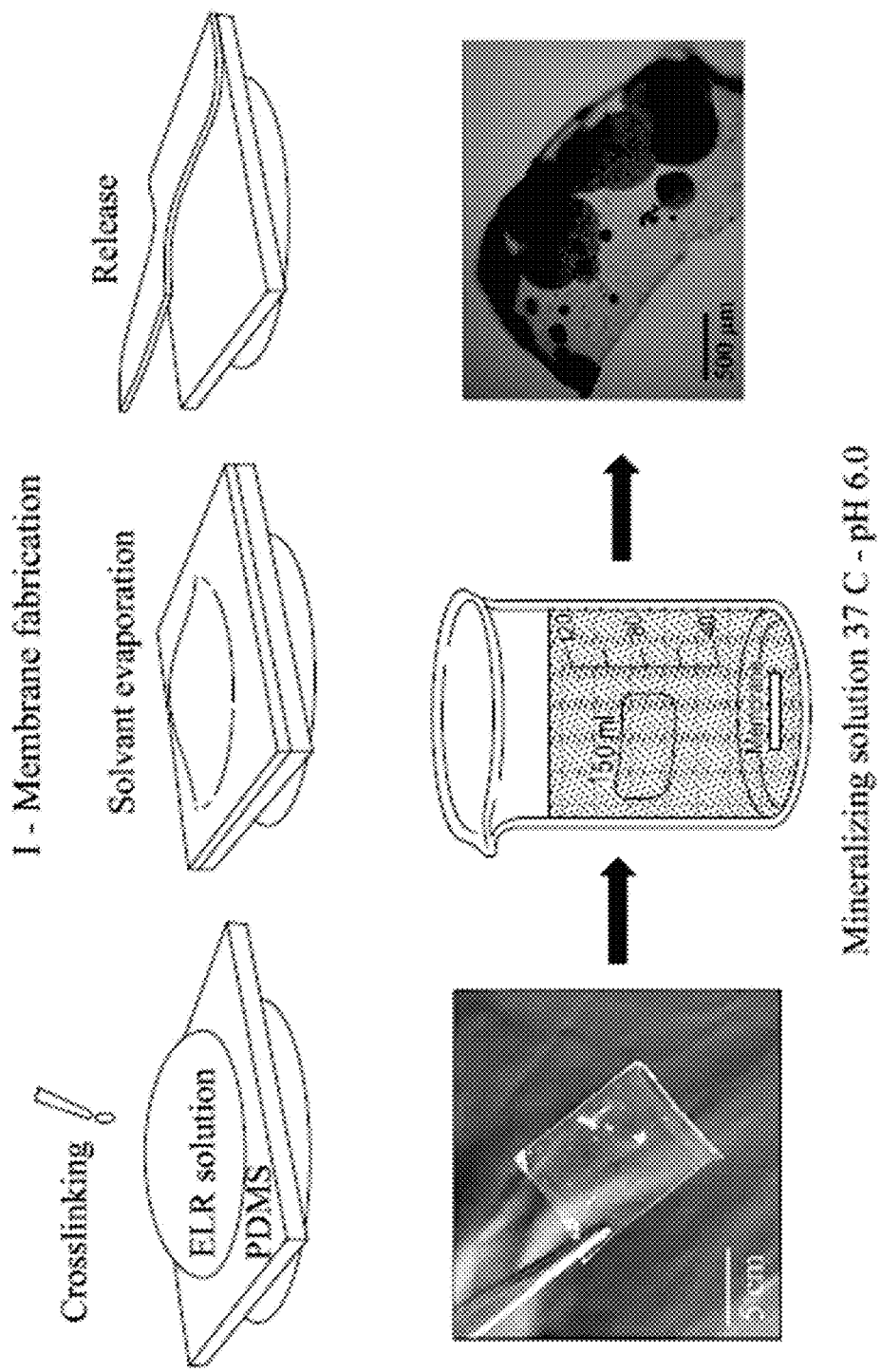
FIG. 2. Table showing the different ELP molecules along with isoelectric points and molecular weights. Bioactive sequences are shown in red. Schematics at the bottom, illustrating the fabrication and mineralization processes.

Accordingly, the ELP membrane or hydrogel may comprise a bioactive sequence selected from the group consisting of MGSSHHHHHHSSGLVPRGSHMESLLP-[[(VPGIG)2(VPGKG)(VPGIG)2]2AVTGRGDSPASS[(VPGIG)2(VPGKG)(VPGIG)2]2]6 (SEQ ID NO:39), RGDS (SEQ ID NO:1) or DDDEEKFLRRIGRFG (SEQ ID NO:2). In one embodiment the ELP membrane or hydrogel comprises one or more bioactive sequence. In one embodiment the ELP membrane or hydrogel comprises two or more bioactive sequences. The skilled person would understand other bioactive epitopes can be incorporated into the ELP membrane to provide specific functionality. In one embodiment, the ELP membrane or hydrogel comprises a bioactive sequence as defined in Table 1 (FIG. 2).

TABLE 1

| Type of ELP | Sequence (bioactive sequence in red) | Isoelectric point (pI) | Molecular weight | Inverse transition temperature (DW) | |
|---|---|---|---|---|---|
| | | | | pH | $T_t$ (° C.) |
| IK | MESLLP-(VPGIG VPGIG VPGKG VPGIG VPGIG)24 (SEQ ID NO: 40) | 11 | 51.9 kDa | 3.5 7.2 10.5 | 39-41 32-34 24-26 |
| SN | MESLLP-[[(VPGIG)2(VPGKG)(VPGIG)2]2 DDDEEKFLRRIGRFG((VPGIG)2(VPGKG)(VPGIG)2]2]3 (SEQ ID NO: 41) | 9.9 | 31.9 kDa | 3.5 2.2 10.5 | >60 23 25 |
| RGDS | MGSSHHHHHHSSGLVPRGSHMESLLP. [[(VPGIG)2(VPGKG)(VPGIG)2]2AVTGRGDSPASS[(VPGIG)2V(PGKG)(VPGIG)2]6 (SEQ ID NO: 39) | 11.1 | 60.6 kDa | 3.5 7.2 10.5 | 39-41 35-37 26-28 |
| SN-RGDS | MESLLP-[[(VPGIG)2(VPGKG)(VPGIG)2]2 DDDEEKFLRRIGRFG[(VPGIG)2(VPGKG)(VPGIG)2]2)4 ([[(VPGIG)2(VPGKG)(VPGIG)2]2 AVTGRGDSPASS [(VPGIG)2(VPGKG)(VPGIG)2]4 (SEQ ID NO: 42) | 10.8 | 80.7 kDa | 3.5 7.2 10.5 | >60 33 25 |

Other materials or molecules may be included in the ELP membrane or hydrogel during the fabrication process. In one embodiment, the ELP membrane or hydrogel comprises collagen, amelogenin, bone sialoprotein, enamelin or phosphorylated serine. In one embodiment the ELP membrane or hydrogel comprises graphene, carbon nanotubules, and/or quantum dots. In one embodiment the ELP membrane or hydrogel comprises sugar, proteins, inorganic particles and/or peptides. The skilled person would understand that a wide range of solvent soluble materials can be incorporated into the ELP membrane.

In one embodiment, the ELP membrane or hydrogel is biocompatible, i.e—it is not harmful or toxic to living tissue. In one embodiment, the ELP membrane or hydrogel is formed from a flexible material.

In one embodiment, the ELP membrane or hydrogel has a β-spiral conformation. The presence of a β-spiral conformation can be confirmed using circular dichroism (CD) spectroscopy.

ELP membranes or hydrogels exhibit reversible-phase behaviour and undergo inverse temperature transition (Urry 1992, 1997). An ELP membrane will be in a disorganised state and will be highly soluble in aqueous solution below the transition temperature. The transition temperature is the temperature at which a substance acquires or loses a distinctive property, for example changing from one crystal state to another. An ELP membrane will transition to an organised, hierarchal crystal structure comprising β-spiral conformations above the inverse transition temperature. The skilled person would understand that the inverse transition temperature will vary dependent on the type of membrane or hydrogel. In one embodiment, the ELP membrane or hydrogel has a β-spiral conformation when hierarchical mineralization takes place above the inverse transition temperature of the ELP membrane. The presence of a β-spiral conformation can be confirmed using circular dichroism (CD) spectroscopy.

In one embodiment, the inverse transition temperature of the ELP membrane is 10° C. to 90° C. In one embodiment, the inverse transition temperature of the ELP membrane is about 33° C. to 41° C. In one embodiment, the inverse transition temperature of the ELP membrane is about 35° C. to 39° C. In one embodiment, the inverse transition temperature of the ELP membrane is about 37° C.

Membranes with Fabricated Topographies

The inventors of the present invention are able to tune the directionality of growth of crystals with hierarchical structure using membranes with fabricated topographies. The geometry of the topography can be used to change the directionality and shape of the crystalline structures.

In one embodiment, the scaffold membrane is a fabricated membrane. In one embodiment, the scaffold membrane is a nanofabricated membrane, a microfabricated membrane or a macrofabricated membrane. In a preferred embodiment, the scaffold membrane is a microfabricated membrane.

The fabricated membrane can have a channelled topography (i.e. it comprises channels). The arrangement and direction of the channels can be used to direct growth of the synthetic crystal structure. The channels are co-planar (or substantially co-planar) with the surface of the membrane. The channels of the membrane can comprise one or more ridges. The ridges can comprise a horizontal and vertical section relative to the flat surface of the membrane. In one embodiment, the membrane comprises one or more ridges or grooves between ridges of adjacent channels. In one embodiment, the angle between horizontal and vertical sections of the channels is from 185° to 355°, 210° to 350°, 210° to 340°, 210° to 330°, 2200 to 320°, 240° to 300°, 250° to 290° or 260° to 280°.

In one embodiment, the scaffold membrane topography comprises channels, grooves, post, holes, hexagons and/or stars. In one embodiment, the angle of the star is 20, 36, 60, 108 or 120 degrees. In one embodiment, the scaffold membrane topography comprises a combination of channels, grooves, post, holes, hexagons and/or stars.

Membranes can be fabricated using known methods, as detailed in Tejeda-Montes et al., 2012.

In one embodiment, a scaffold membrane, optionally a scaffold membrane with a fabricated topography, is incubated with a mineralizing solution of the invention. The step of incubating comprises nucleation followed by crystal growth.

Generally there are two mechanisms of nucleation: homogeneous and heterogeneous. In homogenous nucleation, mineralization occurs in a bulk solution, does not require a substrate or template, and exhibits a spherical nucleus in order to overcome the free energy barrier. On the other hand, heterogeneous nucleation originates from impurities in the system (i.e. surfaces and matrices) and requires less energy than homogeneous nucleation because the surface energy barrier is lowered by the interfacial energy following the Gibbs free energy equations (Wang, L. & Nancollas, G. H. Calcium orthophosphates: Crystallization and Dissolution. *Chemical Reviews* 108, 4628-4669 (2008)).

$$\Delta G_{homogenous} = (4/3\pi r^3 \rho \Delta\mu + 4\pi r^2 \gamma) \quad (1)$$

$$\Delta G_{heterogenous} = \Delta G_{homogenous} * f\theta \quad (2)$$

where; ΔG is the free energy barrier of nucleation, r is the radius of the nucleus, ρ is the density of the new phase, Δμ is the difference in chemical potential between the new phase and the existing phase (also known as supersaturation), γ is the surface tension between the nucleus and bulk solution, and θ is the contact angle between the bulk solution and the substrate in the case of heterogeneous nucleation. Generally speaking, methods of the invention comprise heterogeneous nucleation due to the presence of a scaffold membrane. Heterogeneous nucleation gives more control over the nucleation rate, and the crystal orientation, polymorphism, and morphology are influenced by the type of crystal growth mechanism. Therefore, optimising crystal nucleation and growth by tuning the surface topography of substrates allows the design and engineering of advanced materials, such as the synthetic crystals of the invention (Meldrum, F. C. & Ludwigs, S. Template-directed control of crystal morphologies. Macromolecular Bioscience 7, 152-162, doi:10.1002/mabi.200600191 (2007)).

The membrane can be any membrane as described herein. In one embodiment the membrane is from a material with high mineralizing properties. In one embodiment the membrane is formed of natural elastin. In one embodiment, the elastin comprises the tropoelastin recurrent motif Val-Pro-Gly-X-Gly (VPGXG (SEQ ID NO:19)), where X is any amino acid apart from proline. In another embodiment, the membrane is formed of collagen, amelogenin, Elastin-like protein membrane or Elastin-like protein hydrogel. The Elastin-like protein membrane or Elastin-like protein hydrogel can comprise the tropoelastin recurrent motif Val-Pro-Gly-X-Gly (VPGXG (SEQ ID NO:19)), where X is any amino acid apart from proline.

Hierarchically Ordered Structures

As used herein, the term "hierarchically ordered" refers to the hierarchal ordering of different structures at different length scales. Materials such as bone and enamel have multiple levels of hierarchical structure. The present inventors have, for the first time, generated a synthetic enamel with a hierarchal structure that is similar to natural enamel. The synthetic crystals of the invention comprise an assembly of hierarchically ordered crystallographic, nanostructures, microstructures and macrostructures, as discussed below.

In one embodiment, the synthetic crystalline structures comprise nanostructures, microstructures and macrostructures assembled in an hierarchal order across multiple length-scales. The length-scales can be crystallographic, nanometre, micrometre, one hundred micrometre and millimetre.

In one embodiment, the synthetic crystalline structures comprises three levels, preferably at least four levels of hierarchy. In one embodiment, the four levels of hierarchy are nanometre, micrometre, one hundred micrometre and millimetre. In one embodiment, the five levels of hierarchy are crystallographic, nanometre, micrometre, one hundred micrometre and millimetre. Each level of hierarchy comprises morphologically distinct structures. The hierarchical structure of the synthetic enamel mirrors that found in natural dental enamel. Therefore, the synthetic crystals of the invention have a morphology that approaches or is identical to naturally occurring biological dental enamel.

At the crystallographic length-scale, the material is apatite, with a space group, unit cell size, and structural parameters matching apatite values, as reported in the literature (Young, R. A. & Elliott, J. C. Atomic-scale bases for several properties of apatites. *Archives of Oral Biology* 11, 699-707 (1966)).

At the nanometre length scale the structures of the invention exhibit elongated needle shaped nanocrystals or elongated plate-like shaped nanocrystals. In one embodiment the nanocrystals are up to about 200 nm. In one embodiment the nanocrystals are up to about 120 nm. In one embodiment the nanocrystals are up to about 110 nm. In one embodiment the nanocrystals are up to about 100 nm. In one embodiment the needle shaped nanocrystals are about 10 nm to about 200 nm in width. In one embodiment the needle shaped nanocrystals are about 60 to about 110 nm in width. In one embodiment the needle shaped nanocrystals are about 70 to about 100 nm in width. In one embodiment they are 80 nm to 90 nm. In a preferred embodiment the needle shaped nanocrystals are about 25 to about 120 nm in width, optionally about 85 nm in width. Fluroapatite crystals, in particular, may exhibit such a morphology. In one embodiment, the synthetic crystal is fluorapatite and the nanocrystals are elongated needle shaped nanocrystals.

The plate-like crystals are considered to be plate-like, for example on the basis of their chemistry. Using the microscope to observe the side of the plate-like crystals, it is possible to measure the thickness of the plate-like crystal. In one embodiment the plate-like shaped nanocrystals are at least 1 nm in thickness, optionally up to about 50 nm in thickness. For example the plate-like nanocrystals are from about 1 nm to about 40 nm thick. In one embodiment the plate-like shaped nanocrystals are from about 1 nm to about 40 nm thick. In one embodiment the needle shaped nanocrystals are from about 15 to about 25 nm thick. In one embodiment the plate-like shaped nanocrystals are from about 16 to about 17 nm thick. In one embodiment the plate-like shaped nanocrystals are from about 17 nm thick. In one embodiment, the synthetic crystal is hydroxyapatite and the nanocrystals are plate-like nanocrystals. In one embodiment, the synthetic crystal is hydroxyapatite and the nanocrystals are plate-like nanocrystals that are from about 1 nm to about 40 nm thick. In one embodiment, the synthetic crystal is hydroxyapatite and the nanocrystals are from about 15 to about 25 nm thick. In one embodiment, the synthetic crystal is hydroxyapatite and the nanocrystals are plate-like nanocrystals that are from about 16 to about 17 nm across the plate. In one embodiment, the nanocrystals are organized into about 4 μm thick prism-shaped microstructures, resembling the prism microstructures observed in natural enamel. A prism is a solid geometric figure whose two ends are similar, equal, and parallel rectilinear figures, and whose sides are parallelograms. The term prism is interchangeable with fingers or micro-rods. In one embodiment the nanocrystals are form about 1 to about 90 μm, from about 1 to about 0 μm, from about 1 to about 70 μm, from about 1 to about 60 μm, from about 1 to about 50 μm, from about 1 to about 40 μm, from about 1 to about 30 μm, from about 1 to about 20 μm, from about 1 to about 10 μm, or from about 1 to about 5 μm thick prism-shaped microstructures. In a preferred embodiment the nanocrystals form prism-shaped microstructures having a thickness of about 4 μm.

In one embodiment, the prism-shaped microstructures are aligned or substantially aligned with one another and/or are adjacent or substantially adjacent to one another. In one embodiment, the prism-shaped microstructures recur along the enamel-like microstructures. In one embodiment, the prism-shaped microstructures recur at approximately 1 μm intervals, for example they recur at from 0.1 to 10 μm intervals, or at from 0.5 to 5 μm intervals.

In one embodiment, the nanocrystals are organized into circular concentric ring microstructures.

The microstructures assemble to form circular structures or asymmetrical structures hundreds of microns in diameter that come together to fill macroscopic areas (i.e the microstructures assemble to form macrostructures). An asymmetrical structure can be oval, elongated in shape, non-circular, substantially circular shaped or other non-symmetrical shape. In one embodiment the microstructures of the synthetic crystal assemble to form a circular structure. In one embodiment the microstructures of the synthetic crystal assemble to form an asymmetrical structure.

In one embodiment, the synthetic fluorapatite crystalline structure comprises a four (or five) level hierarchy wherein the four (or five)level hierarchy comprises needle-shaped nanocrystals that are organized into prism-like microstructures, and the prism-like microstructures comprise circular structures hundreds of microns in diameter and can fill macroscopic areas.

In one embodiment, the synthetic fluorapatite crystalline structure comprises a four (or five)level hierarchy wherein the four (or five) level hierarchy comprises needle-shaped nanocrystals that are organized into prism-like microstructures, and the prism-like microstructures comprise asymmetrical structures hundreds of microns in diameter and can fill macroscopic areas.

In one embodiment, the synthetic hydroxyapatite crystalline structure comprises a four (or five) level hierarchy wherein the four (or five) level hierarchy comprises plate-like shaped nanocrystals that are organized into prism-like microstructures, and the prism-like microstructures comprise circular structures hundreds of microns in diameter and can fill macroscopic areas.

In one embodiment, the synthetic hydroxyapatite crystalline structure comprises a four(or five) level hierarchy wherein the four (or five) level hierarchy comprises plate-like shaped nanocrystals that are organized into prism-like microstructures, and the prism-like microstructures comprise asymmetrical structures hundreds of microns in diameter and can fill macroscopic areas.

In one embodiment, the synthetic fluorapatite crystalline structure comprises a four (or five) level hierarchy wherein the four (or five) level hierarchy comprises needle-shaped nanocrystals about 10 nm to about 200 nm in width, optionally about 85 nm in width, that are organized into about 1 to about 90 μm thick prism-like microstructures, and the prism-like microstructures comprise circular structures hundreds of microns in diameter and can fill macroscopic areas.

In one embodiment, the synthetic fluorapatite crystalline structure comprises a four (or five) level hierarchy wherein the four (or five) level hierarchy comprises needle-shaped nanocrystals about 10 nm to about 200 nm in width, optionally about 85 nm in width, that are organized into about 1 to about 90 μm thick prism-like microstructures, and the prism-like microstructures comprise asymmetrical structures hundreds of microns in diameter and can fill macroscopic areas.

In one embodiment, the synthetic hydroxyapatite crystalline structure comprises a four (or five) level hierarchy wherein the four (or five) level hierarchy comprises plate-like shaped nanocrystals about 1 nm to about 40 nm thick, optionally about 17 nm thick, that are organized into about 1 to about 90 μm thick prism-like microstructures, and the prism-like microstructures comprise circular structures hundreds of microns in diameter and can fill macroscopic areas.

In one embodiment, the synthetic hydroxyapatite crystalline structure comprises a four (or five) level hierarchy wherein the four (or five) level hierarchy comprises plate-like shaped nanocrystals about 1 nm to about 40 nm thick, optionally about 17 nm thick, that are organized into about 1 to about 90 μm thick prism-like microstructures, and the prism-like microstructures comprise asymmetrical structures hundreds of microns in diameter and can fill macroscopic areas.

In one embodiment, the synthetic fluorapatite crystalline structure comprises a four (or five) level hierarchy wherein the four (or five) level hierarchy comprises needle-shaped nanocrystals about 25 to about 120 nm in width, optionally about 85 nm in width, that are organized into about 1 to about 5 μm thick prism-like microstructures, and the prism-like microstructures comprise circular structures hundreds of microns in diameter and can fill macroscopic areas.

In one embodiment, the synthetic fluorapatite crystalline structure comprises a four (or five) level hierarchy wherein the four (or five) level hierarchy comprises needle-shaped nanocrystals about 25 to about 120 nm in width, optionally about 85 nm in width, that are organized into about 1 to about 5 μm thick prism-like microstructures, and the prism-like microstructures comprise asymmetrical structures hundreds of microns in diameter and can fill macroscopic areas.

In one embodiment, the synthetic hydroxyapatite crystalline structure comprises a four (or five) level hierarchy wherein the four (or five) level hierarchy comprises plate-like shaped nanocrystals about 1 to about 40 nm thick, optionally about 17 nm thick, that are organized into about 1 to about 5 μm thick prism-like microstructures, and the prism-like microstructures comprise circular structures hundreds of microns in diameter and can fill macroscopic areas.

In one embodiment, the synthetic hydroxyapatite crystalline structure comprises a four (or five) level hierarchy wherein the four (or five) level hierarchy comprises plate-like shaped nanocrystals about 1 to about 40 nm thick, optionally about 17 nm thick, that are organized into about 1 to about 5 μm thick prism-like microstructures, and the prism-like microstructures comprise asymmetrical structures hundreds of microns in diameter and can fill macroscopic areas.

The synthetic crystals of the invention can beneficially be used to enhance or promote desired cell characteristics. A number of benefits can be achieved at the site of implantation or administration. In one embodiment, the synthetic crystals of the invention increase cell adhesion. In one embodiment, the synthetic crystals of the invention increase or promote cell growth. In one embodiment, the synthetic crystals of the invention increase or promote cell migration. In one embodiment, the synthetic crystals of the invention increase or promote cell viability. Cell viability is the cells ability to survive and/or live successfully. In one embodiment, the synthetic crystals of the invention increase or promote tissue regeneration. In one embodiment, the cell is selected from the group consisting of stem cells, odontoblasts, dental stem cells, osteoclasts and osteoblasts.

In one embodiment, the synthetic crystals of the invention are acid-resistant. In one embodiment, the synthetic crystals of the invention are resistant to acid attack. Acid attack is the exposure of an object to acid (i.e. having a Ph less than 7).

The synthetic crystals of the invention include those obtained or obtainable by the methods and processes of the present invention.

In one aspect of the invention there is provided a process for producing hierarchically ordered mineralized structure. The process comprises the step of contacting a protein-scaffold membrane with a mineralizing solution. In one embodiment the mineralizing solution is a supersaturated solution of $Ca^{2+}$ and $PO_4^{3-}$. In one embodiment the mineralizing solution is a supersaturated solution of $Ca^{2+}$, $PO_4^{3-}$, and $F^-$. In one embodiment, the contacting step is performed at physiological Ph and temperature. The step of contacting comprises the terms submerging and/or incubating the scaffold membrane in the mineralizing solution.

Cross Linking

The process of the invention comprises the step of contacting a protein-scaffold membrane with a mineralizing solution. In one preferred embodiment, the ELP membrane or hydrogel can be cross-linked.

For example, the ELP membrane or hydrogel can be cross-linked by chemical cross-linking, enzymatic cross-linking by tissue transglutaminase, photoinitiated and/or γ-irradation cross-linking. In one embodiment, the ELP membrane or hydrogel has a cross linker ratio of greater than about 0.25. In one embodiment, the ELP membrane or hydrogel has a cross linker ratio of between about 0.25 to 24. In one embodiment, the ELP membrane or hydrogel has a cross linker ratio of between about 0.25 to 20. In a preferred embodiment, the ELP membrane or hydrogel has a cross linker ratio of about 0.5 to about 12. In one embodiment, the ELP membrane or hydrogel has a cross linker ratio of about 6 to 12. In one embodiment, the ELP membrane or hydrogel has a cross linker ratio of about 12. In one embodiment, the ELP membrane or hydrogel has a cross linker to lysine ratio of greater than about 0.25. In one embodiment, the ELP membrane or hydrogel has a cross linker to lysine ratio of between about 0.25 to 24.

In one embodiment, the ELP membrane or hydrogel has a cross linker to lysine ratio of between about 0.25 to 20. In a preferred embodiment, the ELP membrane or hydrogel has a cross linker to lysine ratio of about 0.5 to about 12. In one embodiment, the ELP membrane or hydrogel has a cross linker to lysine ratio of about 6 to 12. In one embodiment, the ELP membrane or hydrogel has a cross linker to lysine ratio of about 12. The cross-linker ratio is the ratio of the molar concentration of cross-linker to the molar concentration of amine or carboxylic groups of the ELP membrane or hydrogel, protein, polymer, peptide or amino acid. In one embodiment the cross-linker is hexamethyl diisocyanate.

In some embodiments, the step of cross-linking can occur in vivo. For example, the cross-linking solution can be added to the in vivo location, for example to the tooth or bone of a patient.

Mineralizing Solution

The process of the invention comprises the step of contacting a protein-scaffold membrane with a mineralizing solution. Altering the ionic content of the mineralizing solution changes the chemistry of the resulting apatite. Generally, the mineralizing solution is aqueous.

In one embodiment, the mineralizing solution comprises calcium. In one embodiment, the mineralizing solution contains from about 0.1 Mm to about 1 M $Ca^{2+}$. In one embodiment, the supersaturated solution contains from about 0.1 Mm to about 800 Mm $Ca^{2+}$. In one embodiment, the supersaturated solution contains from about 0.1 Mm to about 600 Mm $Ca^{2+}$. In one embodiment, the supersaturated solution contains from about 0.1 Mm to about 400 Mm $Ca^{2+}$. In one embodiment, the supersaturated solution contains from about 0.1 Mm to about 200 Mm $Ca^{2+}$. In one embodiment, the supersaturated solution contains from about 0.1 Mm to about 100 Mm $Ca^{2+}$. In one embodiment, the mineralizing solution contains about 0.5 to about 10 Mm $Ca^{2+}$. In one embodiment, the supersaturated solution comprises about 9 to about 11 Mm $Ca^{2+}$. In a preferred embodiment, the supersaturated solution comprises about 2.5 to about 10 Mm $Ca^{2+}$.

In one embodiment, the supersaturated solution contains from about 0.1 Mm to about 1 M $PO_4^{3-}$. In one embodiment, the supersaturated solution contains from about 0.1 Mm to about 800 Mm $PO_4^{3-}$. In one embodiment, the supersaturated solution contains about from 0.1 Mm to about 600 Mm $PO_4^{3-}$. In one embodiment, the supersaturated solution contains from about 0.1 Mm to about 400 Mm $PO_4^{3-}$. In one embodiment, the supersaturated solution contains from about 0.1 Mm to about 200 Mm $PO_4^{3-}$. In one embodiment, the supersaturated solution contains from about 0.1 Mm to about 100 Mm $PO_4^{3-}$. In one embodiment, the supersaturated solution contains from about 1 Mm to about 10 Mm $PO_4^{3-}$. In one embodiment, the supersaturated solution contains from about 4 to about 8 Mm $PO_4^{3-}$. In one embodiment, the supersaturated solution contains from about 5 to about 7 Mm $PO_4^{3-}$. In one embodiment, the supersaturated solution contains from about 5.5 to about 6.5 Mm $PO_4^{3-}$. In a preferred embodiment the ration of calcium to phosphate is about 1.67 Mm. In this embodiment the resulting crystalline structure is apatite.

In one embodiment, the mineralizing solution comprises from about 0.01 Mm to about 1 M F−. In one embodiment, the mineralizing solution comprises from about 0.01 Mm to about 800 Mm F−. In one embodiment, the mineralizing solution comprises a from bout 0.01 Mm to about 600 Mm F−. In one embodiment, the mineralizing solution comprises from about 0.01 Mm to about 400 Mm F−. In one embodiment, the mineralizing solution comprises from about 0.01 Mm to about 200 Mm F−. In one embodiment, the mineralizing solution comprises from about 0.01 Mm to about 100 Mm F−. In one embodiment, the mineralizing solution comprises from about 0.01 Mm to about 50 Mm F−. In one embodiment, the mineralizing solution comprises from about 0.1 Mm to about 5 Mm F−. In one embodiment, the mineralizing solution comprises from about 0.1 to about 4 Mm F−. In one embodiment, the supersaturated solution comprises from about 1 to about 3 Mm F−. In one embodiment, the supersaturated solution comprises from about 1.5 to about 2.5 Mm F−. In another embodiment the mineralizing solution does not comprise F−. In such an embodiment, the resulting crystalline structure is hydroxyapatite.

In one embodiment, the mineralizing solution comprises strontium. In one embodiment, the mineralizing solution contains from about 0.5 to about 10 Mm strontium. In one embodiment, the supersaturated solution comprises from about 9 to about 11 Mm strontium. In a preferred embodiment, the supersaturated solution comprises from about 2.5 to about 10 Mm strontium.

In one embodiment, the mineralizing solution comprises zinc. In one embodiment, the mineralizing solution contains about 0.5 to about 10 Mm zinc. In one embodiment, the supersaturated solution comprises about 9 to about 11 Mm zinc. In a preferred embodiment, the supersaturated solution comprises about 2.5 to about 10 Mm zinc.

In one embodiment, the mineralizing solution comprises silver. In one embodiment, the mineralizing solution contains about 0.5 to about 10 Mm silver. In one embodiment, the supersaturated solution comprises about 9 to about 11 Mm silver. In a preferred embodiment, the supersaturated solution comprises about 2.5 to about 10 Mm silver.

In one embodiment, the mineralizing solution comprises barium. In one embodiment, the mineralizing solution contains about 0.5 to about 10 Mm barium. In one embodiment, the supersaturated solution comprises about 9 to about 11 Mm barium. In a preferred embodiment, the supersaturated solution comprises about 2.5 to about 10 Mm barium.

In one embodiment, the mineralizing solution comprises carbonate. In one embodiment, the mineralizing solution contains about 0.5 to about 10 Mm carbonate. In one embodiment, the supersaturated solution comprises about 9 to about 11 Mm carbonate. In a preferred embodiment, the supersaturated solution comprises about 2.5 to about 10 Mm carbonate.

In one embodiment, the mineralizing solution comprises magnesium. In one embodiment, the mineralizing solution contains about 0.5 to about 10 Mm magnesium. In one embodiment, the supersaturated solution comprises about 9 to about 11 Mm magnesium. In a preferred embodiment, the supersaturated solution comprises about 2.5 to about 10 Mm magnesium.

In one embodiment, the mineralizing solution comprises potassium. In one embodiment, the mineralizing solution contains about 0.5 to about 10 Mm potassium. In one embodiment, the supersaturated solution comprises about 9 to about 11 Mm potassium. In a preferred embodiment, the supersaturated solution comprises about 2.5 to about 10 Mm potassium.

In one embodiment, the mineralizing solution comprises iron. In one embodiment, the mineralizing solution contains about 0.5 to about 10 Mm iron. In one embodiment, the supersaturated solution comprises about 9 to about 11 Mm iron. In a preferred embodiment, the supersaturated solution comprises about 2.5 to about 10 Mm iron.

In one embodiment, the mineralizing solution comprises lead. In one embodiment, the mineralizing solution contains about 0.5 to about 10 Mm lead. In one embodiment, the supersaturated solution comprises about 9 to about 11 Mm lead. In a preferred embodiment, the supersaturated solution comprises about 2.5 to about 10 Mm lead.

In one embodiment, the supersaturated solution comprises about 8 to about 12 Mm $Ca^{2+}$, about 4 to about 8 Mm $PO_4^{3}$, optionally further comprising about 0.1 to about 4 Mm F−. In a preferred embodiment the supersaturated solution comprises about 10 Mm $Ca^{2+}$, and about 6 Mm $PO_4^{3-}$, optionally further comprising about 2 Mm F−.

In one embodiment the mineralizing is solution is a bodily fluid. In one embodiment the bodily fluid is saliva, blood, interstitial fluid, serum or plasma. In one embodiment, the step of contacting an elastin-like polypeptide membrane or hydrogel with a solution of calcium and phosphate ions is an in vivo step. In one embodiment, the in vivo step occurs in a mouth, on a bone or on a human tissue.

The protein-scaffold membrane is contacted with solution, in particular a supersaturated solution, having a specific Ph value. In one embodiment the Ph is from about 2 to about 11. In one embodiment the Ph is from about 3 to about 8. In one embodiment the Ph is from 4 to 8. In one embodiment the Ph is from about 4 to about 7. In one embodiment the Ph is from about 5 to about 7. In one embodiment the Ph is about 6.

In one embodiment, the protein-scaffold membrane is contacted with a supersaturated solution at physiological Ph. In one embodiment the physiological Ph is from about 2 to about 11. In one embodiment the Ph is from about 3 to 9. In one embodiment the Ph is from about 4 to 8. In one embodiment the Ph is from about 5 to 8. In one embodiment the Ph is from about 6 to 7. In one embodiment the Ph is 7.4.

In one embodiment, the supersaturated solution comprises about 8 to about 12 Mm $Ca^{2+}$ and about 4 to about 8 Mm $PO_4^3$, and the protein-scaffold membrane is contacted with a supersaturated solution having a Ph value of about 5 to about 7. In a preferred embodiment the supersaturated solution comprises about 10 Mm $Ca^{2+}$ and about 6 Mm $PO_4^3$, and the protein-scaffold membrane is contacted with a supersaturated solution having a Ph value of about 6.

In one embodiment, the supersaturated solution comprises about 8 to about 12 Mm $Ca^{2+}$, about 4 to about 8 Mm $PO_4^3$ and about 0.1 to about 4 Mm F−, and the protein-scaffold membrane is contacted with a supersaturated solution having a Ph value of about 6 to about 7. In a preferred embodiment the supersaturated solution comprises about 10 Mm $Ca^{2+}$, about 6 Mm $PO_4^{3-}$ and about 2 Mm F−, and the protein-scaffold membrane is contacted with a supersaturated solution having a Ph value of about 6.

In some embodiments, two solutions having different Ph values can be used. In particular, two different solutions having different Ph values can be used. Reducing the Ph during mineralization of the ELP membrane can control the size of the hierarchically-ordered crystalline structures. The hierarchically-ordered crystalline structures are up to 70 μm in height and 350 μm in diameter when the starting Ph of the solution is set to 6.0 and drops to 3.7 during mineralization.

In one embodiment, the protein-scaffold membrane is contacted with a supersaturated solution at a first Ph and then contacted at a second, lower Ph. In one embodiment the first Ph is about 5.5 to about 6.5. In one embodiment the second lower Ph is about 3.0 to about 4.0. In one embodiment the first Ph is about 5.5 to about 6.5 and the second lower Ph is about 3.0 to about 4.0. In a preferred embodiment the first Ph is about 6.0 and the second lower Ph is about 3.7. In one embodiment, the ELP membrane is contacted with a supersaturated solution at a first Ph and then contacted at a second lower Ph. In one embodiment the first Ph is about 5.5 to about 6.5. In one embodiment the second, lower Ph is 3.0 to 4.0. In one embodiment the first Ph is about 5.5 to about 6.5 and the second lower Ph is about 3.0 to about 4.0. In a preferred embodiment the first Ph is about 6.0 and the second lower Ph is about 3.7.

Much larger structures can be grown with diameters up to 1 mm when the Ph is controlled throughout the mineralization process, for example using BIS-TRIS buffer, in particular where the Ph drops from 6.0 to 5.7.

In one embodiment the protein-scaffold membrane is contacted with a supersaturated solution at a first Ph and then contacted with a second lower Ph. In one embodiment the first Ph is about 5.5 to about 6.5. In one embodiment the second lower Ph is about 3.0 to about 5.7. In one embodiment the second lower Ph is about 3.0 to about 4.0. In a preferred embodiment the first Ph is about 5.5 to about 6.5 and the second lower Ph is about 3.0 to about 4.0. In a preferred embodiment the first Ph is about 6.0 and the second lower Ph is about 5.7. In one embodiment the ELP membrane or hydrogel is contacted with a supersaturated solution at a first Ph and then contacted with a second lower Ph. In one embodiment the first Ph is about 5.5 to about 6.5. In one embodiment the second lower Ph is about 3.0 to about 5.7. In one embodiment the second lower Ph is about 3.0 to about 4.0. In a preferred embodiment the first Ph is about 5.5 to about 6.5 and the second lower Ph is about 3.0 to about 4.0. In a preferred embodiment the first Ph is about 6.0 and the second lower Ph is about 5.7.

When contacting scaffold membranes with solutions having different Ph values, the method may comprise a step of washing the membrane before contacting the membrane with the second Ph. Alternatively, the Ph may be adjusted in situ.

The time spent at each Ph can vary according to requirements. Generally the scaffold membrane will be incubated for at least 8 hours, at least 10 hours, at least 1 day, at least 4 days and more preferably at least 7 days at each Ph. Preferably the scaffold membrane is incubated for at least 8 hours in each Ph solution.

In one embodiment the protein-scaffold membrane is contacted with a supersaturated solution at a temperature of from about 15° C. to about 90° C. In one embodiment the temperature is from about 30° C. to about 60° C. In one embodiment the temperature is from about 35° C. to about 55° C. In a preferred embodiment the temperature is from about 36.5° C. to about 37.5° C., in particular about 37° C. In one embodiment the ELP membrane or hydrogel is contacted with a supersaturated solution at a temperature of from about 15° C. to about 90° C. In one embodiment the temperature is from about 30° C. to about 60° C. In one embodiment the temperature is from about 35° C. to about 55° C. In a preferred embodiment the temperature is from about 36.5° C. to about 37.5° C., in particular about 37° C.

In one embodiment, the ELP membrane or hydrogel is contacted with a supersaturated solution at or above the inverse transition temperature of the ELP membrane. An ELP membrane will transition to an organised, hierarchal crystal structure comprising β-spiral conformations above the inverse transition temperature. The skilled person would understand that the inverse transition temperature will vary dependent on the type of membrane or hydrogel. In one embodiment, the ELP membrane or hydrogel has a β-spiral conformation when hierarchical mineralization takes place above the inverse transition temperature. The presence of a β-spiral conformation can be confirmed using circular dichroism (CD) spectroscopy.

In one embodiment, the inverse transition temperature of the ELP membrane is about 10° C. to 80° C. In one embodiment, the inverse transition temperature of the ELP membrane is about 33° C. to 41° C. In one embodiment, inverse transition temperature of the ELP membrane is about 35° C. to 39° C. In one embodiment, the inverse transition temperature of the ELP membrane is about 37° C.

In one embodiment, the supersaturated solution comprises about 8 to about 12 Mm $Ca^{2+}$ and about 4 to about 8 Mm $PO_4^{3-}$, and the protein-scaffold membrane is contacted with a supersaturated solution having a Ph value of about 5 to about 7 and at a temperature of about 36.5° C. to about 37.5° C. In a preferred embodiment the supersaturated solution comprises about 10 Mm $Ca^{2+}$ and about 6 Mm $PO_4^{3-}$, and the protein-scaffold membrane is contacted with a supersaturated solution having a Ph value of about 6 and at a temperature of about 36.5° C. to about 37.5° C.

In one embodiment, the supersaturated solution comprises about 8 to about 12 Mm $Ca^{2+}$, about 4 to about 8 Mm $PO_4^{3-}$ and about 0.1 to about 4 Mm F−, and the protein-scaffold membrane is contacted with a supersaturated solution having a Ph value of about 6 to about 7 and at a temperature of about 36.5° C. to about 37.5° C. In a preferred embodiment the supersaturated solution comprises about 10 Mm $Ca^{2+}$, about 6 Mm $PO_4^{3-}$ and about 2 Mm F−, and the protein-scaffold membrane is contacted with a supersaturated solution having a Ph value of about 6 and at a temperature of about 36.5° C. to about 37.5° C.

In one embodiment the protein-scaffold membrane is contacted with a supersaturated solution for about 8 to about 12 hours. In one embodiment the protein-scaffold membrane is contacted with a supersaturated solution for about 10 hours. In one embodiment the protein-scaffold membrane is contacted with a supersaturated solution for at least about 10 hours. In one embodiment the protein-scaffold membrane is contacted with a supersaturated solution for about 1 to about 20 days. In one embodiment the protein-scaffold membrane is contacted with a supersaturated solution for about 5 to about 15 days. In one embodiment the protein-scaffold membrane is contacted with a supersaturated solution for about 5 to about 10 days. In one embodiment the protein-scaffold membrane is contacted with a supersaturated solution for about 7 to about 9 days. In one embodiment the protein-scaffold membrane is contacted with a supersaturated solution for at least about 1 day. In one embodiment the protein-scaffold membrane is contacted with a supersaturated solution for at least about 5 days. In one embodiment the protein-scaffold membrane is contacted with a supersaturated solution for at least about 6 days. In one embodiment the protein-scaffold membrane is contacted with a supersaturated solution for at least about 7 days. In a preferred embodiment the protein-scaffold membrane is contacted with a supersaturated solution for at least about 8 days.

In one embodiment the ELP membrane or hydrogel is contacted with a supersaturated solution for about 1 to about 20 days. In one embodiment the ELP membrane or hydrogel is contacted with a supersaturated solution for about 5 to about 15 days. In one embodiment the ELP membrane or hydrogel is contacted with a supersaturated solution for about 5 to about 10 days. In one embodiment the ELP membrane or hydrogel is contacted with a supersaturated solution for about 7 to about 9 days. In one embodiment the ELP membrane or hydrogel is contacted with a supersaturated solution for at least about 1 day. In one embodiment the ELP membrane or hydrogel is contacted with a supersaturated solution for at least about 5 days. In one embodiment the ELP membrane or hydrogel is contacted with a supersaturated solution for at least about 6 days. In one embodiment the ELP membrane or hydrogel is contacted with a supersaturated solution for at least about 7 days. In a preferred embodiment the ELP membrane or hydrogel is contacted with a supersaturated solution for at least about 8 days.

The ELP membrane or solution is formed by dissolving an ELP in solvent. In one embodiment, the ELP concentration in solvent is from about 1 to about 20% by weight, more particularly from about 1 to about 15% by weight, preferably at least 1% or at least 2%, or at least 3%, or at least 4%, or at least 5% by weight.

In one embodiment the Ph is changed during the step of contacting the ELP membrane or hydrogel with a supersaturated solution. The skilled person would understand how to obtain a supersaturated solution using published methods, for example, Chen, H. et al. Synthesis of Fluorapatite Nanorods and Nanowires by Direct Precipitation from Solution. *Cryst Growth Des* 6, 1504-1508, doi:10.1021/cg0600086 (2006).

In some embodiments, the solution of the invention is supersaturated.

In some embodiments, the methods of the invention are performed in vitro.

Uses

In one aspect of the invention, the synthetic crystals of the invention can be used as dental restorative materials, dental enamel, metallic implants, cements, and ceramics. In one aspect of the invention, the synthetic crystals of the invention can be used in conjunction with dental restorative materials, dental enamel, metallic implants, cements, and ceramics. There is therefore provided dental implants comprising the synthetic crystal of the invention.

In one embodiment of the invention, a method is provided for growing a hierarchical crystalline structure on a dental implant. The method comprises contacting a dental implant comprising a protein-scaffold membrane with a mineralizing solution of the invention. In one embodiment, protein-scaffold membrane is an ELP membrane or an ELP hydrogel. In one embodiment, the crystalline structure is apatite. In one embodiment, the crystalline structure is fluroapatite. In another embodiment, the crystalline structure is hydroxyapatite. The methods are as discussed in connection with the methods and production of the synthetic crystals of the invention.

In one aspect of the invention, the synthetic crystal is used in a method of coating a medical implant or dental implant. The surface may be partially or fully covered with the synthetic crystal. The coating can be chemically bonded to the implant surface.

In one aspect of the invention, the synthetic crystals of the invention can be used as a medical implant, synthetic graft, coating, prosthesis, orthosis, paste, malleable putty or film. In one aspect of the invention, the synthetic crystals of the invention can be used in conjunction with medical implant, synthetic graft, coating, prosthesis, orthosis, paste, malleable putty or film. There is therefore provided medical devices, medical implants, synthetic grafts, coatings, prostheses, orthoses, pastes, malleable putties or films comprising the synthetic crystal of the invention.

In one embodiment of the invention, a method is provided for growing a hierarchical crystalline structure on a medical implant, synthetic graft, prosthesis, orthosis, paste, malleable putty or film. The method comprises contacting a medical implant, synthetic graft, prosthesis, orthosis, paste, malleable putty or film comprising a protein-scaffold membrane with a mineralizing solution of the invention. In one embodiment, protein-scaffold membrane is an ELP membrane or an ELP hydrogel. In one embodiment, the crystalline structure is apatite. In one embodiment, the crystalline structure is fluroapatite. In another embodiment, the crystalline structure is hydroxyapatite. The methods are as discussed in connection with the methods and production of the synthetic crystals of the invention.

In one aspect of the invention, the synthetic crystal is used in a method of coating a medical device, medical implant, synthetic graft, prosthesis or orthosis. The surface may be partially or fully covered with the synthetic crystal. The coating can be chemically bonded to the implant surface.

The synthetic crystals of the invention have numerous advantages properties for a wide variety of uses. In particular, the acid-resistance property of the synthetic crystals allows them to be used as a protective coating for a number of surfaces. In one embodiment, a coating comprising synthetic crystals of the invention is provided. In one embodiment, a acid-resistant coating comprising synthetic crystals of the invention is provided. In one embodiment, a coating comprising synthetic crystals of the invention for use with protective clothing and equipment, military equipment and clothing is provided.

Treatment

In an aspect of the invention, the synthetic crystal or dental implant of the invention may be provided for use in the prevention and/or treatment of dental disease. The dental disease may be dental caries, dental erosion, alveolar bone erosion, periodontitis, peri-implantitis or dental pulp disease. In embodiments of the invention, the synthetic crystal of the invention may be administered in combination with one or more pharmaceutically active agents.

This aspect of the invention therefore also extends to a method of treatment of or prevention of dental disease in a subject, comprising administration to, or implantation into, the subject a synthetic crystal of the invention. In one embodiment, the dental disease may be dental caries, dental erosion, alveolar bone erosion, periodontitis, peri-implantitis or dental pulp disease. In an alternative embodiment, the invention may be seen as providing the use of a synthetic crystal or dental implant of the invention in the preparation of a medicament or dental implant for the treatment and/or prevention of dental disease. In one embodiment, the dental disease may be dental caries, dental erosion, alveolar bone erosion, periodontitis, peri-implantitis or dental pulp disease.

In another aspect of the invention, the synthetic crystal of the invention may be provided for use in the prevention and/or treatment of dental hypersensitivity. In embodiments of the invention, synthetic crystal may be administered in combination with one or more pharmaceutically active agents.

This aspect of the invention therefore also extends to a method of treatment of or prevention of dental hypersensitivity in a subject, comprising administration to the subject a synthetic crystal of the invention. In an alternative embodiment, the invention may be seen as providing the use of a synthetic crystal of the invention in the preparation of a medicament for the treatment and/or prevention of dental hypersensitivity.

In another aspect of the invention, the synthetic crystal of the invention may be provided for use in the prevention and/or treatment of demineralisation of teeth. Demineralisation of teeth may be defined as a loss of hydroxyapatite from the teeth. In embodiments of the invention, synthetic crystal may be administered in combination with one or more pharmaceutically active agents. Preparation and formulation of such compositions would be known by the skilled person.

This aspect of the invention therefore also extends to a method of treatment of or prevention of demineralisation of teeth, comprising administration to the subject a synthetic crystal of the invention. In an alternative embodiment, the invention may be seen as providing the use of a synthetic crystal of the invention in the preparation of a medicament for the treatment and/or prevention of demineralisation of teeth.

The synthetic crystals of the present invention may be employed alone or in conjunction with other compounds, such as therapeutic compounds, e.g. anti-inflammatory drugs, cytotoxic agents, cytostatic agents or antibiotics.

In an aspect of the invention, the synthetic crystal of the invention may be provided for use in the prevention and/or treatment of bone demineralisation, low bone density or osteoporosis. In some embodiments of the invention, there is provided the use of the crystal structures of the invention for increasing bone density. The term low bone density is interchangeable with low bone mass and osteopenia. Low bone density can be considered as bone density that is below the average bone density of a health human. Low bone density can be defined as a T-score of below −1.0 when using the central dual energy x-ray absorptiometry (DXA or DEXA) bone density test. A score of −1.0 to −2 on the central dual energy x-ray absorptiometry (DXA or DEXA) indicates a mildly reduced bone mineral density (BMD) compared to peak bone mass (PBM). A T-score of below −2.5 when using the central dual energy x-ray absorptiometry (DXA or DEXA) bone density test is defined as osteoporosis. Bone demineralization is the loss, decrease or removal of the mineral constituents of bone.

This aspect of the invention therefore also extends to a method of treatment of or prevention of bone demineralisation, low bone density or osteoporosis in a subject, comprising administration to, or implantation into, the subject a synthetic crystal of the invention. In one embodiment, a method of increasing bone density is provided In an alternative embodiment, the invention may be seen as providing the use of a synthetic crystal of the invention in the preparation of a medicament for the treatment and/or prevention of bone demineralisation, low bone density or osteoporosis.

In another aspect of the invention, the synthetic crystal of the invention may be provided for use in the prevention and/or treatment of bone disease. In one embodiment the bone disease is osteoporosis, osteoarthritis, osteosclerosis, osteogenesis imperfecta, Paget's disease of bone, metabolic bone disease, osteomalacia, osteopenia, arthritis or sarcoma. In embodiments of the invention, synthetic crystal may be administered in combination with one or more pharmaceutically active agents.

This aspect of the invention therefore also extends to a method of treatment of or prevention of bone disease in a subject, comprising administration to the subject a synthetic crystal of the invention. In one embodiment the bone disease is osteoporosis, osteoarthritis, osteosclerosis, osteogenesis imperfecta, Paget's disease of bone, metabolic bone disease, osteomalacia, osteopenia, arthritis or sarcoma. In an alternative embodiment, the invention may be seen as providing the use of a synthetic crystal of the invention in the preparation of a medicament for the treatment and/or prevention bone disease. In one embodiment the bone disease is osteoporosis, osteoarthritis, osteosclerosis, osteogenesis imperfecta, Paget's disease of bone, metabolic bone disease, osteomalacia, osteopenia, arthritis or sarcoma.

In another aspect of the invention, the synthetic crystal of the invention may be provided for use in the prevention and/or treatment of a bone defect. In one embodiment, the bone defect is a bone fracture, bone fracture associated with trauma, bone injury, bone cavity or bone lesion. The synthetic crystals of the invention may be useful in treating bone defects associated with the interface of bone with connective tissues such as cartilage, ligaments and tendons. In one embodiment, the bone defect is damage to the bone-cartilage interface, bone-ligament interface or a bone-tendon interface.

In embodiments of the invention, synthetic crystal may be administered in combination with one or more pharmaceutically active agents. Preparation and formulation of such compositions would be known by the skilled person.

This aspect of the invention therefore also extends to a method of treatment of or prevention of bone defect, comprising administration to the subject a synthetic crystal of the invention. In one embodiment, the bone defect is a bone fracture, bone fracture associated with trauma, bone injury, bone cavity or bone lesion. In one embodiment, the bone defect is damage to the bone-cartilage interface, bone-ligament interface or a bone-tendon interface. In an alternative embodiment, the invention may be seen as providing the use of a synthetic crystal of the invention in the preparation of a medicament for the treatment and/or prevention of bone defect. In one embodiment, the bone defect is a bone fracture, bone fracture associated with trauma, bone injury, bone cavity or bone lesion. In one embodiment, the bone defect is damage to the bone-cartilage interface, bone-ligament interface or a bone-tendon interface.

The synthetic crystals of the present invention may be employed alone or in conjunction with other compounds, such as therapeutic compounds, e.g. anti-inflammatory drugs, cytotoxic agents, cytostatic agents or antibiotics.

In one aspect of the invention, there is provided a method comprising contacting an elastin-like polypeptide membrane or hydrogel with a solution of calcium and phosphate ions in vivo. The solution may further comprises fluoride ions, and or other components as described herein. The concentrations of the various ions are discussed elsewhere, and apply equally to this aspect of the invention. In some embodiments, the method comprises the step of administered the membrane or hydrogel to a patient, in particular the surface of a patient, such as a tooth or bone. After contact the membrane or hydrogel with the solution, the ELP membrane or hydrogel and the ions form a synthetic crystal having a hierarchical structure formed on the membrane or hydrogel scaffold. In this way, the crystal structures of the invention can be formed in vivo.

The solution comprising the ions may be an exogenous solution. In such an embodiment, the method may further comprise the step of administering the exogenous solution before, concurrently or after administration of the membrane or hydrogel. In other embodiments, the solution of ions is an endogenous solution. Such an endogenous solution may be a bodily fluid, for example saliva, interstitial fluid, blood or plasma.

In some embodiments, the method further comprises the step of cross-linking in vivo. For example, the cross linker may be added after the membrane or hydrogel is added to the solution (and after the mineralising solution is added, if an exogenous solution is being used).

Hence in one aspect of the invention, the method is a method of treatment and/or prevention. Forming the crystal structures in vivo allows the formation of the crystals directly at the site of application, i.e. the site where the biomimetic structures are required. The method may be a method of treatment and/or prevention of a dental disease or bone disease or a bone defect. The dental disease may be demineralisation of teeth or dental hypersensitivity. The bone disease may be low bone density or osteoporosis, bone disease. Hence the present invention is also useful in increasing bone density and tooth enamel density.

As used herein, the term "treatment" includes any regime that can benefit a human or a non-human animal. The treatment of "non-human animals" extends to the treatment of domestic animals, including horses and companion animals (e.g. cats and dogs) and farm/agricultural animals including members of the ovine, caprine, porcine, bovine and equine families. The treatment of "non-human" animals extends to the treatment of any animal with teeth. The treatment may be in respect of any existing condition or disorder, or may be prophylactic (preventive treatment). The treatment may be of an inherited or an acquired disease. The treatment may be of an acute or chronic condition. Preferably, the treatment is of a condition/disorder associated with inflammation.

The present invention may also find application in veterinary medicine for treatment/prophylaxis of domestic animals including horses and companion animals (e.g. cats and dogs) and farm animals which may include members of the ovine, porcine, caprine, bovine and equine families.

According to a further aspect of the invention, there is provided a pharmaceutical composition comprising a synthetic crystal of the invention.

Suitably, the pharmaceutical composition may be formulated for oral administration or for topical administration in the mouth cavity or on the teeth or gums by way of a coating. The pharmaceutical composition may be an artificial saliva, a mouth wash (buccal wash), tooth paste or cream, moisturiser, chewing gum, drink or other oral healthcare preparation.

Pharmaceutical compositions in accordance with this aspect of the invention may comprise other pharmaceutically active substances, such as anti-bacterial, anti-viral, anti-fungal, analgesic substances. The composition may also comprise pharmacologically acceptable salts such as fluoride salts or phosphate salts, for example a fluoride salt or a phosphate with an alkali metal or an alkaline earth metal, e.g. sodium fluoride (NaF). The pharmaceutical composition may be formulated using any convenient adjuvant and/or physiologically acceptable diluents. Other components may also be present in order to improve "mouthfeel" of the composition, such as sorbitol, xanthan gum, guar gum, and/or cellulose derivatives such as hydroxypropylmethylcellulose (HPMC), sodium carboxymethyl cellulose etc.

Kits

In one embodiment, a kit is provided comprising an ELP membrane or hydrogel of the invention and a mineralising solution of the invention. The mineralising solution can be contacted with the ELP membrane or hydrogel of the invention in vivo. The mineralising solution may be as described above. In one embodiment, a kit is provided comprising an ELP membrane or hydrogel of the invention, a mineralising solution of the invention and a therapeutically active agent. In one aspect, a kit is provided comprising a synthetic crystal of the invention or a pharmaceutical composition comprising the synthetic crystal of the invention and a therapeutically active agent.

In some embodiments, the kit further comprises a cross-linker. Details of the possible cross-linkers that may be included are discussed above.

In some embodiments, the kit further comprises instructions for use.

A major goal in materials science is to develop bioinspired functional materials that can offer precise control of molecular building-blocks across multiple length-scales. The present inventors have discovered they can grow hierarchically-ordered crystal structures, in particular apatite structures, that resemble those found in human dental enamel to a level previously unreported. The structures exhibit elongated needle-like fluorapatite nanocrystals of about 85 nm thick that are organized into approximately 4 μm thick prism-like microstructures, which assemble to form circular structures hundreds of microns in diameter that come together to fill macroscopic areas.

In one embodiment, the method comprises the step of contacting an ELP membrane with a solution of calcium, phosphate and fluoride mineralizing ions wherein the contacting step is performed at about Ph 6 to 7 and about 35° C. to 40° C.

The preferred features or the second and subsequence aspects of the invention are as provided for the first aspect mutatis mutandis.

The invention will now be described with reference to the following Examples, which are presented for the purposes of reference only and are not intended to be limiting on the scope of the invention.

EXAMPLES

Example 1

Materials and Methodology
Membrane Fabrication and ELP Glass Coating

Membranes were fabricated using a recently published method, and as detailed further below (Tejeda-Montes, E. et al. Engineering membrane scaffolds with both physical and biomolecular signaling. *Acta Biomaterialia* 8, 998-1009 (2012)) and with systematic processing variations in order to control, where different ELP molecules as shown in Table 2 were dissolved in anhydrous dimethylformamide (DMF) at room temperature in a low-humidity conditions (less than 20%) inside a polymer glove box.

Then the resultant solution was cross-linked using hexamethyl diisocyanate (HDI), left to dry overnight, and then washed with deionized water for three days and stored at 4° C. Collagen membranes supplied from Viscofan Bioengineering (Weinheim, Germany) were used as controls. Similar fabrication procedures were undertaken to fabricate membranes on the dental enamel/dentine substrates. For ELP glass coating, 100 μg of ELP dissolved in deionized water and drop-casted onto the borosilicate glass substrates, and left to dry.

Detailed Method for Crosslinking Solution and Membrane Fabrication

The general process of membrane fabrication is a drop-casting technique that includes four steps:
(i) preparation of ELP and cross-linker solutions;
(ii) mixing of solutions and onset of ELP cross-linking;
(iii) spin-coating of ELP during cross-linking; and finally
(iv) solvent evaporation, cross-linked ELP assembly and membrane release.

A variety of key fabrication parameters were optimized in order to maximize the ELP cross-linking and the subsequent membrane strength/thickness ratio. The key fabrication variables investigated included surface (mold or smooth substrate)

1) Wettability; varies from 20-115 degrees of contact angle.
2) ELP concentration varies from 1 to 15%, preferred 5%
3) Temperature, varies from 4 to 90c, preferred according to each the ELP transition temperature; just below the transition temperature by 10c or above the transition temperature by 10c.
4) Humidity, varies from 0.1 to 80% preferred is 18%
5) solvent evaporation time, varies from 10 to 540 minutes, preferred 360 minutes.

The ELPs were dissolved in anhydrous dimethylformamide (Sigma-Aldrich, Germany) at room temperature at a concentration of 5% (50 mg/ml). The ELP solution was then mixed with hexamethyl diisocyanate (HDI) (Sigma-Aldrich, Germany) at a ratio of available lysine side chains to HDI molecules of 2:3, thus providing an excess of cross-linker. The crosslinker ratio can be varied from 1:0.25, 1:0.5, 1:1, 1:3, 1:6, 1:12, 1:24. This cross-linker has been previously used in both in vitro (Srivastava G K, Martin L, Singh A K, Fernandez-Bueno I, Gayoso M J, Garcia-Gutierrez M T, et al. Elastin-like recombinamers as substrates for retinal pigment epithelial cell growth. J Biomed Mater Res A 2011; 97A:243-50) and in vivo (clinical) applications (Hsu P W, Salgado C J, Kent K, Finnegan M, Pello M, Simons R, et al. Evaluation of porcine dermal collagen (Permacol) used in abdominal wall reconstruction. J Plastic Reconst Aesthetic Surg 2009; 62:1484-9). The cross-linking reaction was left to proceed under a nitrogen atmosphere using a polymer glovebox (Cleaver Scientific, Wolf Laboratories Ltd., UK). Different volumes of the cross-linked polymer solution were added to the surface of pieces of polydimethylsiloxane (PDMS) (Sylgard 184, Dow Corning, USA) or bare or photopatterned resist on a (1 1 1)-oriented silicon wafer (Siltronix, France). The solution was allowed to air-dry on top of the substrates either statically or while spinning constantly on a spin-coater (Ws-650Sz, Laurell Technologies, USA) to allow solvent evaporation, ELP assembly, and a precise and reproducible membrane thickness. Finally, the membrane was released from the substrate. The same protocol was repeated for membranes composed of multiple ELP layers to form a second ELP assembly on top of the first one. In order to re-move any residual solvent or cross-linker that would be toxic to the cells, the membranes were washed over a period of 7 days with various substances. First, they were placed in a Buchner funnel, where 20 ml of 100% dimethylsulfoxide (DMSO) was added drop-wise to the top of each membrane, which caused them to swell considerably. They were then left overnight immersed in 10% DMSO in water. This was followed by soaking in cold (below the Tt) MilliQ water, with several exchanges over a 24 h period. The membranes were then submerged in a cold 0.03 M solution of Tween 20 in water with constant agitation for 15 min and rinsed thoroughly with MilliQ water for 48 h. Following this, a 0.15% solution of glycine in water was used to deactivate any residual cross-linker by reacting with any isocyanate groups still present. Further washing in cold MilliQ water was then carried out for 48 h.

TABLE 2

Table showing the different ELP molecules used during the study along with isoelectric points and molecular weights. Bioactive sequences are shown in red.

| Type of ELP | Sequence (bioactive sequence in red) | Isoelectric point (pI) | Molecular weight |
|---|---|---|---|
| IK | MESLLP-(VPGIG VPGIG VPGKG VPGIG VPGIG)$_{24}$ | 11 | 51.9 kDa |
| SN | MESLLP-[[(VPGIG)$_2$(VPGKG)(VPGIG)$_2$]$_2$ DDDEEKFLRRIGRFG[[(VPGIG)$_2$(VPGKG)(VPGIG)$_2$]$_2$]$_3$ | 9.9 | 31.9 kDa |
| RGDS | MGSSHHHHHHSSGLVPRGSHMESLLP-[[(VPGIG)$_2$(VPGKG)(VPGIG)$_2$]$_2$AVTGRGDSPASS((VPGIG)$_2$(VPGKG)(VPGIG)$_2$]$_2$]$_6$ | 11.1 | 60.6 kDa |

Enamel and Dentine Discs Preparation:

Extracted human non-carious teeth (with approval from Queen Mary Research Ethics Committee QMREC2008/57) were stored at 4° C. in deionized water refreshed every 7 days until needed. Each tooth was carefully mounted on a holder and placed inside the diamond cut-off machine (Accutom-5, Struers A/S, Ballerup, Denmark) by aid of a compound material, the required X and Y starting positions along with Y stop position were selected and saved. Teeth were cut along their cross sections into discs, the thickness of each disk comprising both dental enamel and dentine was 500 µm. The tooth sections were carefully polished using a polishing unit (Kent 4, automatic lapping and polishing unit) by aid of silicon carbide (SiC) grinding papers (CarbiMet™) from coarse to fine as follows (P600, P1000, P2500, P4000). Subsequently, the samples were polished using polishing cloth and diamond suspension waterbase (Metprep™) as follows (3, 1, 0.25 µm). Finally, the discs were acid etched using 6% citric acid for 2 minutes, however, enamel samples (longitudinal sections) that were used as controls for SEM images were etched using 38% phosphoric acid for 30 seconds. Fabrication of the ELP membranes in situ on dental discs was performed as described above (Membrane fabrication and ELP glass coating).

Crystal Growth Experiment:

This method used a previously published protocol (Chen, H. et al. Synthesis of Fluorapatite Nanorods and Nanowires by Direct Precipitation from Solution. *Cryst Growth Des* 6 (2006)), whereby 2 Mm of Hap powder and 2 Mm of sodium fluoride were added to 100 ml of deionized water with continuous stirring.

Subsequently, 69% nitric acid was added dropwise into the solution very slowly until the powder was completely dissolved. 30% ammonium hydroxide solution was added dropwise until the Ph was readjusted to 6.0, and then different ELP membranes were placed at the bottom of beaker and incubated for eight days at 37° C. using a temperature-controlled incubator (LTE Scientific, Oldham, UK).

Scanning Electron Microscopy (SEM), Density Dependent Color SEM and Energy Dispersive x-Ray (EDX) Spectroscopy:

Samples were mounted after being dried on aluminum stubs via self-adhesive tape and were coated by auto sputter coating machine with a conductive material. Samples were analyzed using an FEI Inspect F (Hillsboro, OR, USA). Their surface topography was observed using a secondary electron detector. A backscattered electron (BSE) detector was used to assess the variation in density within each sample. Furthermore, the elemental analysis was carried out using INCA software. Point and mapping spectra collection at areas of interest were carried out using an EDX detector (INCA x-act, Oxford Instruments) at an accelerating voltage of 10 kV. In other instances, samples were investigated using SEM (Gemini 1525 FEGSEM), operated at 10 Kv. The instrument was equipped with both an inlens detector that recorded secondary electrons, and a backscatter electron detector. The DDC-SEM images were obtained by imaging the same region with both inlens mode and backscatter mode. Using ImageJ software, both images were stacked and the inlens image was assigned to the green channel whereas the backscatter image was assigned to the red channel (Bertazzo, S. et al. Nano-analytical electron microscopy reveals fundamental insights into human cardiovascular tissue calcification. *Nature Materials* 12, 576-583 (2013)).

Focused Ion Beam-Scanning Electron Microscopy

Focused ion beam-scanning electron microscopy (FIB-SEM) was undertaken using FEI Quanta 3D ESEM (Hillsboro, OR, USA) following a recently published protocol (Bushby et al., 2011) for which the gallium ion beam parameters were set to 30 Kv and 1 Na in order to cut trenches, each slice was 73 µm wide, 65 µm tall and 20 µm deep, while the images were captured at 5 Kv with magnification of 4000× after each cut using auto slice and view software (FEI) with resolution of 1024×884. The data were then three dimensionally reconstructed using ImageJ (National Institute of Health, USA) and Drishti (Australia National University, Canberra, Australia) softwares.

Fourier Transform Infra-Red Spectroscopy (FT-IR)

FTIR analysis was conducted using the FTIR Spectrum GX (PerkinElmer®, Waltham, MA, USA). Membranes before and after mineralization were placed over the IR window without any grinding but covered, then scanned. The program was set to take the average of thirty scans after subtracting the background, and were analyzed at a wavenumber of 4000 cm$^{-1}$ to 450 cm$^{-1}$ in respect to % of transmittance. The data were normalized from 500 to 1800 cm$^{-1}$. Human non-carious dental enamel powder (kindly supplied by Prof. Colin Robinson, University of Leeds) was also analyzed for comparison purposes.

X-Ray Diffraction (XRD)

Powder diffraction was conducted at room temperature to elucidate the phase composition of the mineralized membrane, using an X'Pert Pro X-ray diffractometer (PANalytical, B.V., Almelo, Netherlands) with flat plate θ/θ geometry and Ni-filtered Cu-Kα radiation at 45 Kv and 40 Ma, where Kα1 and Kα2 equal 1.540598 and 1.5444260 Å respectively. The 2θ range of the diffraction pattern was taken from 5-70° with a step size 0.0334° and data was collected continuously with an equivalent step time of 1600 seconds using a PANalytical X'Celerator solid-state RTMS detector. Rietveld refinement was performed using GSAS software40.

$^{19}$F Magic Angle Spin-Nuclear Magnetic Resonance (MAS-NMR):

In order to investigate the fluoride interactions present in both the powder collected from base of the beakers with no ELP membranes (as a control) and the mineralized membranes, all samples were crushed into fine powder using pestle and mortar, and then analyzed. Solid-state $^{19}$F MAS-NMR analysis was conducted using a 14.1 Tesla spectrometer (600 MHz Bruker, Coventry, UK) at a Larmor frequency of 564.5 Mega Hertz (MHz) under spinning conditions of 22 kHz in a 2.5 mm rotor. The spectra were acquired from a single-pulse experiment of 60 seconds recycle duration, by using a fluorine free background probe. The $^{19}$F chemical shift scale was calibrated using the −120 ppm peak of 1 M of NaF solution along with trichloro-fluoro-methane ($CFCl_3$), as a second reference. Spectra were acquired for 4 hours with accumulation of 240 scans, while for the protein membranes there was an accumulation of 4 runs each for 4 hours.

Live Timelapse Optical Microscopy Studies:

Live timelapse microscopy was performed using Zeiss Axiovert 200M microscope (motorized epi-fluorescence inverted microscope) equipped with a temperature-controlled chamber for live imaging. Imaging setup and acquisition was controlled by AxioVision software with a temporal resolution of 15 minutes with Zeiss AxioCam MRm camera. The objective used for the imaging was an LD Aplan 20×/0.3 Ph1 as required for phase contrast. The images were then compiled into a video for visualization.

Moreover, the images were segmented using Avizo software (FEI) to allow quantitative analysis of the growth as a function of time.

TEM:

Transmission electron microscopy was performed on the FIB-prepared lamellas using a JEOL JEM 2010 (JEOL Ltd., Tokyo, Japan) operated at 120 Kv. The obtained images were analyzed using the Gatan Microscopy Suite® (GMS 3) software. For the analysis of crystal phases present in the samples, d-values obtained from SAED patterns were compared with d-values obtained from the same samples using XRD measurements and the Powder diffraction file—PDF2 database (ICDD, USA, release 2009).

AFM Nanoindentation:

Samples were attached to a petri dish using a drop of cyanoacrylate adhesive, and left for a minute for the adhesive to dry. Samples were then immersed in distilled water. Young's modulus measurements were taken with a JPK Nanowizard-1 (JPK Instruments, Germany) in force spectroscopy mode, mounted on an inverted optical microscope (IX-81; Olympus, Japan). Quadratic pyramidal cantilevers (MLCT; Bruker, MA, USA) with a spring constant of 0.07 N/m or 0.5 N/m (for larger loads) and half-angle to face of 17.5° were used for indentation. The sensitivity of cantilevers was determined before measurements by measuring the slope of the force-distance curve in the AFM software on an empty region of a petri dish. Indentation was carried out with an approach speed of 5 μm/s and a maximum set force of 1 Nn. Measurements were taken multiple times per region and in multiple regions per sample. The Young's modulus was calculated by fitting the contact region of the approach curve with the Hertz Contact model (Harris, A. R. & Charras, G. T. Experimental validation of atomic force microscopy-based cell elasticity measurements. Nanotechnology 22, (2011)) using the JPK software, using the above constants and calibrated cantilever sensitivity. Graphs were plotted with GraphPad Prism software, using a P value of 0.05.

Circular Dichroism:

Spectra were recorded using a Chirascan spectropolarimeter (Applied Photophysics, UK). ELR samples were dissolved in an optimized concentration of 0.01% w/v in 0.01 mm thick cuvette. Spectra are presented with a 0.5 nm step, 1 nm bandwidth, and 0.5 second collection time per step at 4, 25, and 37° C. The post-acquisition smoothing tool from Chirascan software was used to remove random noise elements from the averaged spectra. The CD signal from the water was subtracted from the CD data of the peptide solutions.

Zeta Potential (ζ) and Hydrodynamic Radii Measurements:

Dynamic light scattering using a Zetasizer (Nano-ZS ZEN 3600, Malvern Instruments, UK) was used to measure both zeta potential (ζ) and hydrodynamic radii of the statherin-ELR molecules to investigate the charge and size respectively, at constant Ph of 6.0, while varying calcium concentration whether 0 Mm or 10 Mm in order to investigate its calcium binding affinity at different temperatures (4, 25, 37° C.). Samples were incubated for 5 minutes at the desired temperature before measurements.

Acid Attack Experiments:

Both human dental enamel and mineralized membranes were subjected to 0.1 M of acetic acid adjusted to Ph 4.0 and incubated at 37° C. for different timepoints (Mohammed, N. R., Lynch, R. J. M. & Anderson, P. Inhibitory Effects of Zinc Ions on Enamel Demineralisation Kinetics in vitro. Caries Research 49, 600-605, (2015)).

Enzymatic Digestion:

Mineralized membranes were subjected to elastase (from hog pancreas source) digestion after optimization of the concentration adjusted to 15 U/ml for 72 hours at 37° (Greenwald, S. E., Moore Jr, J. E., Rachev, A., Kane, T. P. C. & Meister, J. J. Experimental investigation of the distribution of residual strains in the artery wall. Journal of Biomechanical Engineering 119, 438-444 (1997)).

Swelling Measurements to Yield Diffusion Coefficient Values at Different Crosslink Densities:

A circle was punched out of each ELR membrane (different crosslink densities) using a 0.5 cm biopsy punch. The dry weight and dimensions of each membrane were then recorded using a micro-balance and micrometer. Each membrane was immersed in a petri dish full of deionized water. The petri dish was placed under an optical microscope with a calibrated scale and the diameter and thickness of the membrane was measured as a function of time over the following time points: at 30 second intervals from 0-10 minutes, at 10 minute intervals from 10-60 minutes, at 60 minute intervals from 60-480 minutes and at 24 hour intervals between 480-2880 hours. The moment the membrane was placed inside the petri dish was taken as t=0. These measurements were carried out at room temperature. Analyses and calculations were conducted using ImageJ implementing Tanaka and Fillmore equations (Tanaka, T. & Fillmore, D. J. Kinetics of swelling of gels. The Journal of Chemical Physics 70, 1214-1218 (1979)).

Example 1. Discussion and Results

Figure 35:
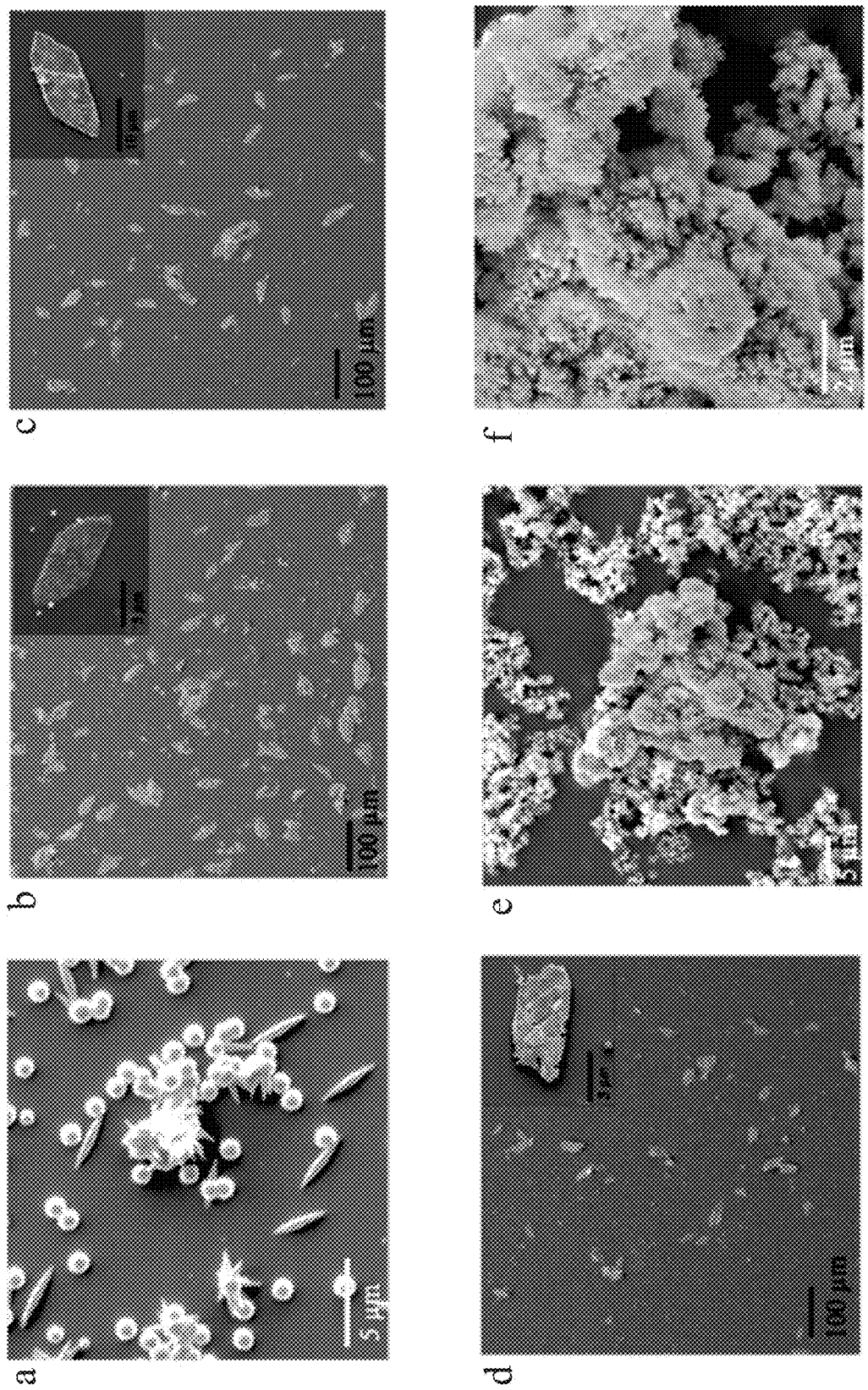
FIG. 35. SEM images of the crystal morphology on; a) uncoated borosilicate glass showing the characteristic needle-like and ball-like morphology; and borosilicate glass coated with ELPs b) IK, c) SN, and d) RGDS (SEQ ID NO:1) showing flat plate-like crystals. Similarly e-f) collagen membranes showed disordered crystal growth.

Membranes were fabricated as detailed above using three different ELPs comprising a statherin-derived peptide (SN), RGDS (SEQ ID NO:1), or no bioactive segment (IK), where the only molecular difference is the presence of the bioactive sequence (Table 2). SN membranes have been shown to enhance mineralisation and therefore were used as the main experimental group in this study, while RGDS (SEQ ID NO:1) membranes were used for comparison, and IK membranes and borosilicate glass substrates coated with the different ELP molecules were used as controls. Surprisingly, upon incubation in a supersaturated solution rich in $Ca^{2+}$, $PO_4^{3-}$, and $F^-$ (10, 6, and 2 Mm, respectively) at near physiological conditions (37° C. and Ph 6.0), distinctive hierarchically mineralized structures (FIG. 30a-c) were observed on both sides of the SN and IK membranes (FIG. 30b) and not on the ELP-coated glass surfaces, which only showed flat platelet-like crystals (FIG. 35a-d). The results were verified by repeating the experiments and including RGDS-containing ELP membranes and collagen membranes, and observing that the hierarchically mineralized structures formed only on ELP membranes, confirming that the ELP sequence, and not the bioactive components, is responsible for the formation of the hierarchically mineralized structures (FIG. 35e-f).

Figure 13:
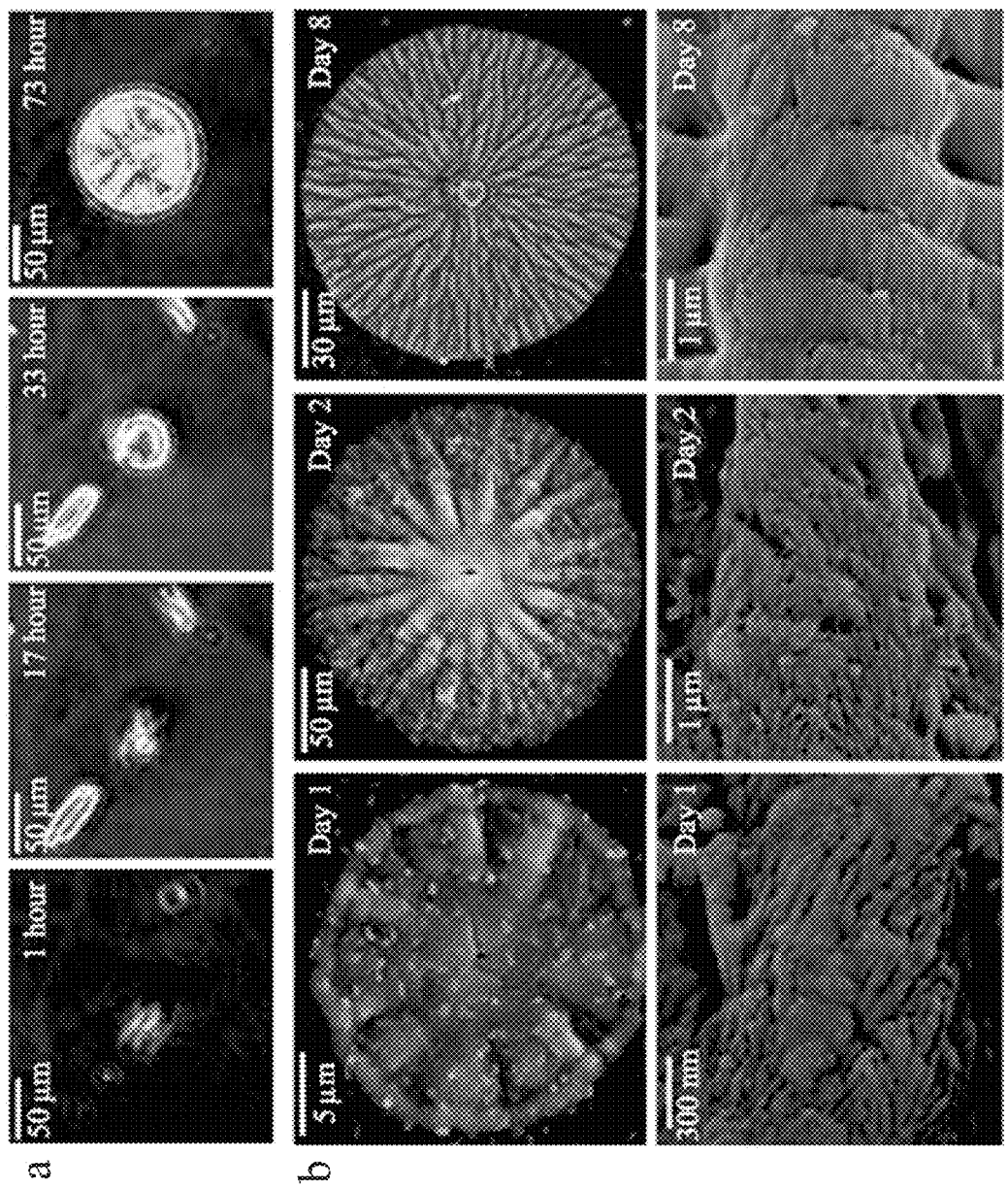
FIG. 13. a) Time-lapse microscopy demonstrating the emergence and centripetal growth of the structures by phase contrast imaging. b) DDC-SEM images of day 1, 2, and 8 at different size scales, demonstrating that the structures gain hierarchical definition as a function of time. The accumulation of the less-dense material (green) is clearly observed at the interprismatic areas at the different time-points. c) Graphs showing the increase in volume during the morphogenesis of the hierarchical mineralized structures (left) and the significant improve of the stiffness as a function of time (right). d) Ion selective electrode (ISE) measurements and SEM images (right), showing the free ion concentration in the system as a function of time with (bottom) or without (top) the use of the BIS-TRIS buffer (top), that controls the pH of the system, the system reaches steady-state conditions earlier under constant pH, and hence more calcium consumption, faster mineralization, and larger mineralized structures (bottom) up to almost 1 mm in diameter. e) XRD at different timepoints clearly shows the phase transformation. Brushite (B) is observed during the first hour of the mineralization, while it starts to dissolve by time transforming into the more stable phase of Fluorapatite (F) after the first day.
Figure 13:
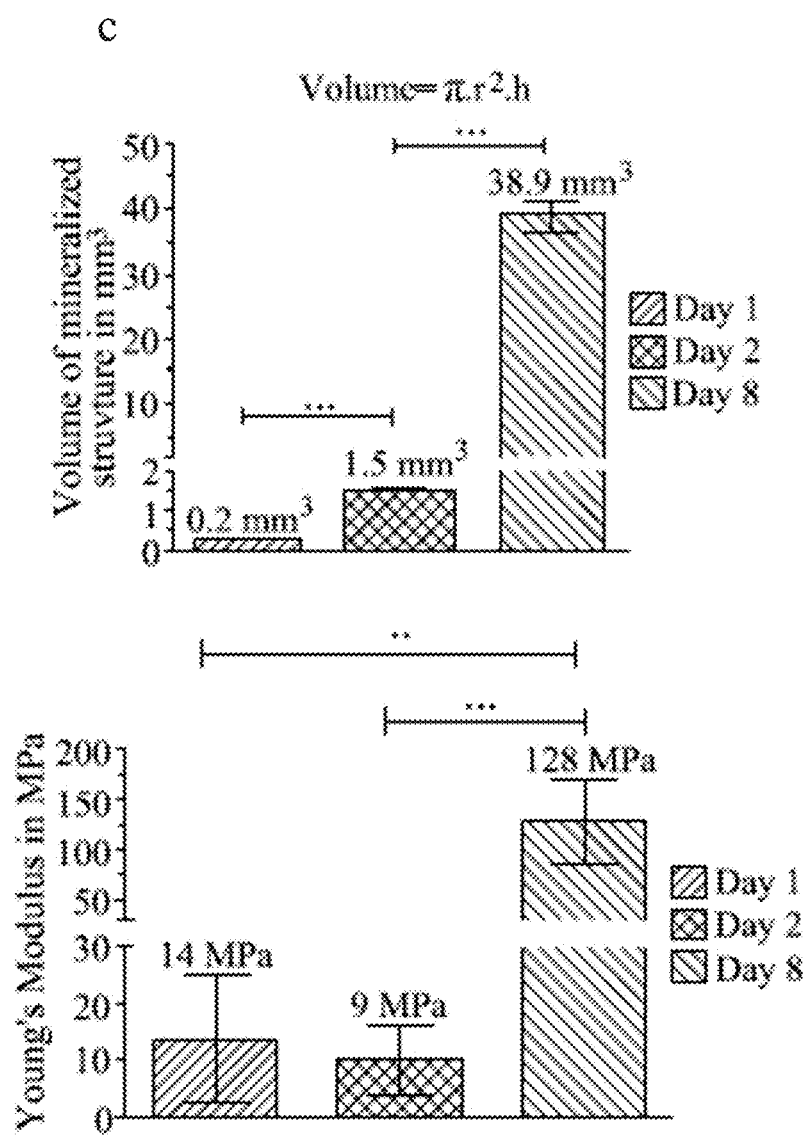
Figure 13:
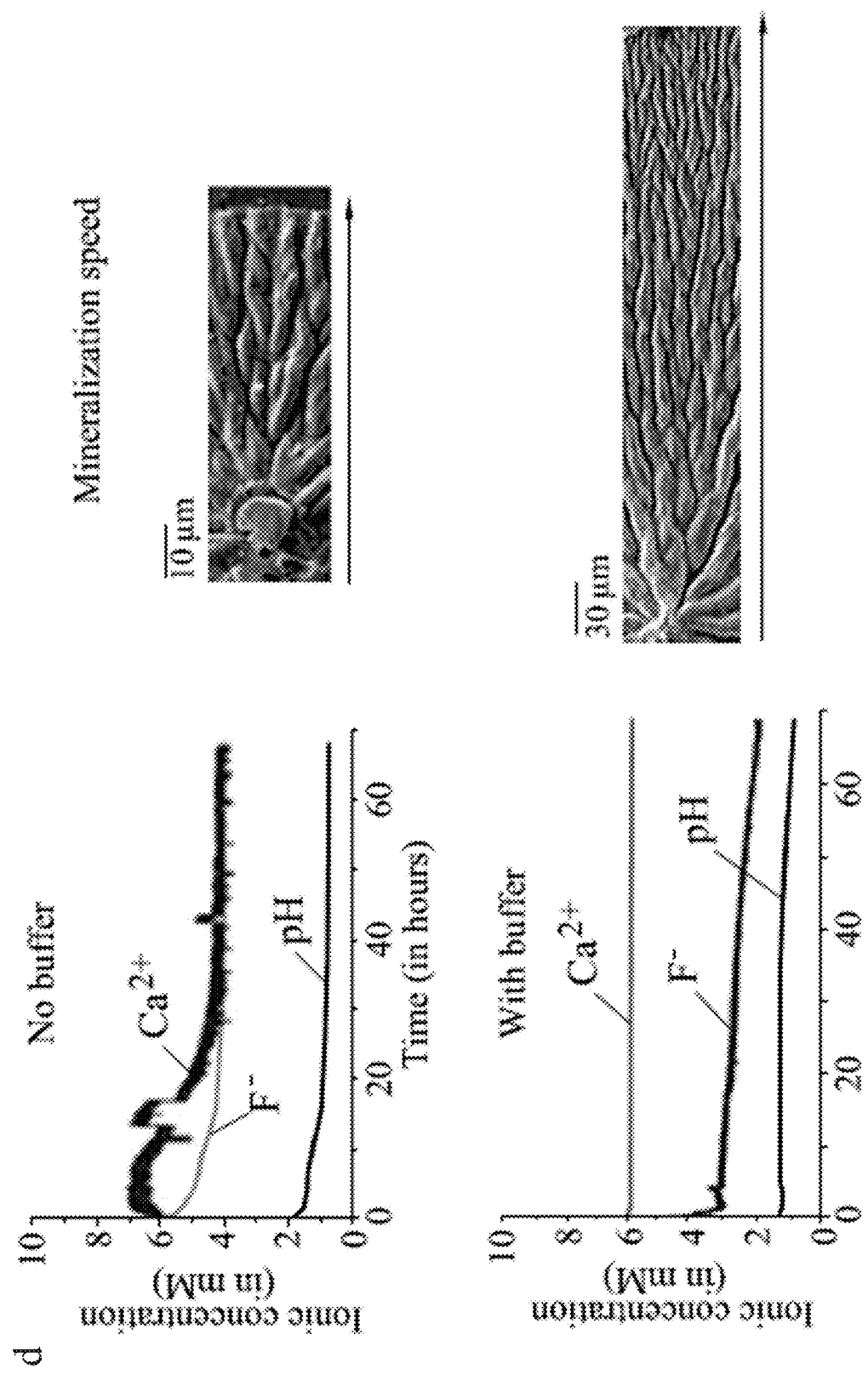
Figure 13:
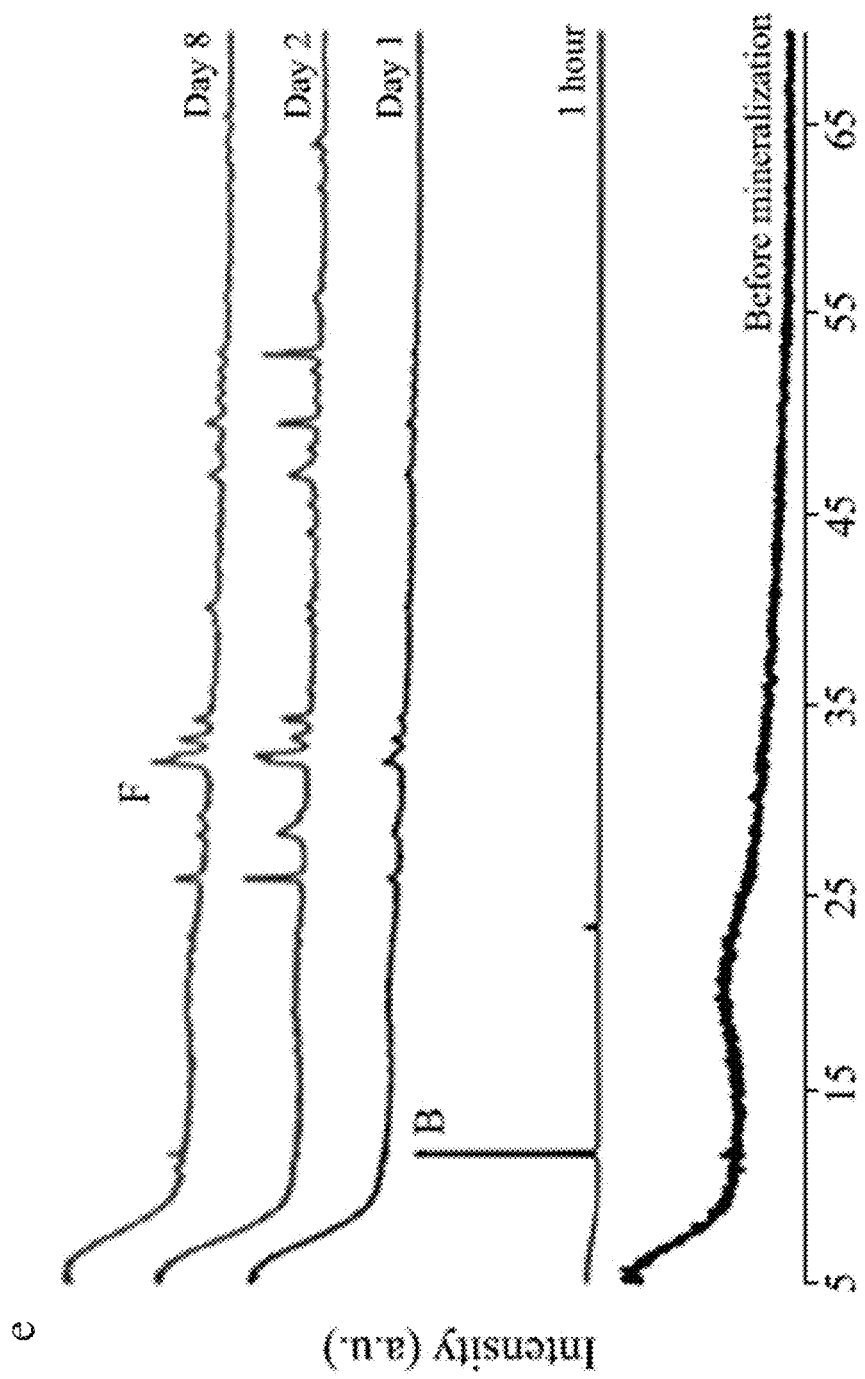

The hierarchically-ordered crystalline structures are up to 70 μm in height and 350 μm in diameter (FIG. 30b-c) when the starting Ph of the solution is set to 6.0 and drops to 3.7 during mineralization. However, much larger structures can be grown with diameters up to 1 mm when the Ph is controlled throughout the mineralization process using BIS-TRIS buffer, where the Ph drops from 6.0 to 5.7. It is possible that this increased growth takes place as a result of the system reaching steady-state conditions earlier under controlled Ph, and therefore enabling more calcium consumption as evidenced by ion-selective electrode (ISE) measurements (FIG. 13d). These structures exhibit a distinctive hierarchical architecture that mimics natural enamel. At the crystallographic length-scale, the material is apatite (FIG. 31) in the form of elongated needle-like nanocrystals of about 85±22 nm thick. At the microscale, these crystals are organized further into enamel prism-like microstructures of about 3.8±0.9 μm thick and tens of microns long. These microstructures radiate outward forming the macroscopic circular structures (FIG. 30c-f, 33a-d). Furthermore, the enamel-like structures display a remarkable periodicity of approximately 1 μm intervals (FIG. 30f) along the prism-like structures, incidentally mimicking the daily incremental lines of dental hard tissues (Boyde, A. Microstructure of enamel. *CIBA Foundation Symposia*, 18-31 (1997)).

Figure 8:
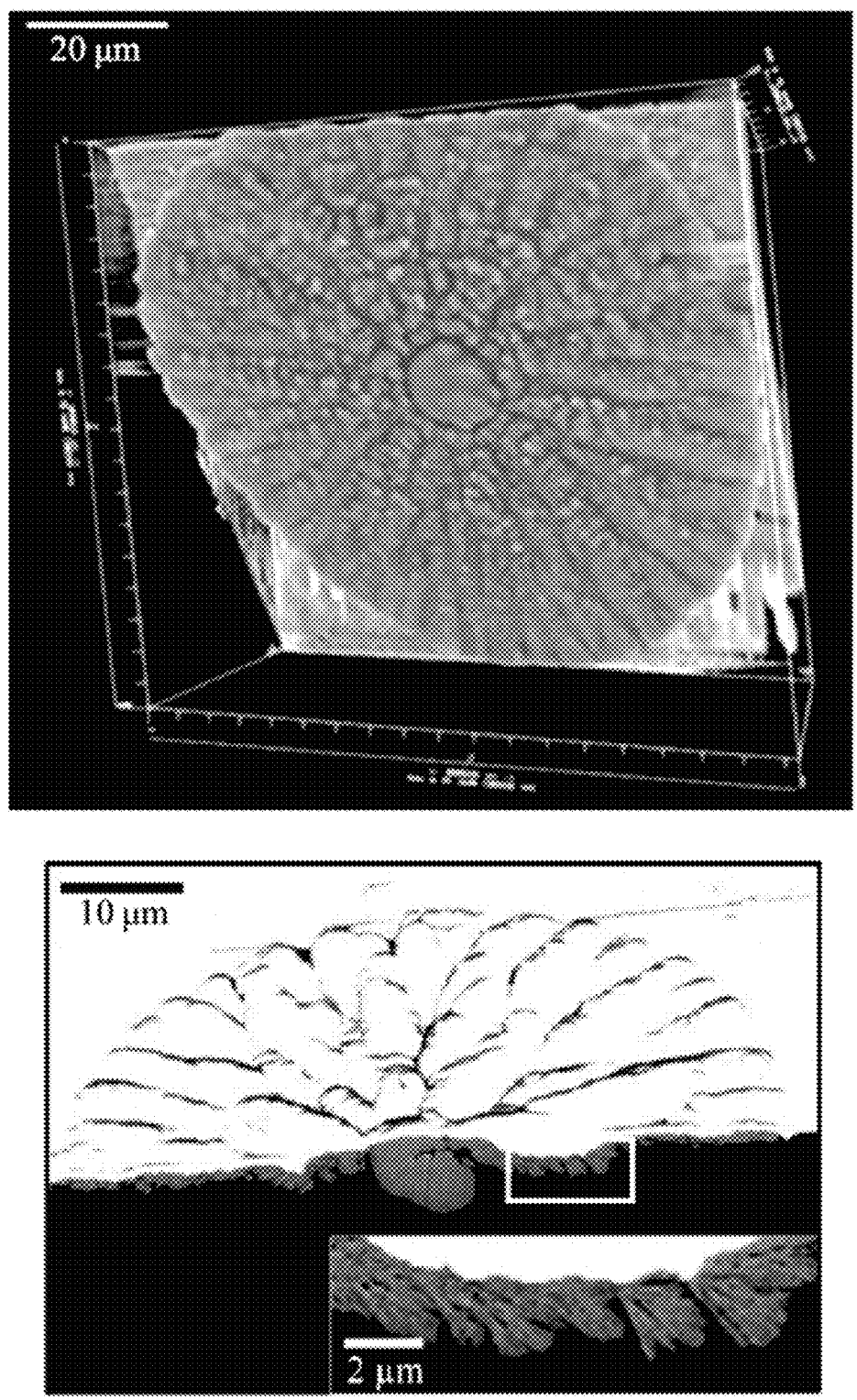
FIG. 8. 3D reconstruction of serial FIB-SEM imaging. The angle of visualization is modified in order to be able look at the structures from within the membrane, which also clearly shows the core structure at the centre (left). Scanning electron microscopy (SEM) using the backscattered electron mode (BSE) and focused ion beam (FIB) revealed that the mineralized structures exhibit a mineralized core deep within the membrane made from similar elongated and aligned nanocrystals (right).

Scanning electron microscopy (SEM) using the backscattered electron mode (BSE) (FIG. 30g-h) and focused ion beam-scanning electron microscope (FIB-SEM) (FIG. 30i) revealed that the mineralized material is present deep within the membrane in a root-like formation with a similar elongated crystallite/prism architecture, located directly below the centre of the circular macrostructures. The orientation of the nanocrystals and the prism-like microstructures, however, changed from being parallel to the surface when located on the surface of the membrane (FIG. 30j) to perpendicular to the surface within the root-like structures (FIG. 8).

After Rietveld refinement, the hexagonal unit cell parameters (space group P63/m No. 176) are a=9.3757(16) and c=6.8841(12) Angstroms. The unit cell therefore has a volume of 524.1 (1) cubic Angstroms. This results further confirm that the crystalline phase of the structures is fluorapatite (Fap) with a space group, unit cell size and structural parameters matching Fap values, as reported in the literature (Sudarsanan, K., Mackie, P. E. & Young, R. A. Comparison of synthetic and mineral fluorapatite, Ca5 (P04)3F, in crystallographic detail. *Materials Research Bulletin* 7, 1331-1337 (1972)) (FIG. 31a).

Figure 36:
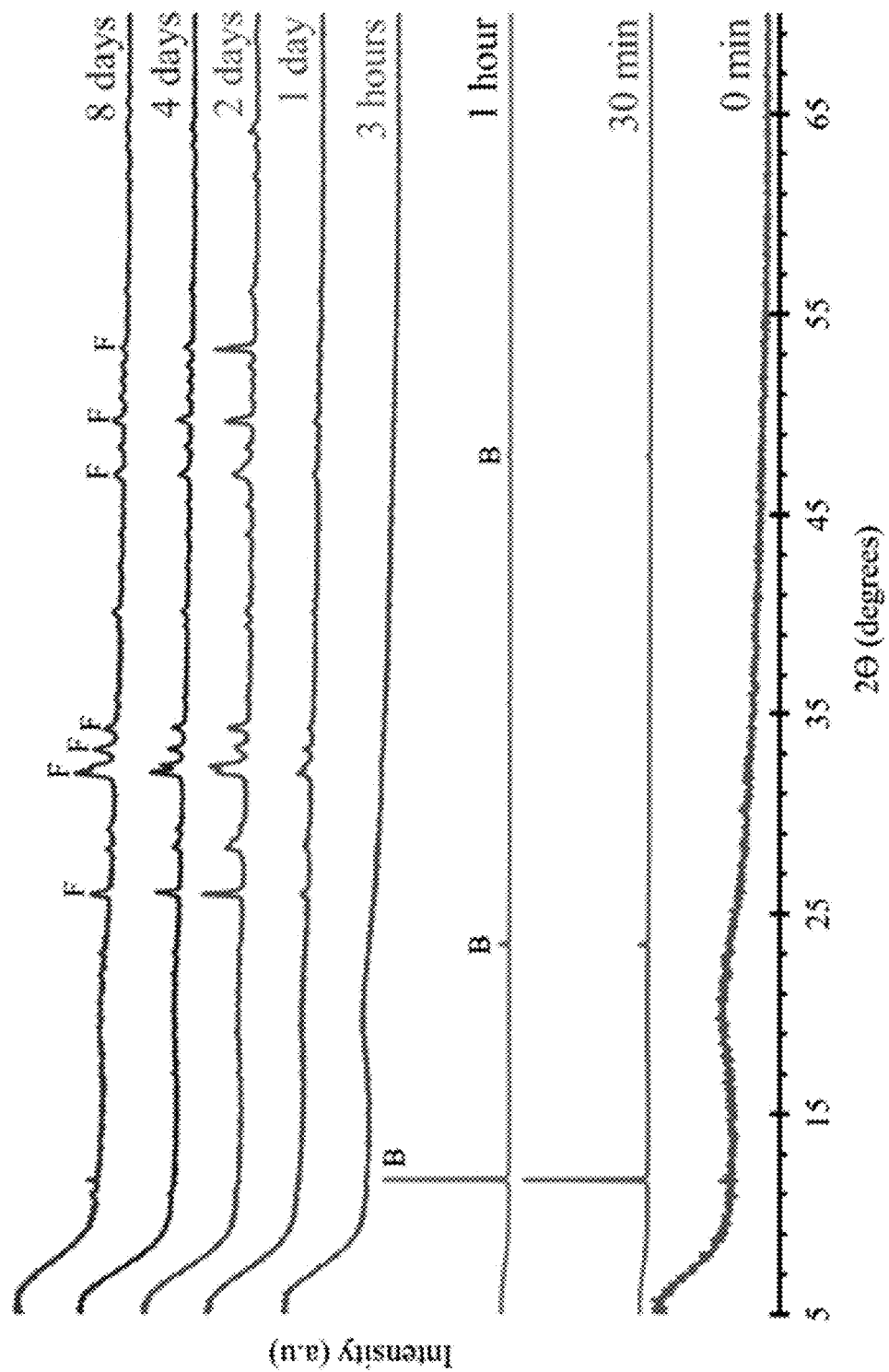
FIG. 36. XRD at different timepoints clearly show the phase transformation. Brushite (B) is observed during the first hour of the mineralisation, while it starts to dissolve by time transforming into the more stable phase of Fluorapatite (F) after the first day.
Figure 37:
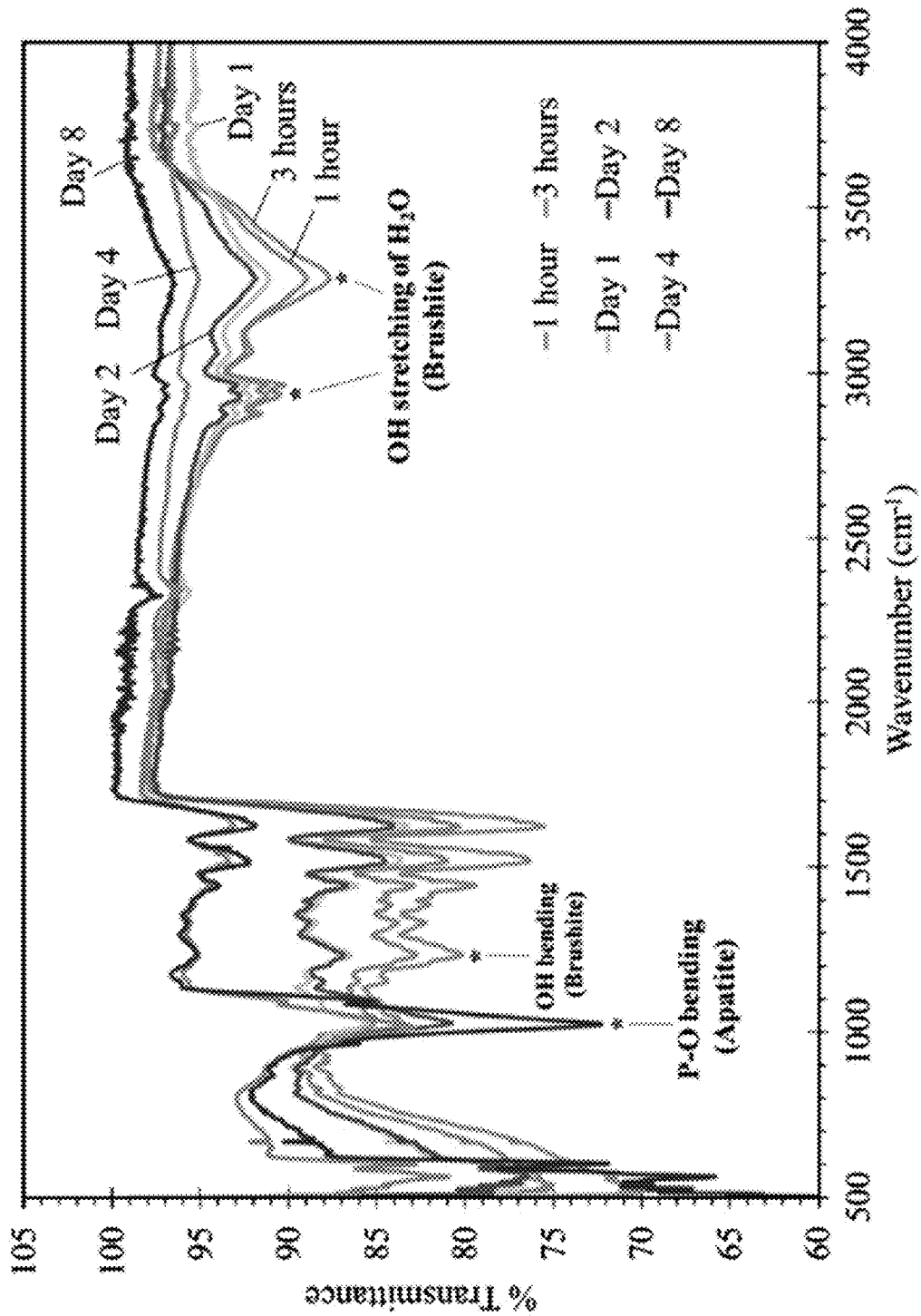
FIG. 37. FTIR spectra of the mineralising ELP membrane at different timepoints (1 hour, 3 hours, 1 day, 2, 4, and 8 days). At early timepoints, the spectra exhibit the characteristic sharp peak of OH bending of brushite ($CaHPO_4 \cdot 2H_2O$) at 1238 cm−1, and OH stretching peak of water molecule of brushite. As a function of time, the % transmittance of the brushite peaks decrease at the expense of the apatite's phosphate peaks, this confirms that brushite is the intermediate crystalline phase before transformation to fluorapatite.
Figure 38:
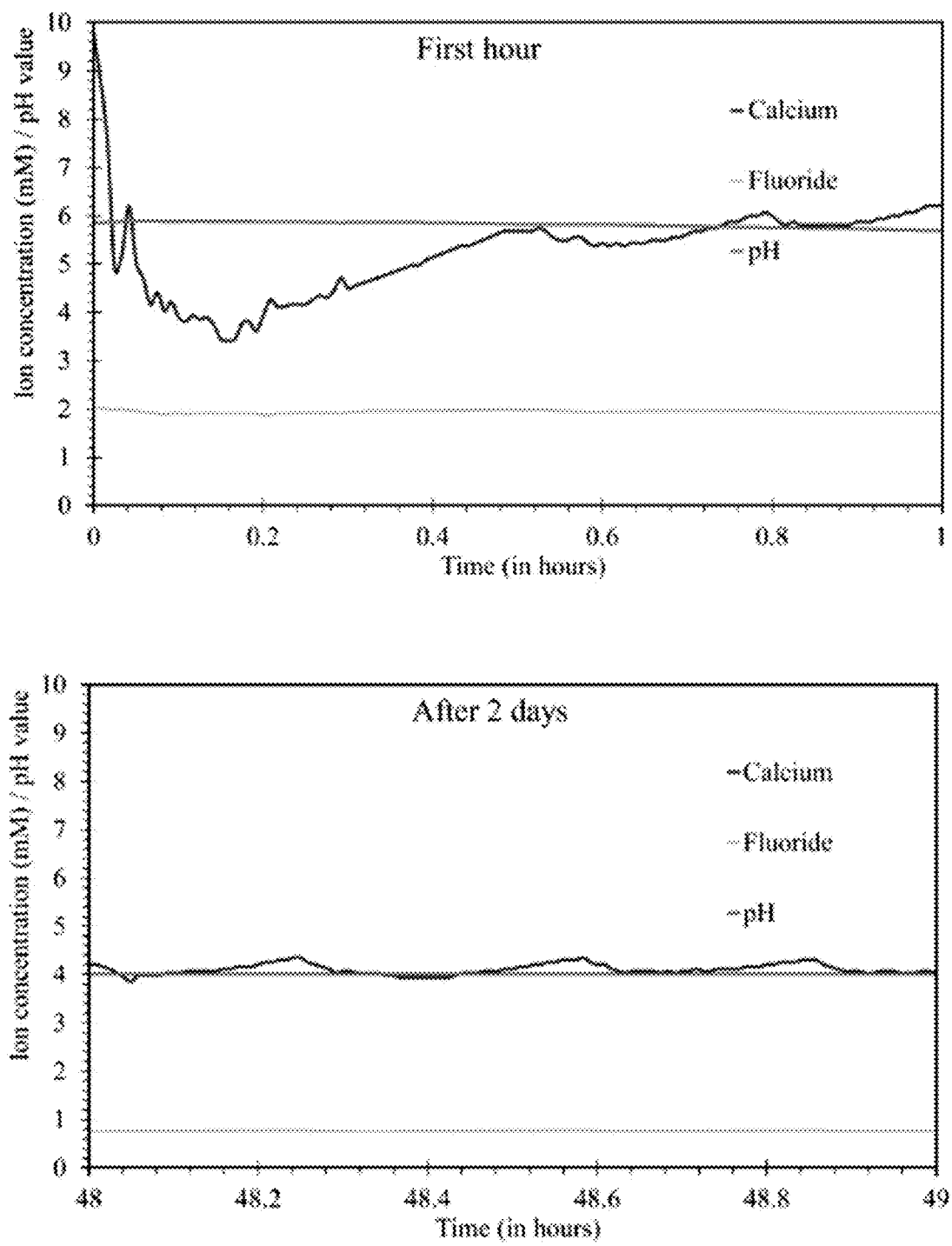
FIG. 38. ISE measurements during a) the first hour and b) after 48 hours. During the first hour, a significant drop in the free calcium ion concentration from 10 mM (initial concentration) to about 3.7 mM is observed, while the fluoride concentration remains fairly constant (a slight drop from 2 mM to 1.9 mM). During the first hour, the consumed calcium to fluoride ratio is about 7:0.1, giving an indication that the precipitated phase does not contain fluoride and therefore is not fluorapatite where the Ca:F ratio equals 10:6, rather another intermediate phase. This intermediate phase has been identified as brushite using XRD and FTIR (FIGS. 36 and 137). After 48 hours, it is clearly seen that the fluoride concentration drops to half of the initial concentration, giving an indication of phase transformation to fluorapatite under acidic conditions (pH=4.0).

Fourier transform infra-red (FTIR) spectroscopy analysis revealed spectra exhibiting amide peaks before undergoing mineralization (corresponding to the ELP material), while after mineralization they exhibited hydroxyl-free apatite peaks (Baddiel, C. B. & Berry, E. E. Spectra structure correlations in hydroxy and fluorapatite. *Spectrochimica Acta* 22, 1407-1416 (1966)) (FIG. 31b). This result suggests substitution of hydroxyl groups by fluoride ions in the crystal lattice (Elliott, J. C. Structure, crystal chemistry and density of enamel apatites. *CIBA Foundation Symposia*, 54-72 (1997)). On the other hand, at earlier time-points, XRD confirmed that brushite ($CaHPO_4 \cdot 2H2O$) was an intermediate crystalline phase within the membrane, which, in agreement with FTIR spectra and ISE measurements, is transformed into the more stable fluorapatite phase (Elliott, J. C. Structure, crystal chemistry and density of enamel apatites. *CIBA Foundation Symposia*, 54-72 (1997)) at later stages (FIGS. 36, 37 and 38). In addition, energy dispersive x-ray (EDX) spectroscopy point and mapping spectra showed the presence of calcium, phosphorus, and fluoride (FIG. 31c) with atomic ratios similar to stoichiometric apatite crystals and dental hard tissues (Elliott, J. C. Structure, crystal chemistry and density of enamel apatites. *CIBA Foundation Symposia*, 54-72 (1997)). This same crystalline phase was further confirmed by $^{19}F$ MAS-NMR spectra (FIG. 31d), which demonstrated the presence of a Fap peak at −103 ppm and of a fluorite ($CaF_2$) peak at −108 ppm (Mohammed, N. R. et al. Effects of fluoride on in vitro enamel demineralization analyzed by 19F MAS-NMR. *Caries Research* 47, 421-428 (2013)). The fluorite phase was not clearly observed in the diffraction data, mainly due to broad peaks arising from small crystallite size and peak overlap with the Fap crystalline phase.

Figure 14:
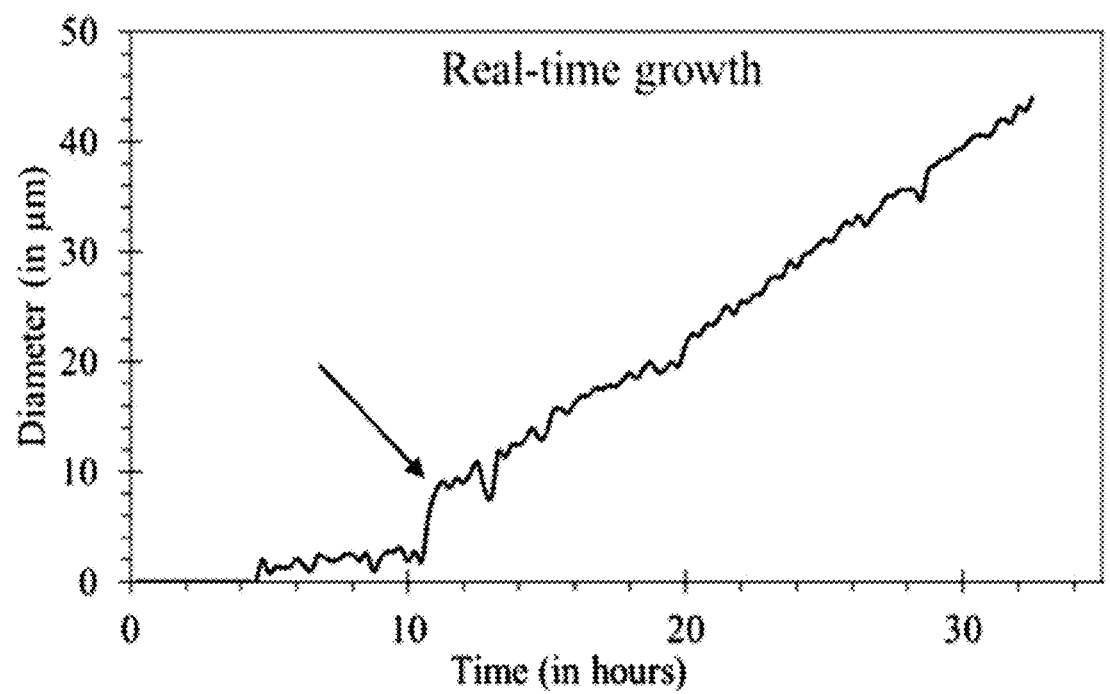
FIG. 14. The time-dependent mineralisation and growth behaviour of the structures on the membrane surface were traced in real-time using time-lapse phase-contrast optical microscopy and demonstrated an outward radial growth of the structures. As evidenced from the quantitative data, the structure starts to grow after about 5 hours of incubation, and then it passes through a quiescent state (between 5 to 10 hours) until a rapid growth stage takes place after 10 hours (arrow), subsequently growth takes a linear trend as a function of time.
Figure 32:
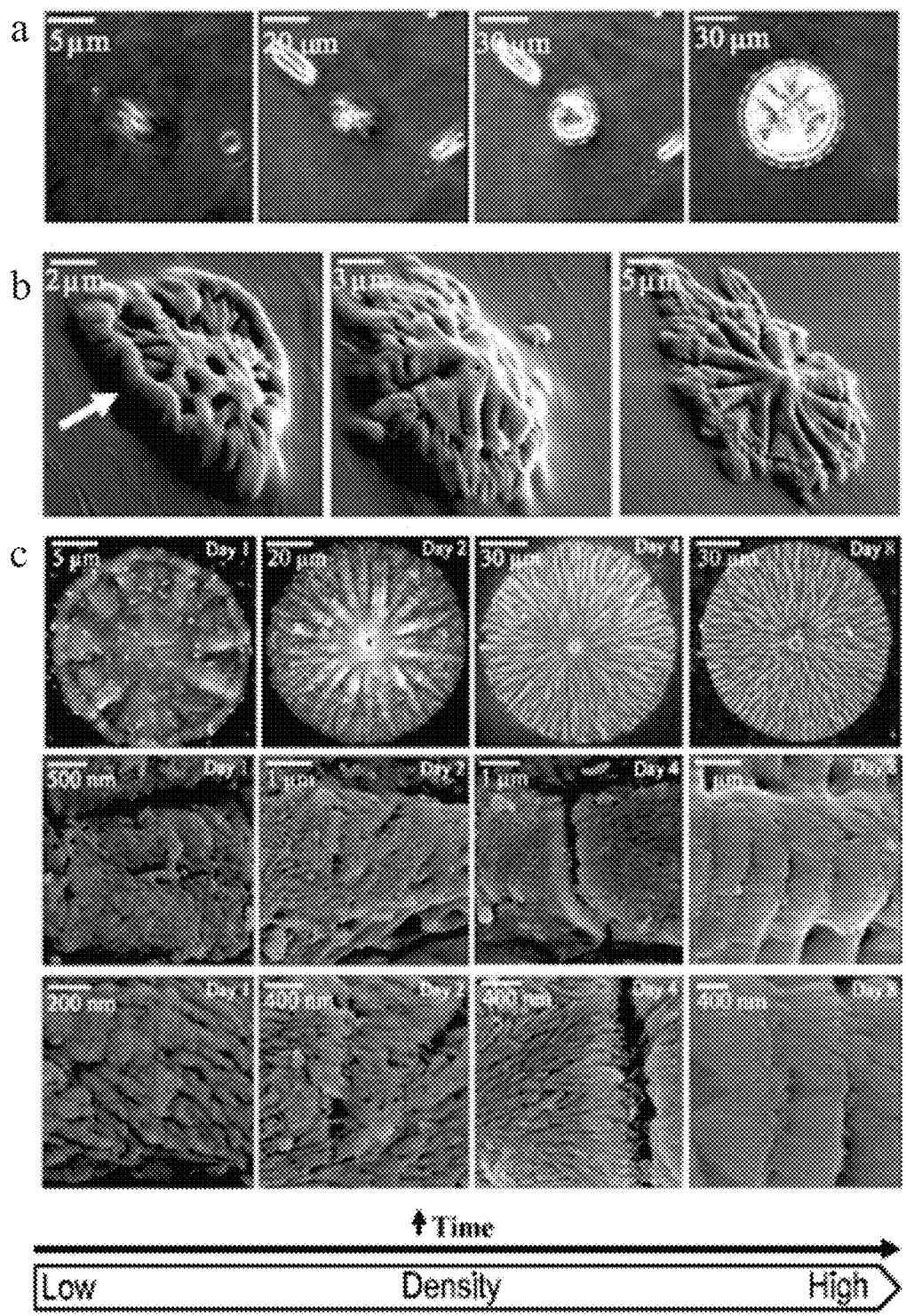
FIG. 32. Growth of the hierarchically-ordered mineralized structures. a,b) Time-lapse microscopy demonstrating a) the emergence and centripetal growth of the structures by phase contrast imaging and b) their initial stages of organization at the surface of an ELP membrane by SEM imaging. Outward bursting and growth is evidenced by thickening of the advancing front (arrow). c) DDC-SEM images of day 1, 2, 4, and 8 at different size scales, demonstrating that the structures gain hierarchical definition as a function of time. The accumulation of the less-dense material is clearly observed at the interprismatic areas at the different timepoints. d) Cross-section of an ELP membrane after 8 days of mineralization. e) EDX mapping at the same area of the SEM image (d). Near the surface of the ELP membrane, calcium, phosphorus, fluoride, and oxygen are abundant representing the prism-like crystalline structures. Away from the surface, carbon, nitrogen, and oxygen elements exhibit higher signals reflecting the organic nature of the membrane. This elemental distribution gives an indication of the presence of both organic and inorganic materials. f,h) DDC-SEM images of the areas within the white squares (d) showing the prism-like and round structures comprising of a dense material covered by a less dense material. g) EDX spectroscopy confirms the presence of both organic and inorganic materials. i) DDC-SEM image shows the less dense organic shell (green) surrounding the dense inorganic material (orange) at day 2. At higher magnification, the green rim is seen surrounding the round dense structure (inset).
Figure 32:
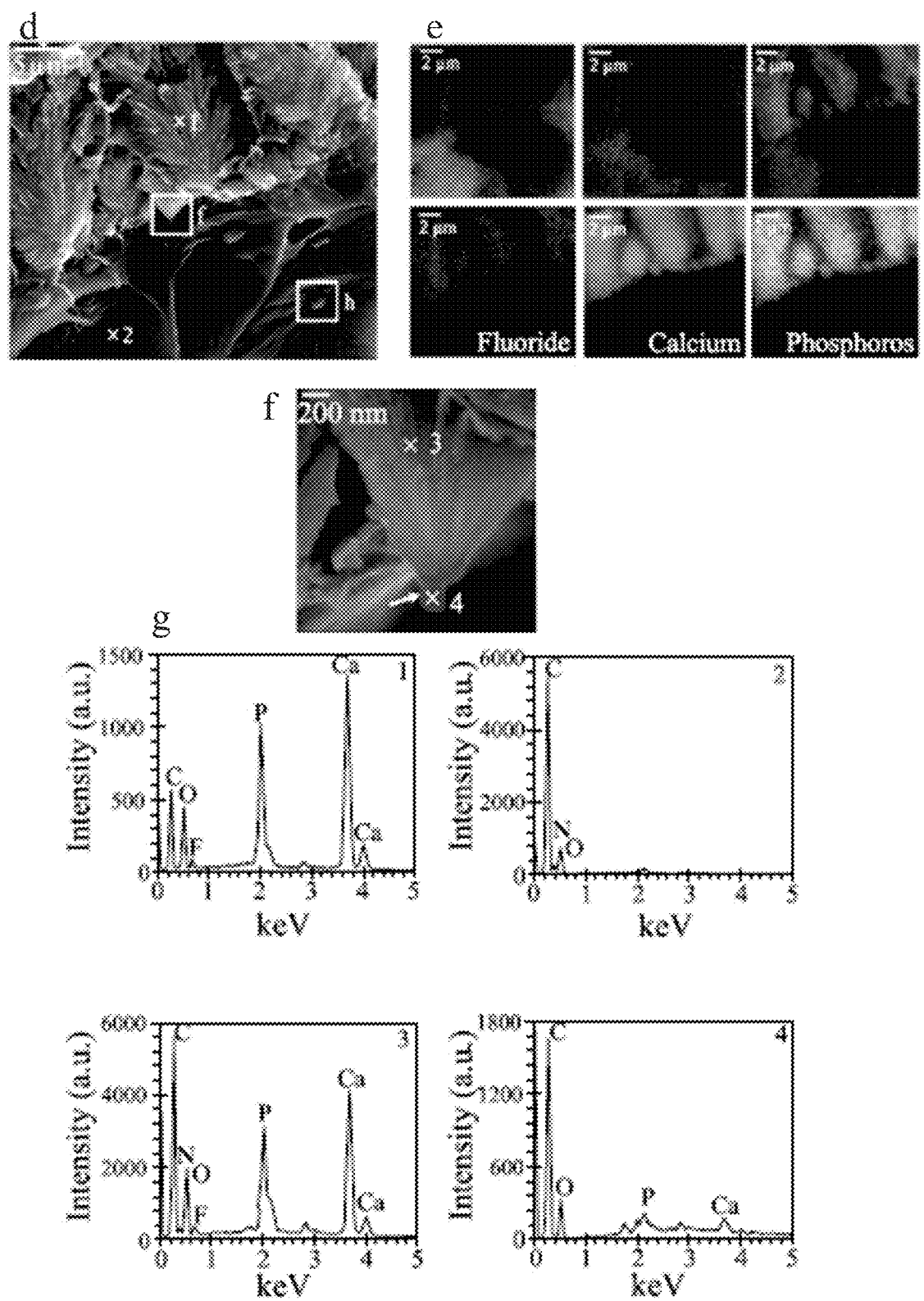
Figure 32:
Figure 32:
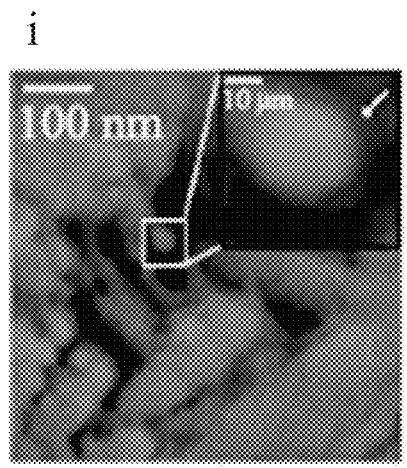
Figure 33:
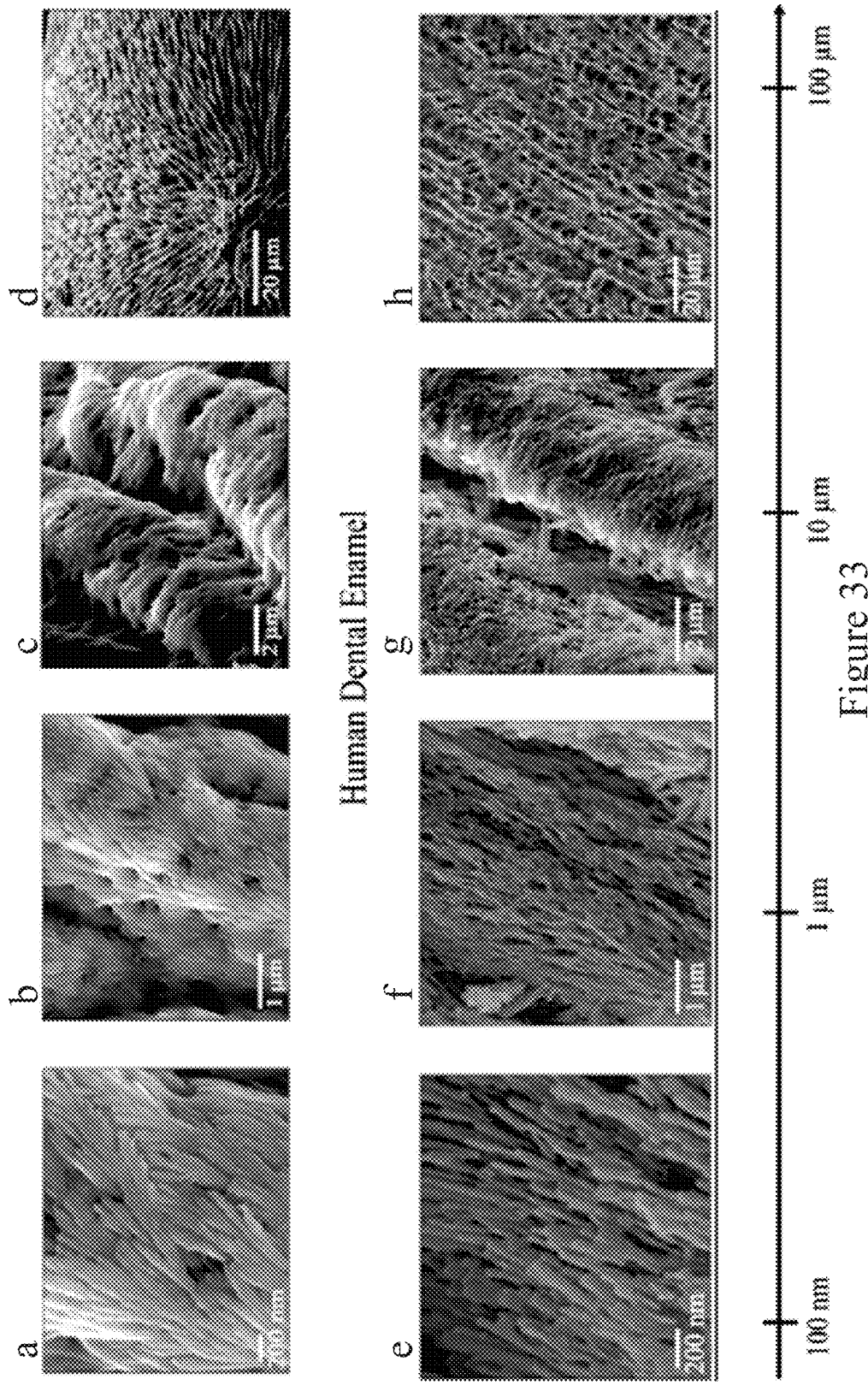
FIG. 33. Morphological comparison between the synthetic enamel-like hierarchically-ordered mineralized structures and human dental enamel. SEM images depicting the morphological similarities at different length-scales between the synthetic and natural tissues including a,e) apatite nanocrystals with similar crystal morphology, b-g) prism-like/interprism-like microstructures, and d,h) prism assemblies into macroscopic structures. The synthetic structures exhibit a centripetal pattern rather than the linear pattern that forms human dental enamel.

The time-dependent mineralization and growth behavior of the structures on the membrane surface were traced in real-time using time-lapse phase-contrast optical microscopy and demonstrated an outward radial growth of the structures with a linear trend (FIG. 32a, FIG. 14). This centripetal growth suggests that single nanocrystals self-organize close to each other and tend to slightly separate as they grow outwards as confirmed by SEM (FIG. 32b). Interestingly, density dependent color SEM (DDC-SEM) analysis at different time points, which simultaneously enables topographical and density assessment (Bertazzo, S. et al. Nano-analytical electron microscopy reveals fundamental insights into human cardiovascular tissue calcification. *Nature Materials* 12, 576-583 (2013)), revealed that the structures seem to acquire hierarchical definition as a function of time (FIG. 32c), a process that is also observed during the development of human dental enamel (Simmons, L. M., Montgomery, J., Beaumont, J., Davis, G. R. & Al-Jawad, M. Mapping the spatial and temporal progression of human dental enamel biomineralization using synchrotron X-ray diffraction. *Arch Oral Biol* 58 (2013)).

Figure 30:
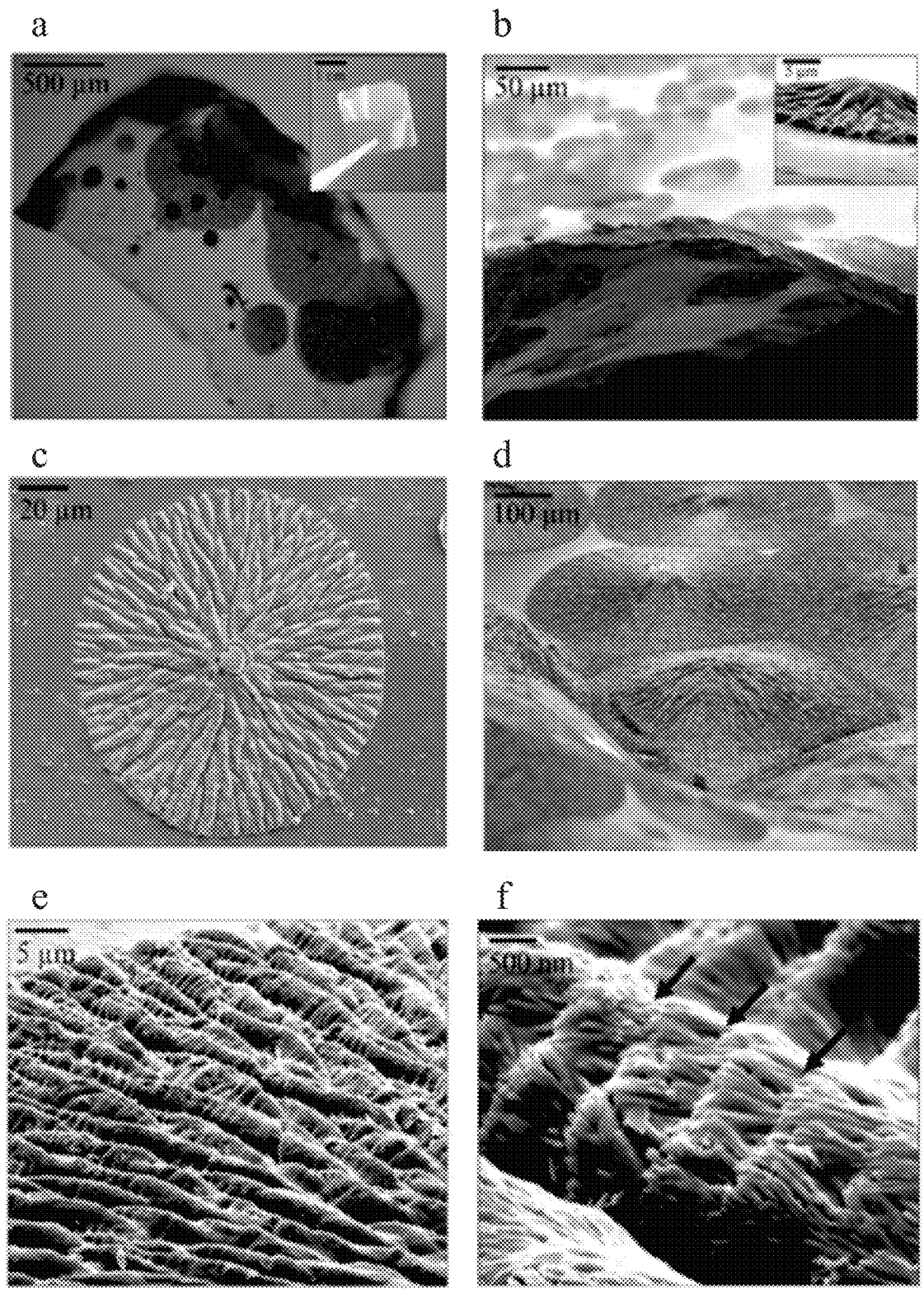
FIG. 30. Morphological description of hierarchically-ordered mineralized structures. a) Bright-field and b) SEM images of macroscopic circular structures grown on both sides of transparent and flexible ELP membranes (inset). SEM images showing c) the circular morphology of the hierarchical mineralized structures, d) their capacity to grow until adjacently assembling into a coating-like macrostructure on the surface of the ELP membrane, and e,f) the aligned nanocrystals organized in prism-like structures parallel to the surface of the membrane and exhibiting incremental growth lines (arrows). g,h) BSE images showing brighter areas at the centre of the structures that indicate the presence of mineral deep within the membrane. i,j) FIB sectioning of the hierarchically mineralized structures resolving the deeper root-like structures located underneath the centre of the circular structures and j) the nanocrystals within the ELP membrane and aligned perpendicular to the surface of the membrane.
Figure 30:
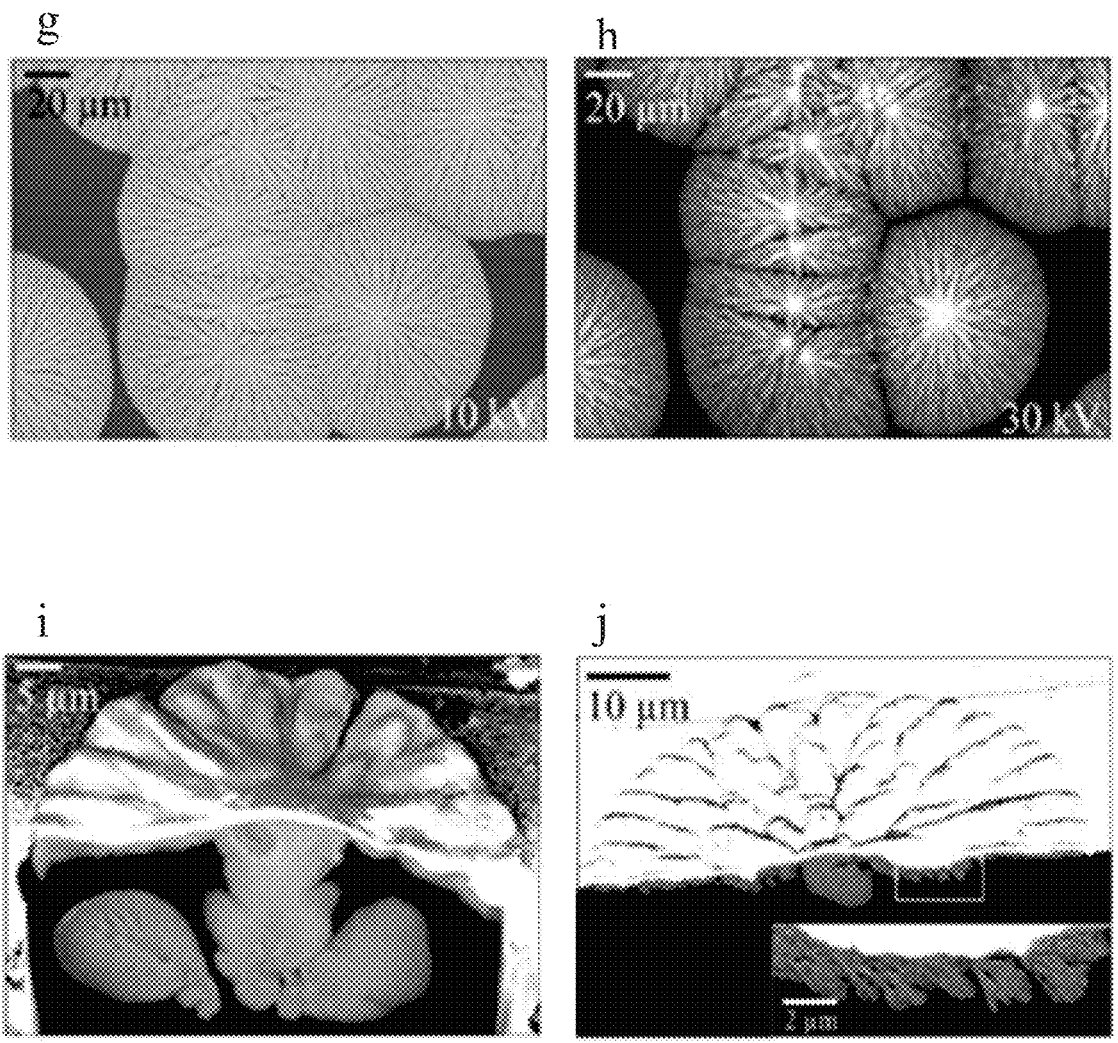
Figure 31:
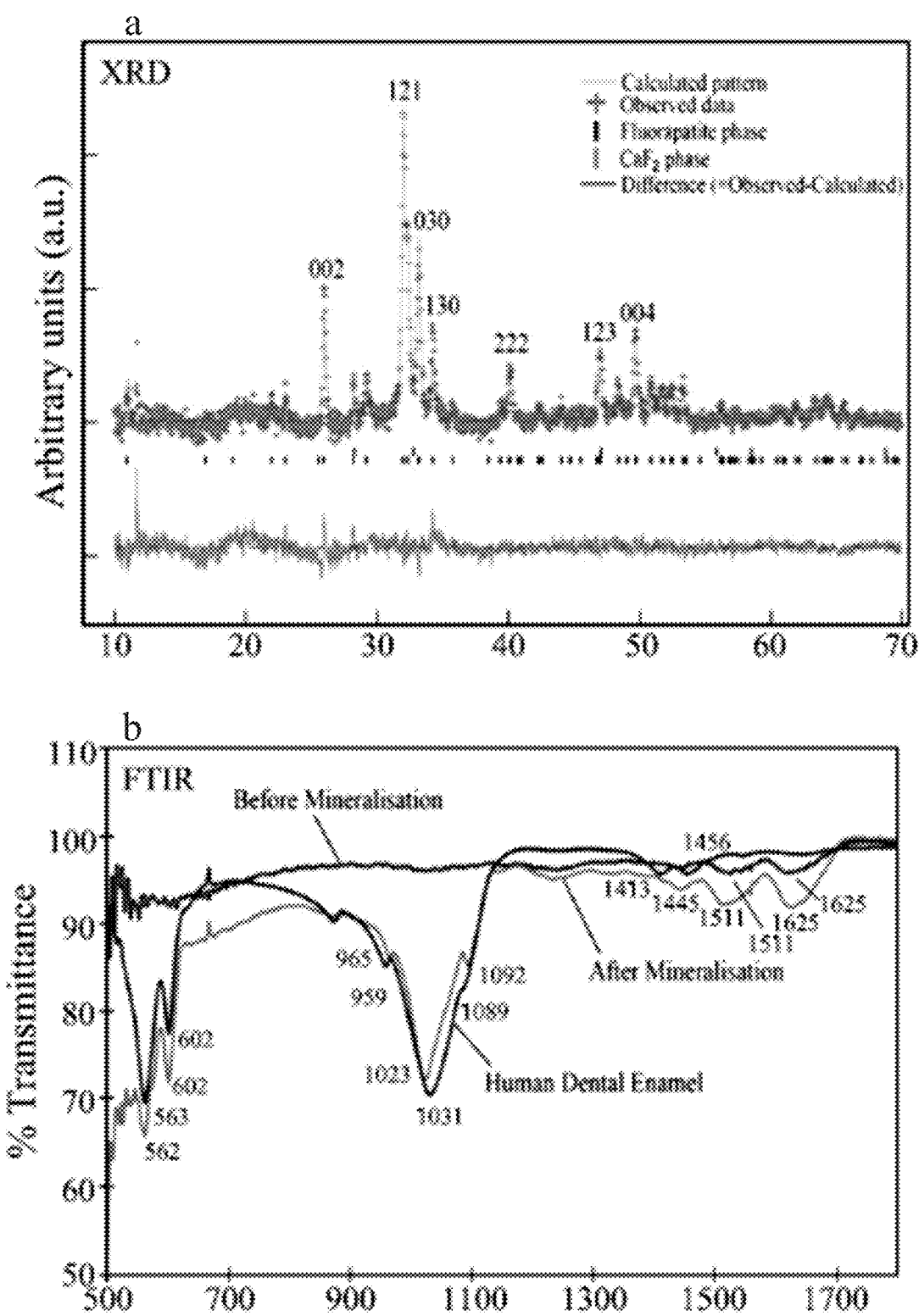
FIG. 31. Chemical characterization of the highly-ordered mineralized structures. a) Rietveld refinement of XRD pattern of mineralized membranes showing the fluorapatite nature of the crystalline phase with the typical Bragg peaks of apatite. b) FTIR spectra of the ELP membrane before mineralization (red) depicting the amide peaks at 1511 and 1625 cm-1, clearly reflecting its organic nature, while after mineralization (blue) showing typical apatite peaks from P—O bending assignments at 562 and 602 cm-1, symmetric P—O bending at 965, and asymmetric P—O bending at 1023 and 1092 cm-1. The absence of OH stretch at 631 cm-1 associated to the hydroxyapatite crystalline phase gives an indication of the OH substitution inside the crystal lattice. The carbonate stretch peak is present at 1445 cm-1. The overall spectrum shows a close compositional resemblance to the human dental enamel spectrum (purple). c) The EDX sum spectrum from the mineralized structure (box), confirms the presence of calcium, phosphorus, oxygen, and fluoride in the structure. d) 19F solid-state MAS-NMR spectra confirm the presence of fluorapatite and fluorite phase at −103 and −108 ppm, respectively, with increasing FAp peak intensity on the mineralized membrane (I) compared to without the ELP membrane (II) at the same conditions.
Figure 31:
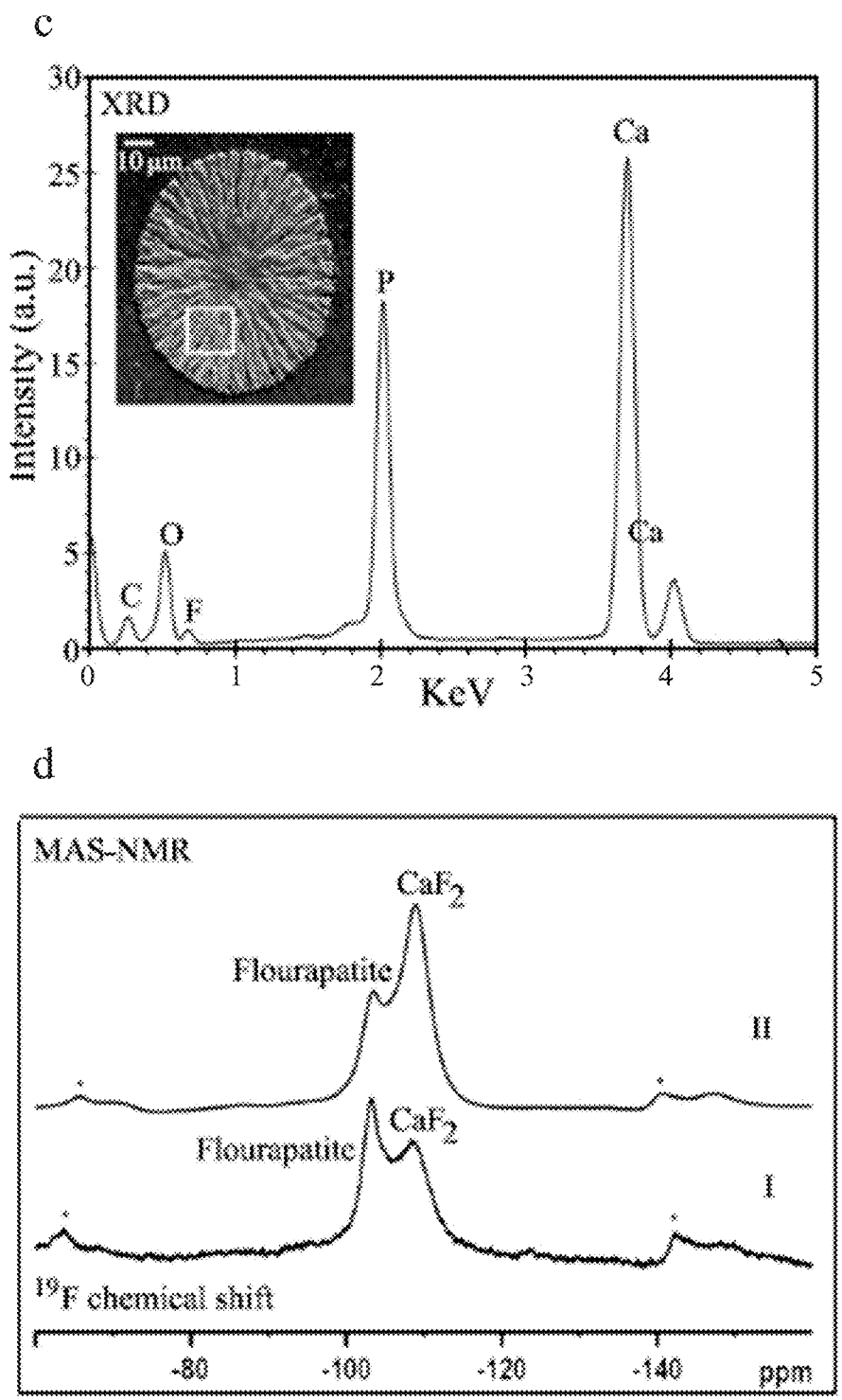
Figure 39:
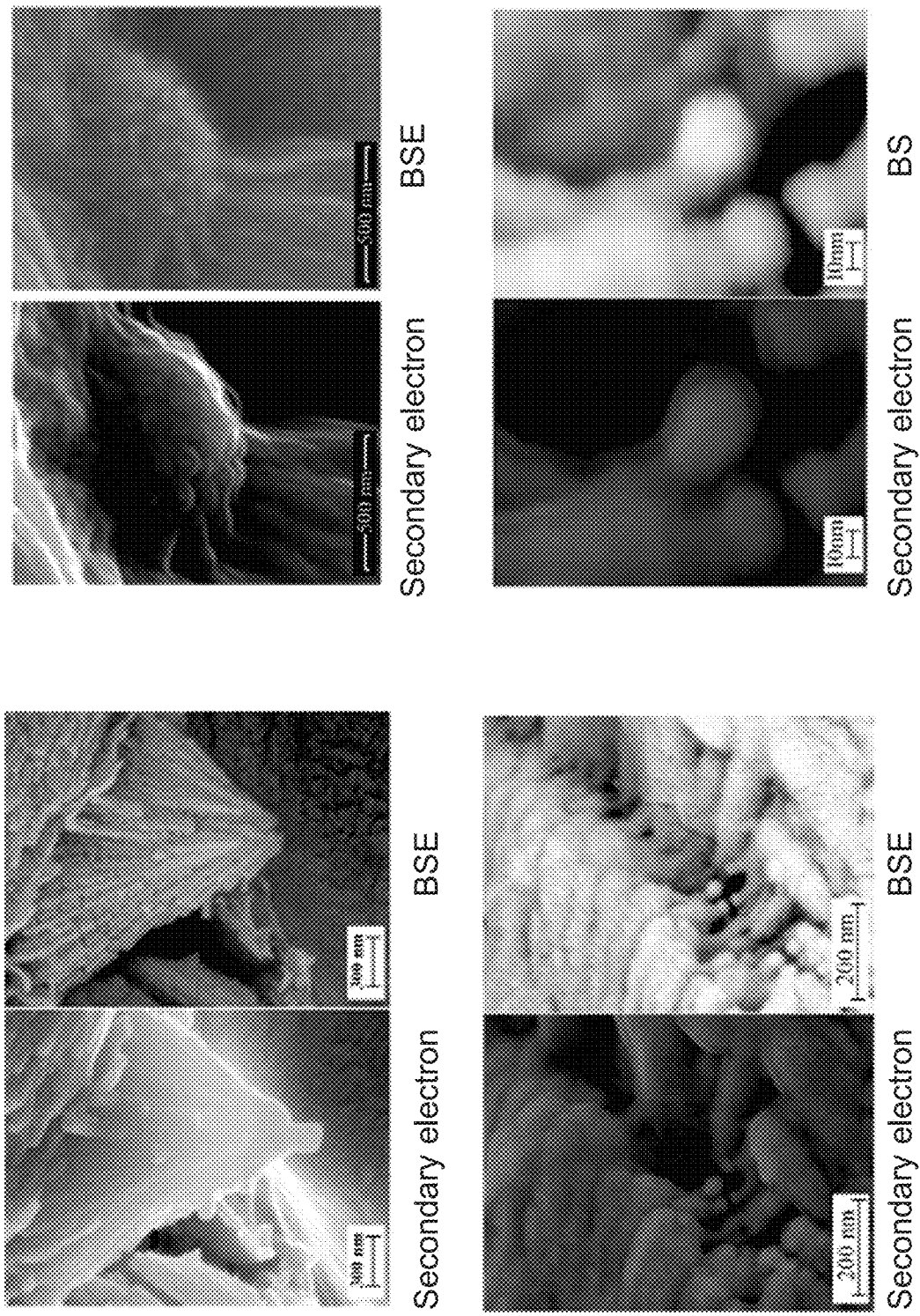
FIG. 39. SEM and BSE images taken simultaneously from same area to allow density-dependent analyses (DDC-SEM). BSE images show clearly the disappearance of the thin coating around the crystals giving an indication of the presence of the less dense material surrounding the crystals. The less dense material is confirmed previously (FIG. 32) to be rich of carbon, nitrogen and oxygen, giving indication of its organic nature.

Mineral growth was further investigated conducting DDC-SEM and EDX spectroscopy on cross-sections of membranes mineralized for 8 days (FIG. 32d and FIG. 39). The results revealed that the elongated nanocrystals seem to sprout symmetrically outwards at an angle of 102±6° with respect to the surface of the membrane and organize in well-defined prism-like structures similar to those found on the surface of the membrane. In combination with the FIB-SEM investigations (FIG. 30i-j), these observations suggest that the hierarchical structures nucleate within the membrane and erupt outwards towards the surface (FIG. 32*f*). In addition, repeated round structures exhibiting a dense pattern of regular bumps on their surface were also observed at different depths within the cross-section of the membrane (FIG. 32*h*). It is possible that these round structures are the sites at which the nanocrystals nucleate and grow into the hierarchical structures. To confirm this hypothesis, closer examination was performed using DDC-SEM and revealed a thin less dense material surrounding both the round and prism structures at multiple lengthscales. Furthermore, BSE imaging/EDX spectral mapping of the cross-sections revealed abundance of calcium and phosphorus peaks in the denser material, and carbon and nitrogen in the less dense areas (FIG. 32*e-g*). These results suggest that heterogeneous nucleation is taking place within the ELP membrane, which in turn acts as an insoluble macromolecular framework (FIG. 32*c-f-h-i*) leading to the high-order assembly of crystallites at multiple length-scales (Mann, S. *Biomineralization: principles and concepts in bioinorganic materials chemistry*. (Oxford University Press, 2001)), and in turn the distinctive hierarchical architecture (FIG. 30*c*). It is well established that organic matrices play a key role in biomineralization processes (Kato, T., Sakamoto, T. & Nishimura, T. Macromolecular templating for the formation of inorganic-organic hybrid structures. *MRS Bulletin* 35, 127-132 (2010)). For example, hierarchical $CaCO_3$ structures have been generated on surfaces using organic hydrogels that facilitate diffusion through the gel and the formation of an optimal ionic concentration/environment (Sakamoto, T. et al. Three-dimensional relief structures of CaCO3 crystal assemblies formed by spontaneous two-step crystal growth on a polymer thin film. *Crystal Growth and Design* 9 (2009)).

The biomedical field would particularly benefit from materials with a well-defined hierarchical organization that, like biological structures such as dental enamel, offer outstanding properties. However, while there is great interest in developing ordered mineralized materials (Kato, T., Sakamoto, T. & Nishimura, T. Macromolecular templating for the formation of inorganic-organic hybrid structures. *MRS Bulletin* 35, 127-132 (2010), Chen, H. et al. Acellular synthesis of a human enamel-like microstructure. *Advanced Materials* 18, 1846-1851 (2006), Simon, P., Schwarz, U. & Kniep, R. Hierarchical architecture and real structure in a biomimetic nano-composite of fluorapatite with gelatine: A model system for steps in dentino—And osteogenesis? *Journal of Materials Chemistry* 15, 4992-4996 (2005)), synthetic hierarchical apatite structures have not been achieved. The mineralized hierarchical structures reported here are the first synthetically generated material that resembles enamel in nano- and micro-morphology and chemical composition. Like enamel, the structures exhibit aligned crystallites at the nanoscale (FIG. 33*a*), aligned prism-like and interprism-like regions with incremental lines at the microscale (FIG. 33*c-g*), and macroscopic growth. Chemically, the structures consist of Fap rather than Hap (FIG. 31), which could improve resistance to acid environments that increase during dental caries and erosion. Finally, the structures are grown on a flexible, transparent, and robust biocompatible membrane, which facilitates both its formation and functionality.

Figure 34:
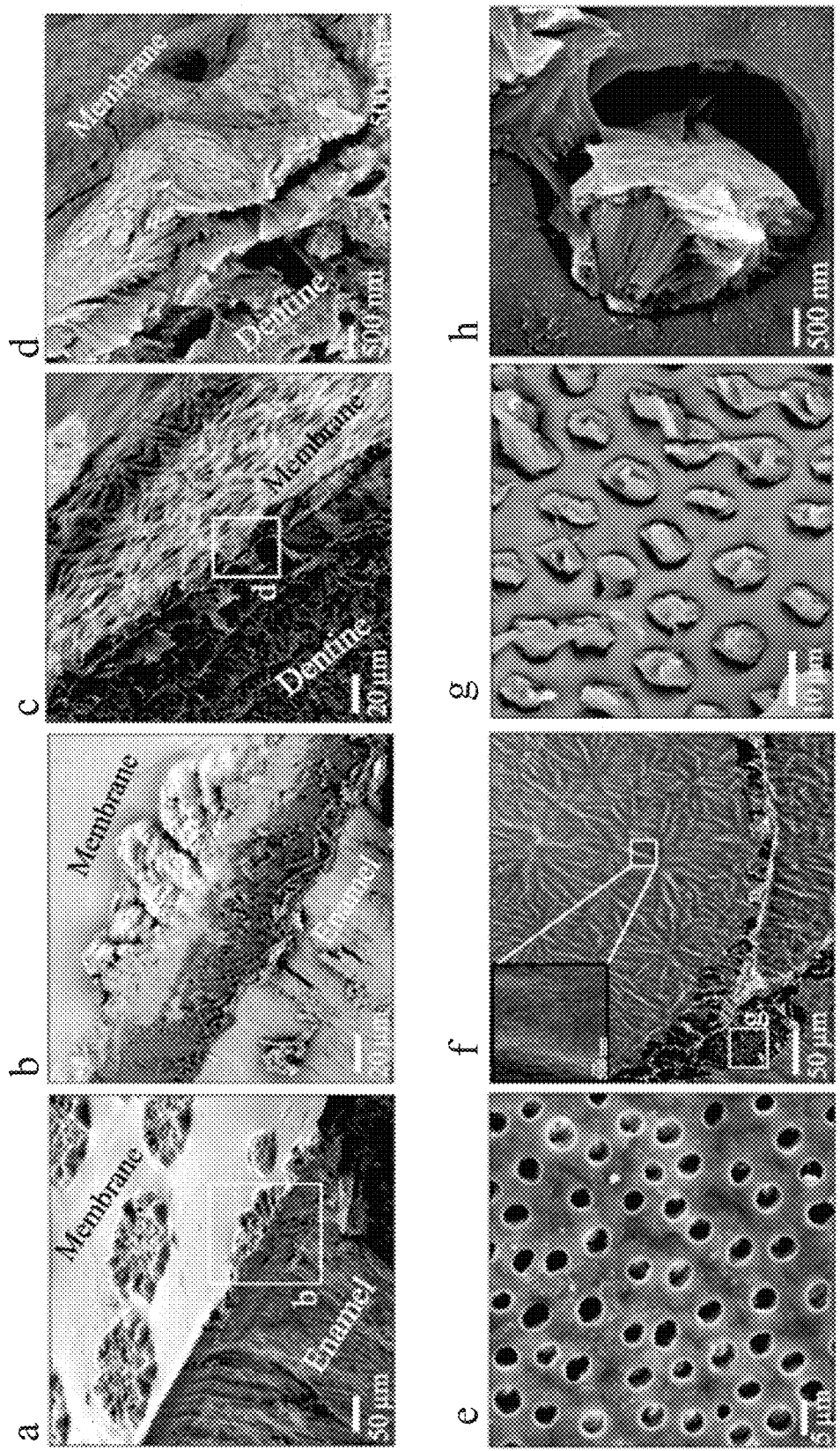
FIG. 34. Application of the hierarchically ordered enamel-like material on enamel and dentine. a) SEM image showing the in-situ cross-linked ELP membrane conformed over dental enamel, exhibiting the enamel-like structures. b) BSE image showing a closer magnification of (a), where the mineralized structures are located away from the dental enamel as a result of the membrane (less dense material) thickness. c) SEM and d) BSE images of much thinner membranes capable of growing the hierarchically organized structures but in close contact to the underlying tissue. SEM images of e) open dentinal tubules before treatment and f) a dentine disc treated with the ELP membrane exhibiting the hierarchically organized structures growing on the surface and assembling into a mineralized coating. g) BSE image showing a closer view of the dentinal tubules after treatment, exhibiting the occlusion of all the tubules as a result of h) infiltrated nanocrystals emerging from the hierarchically organized structures growing on the ELP membrane.

Given the structural and chemical characteristics of the generated material and the current need to regenerate enamel, we conducted in vitro studies to investigate the possibility of applying the mineralizing ELP membranes to both regenerate enamel and to occlude exposed dentinal tubules. Membranes that were about 80 μm thick were fabricated directly on both human enamel and dentine samples (FIG. 34*a-d*) and incubated at near physiological conditions as described earlier. SEM observations confirmed that the membranes adhered and conformed to the surface of the dental tissues and that similar hierarchical mineralized enamel-like structures were grown on these membranes on both enamel and dentine (FIG. 34*b-d*). By decreasing the thickness of the membranes to less than 20 μm, it was possible to grow the enamel-like structures in closer contact with the natural tissues (FIG. 34*c-d*), facilitating integration with the native tissue. For example, in the dentine samples coated with the ELP membranes (FIG. 34*f-h*), directly below the bed of mineralized structures, aligned apatite nanocrystals emanating from the ELP membrane were observed to infiltrate and block dentinal tubules (FIG. 34*e-h*). These results are promising for a variety of dental applications such as treating dentine hypersensitivity, which affects about 30% of dental patients and is caused by open dentinal tubules exposed to the oral environment (Orchardson, R. & Gillam, D. G. Managing dentin hypersensitivity. *Journal of the American Dental Association* 137, 990-998 (2006)). Other potential applications include treatment modalities for dental caries and erosion, which are currently treated by isotropic materials like resin-based composites that tend to fail and do not regenerate the native tissue. The ELP membranes could potentially improve patient outcomes compared to desensitizing toothpastes/agents with the same advantages of fluoride inclusion by treating large damaged areas, be precisely localized, improve mechanical properties, and have the capacity to both regenerate enamel and block dentinal tubules.

This work demonstrates the possibility to grow complex hierarchically-ordered Fap structures that resemble those found in human dental enamel, which has not been previously achieved. The structures exhibit high spatial organization at multiple length scales beginning from well-defined elongated needle-like Fap nanocrystals that come together into adjacent enamel prism-like geometries, which are organized in circular structures hundreds of microns in diameter that collectively assemble to cover macroscopic areas. The structures are grown on a biocompatible, transparent, flexible, and robust ELP-based membrane, which facilitates its application. We explored the system's functionality by growing the hierarchically mineralized structures in vitro on both human dental enamel and exposed dentinal tubules and demonstrated their capacity to grow and bind to the underlying natural dental hard tissues as well as infiltrate and block dentinal tubules. The mineralizing membrane could potentially replace isotropic restorative materials and provide a leap forward by not only treating caries, dental erosion, and hypersensitivity, but enabling the regeneration of enamel.

Example 2 Micro-Fabricated ELP-Based Membranes

Method

Direct write laser lithograpy was used to fabricate a silicon chrome photomask. A (111)-oriented silicon wafer was coated with an 8 um thick layer of SU8-10 photoresist, soft baked (65 C for 2 minutes and 950 C for 5 minutes), and then exposed through the silicon chrome photomask (30 mWcm−2 for 3.3 seconds). It was subsequently post-exposure baked (65 C for 1 min and 950 C for 5 min) and developed using SU8 developer for 30 s. Topographies were transferred to polydimethylsiloxane (PDMS) using a standard soft lithography process. The PDMS prepolymer was poured on top of the patterned master, degassed under vacuum for 7 min, and then cured at 650 C for 2 hours. The resulting topographically patterned mold was subsequently used to create membranes with the different structural components using similar dropcasting method as mentioned for the smooth membranes.

Results

FIG. 14 shows the preferential nucleation and growth of fluorapatite crystals on a channel-containing a microfabricated ELP-based membrane. The membrane was fabricated according to the method described in Tejeda-Montes et al., 2012 (Tejeda-Montes, E. et al. Engineering membrane scaffolds with both physical and biomolecular signaling. Acta Biomaterialia 8, 998-1009 (2012)) and as detailed above. The apatite crystals grew and arranged preferentially along the ridges of the channels and were absent in the channel grooves. Moreover, more crystals were observed to be present in areas where the horizontal and vertical sections of the channels would meet creating a 270° angle compared to flat surfaces, which could be due to reduction of the energy barrier.

Discussion of FIGS. 1 to 6

Figure 3:
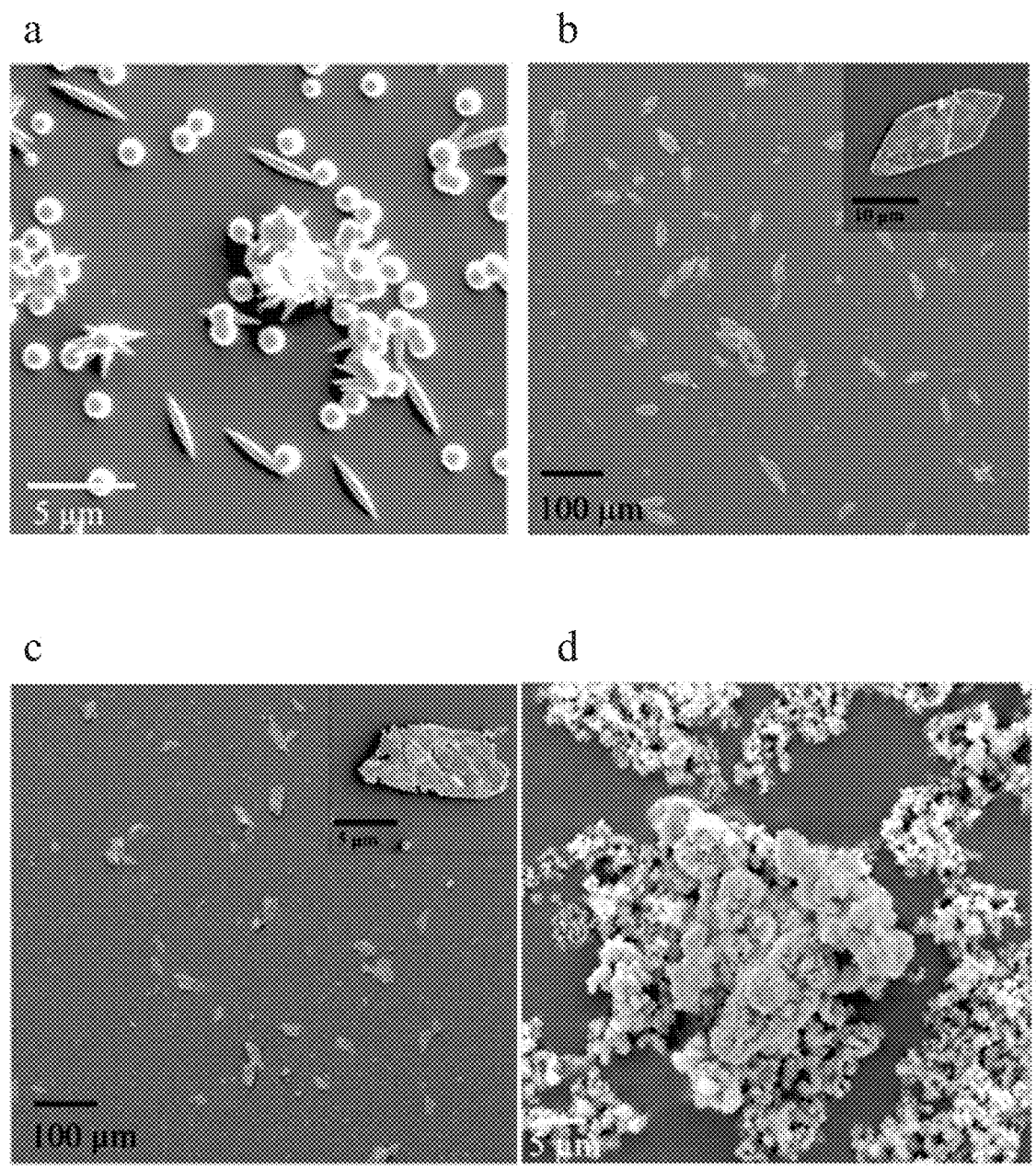
FIG. 3. SEM images of the crystal morphology on; a) uncoated borosilicate glass showing the characteristic needle-like and ball-like morphology; and borosilicate glass coated with ELPs b) statherin-ELP, and c) RGDS-rich ELP showing flat plate-like crystals. Similarly collagen membranes showed disordered crystal growth (d).
Figure 4:
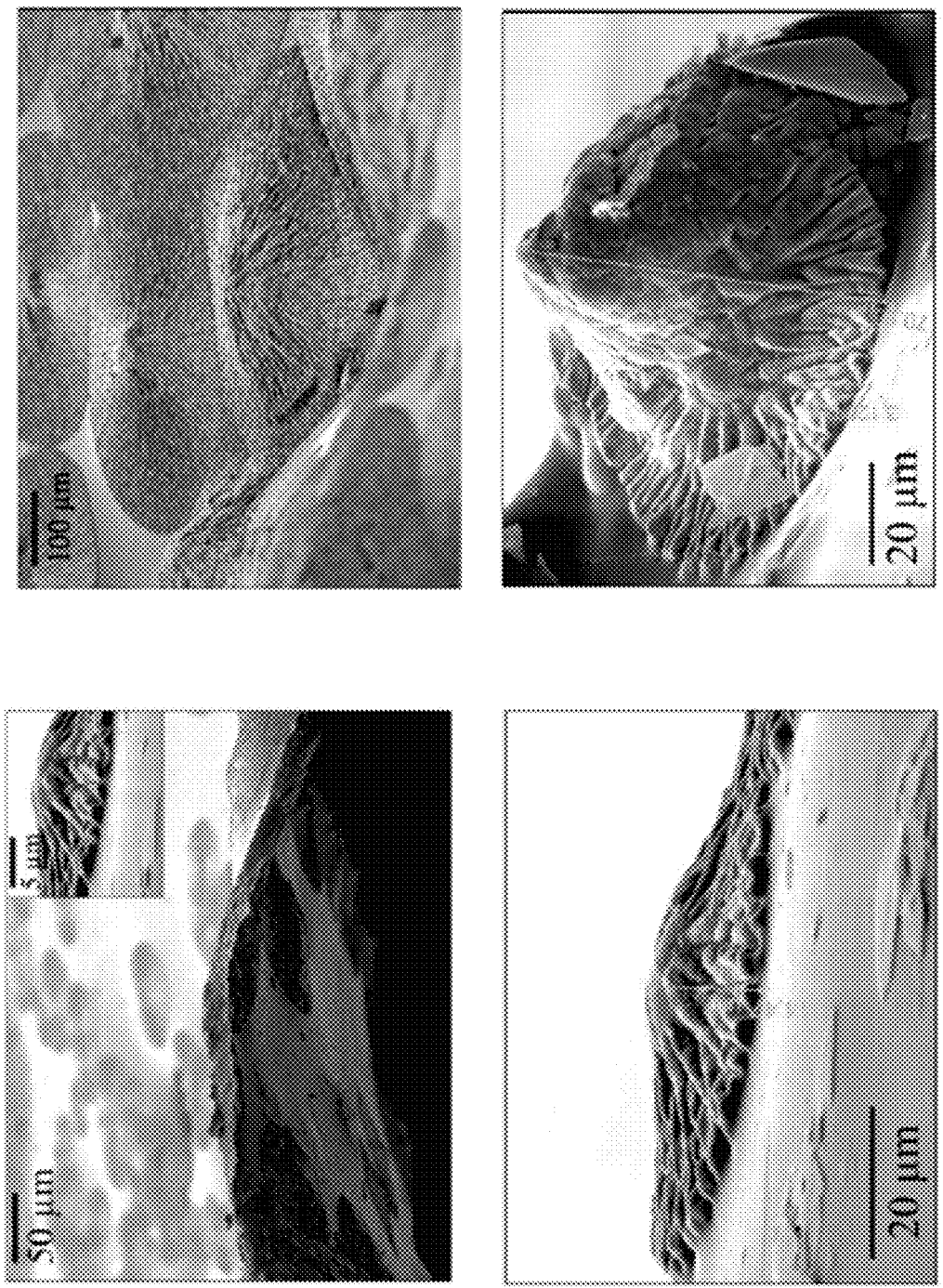
FIG. 4. SEM image showing the growth of the hierarchical mineralized structures on both sides of the RGDS-rich ELP membranes. Below images showing a side view of the structures with different heights.
Figure 5:
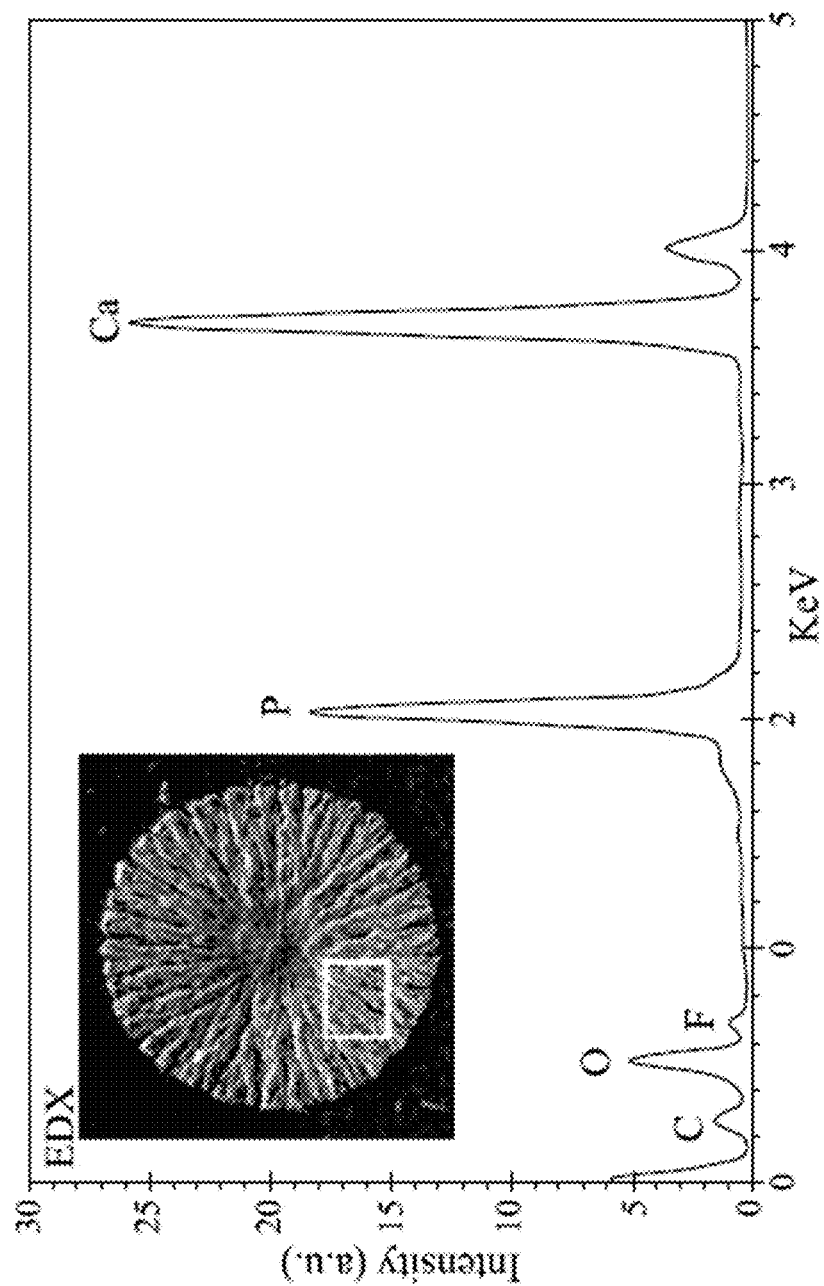
FIG. 5. EDX mapping (top) of the structures showing the presence of calcium, phosphorus, and fluoride with atomic ratios similar to stoichiometric apatite crystals and dental hard tissues. Fourier transform infra-red (FTIR) spectroscopy analysis (below), which revealed spectra exhibiting amide peaks before undergoing mineralization (corresponding to the statherin-rich ELP material), while after mineralization they exhibited hydroxyl-free apatite peaks.
Figure 5:
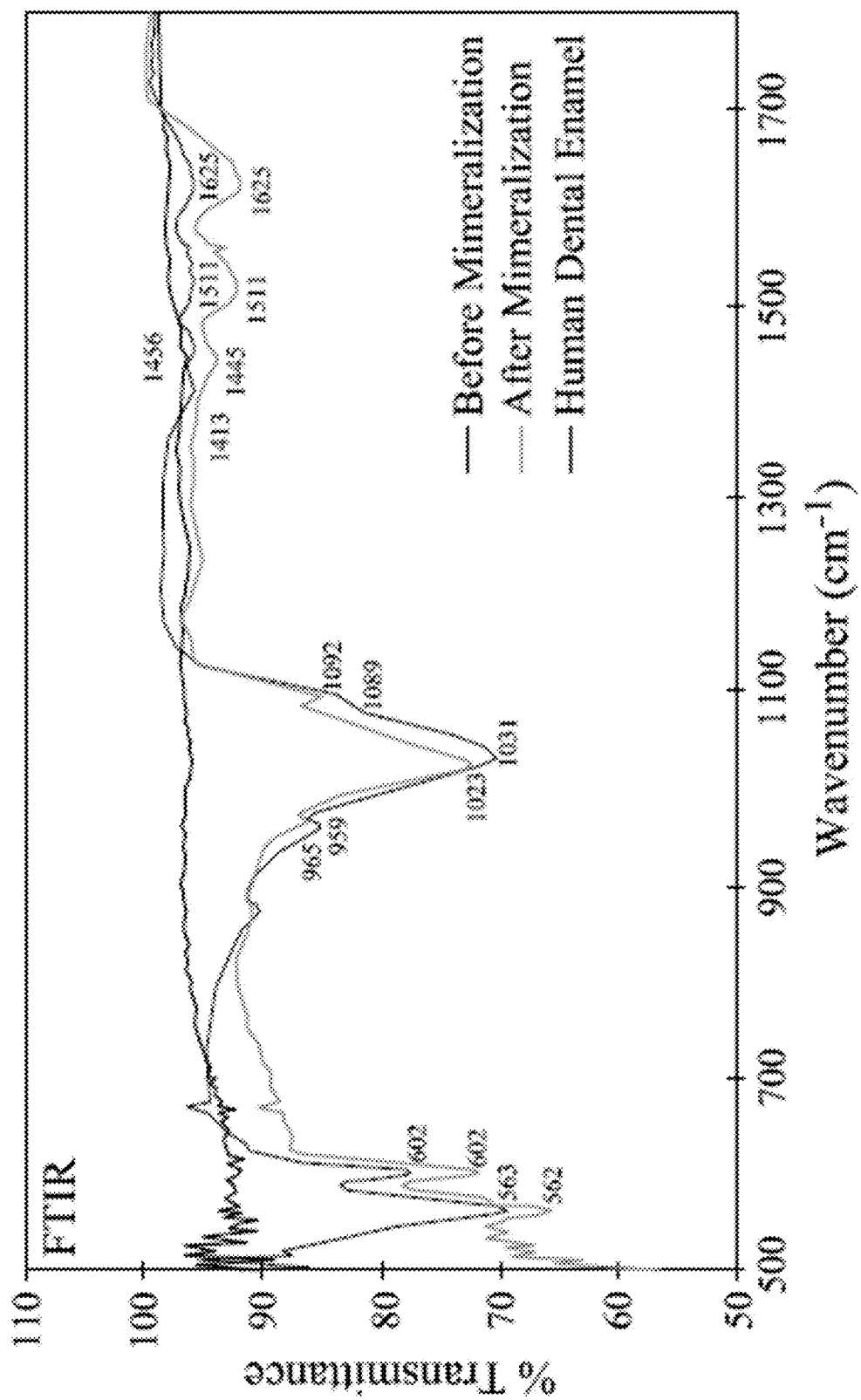
Figure 6:
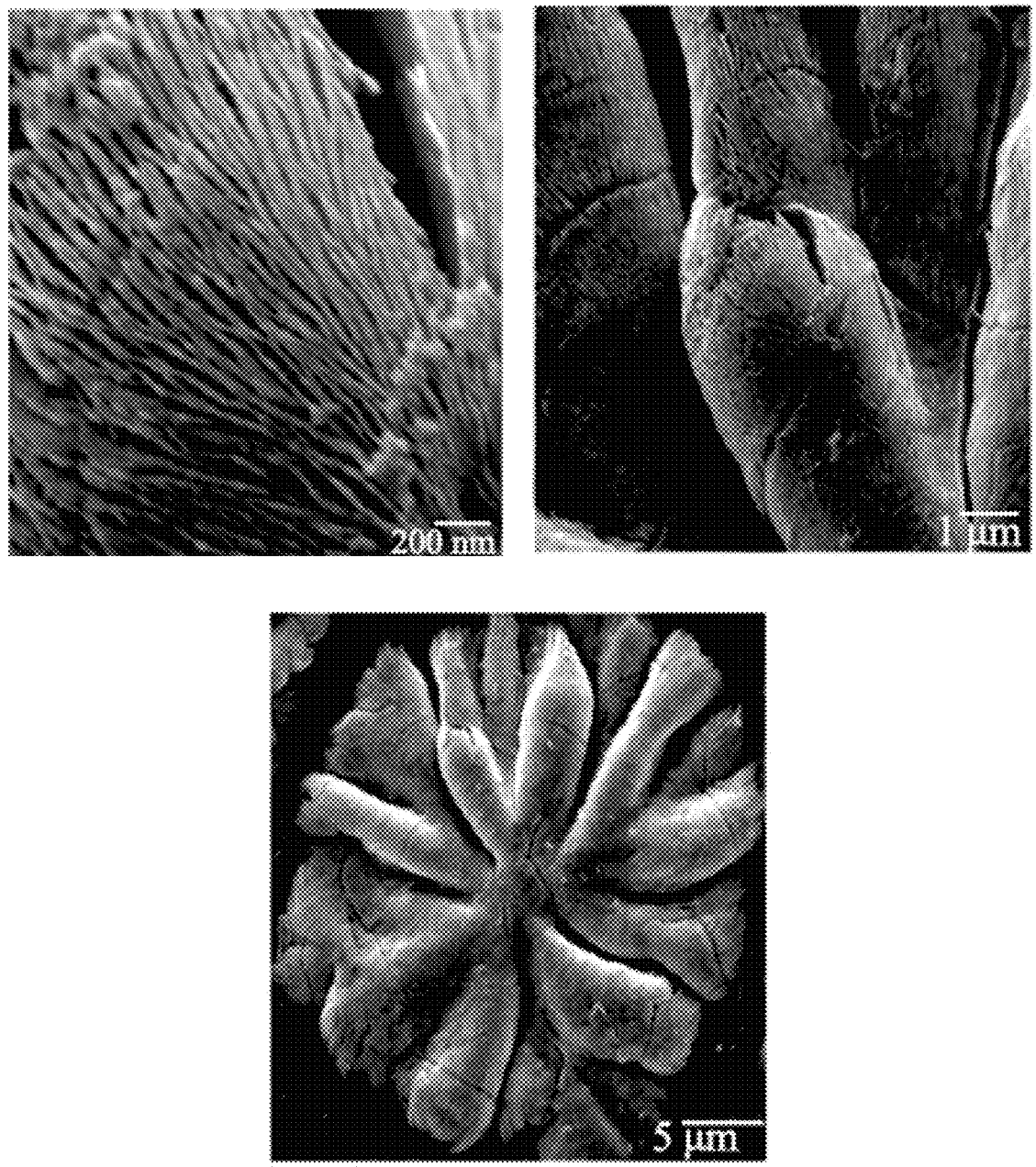
FIG. 6. SEM images of RGDS-ELP membranes, when mineralised without the use of fluoride, showing a similar hierarchical organization with those formed with fluorine. However, the morphology of nanocrystals changed to elongated plate-like due to the different chemistry. We are not restricted in using fluorine to grow the structures; we can grow them in a fluorine free conditions.

The biomineralization system takes place within the bulk of a transparent ELP membrane (FIG. 1b) when combined with a supersaturated solution in respect to apatite at physiological ionic concentrations and environmental conditions. The ELP molecule used is a 32 kDa molecular weight ELP comprising a main hydrophobic framework (VPGIG (SEQ ID NO:43)) and the highly-acidic hydroxyapatite-binding statherin-derived peptide DDDEEKFLRRIGRFG (SEQ ID NO:2) (FIG. 2). Collagen membranes, ELP-coated glass, and membranes made from similar ELP molecules without the statherin-derived peptide or with the cell adhesive RGDS (SEQ ID NO:1) were used as controls (FIG. 3).

Figure 20:
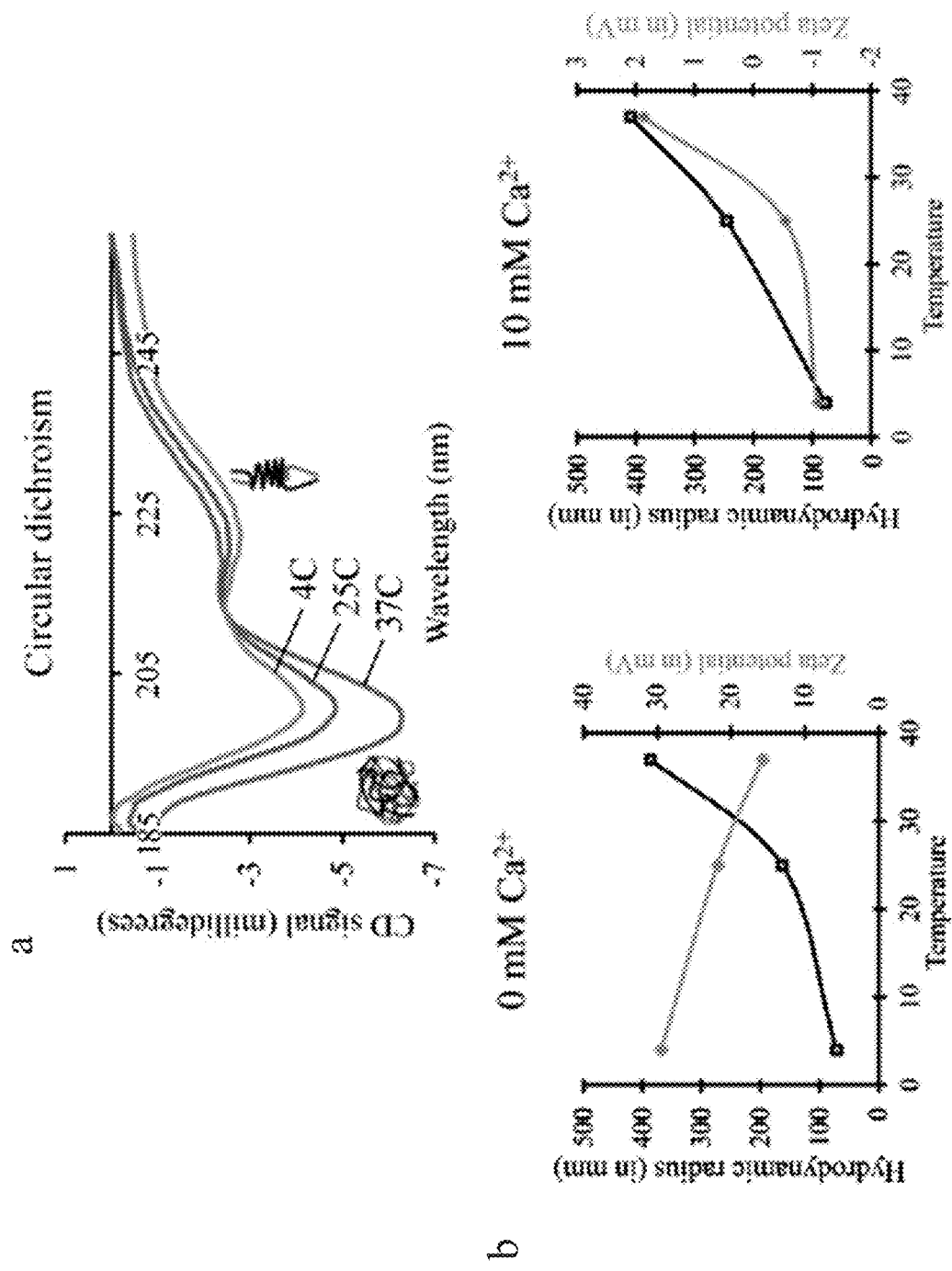
FIG. 20. a) Circular dichroism (CD) of the statherin-ELP molecule at 4, 25, and 37° C.; showing an increase in β-spiral population at the expense of the random-coils, above its inverse transition temperature. b) Dynamic light scattering showing both the hydrodynamic radii and zeta potential of the statherin-ELP in deionized water (left) and in 10 mM calcium solution (right), evidencing the strong calcium binding to the statherin-ELP polypeptides. c) SEM images of the mineralization of the membranes at different temperatures below (4 and 21° C.) and above the Tt (37° C.). The hierarchical mineralized structures were observed at temperatures above the Tt. d) Quantification of the number and size of the hierarchical mineralized structures of different molecules, showing an increase in number and decrease of sizes of the structures grown on statherin-ELP membrane compared to the bigger sized but fewer structures when grown on RGDS-ELP membranes. e) Schematic depicting the mechanism of growth of the hierarchical mineralized structures at the molecular level as function of temperature and calcium binding FIG. 21. SEM images of mineralized membranes at small increments of temperature to see the effect of the transition temperature of the molecules on the formation of the hierarchy.
Figure 20:
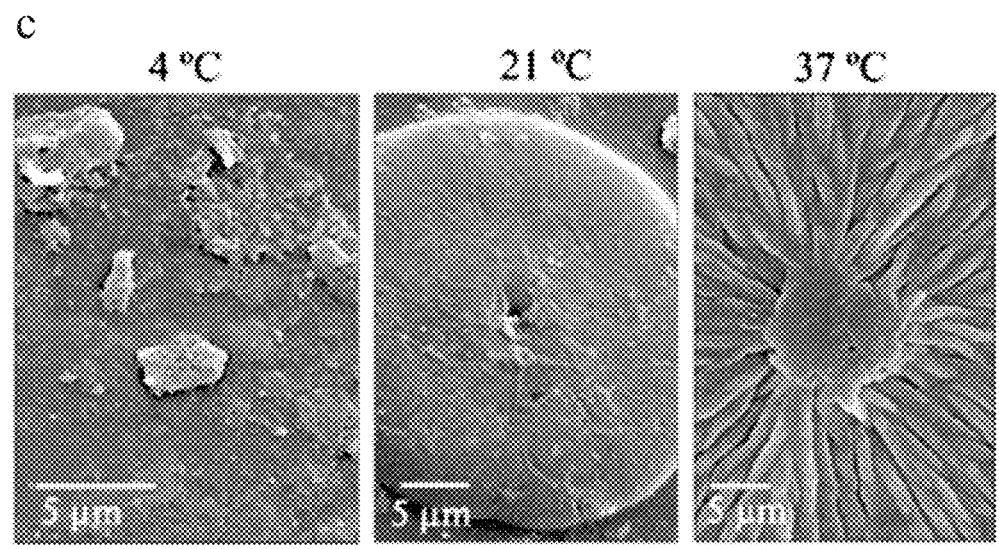
Figure 20:
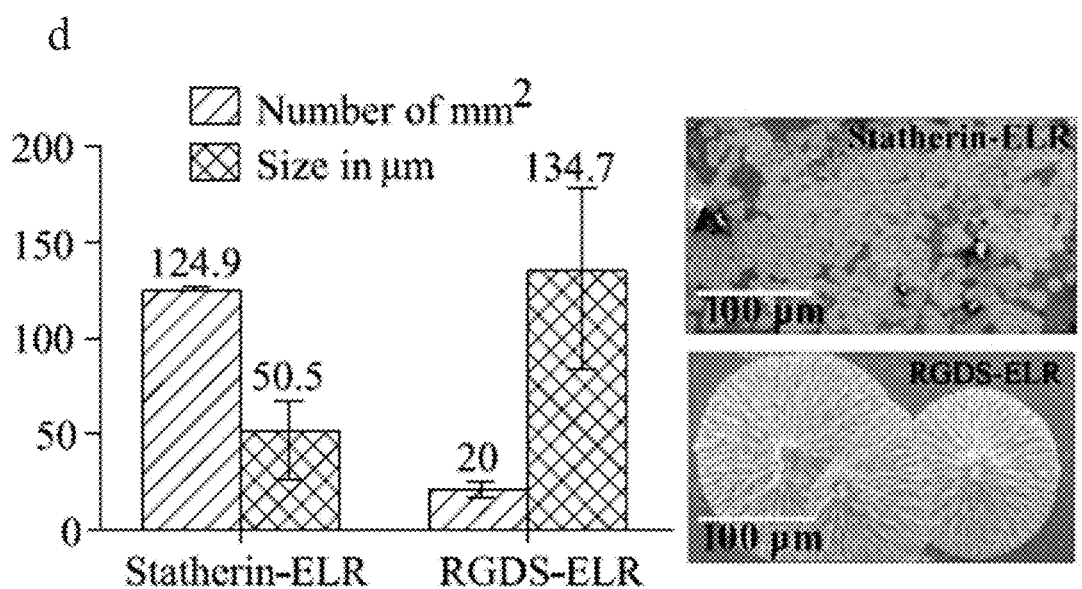
Figure 20:
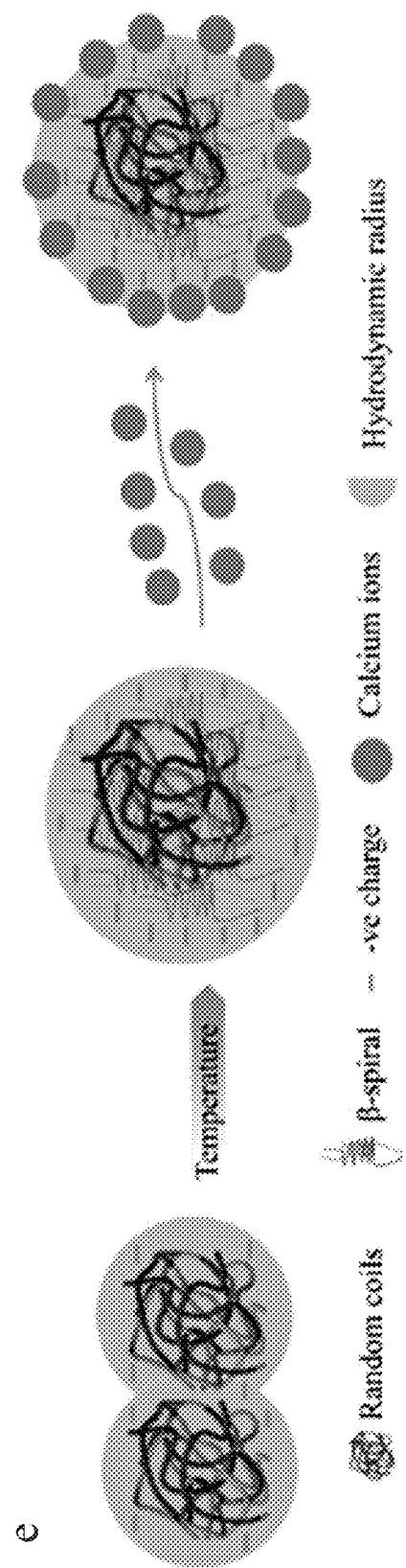

Upon incubation in the supersaturated solution as described in the methodology section, a mineralization process develops within the bulk of the ELP membrane (FIG. 2), which results in the growth of a distinctive hierarchically-ordered mineralized structure (FIG. 1a-d-e-f-g) on both sides of the membrane (FIG. 20). The structures were not observed on the collagen membrane controls (FIG. 3d) while the ELP-coated glass surfaces only exhibited flat platelet-like crystals (FIG. 3b-c). Interestingly, the control ELP membranes exhibited similar hierarchical structures but less in number compared to membranes made with the statherin-derived ELP. As elaborated below, while both the statherin-derived and ELP sequences play a role in the mineralization process, an optimum physicochemical environment within the membrane is of fundamental importance.

The mineralized structures exhibit a distinctive hierarchical architecture that mimics natural enamel at several length-scales (FIG. 1a). At the crystallographic length-scale, the material is apatitic (FIG. 1h) in the form of elongated nanocrystals of on average 85±22 nm thick (FIG. 1a). At the microscale, these crystals are organized further into enamel prism-like microstructures of on average 3.8±0.9 µm thick and tens of microns long (FIG. 1a). These microstructures grow radially and assemble into circular structures that can reach up to 1 mm (FIG. 1d) in diameter and 70 µm in height (FIG. 20), while coming together, interlocking (FIG. 1e-g) and populating large areas (FIG. 1e-f). This hierarchical mineralization can produce membranes that are fully mineralized not only on the surface but throughout their cross-section (FIG. 1f). Highly aligned nanocrystals covering large surfaces aiming to recreate enamel, using either wet chemical processes (Chen, H. et al. Acellular synthesis of a human enamel-like microstructure. Advanced Materials 18, 1846-1851 (2006), Chen, H. et al. Synthesis of Fluorapatite Nanorods and Nanowires by Direct Precipitation from Solution. Cryst Growth Des 6, 1504-1508 (2006)) or organic matrices (Busch, S. Regeneration of human tooth enamel. Angewandte Chemie—International Edition 43, 1428-1431 (2004), Mukherjee, K., Ruan, Q., Liberman, D., White, S. N. & Moradian-Oldak, J. Repairing human tooth enamel with leucine-rich amelogenin peptide-chitosan hydrogel. Journal of Materials Research 31, 556-563 (2016)), have been reported. However, our system enables the growth of apatite crystals with a distinctive hierarchical order, expanding from the crystallographic-, nano-, micro-, and up to the macro-scale. Furthermore, the prismatic structures not only exhibit regular and reproducible sizes comparable to native enamel prisms, they also display a periodicity of approximately 1 µm intervals (FIG. 1g), incidentally mimicking the daily incremental lines of dental hard tissues. To demonstrate the importance of such hierarchical organization, we conducted nanoindentation tests using an atomic force microscope (AFM). Remarkably, the Young's modulus of the mineralized membranes (127.7 Mpa±41.8 Mpa) was just under three times higher than that of human dental enamel (46.3 Mpa±16.1 Mpa) and comparable to sapphire (161.3 Mpa±12.1 Mpa) (FIG. 1c). It is important to keep in mind that, while the nanoindentation test used is highly localized (test radius of 50-100 nm), it is a well-established method that accurately provides an estimation of bulk mechanics, which is especially useful when comparing different materials (Dickinson, M. E. & Schirer, J. P. Probing more than the surface. Materials Today 12, 46-50 (2009)). In contrast, previous studies aiming to recreate enamel through highly aligned nanocrystals have resulted in lower Young's moduli compared to enamel, which has been associated with the lack of hierarchical prismatic-interprismatic structure (Ruan, Q. & Moradian-Oldak, J. Development of amelogenin-chitosan hydrogel for In Vitro enamel regrowth with a dense interface. Journal of Visualized Experiments (2014)).

Figure 26:
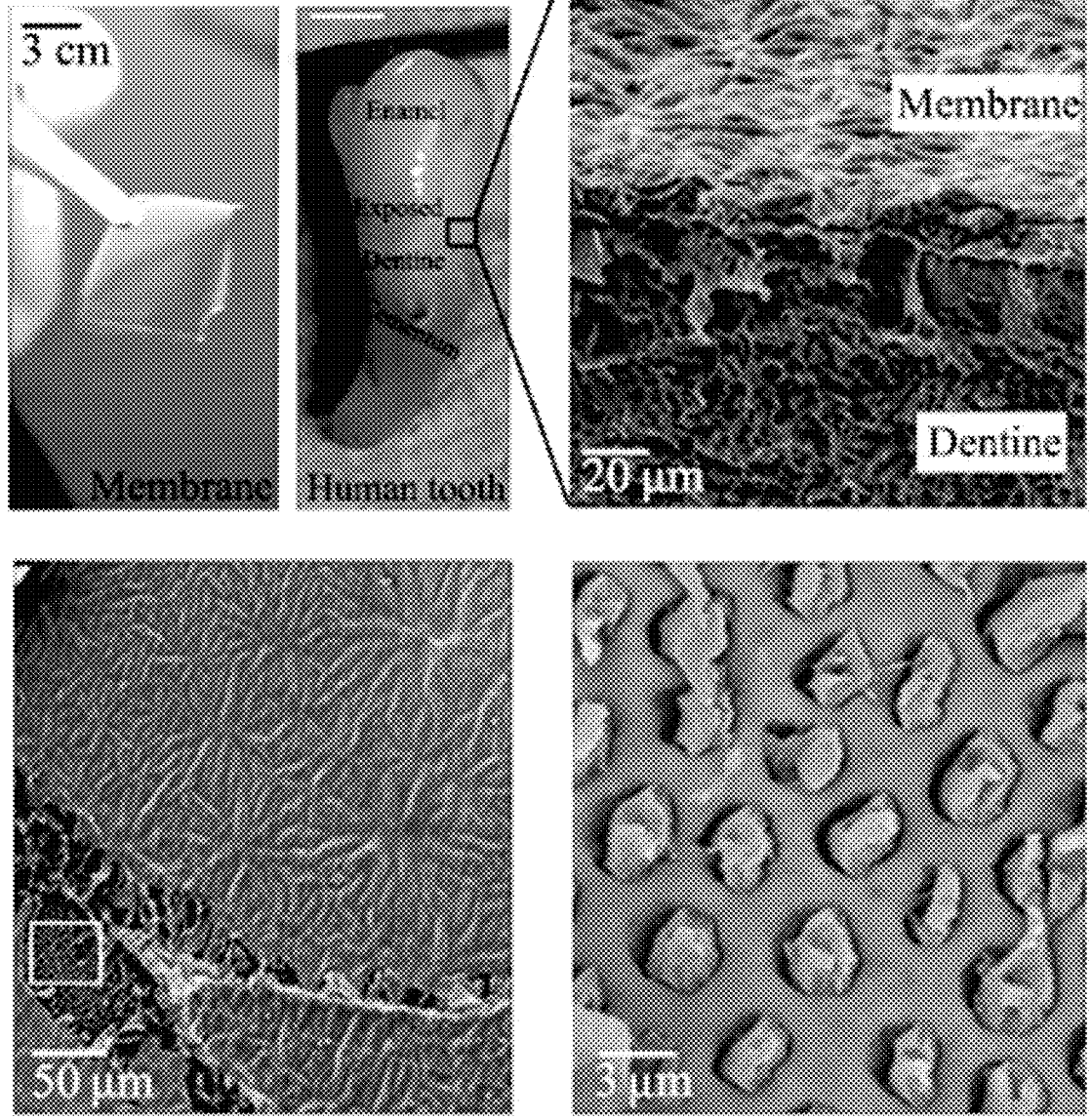
FIG. 26. a) Application of the in-situ cross-linked ELP membrane conformed over the rough and uneven surface of exposed human dentine, exhibiting the hierarchical mineralized structures as a coating on top of the native tissue. At closer magnification, the membranes were able to infiltrate, bind, and occlude the open dentinal tubules structures. b) FIB milling of the mineralized coating at different depths to observe the dentine-membrane interface, where the thickness of the coating is about 10 μm, at which it exhibits infiltration of nanocrystals emerging from the hierarchically organized structures grown from the ELP membrane, and in turn blockage of the dentinal tubules. c) SEM images showing the effect of the acid attack at different timepoints (0, 15 minutes, and 7 days) on both human dental enamel (top) and the hierarchical mineralized structures (bottom), both showing a level of resistance of the nanocrystals to the acid at early time-point in comparison to 7 days. d) Graph illustrating the stiffness of the different treated mineralized, unmineralized membranes, and human enamel to the acid attacks. e) DDC-SEM images of the hierarchical mineralized structures after the enzymatic digestion, showing less dense organic material (arrow) in comparison to before treatment (more green), however, no effect was observed on the highly dense inorganic nanocrystals after the ELP degradation.
Figure 26:
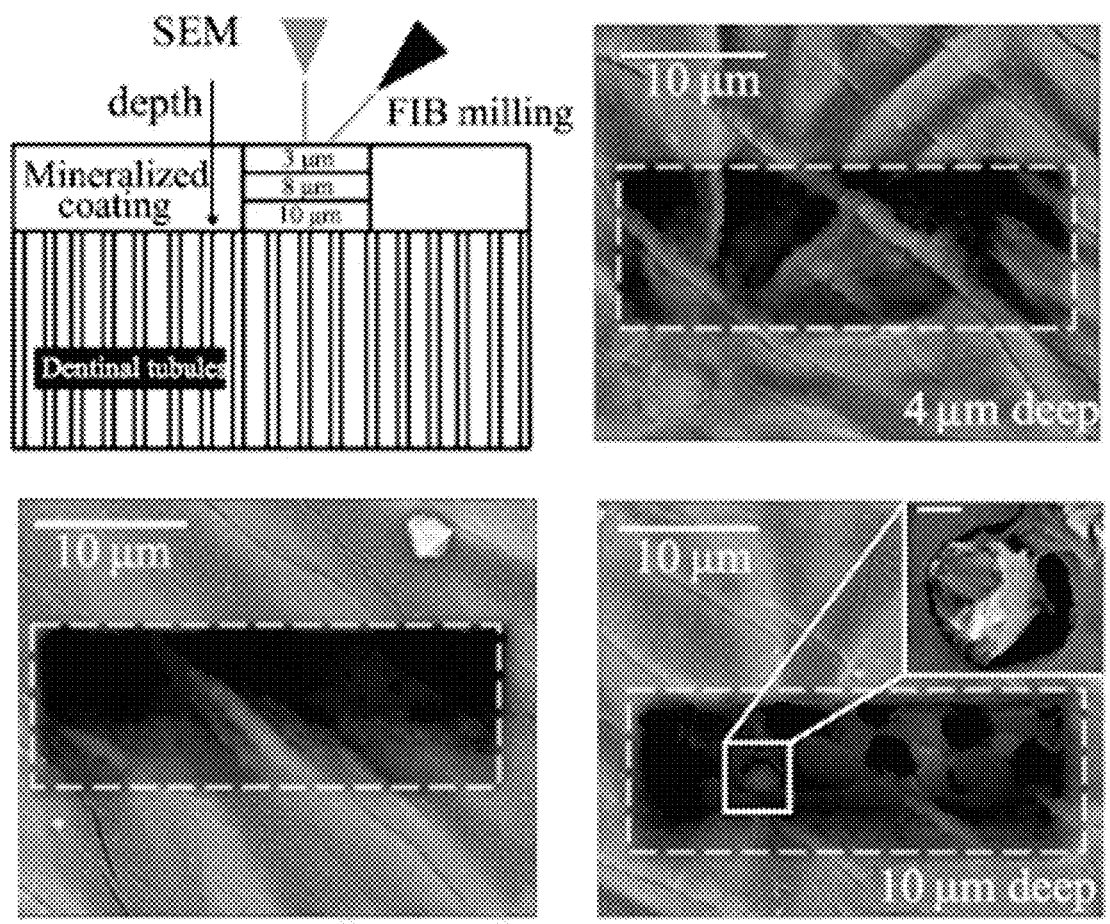
Figure 26:
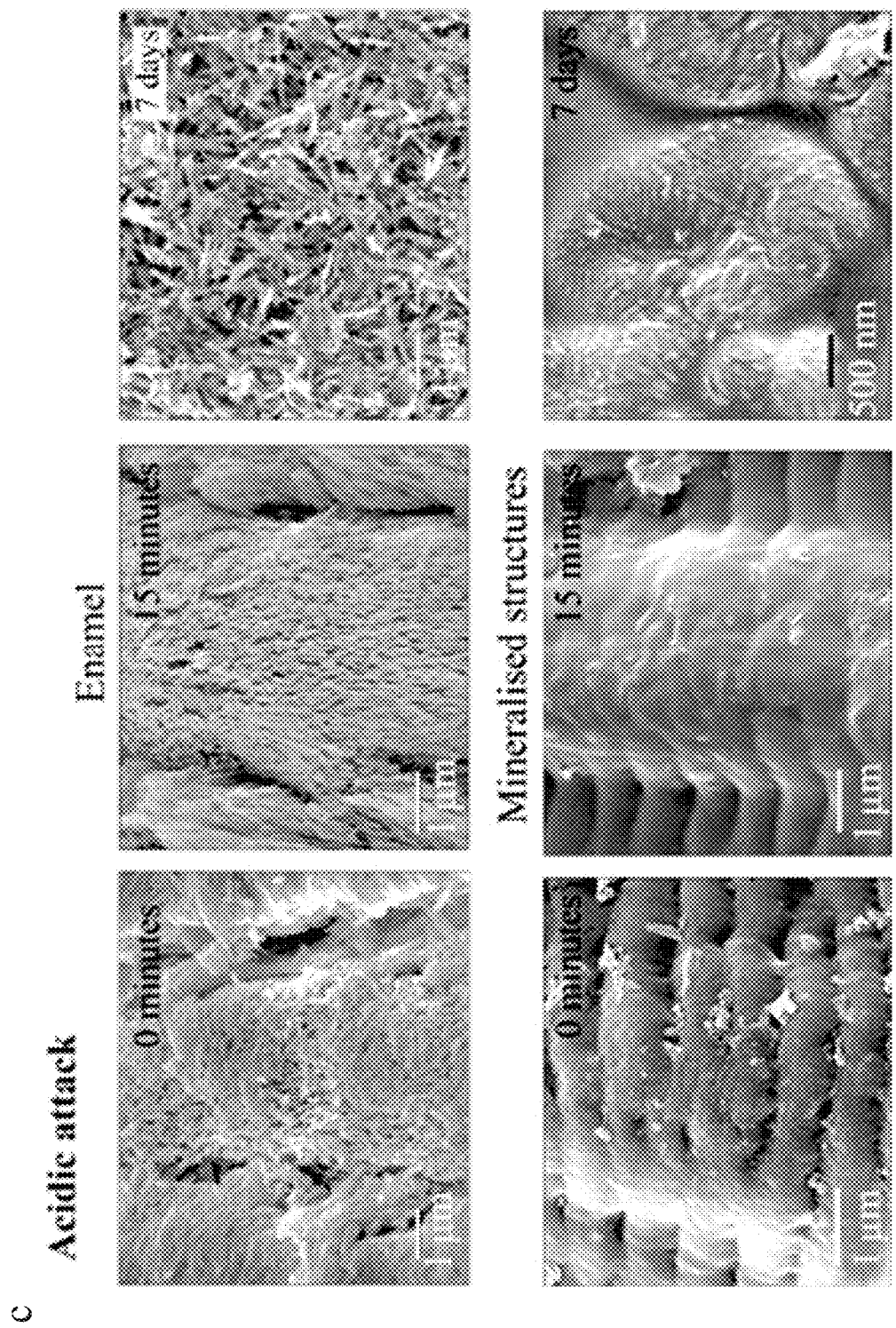
Figure 26:
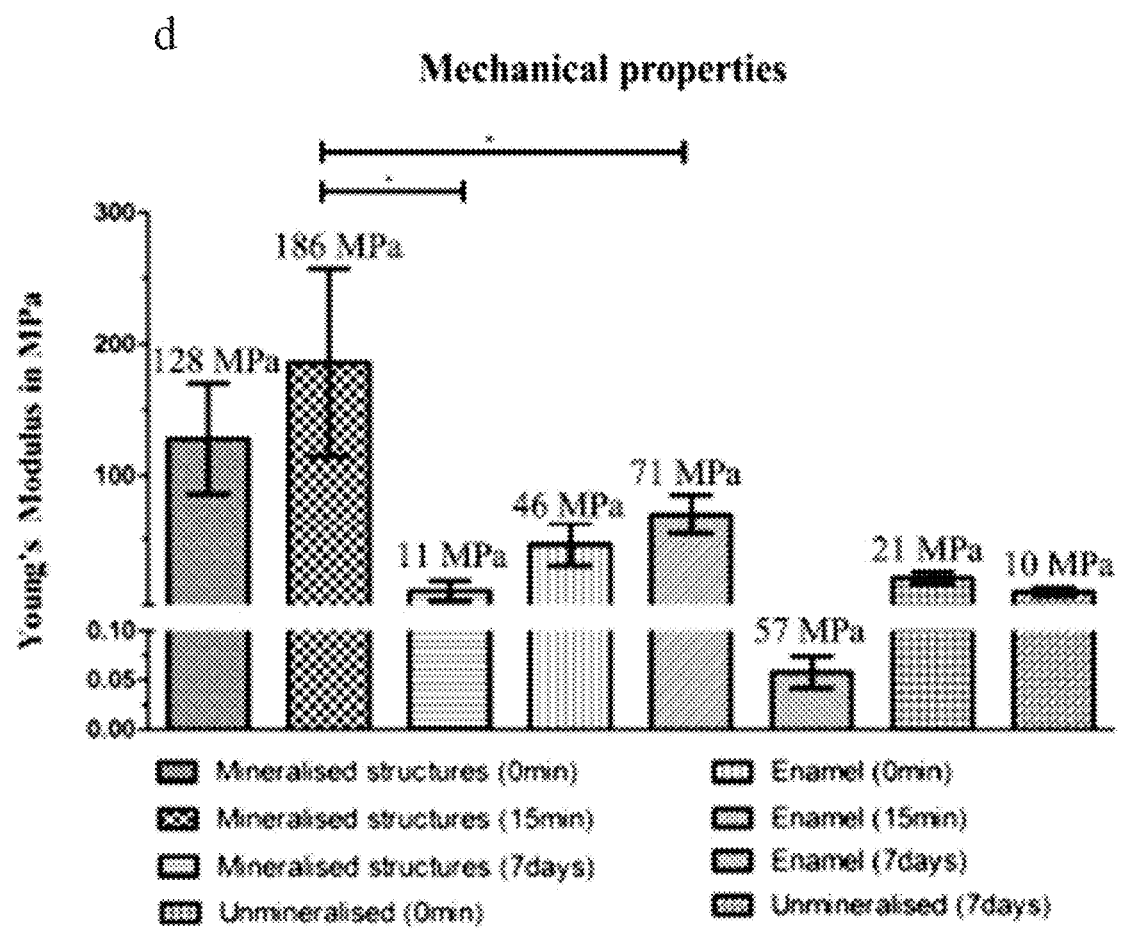
Figure 26:
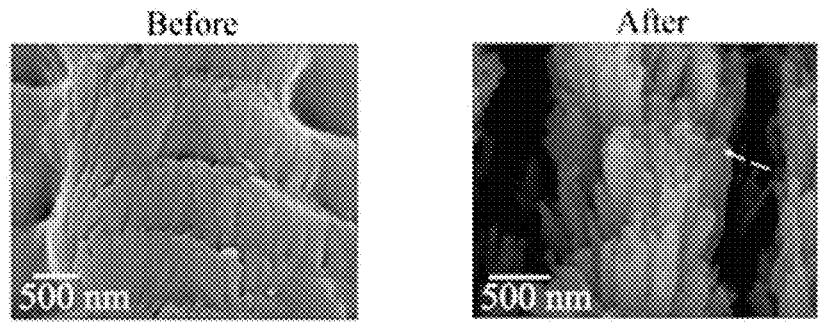

Rietveld modelling of X-ray diffraction (XRD) demonstrated that the crystalline phase of the structures matches fluorapatite (Fap) with a space group, unit cell size, and structural parameters matching Fap values, as reported in the literature (FIG. 1h). The results are confirmed by Fourier Transform infra-red (FTIR) spectroscopy analysis, which revealed spectra exhibiting amide peaks before undergoing mineralization (corresponding to the ELP material), while after mineralization they exhibited hydroxyl-free apatite peaks (FIG. 23) (Baddiel, C. B. & Berry, E. E. Spectra structure correlations in hydroxy and fluorapatite. Spectrochimica Acta 22, 1407-1416 (1966)). This suggests substitution of hydroxyl groups by fluoride ions into the crystal lattice (Elliott, J. C. Structure, crystal chemistry and density of enamel apatites. CIBA Foundation Symposia, 54-72 (1997)). In addition, energy dispersive X-ray (EDX) spectroscopy point and mapping spectra also indicated the presence of calcium, phosphorus, and fluoride (FIG. 23) with atomic ratios similar to stoichiometric apatite crystals and dental hard tissues. This crystalline phase was further confirmed by 19F MAS-NMR spectra (Mohammed, N. R. et al. Effects of fluoride on in vitro enamel demineralization analyzed by 19F MAS-NMR. Caries Research 47, 421-428 (2013)), which verified the presence of a Fap peak at −103 ppm (FIG. 1i). A fluorite (CaF2) peak at −108 ppm was also observed. However, the presence of the organic ELP matrix increased the Fap phase at the expense of the undesirable fluorite phase, which would further benefit its application. In addition, our system also enables the formation of similar hierarchical structures but without the use of fluoride, which results in similar microscopic prisms made of assembled elongated plate-like apatite nanocrystals (FIG. 26).

Figure 7:
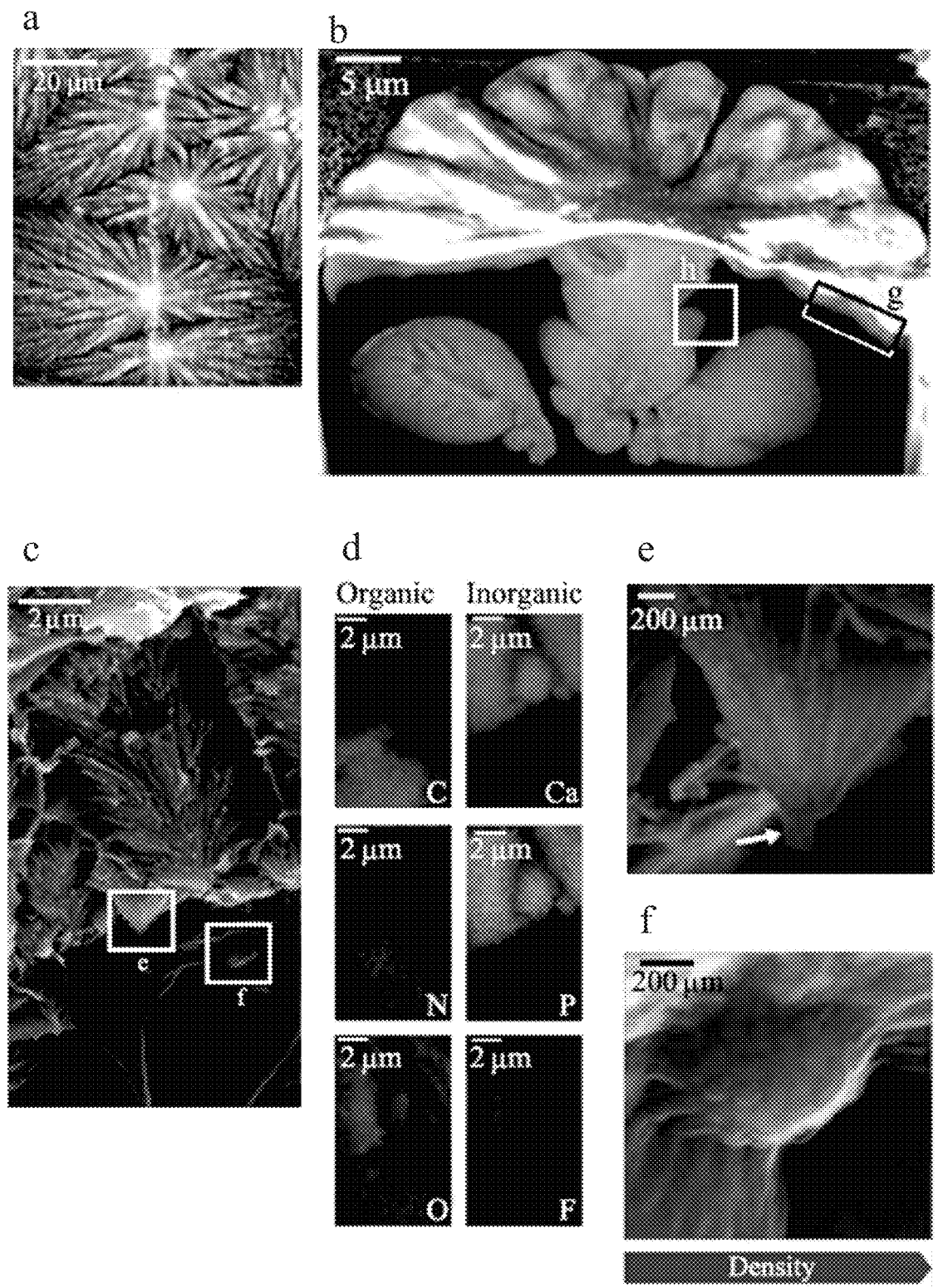
FIG. 7. a) BSE images showing brighter areas at the centre of the structures that indicate the presence of mineral deep within the membrane. b) FIB sectioning of the hierarchically mineralized structure on RGDS-ELP resolving the deeper mineralized core structures located underneath the centre of the structures. c) Cross-section of the RGDS-ELP membrane after 8 days of mineralization showing the two different morphologies found within the bulk; enamel prism-like (e) and round structures (f) found within the membrane and suggesting the presence of ionic gradient. d) EDX mapping at the same area of the SEM image (c), near the surface of the membrane, calcium, phosphorus, fluoride, and oxygen are abundant representing the enamel prism-like crystalline structures. Away from the surface, carbon, nitrogen, and oxygen elements exhibit higher signals reflecting the organic nature of the membrane. This elemental distribution gives an indication of the presence of both organic and inorganic materials. e,f) DDC-SEM images showing the enamel prism-like and round structures comprising of a dense material covered by a less dense material. g) TEM image from a FIB milling liftout from a region of (b), showing a higher magnification of the prismatic structure and its corresponding directionality and co-alignment of the crystals. h) TEM image at the growing interface between the inorganic crystals and organic material with corresponding SAED patterns. i) High-resolution TEM images and their Fast Fourier Transforms showing the arrangement of the apatite crystals and its 10° co-alignment.
Figure 7:
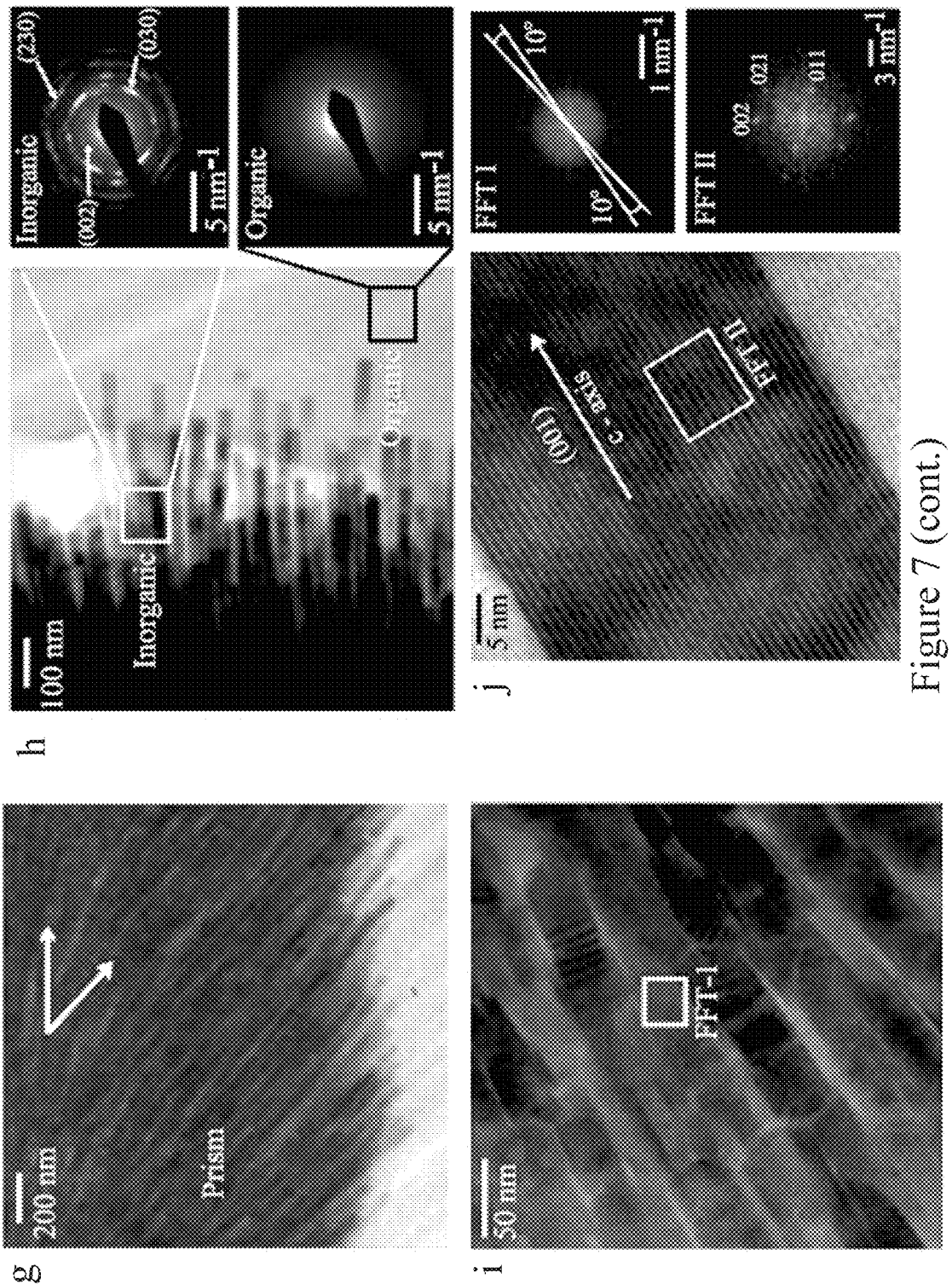
Figure 9:
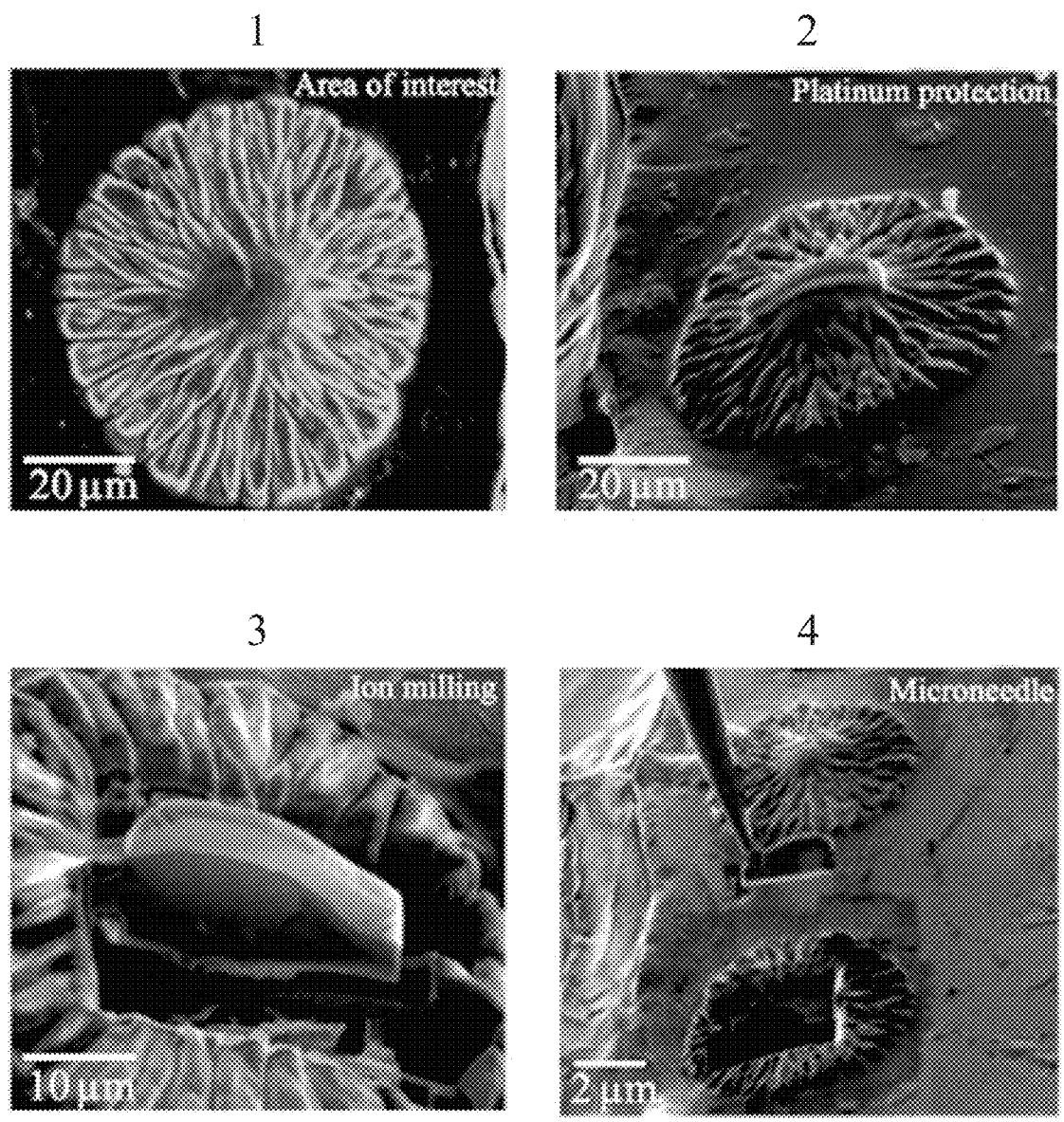
FIG. 9. Series of SEM images (1-6) showing the procedures followed to prepare the samples for the TEM liftout using FIB. The lamella is thinned down in order to be transmitting electrons through using the TEM for structural and crystallographic information (7).
Figure 9:
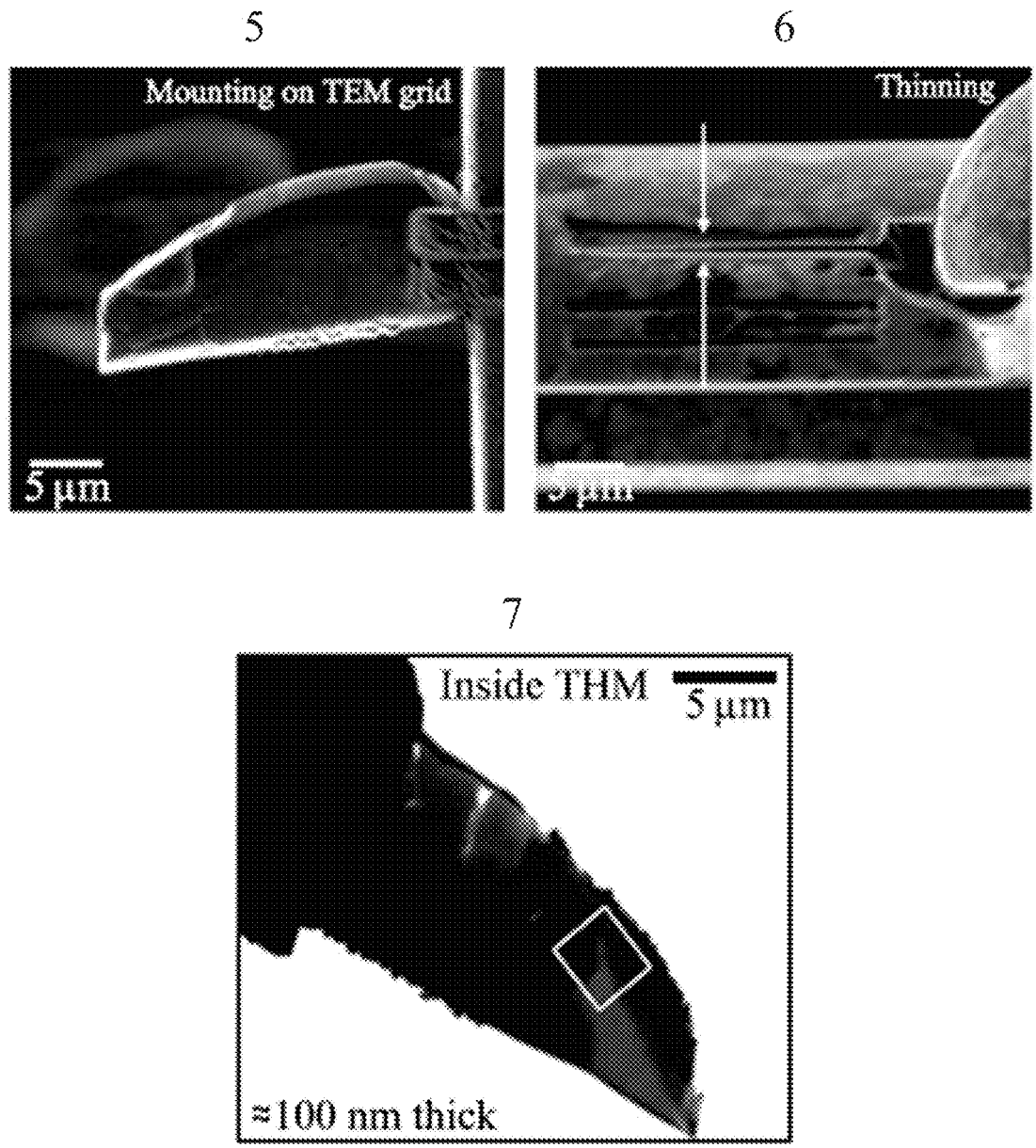
Figure 10:
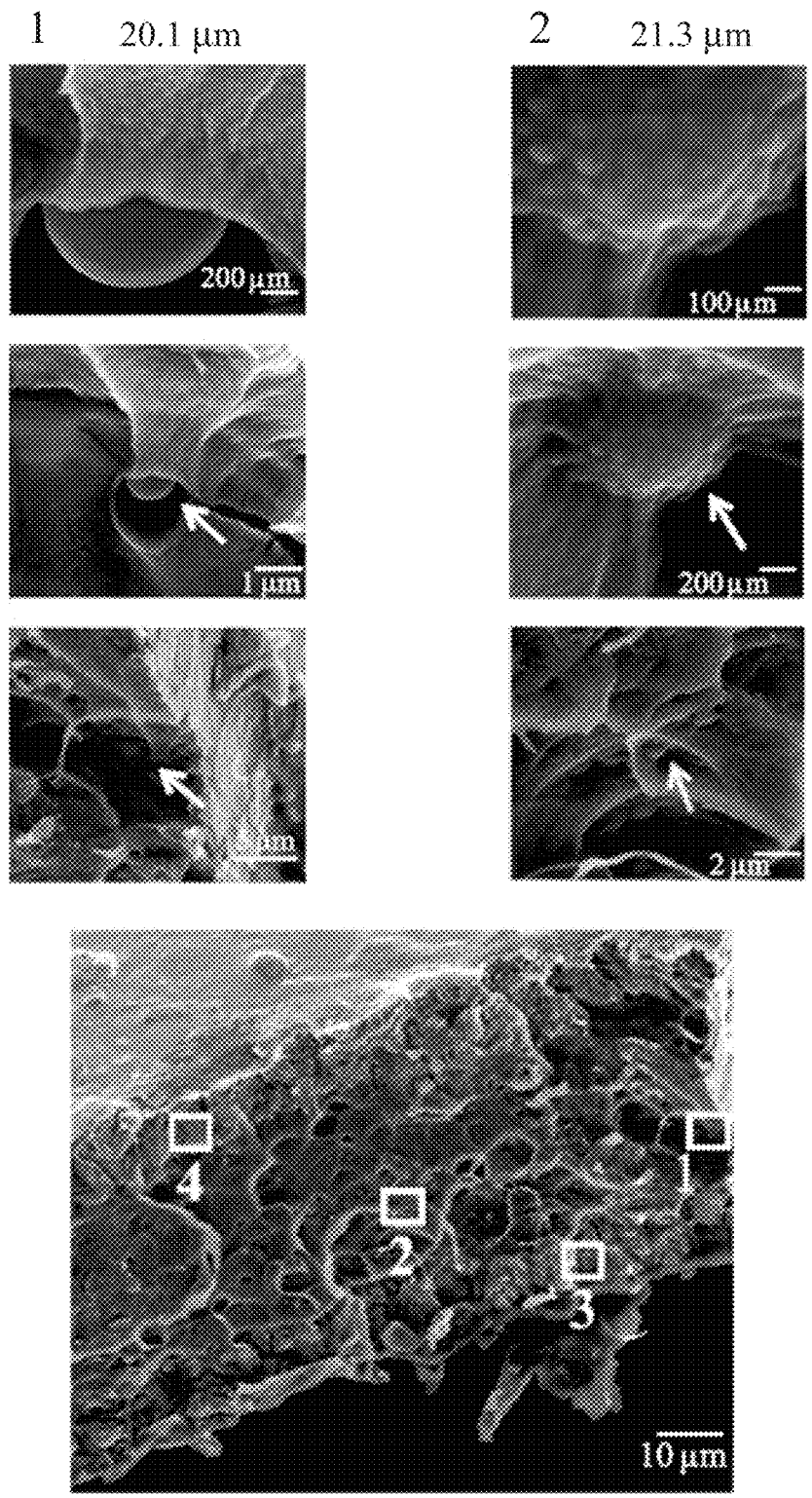
FIG. 10. SEM images showing the nucleation and crystal growth within the bulk of the organic matrix revealed different structures. Round structures exhibiting a dense pattern of regular granular regions were observed deep within the bulk of the membrane while core structures made from nanocrystals oriented at 102±6° with respect to the surface of the membrane were observed nearer the surface. It is possible that these two types of structures represent different stages of development of the mineralized cores, suggesting the presence of an ionic gradient across the cross-section of the organic matrix.
Figure 10:
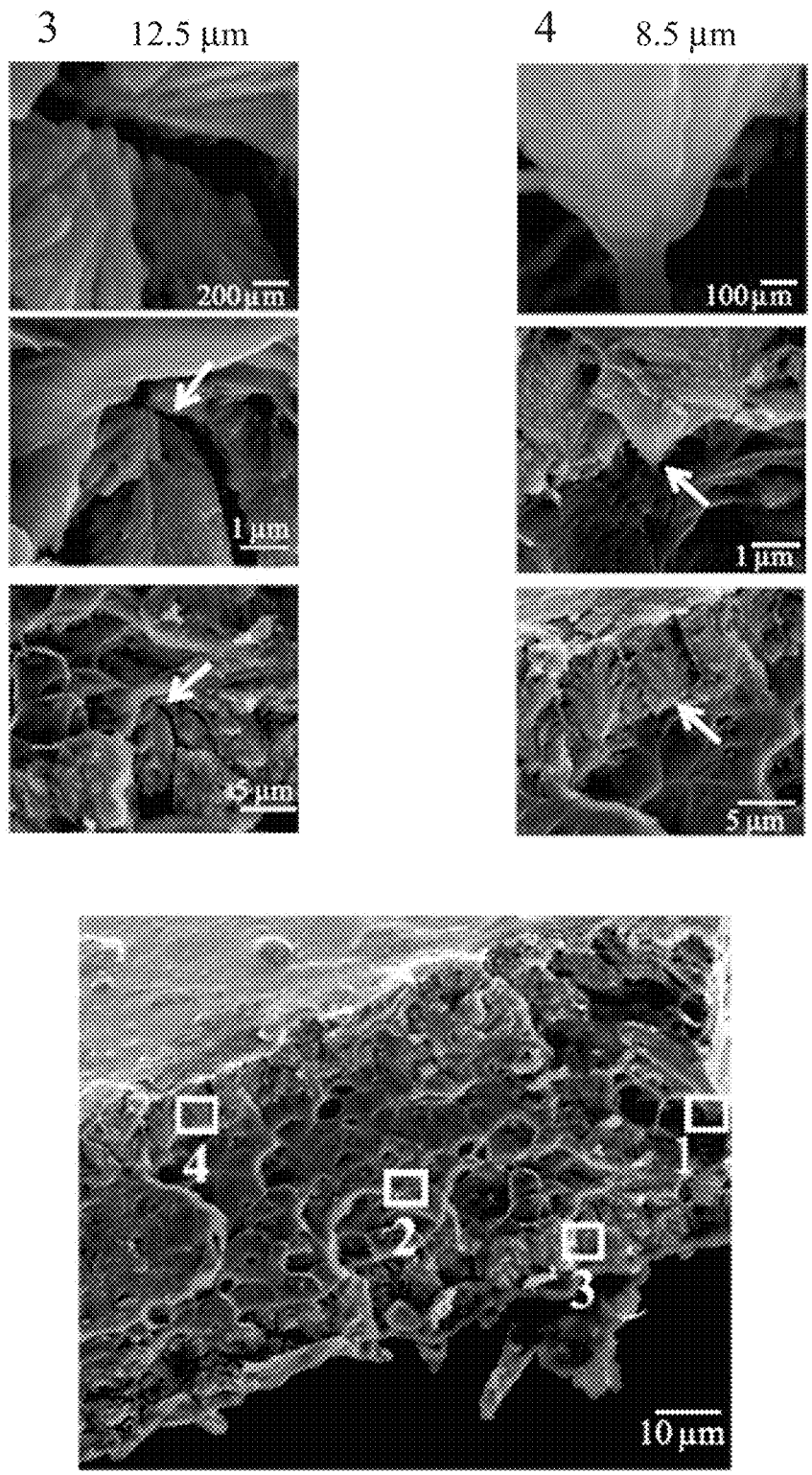
Figure 11:
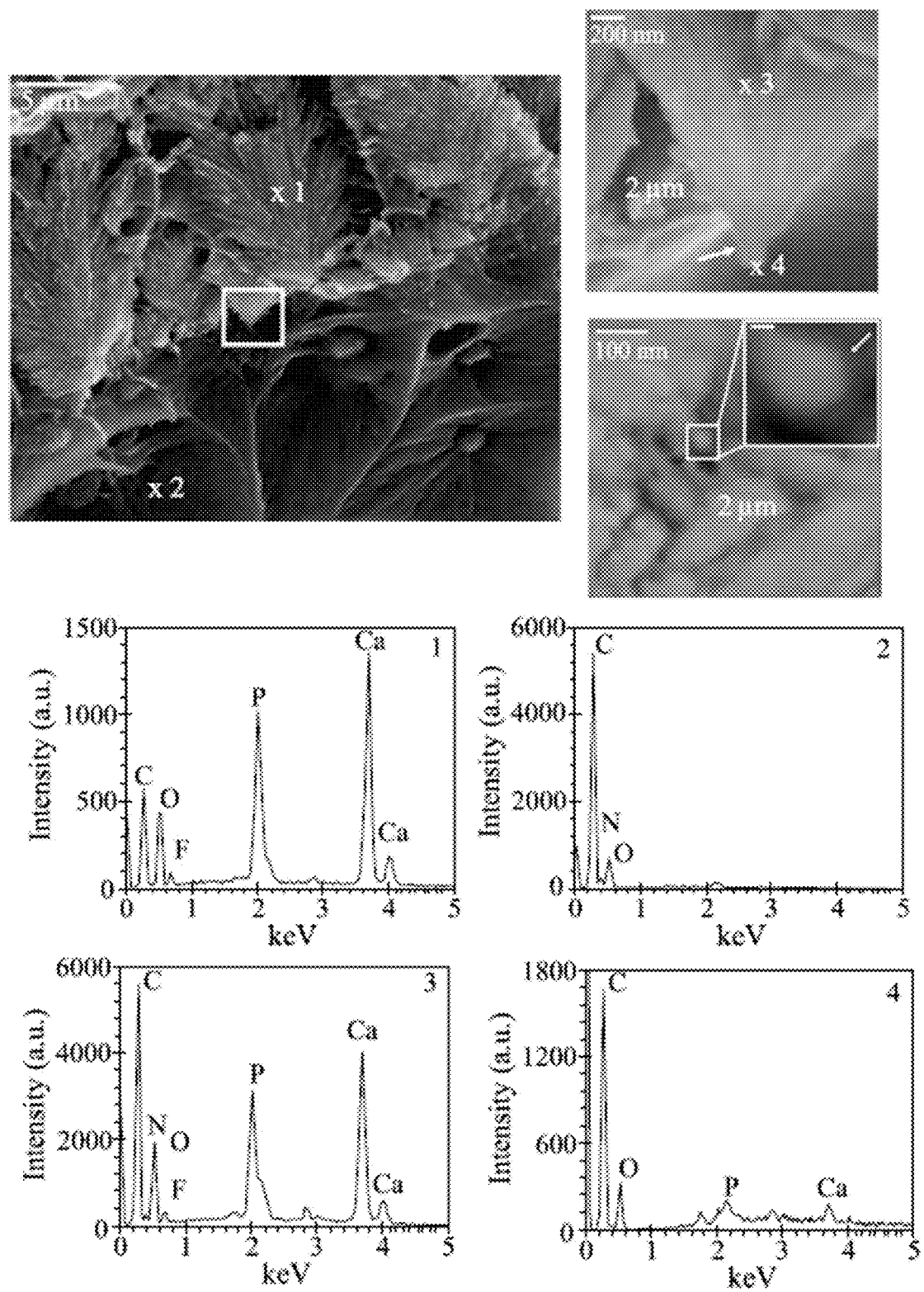
FIG. 11. Closer examination using DDC-SEM and EDX spectral mapping of both of these structures revealed a thin less dense material (green) surrounding a denser (orange) material. The less dense material was found to be rich in carbon, oxygen, and nitrogen, which is commonly found in organic material. In contrast, the denser material exhibited abundance of calcium and phosphorus, which reflects its inorganic nature.
Figure 12:
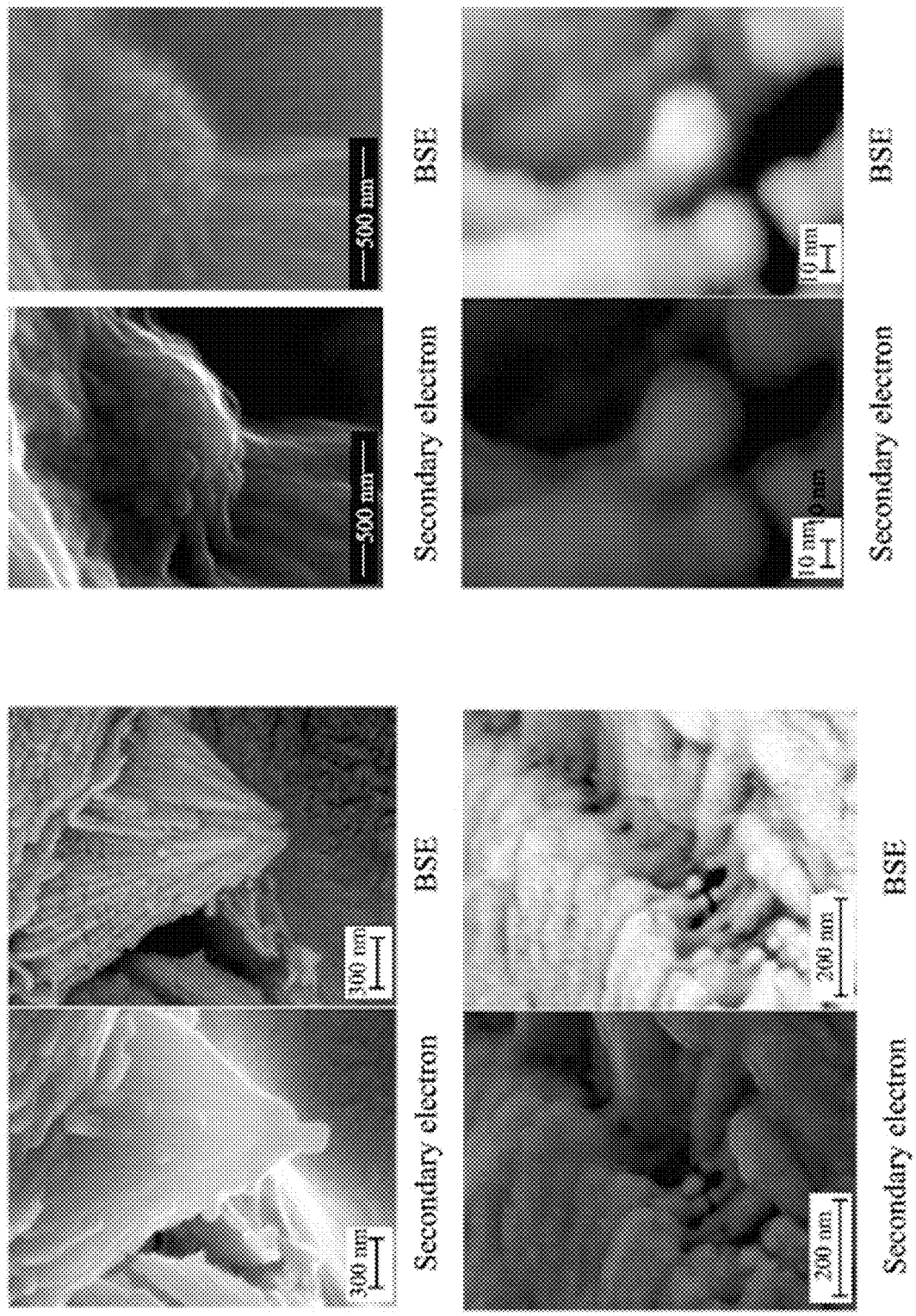
FIG. 12. SEM and BSE images taken simultaneously from same area to allow density-dependent analyses (DDC-SEM). BSE images show clearly the disappearance of the thin coating around the crystals giving an indication of the presence of the less dense material surrounding the crystals. The less dense material is confirmed in to be rich of carbon, nitrogen and oxygen, giving indication of its organic nature according to EDX data (FIG. 11).

Discussion of FIGS. 7 to 12 electron microscopy (SEM) using the backscattered electron mode (BSE) (FIG. 7a) and focused ion beam (FIB) revealed that the mineralized structures exhibit a mineralized core deep within the membrane made from similar elongated and aligned nanocrystals (FIG. 7b and FIG. 8). As the hierarchical structures spread radially on the surface, the nanocrystals within the prisms in closer proximity to the ELP matrix change their orientation gradually from parallel to the surface towards the inside of the membrane (FIG. 7g). This suggests that there is a preference for the nanocrystals to grow in the presence of the organic ELP matrix. To further investigate this organic-inorganic relationship within the system and its effect on the crystallographic orientation of the nanocrystals, ultrathin sections were milled via FIB and analyzed by transmission electron microcopy (TEM) and selected area electron diffraction (SAED) (FIG. 7g-h, and FIG. 9). The results further confirm this intimate relationship; first by the presence of embedded nanocrystals within the amorphous organic material and second by the flat geometry at the end of the nanocrystals (FIG. 7h), which suggest their continuous growth within the matrix. Organic matrices have been used to grow aligned needle-like nanocrystals (Ruan, Q., Zhang, Y., Yang, X., Nutt, S. & Moradian-Oldak, J. An amelogenin-chitosan matrix promotes assembly of an enamel-like layer with a dense interface. Acta Biomaterialia 9, 7289-7297 (2013)), a geometry that is observed in systems that do not rely on organic matrices (Chen, H. et al. Synthesis of Fluorapatite Nanorods and Nanowires by Direct Precipitation from Solution. Cryst Growth Des 6, 1504-1508 (2006)). In contrast, our system enables the growth of embedded flat-ended nanocrystals at the c-axis (FIG. 7h-i-j), which resembles the crystal growth in developing biomineralized tissues such as dental enamel where an organic matrix plays a central role (Simmer, J. P. & Fincham, A. G. Molecular mechanisms of dental enamel formation. Critical Reviews in Oral Biology and Medicine 6, 84-108 (1995)). To better understand the mineralization within the bulk of the organic matrix, Fast Fourier Transform (FFT) analysis was conducted and revealed that the nanocrystals are stacked and oriented towards the c-axis with a 10° co-alignment, which may contribute to the spherulitic radial geometry of the hierarchical structures (FIG. 7i-j) (Shtukenberg, A. G., Punin, Y. O., Gunn, E. & Kahr, B. Spherulites. Chemical Reviews 112, 1805-1838 (2012)). This result further demonstrates the central role of the organic matrix in our mineralization system (Van de Locht, R. et al. Microstructural evolution and nanoscale crystallography in scleractinian coral spherulites. Journal of Structural Biology 183, 57-65 (2013)). Further analysis using density-dependent color SEM (DDC-SEM) and EDX spectroscopy of the nucleation and crystal growth within the bulk of the organic matrix revealed different structures (FIG. 7b-c and FIG. 10). Round sub-micron structures exhibiting a dense pattern of regular granular regions were observed deep within the bulk of the membrane (FIG. 7f) while core structures made from nanocrystals oriented at $102\pm_6°$ with respect to the surface of the membrane were observed nearer the surface (FIG. 7e and FIG. 11). It is possible that these two types of structures represent different stages of development of the mineralized cores, which, as elaborated later, suggests the presence of an ionic gradient across the cross-section of the organic matrix. Closer examination using DDC-SEM and EDX spectral mapping of both of these structures revealed a thin less dense material (green) surrounding a denser (orange) material. The less dense material was found to be rich in carbon, oxygen, and nitrogen, which are commonly found in organic material. In contrast, the denser material exhibited abundance of calcium and phosphorus, which reflects its inorganic nature (FIG. 7d-e-f and FIG. 11-12). This result confirms further the presence of organic-inorganic interactions that take place within the system.

Discussion of FIGS. 13 to 19

Figure 15:
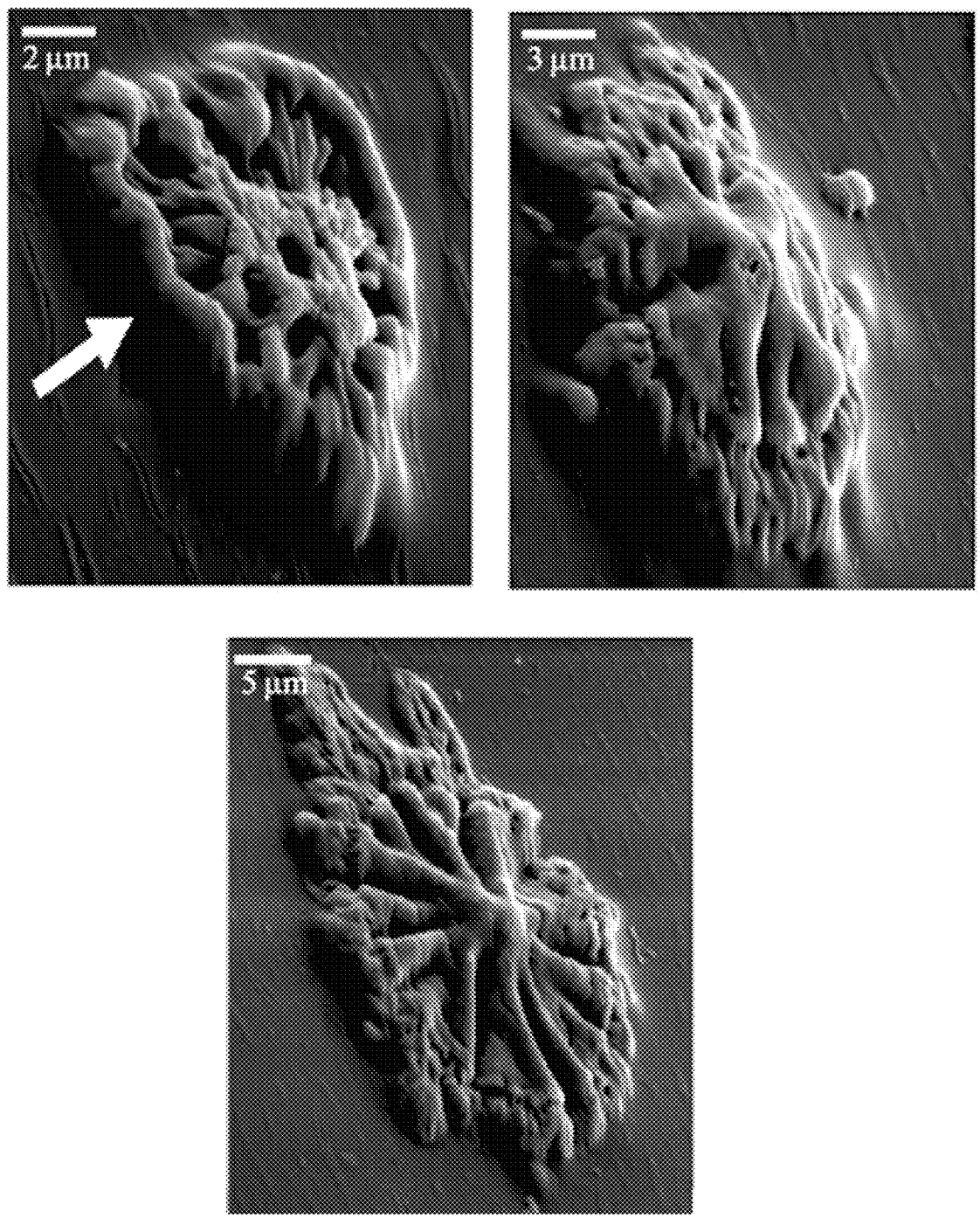
FIG. 15. SEM images showing the progression of the centripetal growth of the hierarchical mineralized structures at different developmental stages (left to right).
Figure 16:
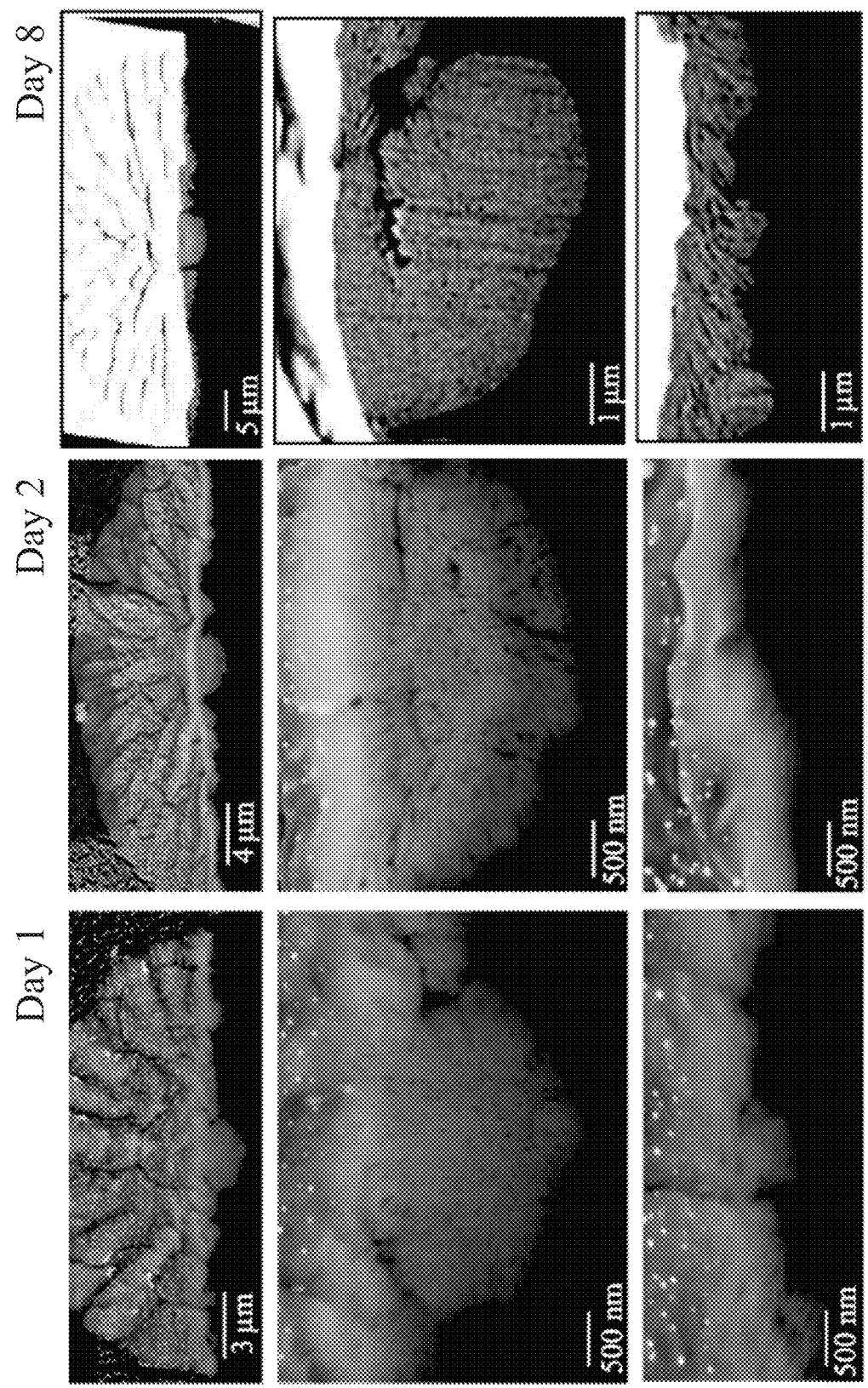
FIG. 16. FIB-SEM analysis of RGDS-ELP revealed that the structures acquired hierarchical definition (FIG. 3b) and volume as a function of time, respectively.
Figure 17:
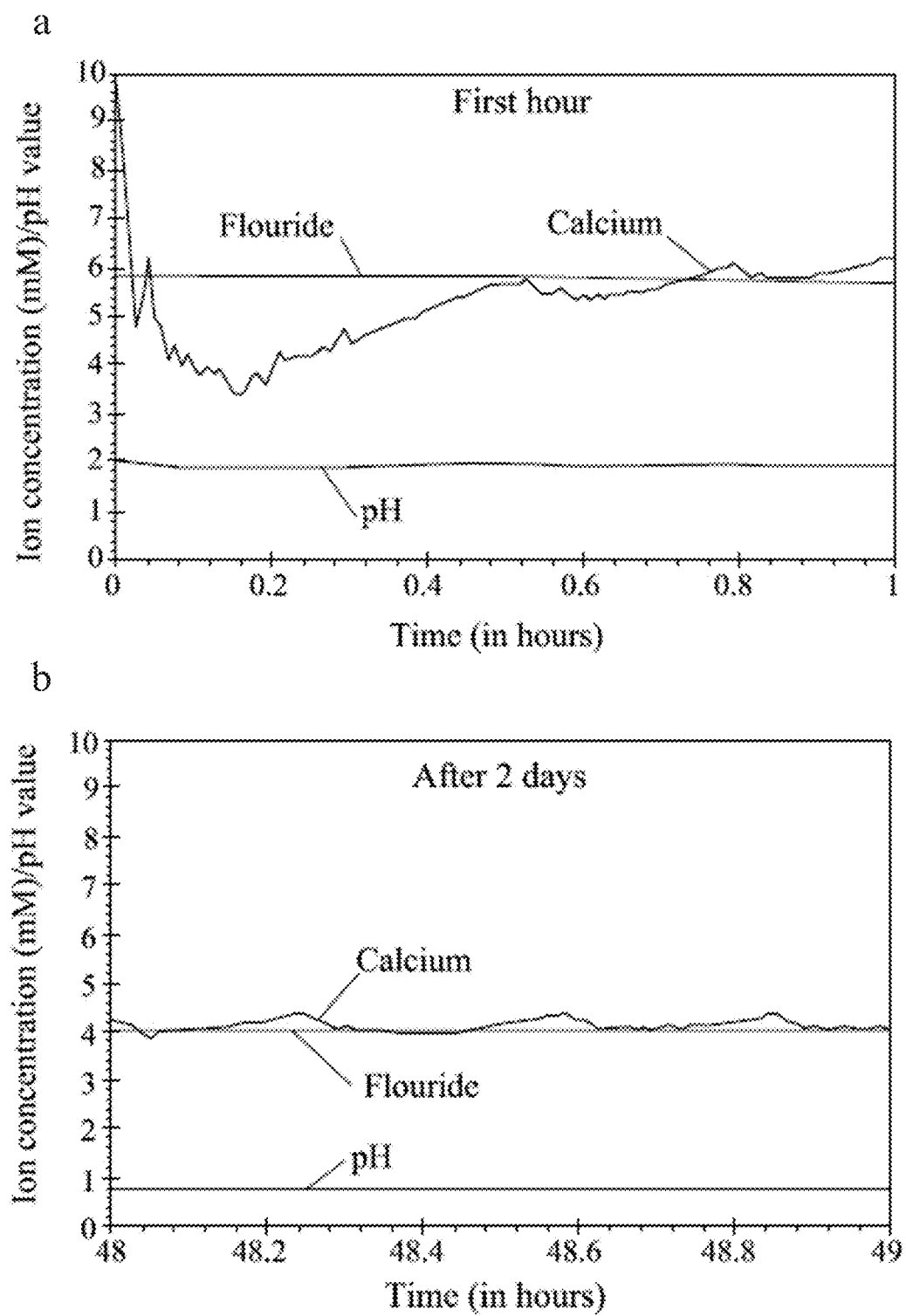
FIG. 17. ISE measurements during a) the first hour and b) after 48 hours. During the first hour, a significant drop in the free calcium ion concentration from 10 mM (initial concentration) to about 3.7 mM is observed, while the fluoride concentration remains fairly constant (a slight drop from 2 mM to 1.9 mM). During the first hour, the consumed calcium to fluoride ratio is about 7:0.1, giving an indication that the precipitated phase does not contain fluoride and therefore it is not fluorapatite where the Ca:F ratio equals 10:6, rather another intermediate phase. This intermediate phase has been identified as brushite using XRD and FTIR. After 48 hours, it is clearly seen that the fluoride concentration drops to half of the initial concentration, giving an indication of phase transformation to fluorapatite under acidic conditions (pH=4.0).
Figure 18:
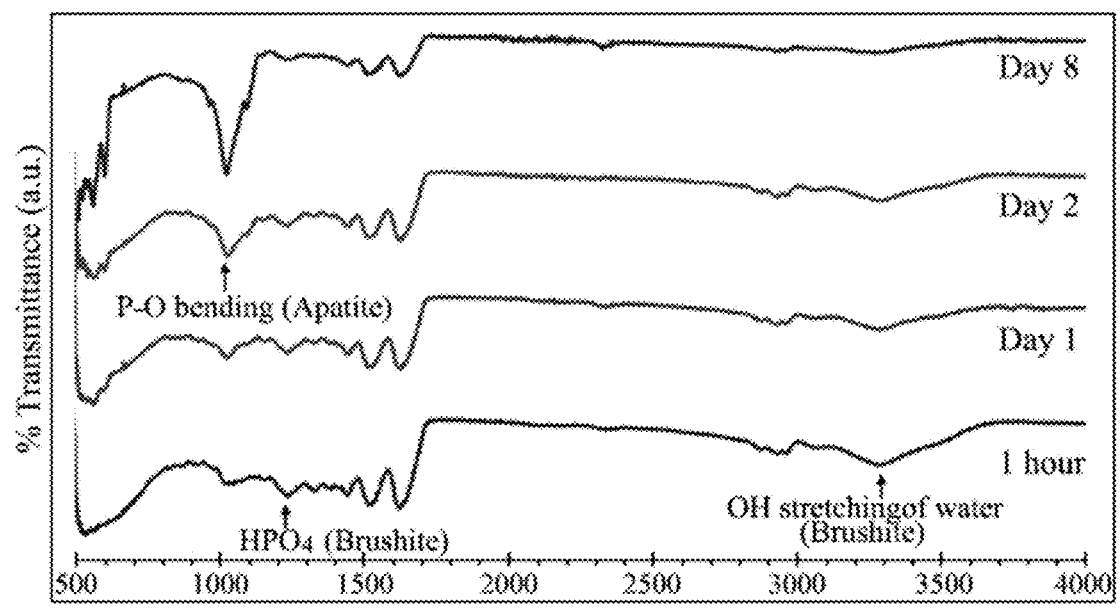
FIG. 18. FTIR spectra of the mineralizing statherin-ELP membrane at different timepoints (1 hour, 1 day, 2 days, and 8 days). At early timepoints, the spectra exhibit the characteristic sharp peak of HPO4-vibration characteristic to brushite (CaHPO4·2H2O) at 1238 cm−1, and OH stretching peak of water molecule of brushite. As a function of time, the % transmittance of the brushite peaks decrease at the expense of the apatite's phosphate peaks, this confirms that brushite is the intermediate crystalline phase before transformation to fluorapatite.
Figure 19:
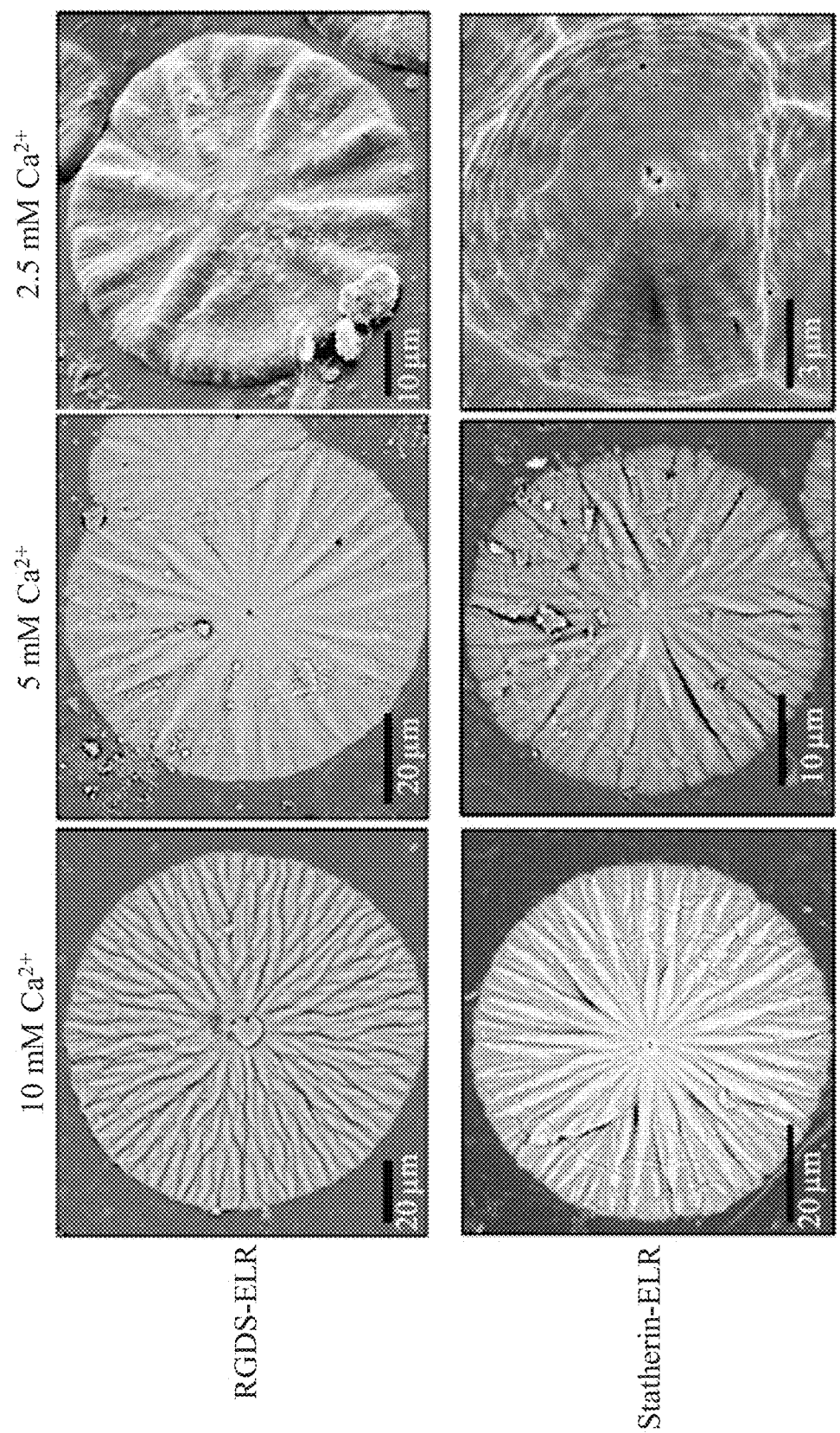
FIG. 19. SEM of images of mineralized membranes at different initial ionic concentrations ranging from 2.5-10.0 mM of $Ca^{2+}$, 1.6-6.0 mM of $PO_4^{3-}$, and 0.5-2.0 of $F^-$, demonstrating that the hierarchical structures form in all conditions independently of the initial ionic strength.

The mineralization process on the surface of the membranes was traced in real-time using time-lapse phase-contrast optical microscopy and confirmed an outward radial growth of the structures (FIG. 13a, and FIGS. 14-15). This centripetal growth may result from the 10° co-alignment along the c-axis of the nanocrystals measured at the crystallographic scale (FIG. 7i). Interestingly, DDC-SEM, which simultaneously enables topographical and density assessment (Bertazzo, S. et al. Nano-analytical electron microscopy reveals fundamental insights into human cardiovascular tissue calcification. Nature Materials 12, 576-583 (2013)), and FIB-SEM analysis revealed that the structures acquired hierarchical definition (FIG. 13b) and volume (FIG. 13c and FIG. 16) as a function of time, respectively. This enhanced hierarchy dramatically increased the stiffness of the structures from 14 Mpa after 1 day of mineralization to 128 Mpa after 8 days (FIG. 13c). This evolving spatiotemporal structure-function relationship is also observed during human dental enamel biomineralization (Simmons, L. M., Montgomery, J., Beaumont, J., Davis, G. R. & Al-Jawad, M. Mapping the spatial and temporal progression of human dental enamel biomineralization using synchrotron X-ray diffraction. Arch Oral Biol 58, 1726-1734 (2013), Cuy, J. L., Mann, A. B., Livi, K. J., Teaford, M. F. & Weihs, T. P. Nanoindentation mapping of the mechanical properties of human molar tooth enamel. Archives of Oral Biology 47, 281-291 (2002)). In order to elucidate this hierarchical progression, XRD was used to analyze the chemical composition at different time points. The results indicate the presence of brushite ($CaHPO_4 \cdot 2H_2O$) on and within the membrane during the first hour, its dissolution in time, and the formation of the more stable Fap phase at later timepoints (FIG. 13e and FIG. 17). FTIR spectra and ion selective electrode (ISE) measurements confirmed this transition (FIG. 17 and FIG. 18). To further investigate the kinetics behind the mineralization process with respect to the ionic availability in the solution, we mineralized the membranes at different initial ionic strength ranging from 2.5-10.0 Mm of $Ca^{2+}$, 1.6-6.0 Mm of $PO_4^{3-}$, and 0.5-2.0 of F−. Interestingly, the results demonstrate that the hierarchical structures form in all conditions independently of the initial ionic concentration. However, the size and hierarchical definition tended to increase with increasing ionic concentrations (FIG. 19). This result demonstrates that the hierarchical mineralization can take place at physiological ionic concentrations (2.5 Mm $Ca^{2+}$, 1.5 Mm $PO_4^{3-}$) and can be accelerated by increasing the concentration of available ions. Furthermore, controlling the kinetics of ionic consumption by maintaining a constant Ph during the mineralization process considerably increases the size of the hierarchical structures up to a millimeter in diameter (FIG. 13d).

Figure 21:
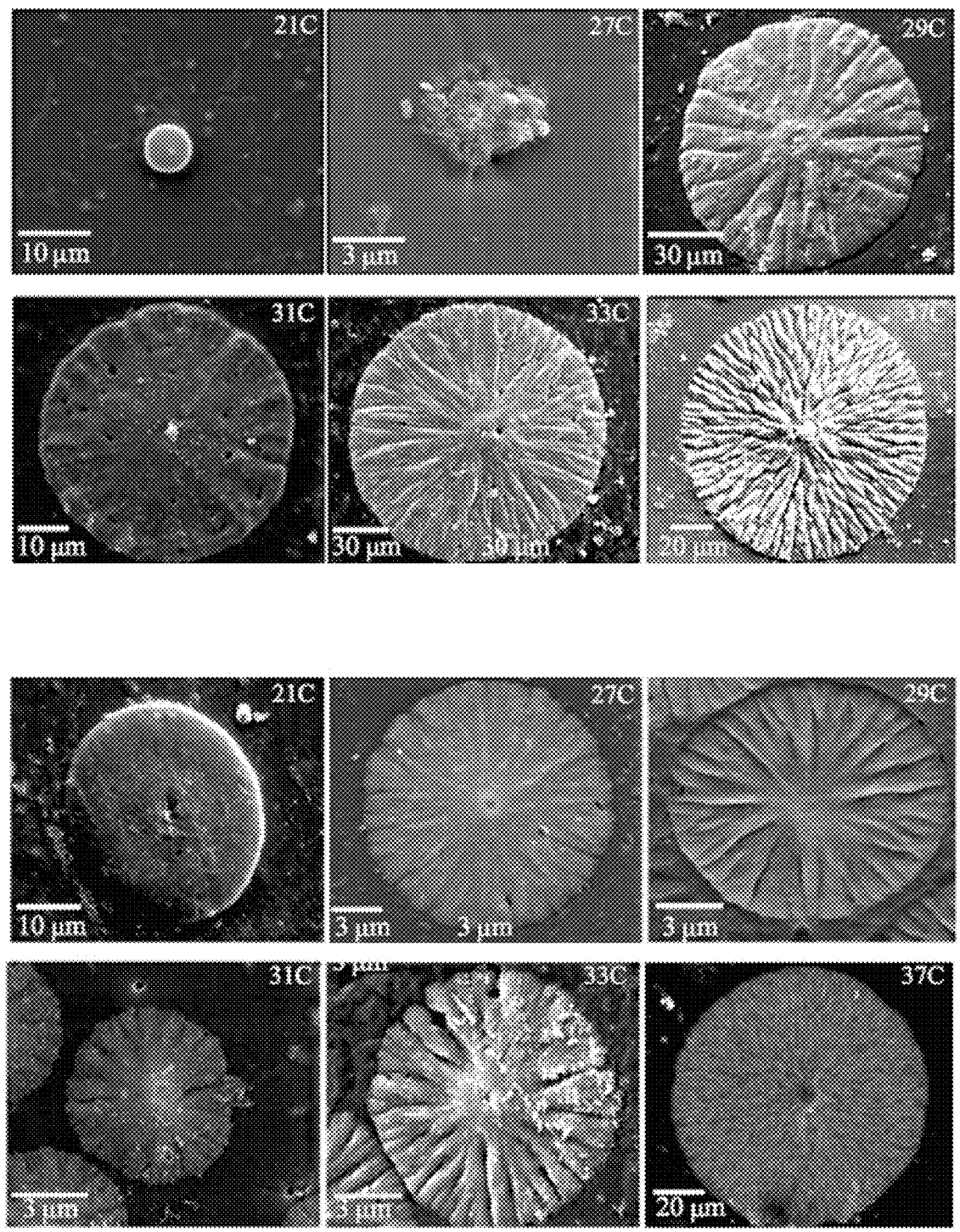
Figure 22:
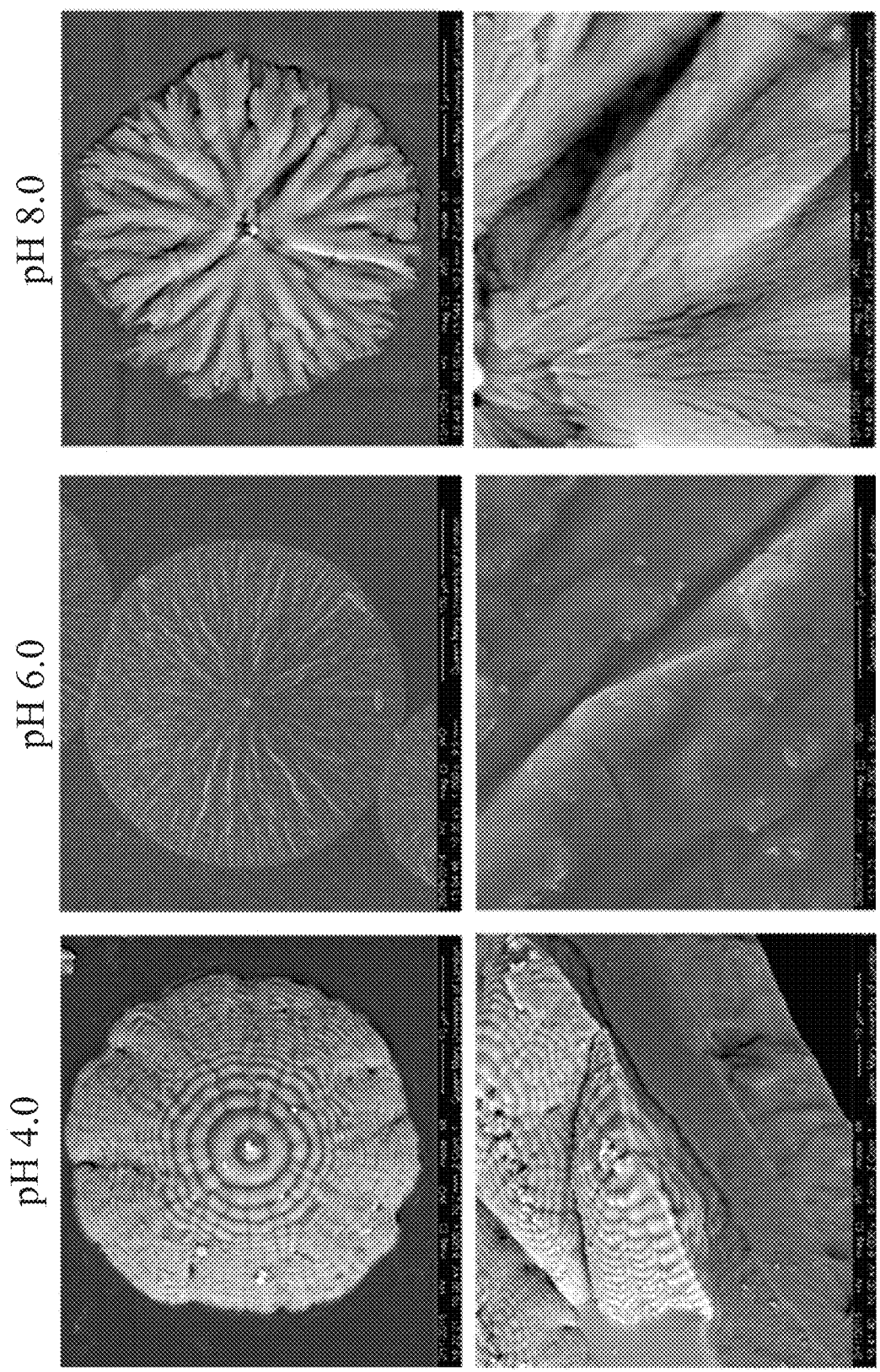
FIG. 22. SEM images of mineralized membranes at different pH 4, 6, and 8.

Discussion of FIGS. 20 to 22

At the molecular level, the ELP molecules exhibit a reversible-phase behavior, known as inverse transition temperature (Tt), where below its Tt, the molecules are well-solvated, surrounded by highly-ordered water structures, and possess a random coil conformation. Above the Tt, the ELP chain aggregates due to a hydrophobic collapse disturbing the ordered water molecules and gaining a β-spiral conformation. This behavior provides an opportunity when designing and modulating a 3D organic matrix environment for biomineralization (Weiner, S. & Addadi, L. Design strategies in mineralized biological materials. Journal of Materials Chemistry 7, 689-702 (1997)). In addition, β-sheet conformation in proteins is known to promote preferential stereochemical interactions between the protein and crystal faces during biomineralization (Addadi, L., Weiner, S. & Geva, M. On how proteins interact with crystals and their effect on crystal formation. Zeitschrift fur Kardiologie 90, 92-98 (2001), Fujisawa, R. & Kuboki, Y. Conformation of dentin phosphophoryn adsorbed on hydroxyapatite crystals. European Journal of Oral Sciences 106, 249-253 (1998)). The acquisition of β-spiral conformation by the statherin-rich ELP molecules was confirmed by circular dichroism (CD) measurements (FIG. 20a). This behavior would explain the profound difference exhibited by membranes mineralized slightly below and above the Tt, where the β-spiral-rich ELP membranes exhibit the hierarchical biomineralization (FIG. 20c and FIG. 21). In addition, above the Tt, the ELP molecule is known to aggregate and display the hydrophilic domains on its exterior (Urry, D. W. What sustains life?: Consilient mechanisms for protein-based machines and materials (2006)). Similarly, our statherin-rich ELP molecules (DDDEEKFLRRIGRFG (SEQ ID NO:2)), which exhibit highly acidic and negatively charged hydrophilic domains, leads to higher calcium binding affinity above the Tt, as evidenced by zeta potential ($\zeta$) (FIG. 20b) and hydrodynamic radii measurements (FIG. 20b). This behavior is in accordance with the well-known nucleating role of negatively charged acidic residues in biomineralized tissues (Addadi, L. & Weiner, S. Interactions between acidic proteins and crystals: Stereochemical requirements in biomineralization. Proceedings of the National Academy of Sciences of the United States of America 82, 4110-4114 (1985)). This mechanism is further supported by the significant increase in number of hierarchical structures growing within statherin-rich ELP membranes (125±0.34 per mm2) compared to RGDS-rich ELP membranes (20±4 per mm2) (FIG. 20d). In addition, the role of the hydrophobic macromolecular framework guiding the hierarchical mineralization of tissues is well-established (Greenfield, E. M., Wilson, D. C. & Crenshaw, M. A. Ionotropic nucleation of calcium carbonate by molluscan matrix. Integrative and Comparative Biology 24, 925-932, (1984), Weiner, S. Organization of organic matrix components in mineralized tissues. Integrative and Comparative Biology 24, 945-951, (1984)). We hypothesize that the hydrophobic segments of the ELP chains may play a similar role as a structural framework for the hierarchical mineralized structures, which explains the presence of mineralized structures on membranes made from control ELP molecules (FIG. 21). All together, these results demonstrate that our system requires a distinctive aggregated (FIG. 20e) macromolecular organic environment (FIG. 20b-c) that enables β-spirals (FIG. 20a) and increases charge density (FIG. 20b) to promote nucleation and hierarchical mineralization (FIG. 20c).

Figure 23:
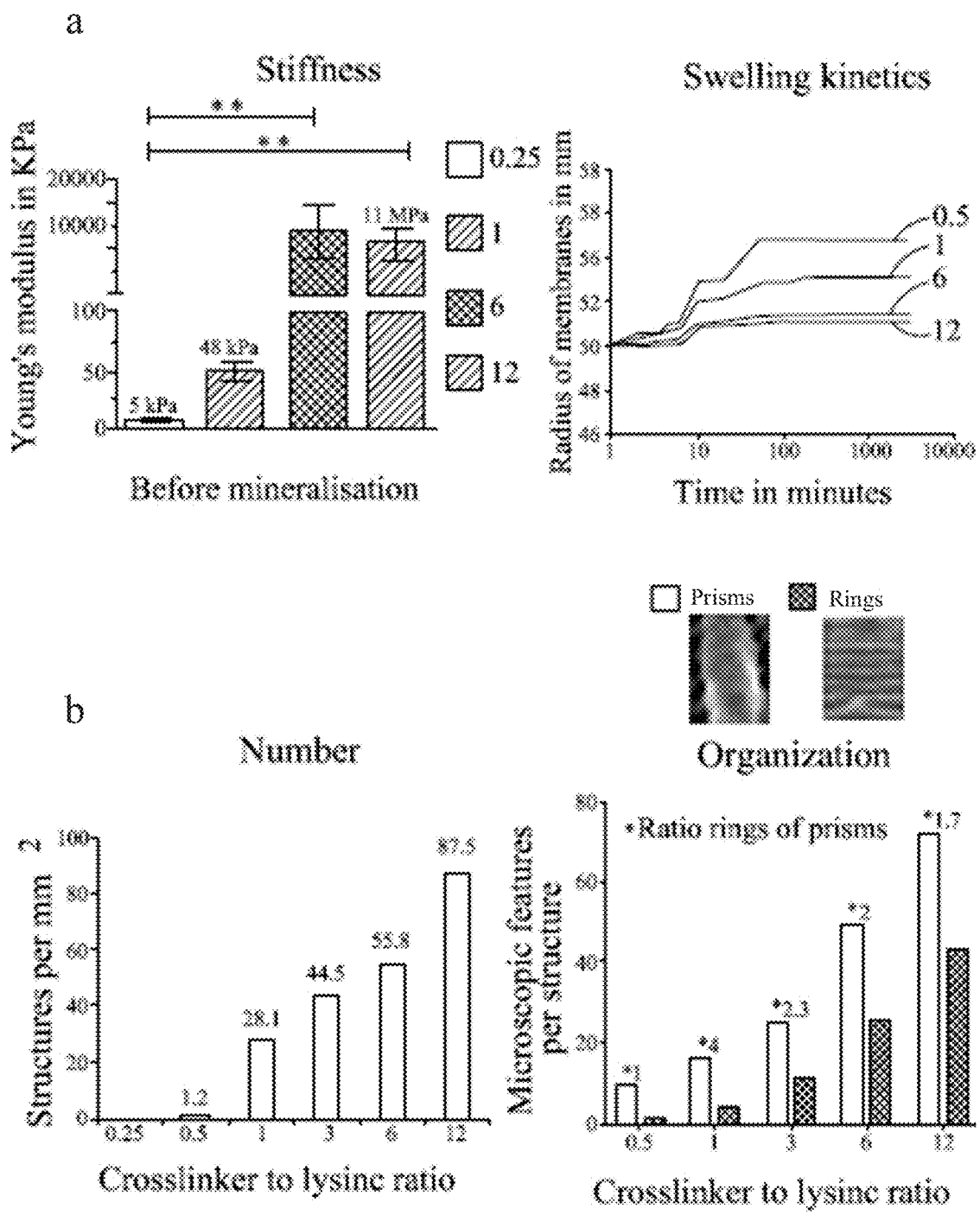
FIG. 23. a) Graphs showing of the stiffness of the unmineralized membranes fabricated with different ELP to cross-linker ratio (left), where a significant increase in the Young's moduli is observed with the highly crosslinked membranes in comparison to the less crosslinked membranes. As a result, the swelling measurements (right) evidence that the higher the stiffness (crosslinking), the lower the diffusion and swelling. b) Graphs showing the increase in both the number and the level of the organization of the hierarchical mineralized structures as a function of stiffness. c) SEM images showing that the hierarchical organization of the crystals is affected to the surrounding physical properties. After the mineralization of the different crosslinked membranes, showing an increase of the prismatic structures at the expense of the concentric rings with increasing stiffness. d) Schematic illustrating the mechanism of growth of the hierarchical mineralized structures at the membrane level with different ratios of crosslinking, diffusion, and stiffness.
Figure 23:
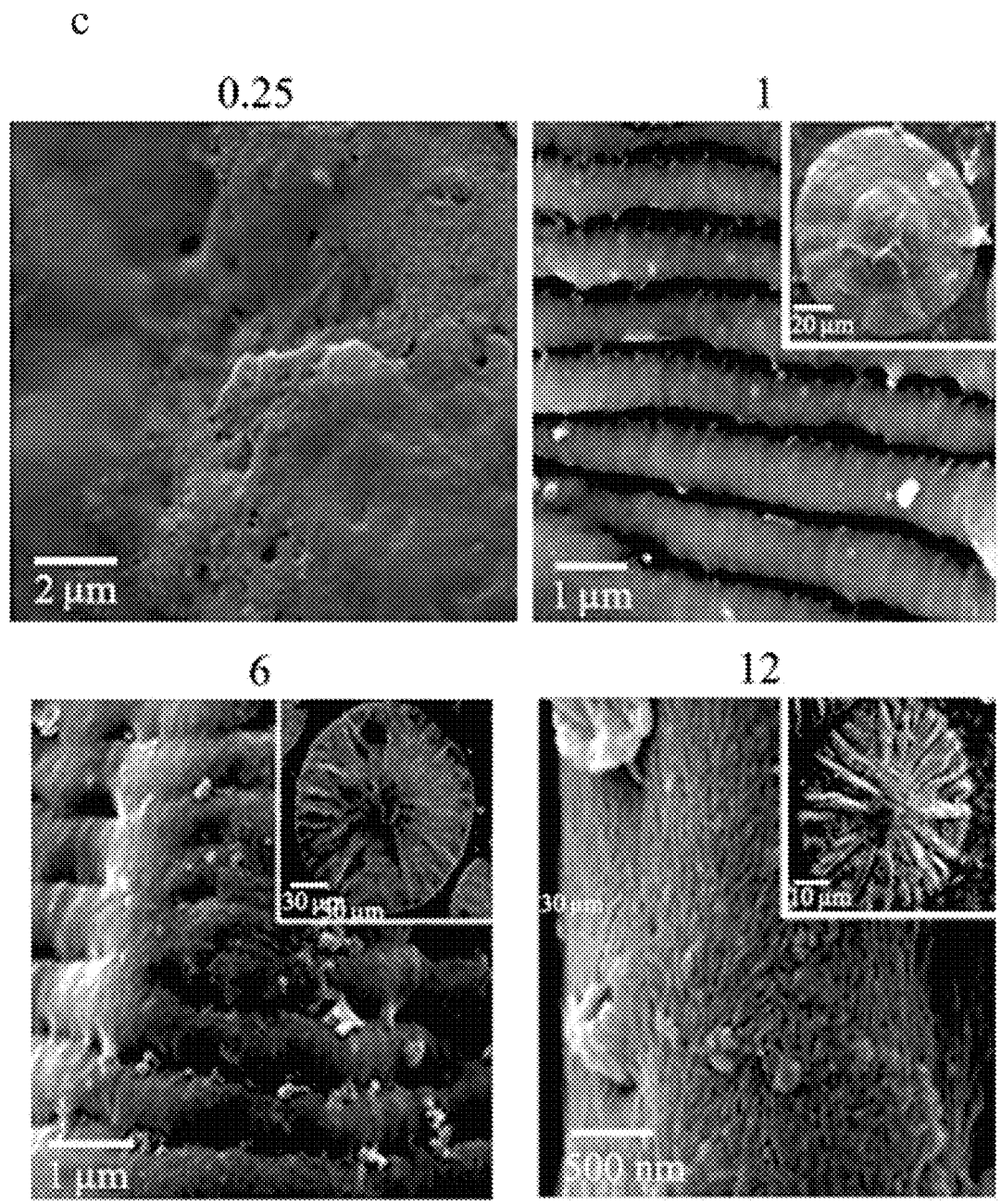
Figure 23:
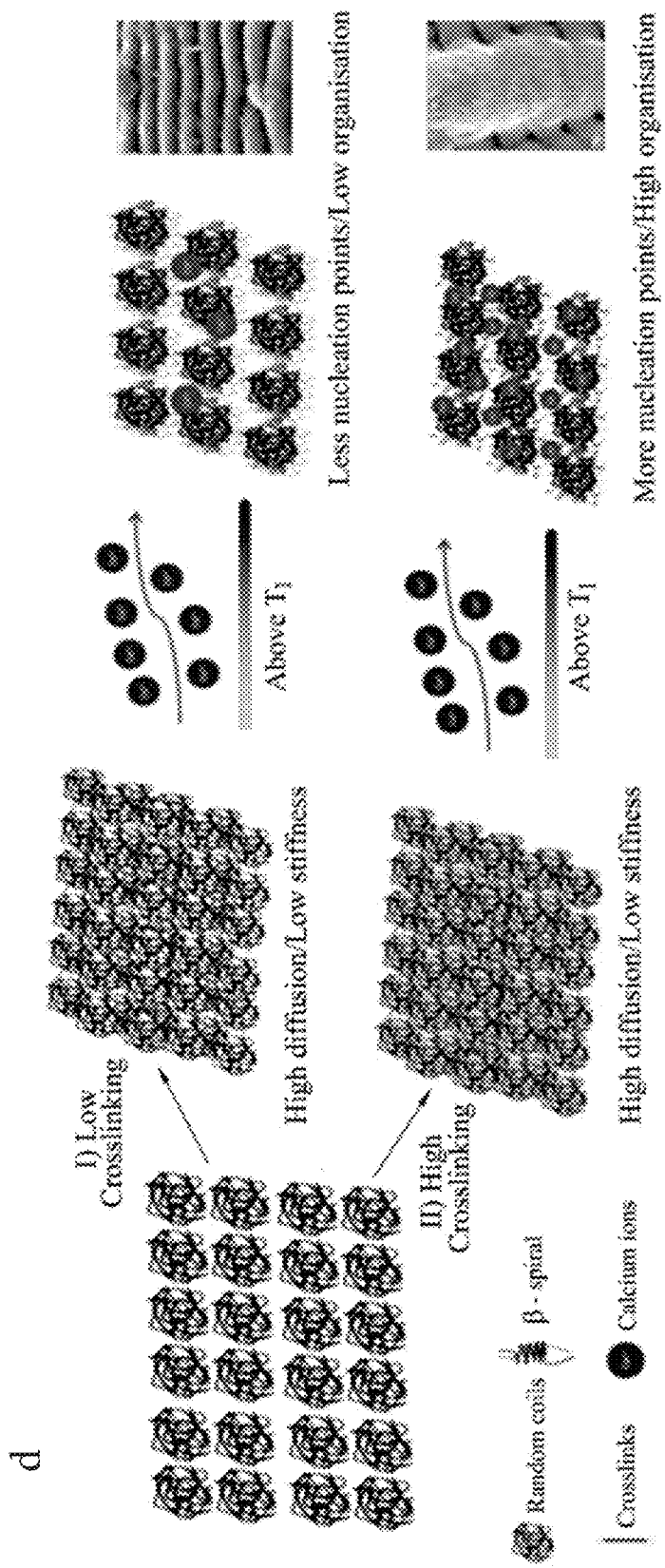
Figure 25:
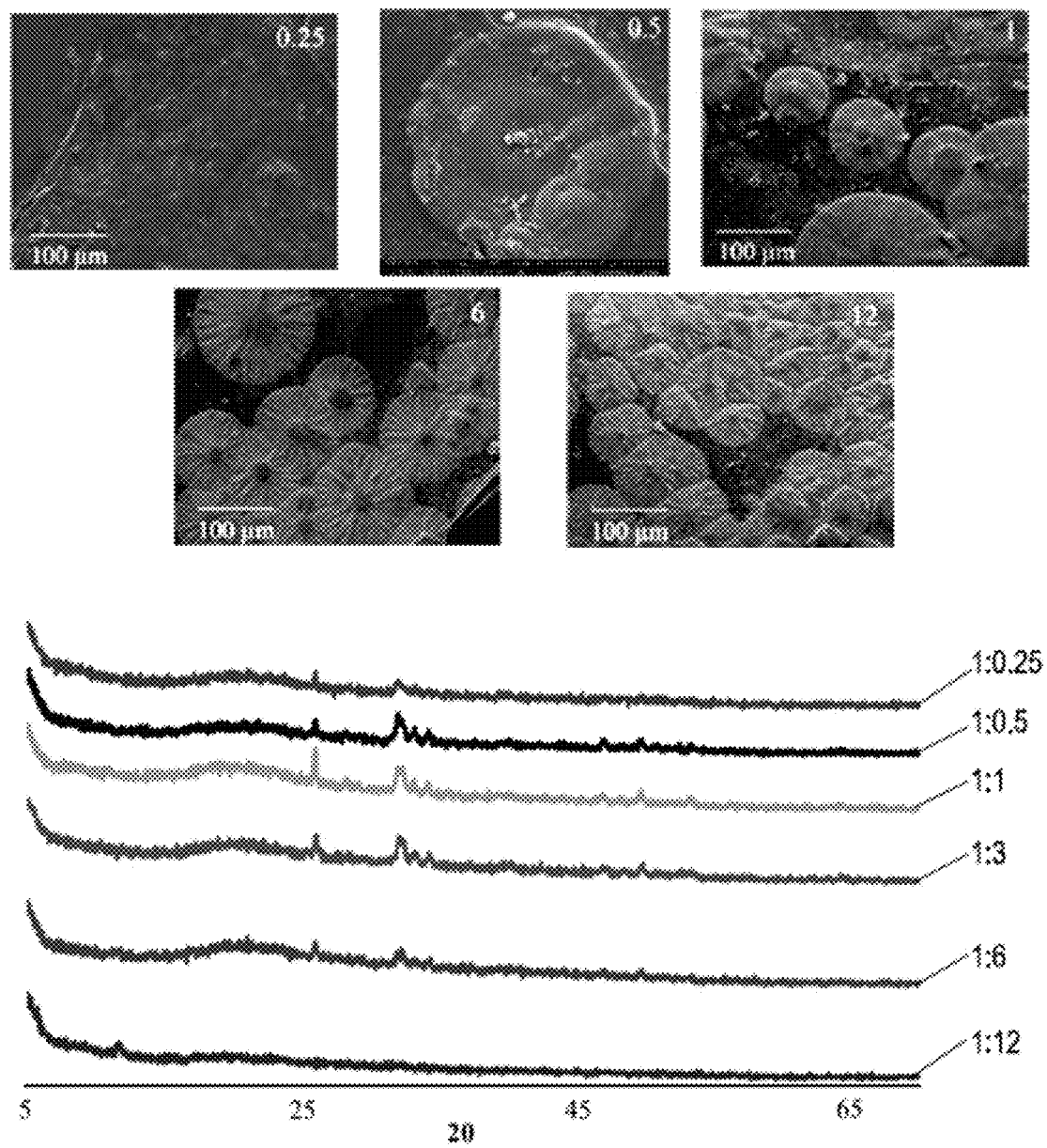
FIG. 25. The apatite chemical composition of the different organized structures, remains the same as evidenced by XRD at different crosslinking ratios. Note the increase in the number of the structures at high crosslinking.

Discussion of FIGS. 23 to 25

Diffusion and the corresponding degree of supersaturation are well known to affect the morphological evolution of mineralized structures (Oaki, Y. & Imai, H. Experimental demonstration for the morphological evolution of crystals grown in gel media. Crystal Growth and Design 3, 711-716 (2003)). To elucidate the role of this mechanism, systematic studies were conducted using membranes with increasing amounts of crosslinking. Diffusion coefficients (D) were calculated based on membrane swelling measurements following Tanaka and Fillmore equations (Tanaka, T. & Fillmore, D. J. Kinetics of swelling of gels. The Journal of Chemical Physics 70, 1214-1218 (1979)), which were inversely proportional to the degree of the crosslinking (FIG. 23a and FIG. 24). We hypothesize that membranes with lower diffusion coefficient would enhance local supersaturation within the bulk of the membrane by concentrating ions from the solution. To confirm this hypothesis, we mineralized the membranes with increasing amounts of crosslinking, and therefore with increasing stiffness (FIG. 23a). The results confirm that higher number (FIG. 23b) of mineralized structures were present in membranes with lower diffusion coefficient and higher stiffness. It is possible that a denser matrix with ELP chains in closer proximity promotes a more favorable environment for the formation of critical-sized nuclei. In addition, the mineralized structures exhibit a higher degree of hierarchical organization in membranes with higher crosslinking (FIG. 23b-c), evolving from no observable mineralized structures in the lowest crosslinked membranes, to macroscopic structures with concentric rings, to the macroscopic structures with the aligned prisms in those with highest crosslinking (FIG. 23c). In addition to decreased swelling, the increasing crosslinking also generates stiffer membranes, which suggests that the physical environment plays a major role in controlling the level of hierarchical order generated by our system. While distinct morphologies result from denser and stiffer membranes, the chemical composition of these structures remains the same as evidenced by XRD (FIG. 25), which confirms that the organic-inorganic bulk environment plays a critical role in guiding both nucleation and crystal growth. These results demonstrate that the mechanism behind the hierarchical biomineralization of our system, relies on the formation of an organic-inorganic environment (FIG. 23d) that enables appropriate molecular aggregation and confinement (FIG. 20 and FIG. 23), controlled ionic diffusion (FIG. 23a), and a suitable physical environment (FIG. 23a-c).

Figure 27:
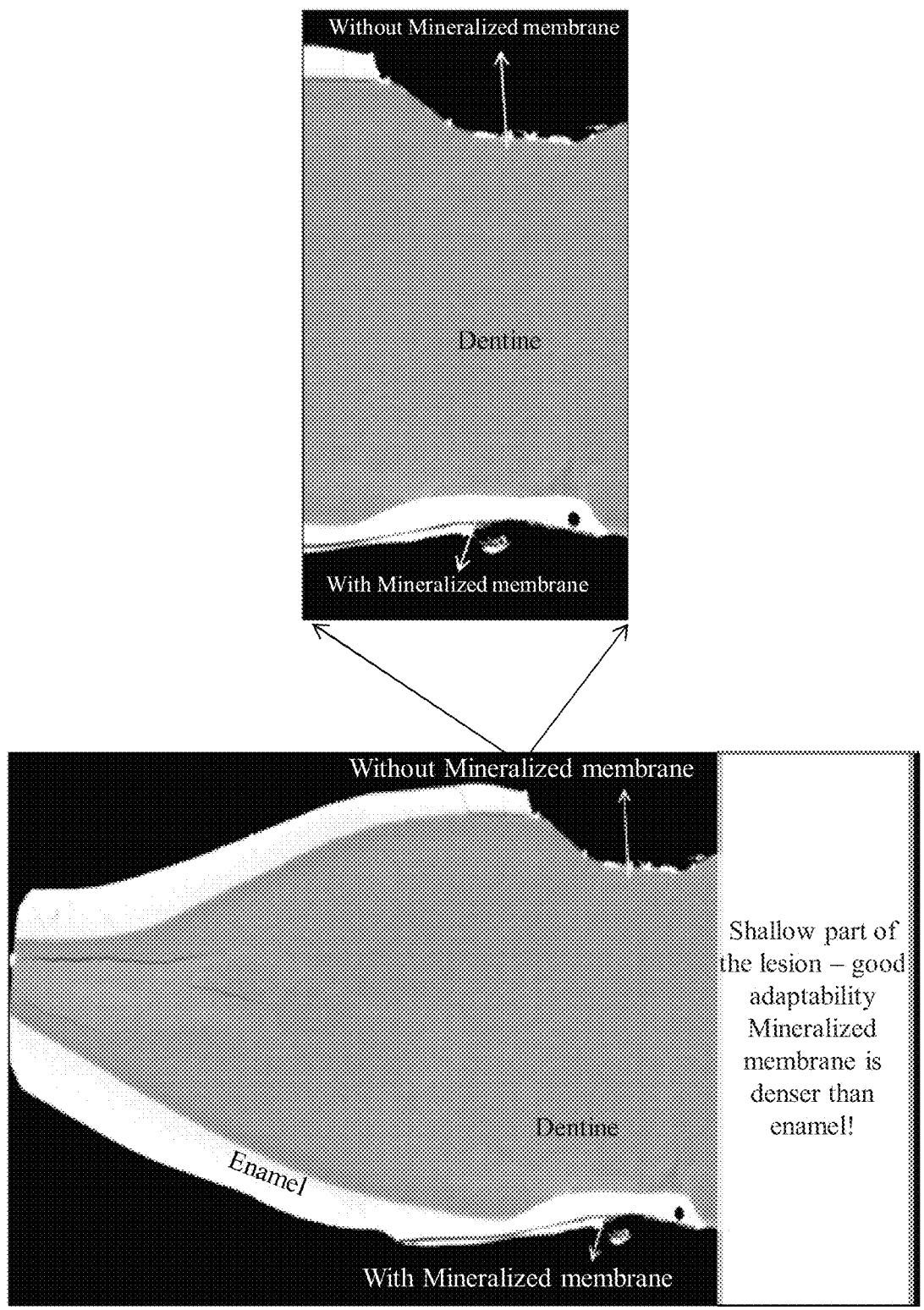
FIG. 27. XMT showing that the mineralized membrane can not only fill and occlude large cervical defects of teeth that are major cause for dentine hypersensitivity, but also with a high density of mineral.

Discussion of FIGS. 26 to 27

Dental enamel exhibits outstanding hardness and resistance to various masticatory forces and harsh intra-oral conditions thanks to its unique well-defined hierarchical mineralized structure (Boyde, A. Microstructure of enamel. CIBA Foundation Symposia, 18-31 (1997)). However, once lost, enamel cannot regenerate nor be healed clinically (Galler, K. M., D'Souza, R. N. & Hartgerink, J. D. Biomaterials and their potential applications for dental tissue engineering. Journal of Materials Chemistry 20, 8730-8746 (2010)). This situation leads to exposure of the dentinal tissue and consequently dentine hypersensitivity, a painful condition affecting 52% of the world population (Taani, D. Q. & Awartani, F. Prevalence and distribution of dentin hypersensitivity and plaque in a dental hospital population. Quintessence International 32, 372-376 (2001), Gillam, D. G. Dentine hypersensitivity: advances in diagnosis, management, and treatment. (2016)). Currently, restorative materials used to replace lost/diseased dental enamel lack the distinctive anisotropic structure and properties of dental enamel, which leads to surface mismatch, marginal damage and leakage, and further loss of dental tissues. Given the capacity to grow hierarchically mineralized apatite structures into stiff, yet conformable, membranes and coatings (FIG. 1), we conducted in vitro proof-of-concept studies to investigate its potential as a mineralizing bandage to regenerate lost dental enamel and/or to occlude exposed dentinal tubules.

Membranes were fabricated directly on both etched and rough surfaces of human dentine (FIG. 26a) and mineralized for 8 days. SEM observations confirmed that the hierarchically mineralized membranes grew, adhered, and conformed to the surface of the etched dental tissues (FIG. 26a-b). Integration between the hierarchical structures and the dental tissues was enhanced by decreasing membrane thickness to less than 20 ☐m, as observed by FIB milling of the mineralized coating at dentine-membrane interface (FIG. 26b). This behavior was particularly clear when growing the hierarchically mineralized coating on dentine tissue, where the growing aligned nanocrystals were observed to infiltrate and block dentinal tubules (FIG. 26a-b). Dental hard tissue destruction is primarily caused by the acid produced during dental caries and dental erosion either from acids produced during the metabolic activity of cariogenic bacteria or from dietary sources, respectively (Kidd, E. A. M. Essentials of dental caries. 3rd edn, (Oxford University Press, 2005)). To investigate the acid resistance properties of the hierarchically mineralized structures, acid attack experiments were conducted on mineralized membranes and compared to dental enamel. The mineralized structures exhibited higher acid resistance after 15 minutes of exposure compared to dental enamel by better maintaining their morphological structure (FIG. 6c) and mechanical properties (FIG. 6d), as evidenced by SEM observations and AFM nanoindentation, respectively. It is probable that the enhanced acid resistance exhibited by our mineralized structures is related to their intrinsic Fap crystalline phase in comparison to the carbonated hydroxyapatite phase found in enamel62. As expected, after 7 days in the acid exposure, the inorganic content of the mineralized membranes and dental enamel were significantly disturbed as observed by the SEM images (FIG. 26c). This result is confirmed by the nanoindentation studies where both the mineralized and unmineralized membranes exposed to the acid attack for 7 days exhibit a similar stiffness, suggesting that the organic matrix is maintained. The preservation of the organic matrix could enable a remineralization treatment once the acid attack subsides. However, confirmation of this hypothesis would require further experimentation, which is beyond the scope of the current study. Another potential challenge encountered by dental tissues is exposure to proteases in saliva (Pashley, D. H. et al. Collagen degradation by host-derived enzymes during aging. Journal of Dental Research 83, 216-221 (2004), Chaussain-Miller, C., Fioretti, F., Goldberg, M. & Menashi, S. The role of matrix metalloproteinases (MMPs) in human caries. Journal of Dental Research 85, 22-32, (2006)). To investigate the stability of the hierarchically mineralized structures, membranes were tested for enzymatic degradation by elastase exposure. DDC-SEM observations confirmed the presence of the nanocrystals (high-density material) and a reduction of the low-density material (organic matrix) (FIG. 26e). This result demonstrates that the prismatic structures maintain their hierarchical organization in spite of the reduction of the organic matrix around them. Altogether, these results suggest that our system provides an exciting regenerative alternative for a variety of dental applications such as dentine hypersensitivity, dental caries, and erosion through hierarchically mineralizing materials that mimic natural tissues in both structural organization and chemical composition.

Figure 28:
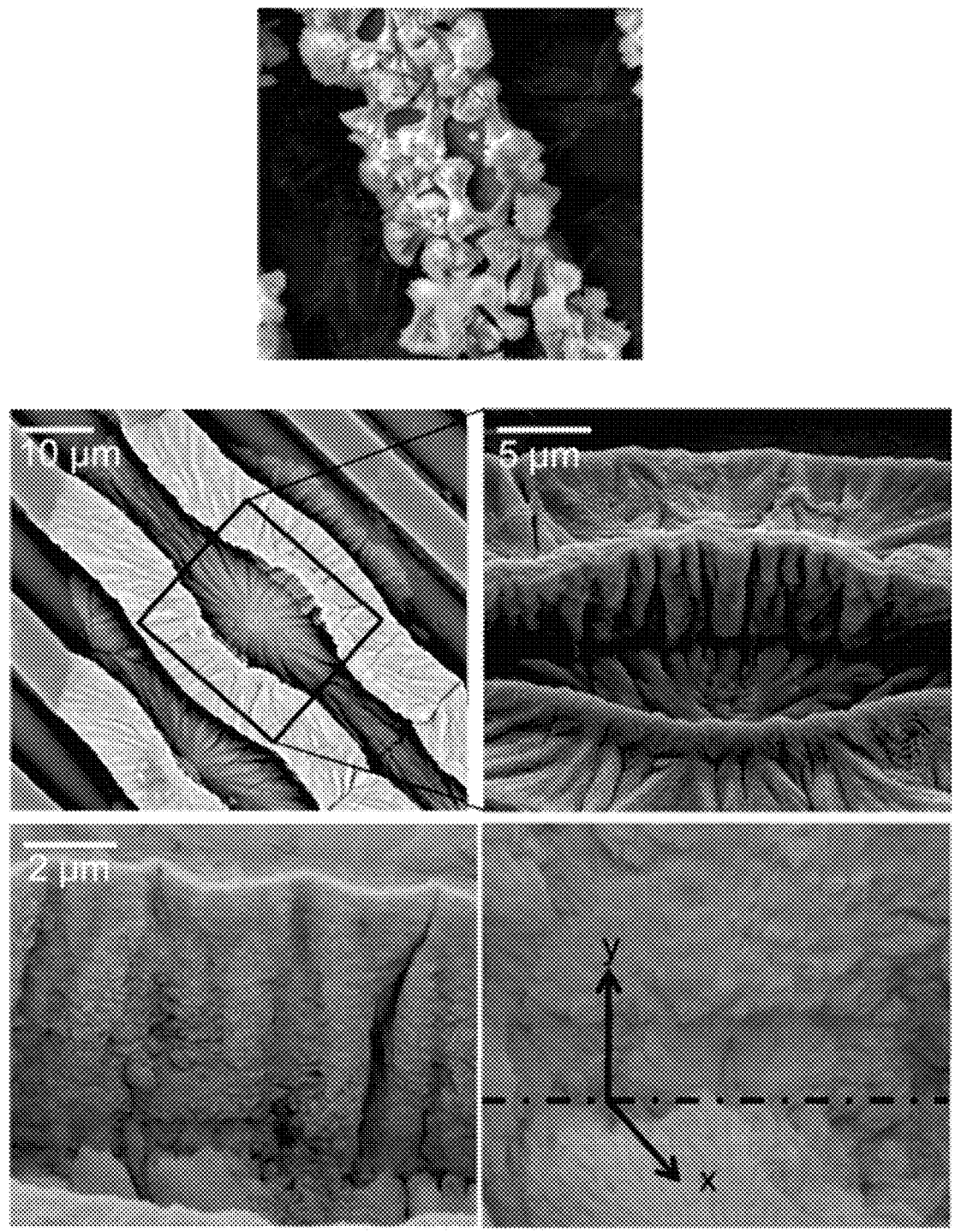
FIG. 28. Effect of microfabricated topography on the growth of the hierarchical structures. Microfabricated topographies were used to tune the directionality of the structures. The structures can be asymmetrical in comparison to the symmetric circular structures on the surfaces. The crystal orientation changes at the 90° and 270°.
Figure 29:
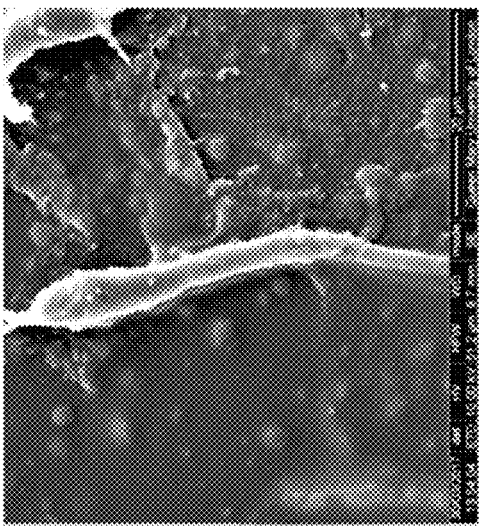
FIG. 29. Cell viability studies of Human adipose derived stem cells (hADSC) on the mineralized structures SEM images showing the extent of viability, spread, and attachment of the hADSCs on the hierarchical structures grown on SN-RGDS-ELP membrane at day 1 (a-b). At day 7, SEM and live-dead imaging showing the significant amount of viable cells on top of the mineralized structures as seen in confocal microscopy (b-c). e) SEM image that shows that the cells on the unmineralized membranes didn't spread in comparison to the mineralized on at day 7.
Figure 29:
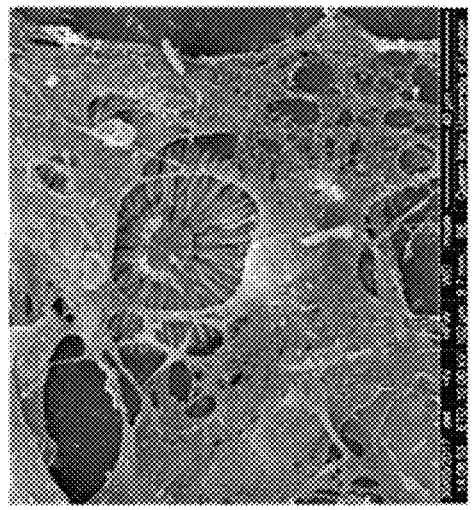
Figure 29:
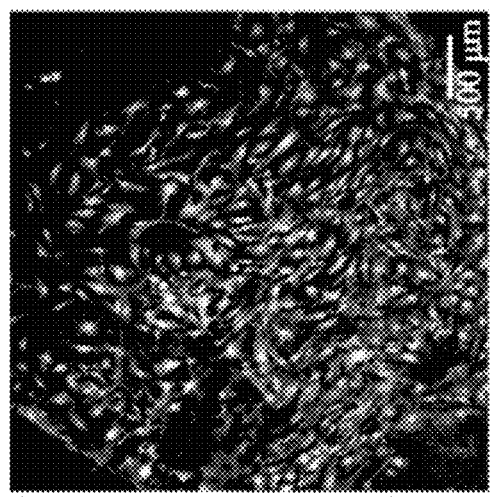
Figure 29:
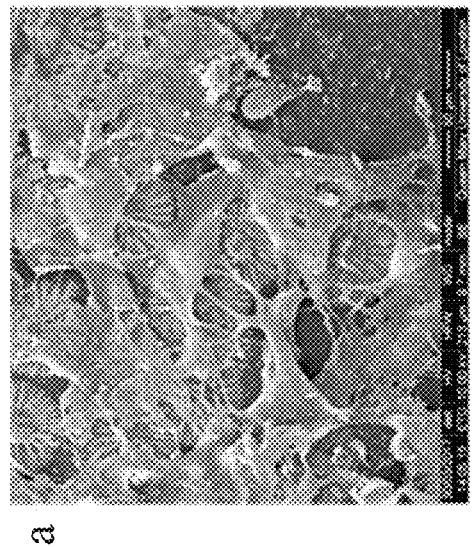
Figure 29:
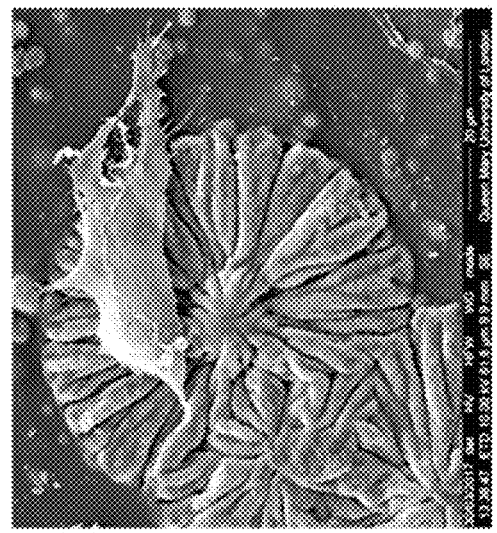

Discussion of FIGS. 28 and 29

As seen in FIG. 28, we have discovered ways where we can change to directionality of the structures from being symmetrical to be asymmetrical. This has been achieved through the fabrication of geometrical topography on the surface of the membranes. The nanocrystals within the hierarchical structures change their orientation following the topography that has been fabricated at 90 and 270 degrees. The previous observation, would allow tuning of the structures from being circular to be linear, and would allow the growth the structures into different directions following the shapes that we can generate with the micro/nano topographies.

As seen in FIG. 29, upon culturing human derived adipose stem cells on the hierarchical structures, the cells were seen to be viable, attached and spread over the mineralised surfaces in comparison to the unmineralised ones. These observations provide evidence of the promising biological properties and biocompatibility of the structures to be used for tissue engineering applications (including bone regeneration).

The invention claimed is:

1. A hybrid organic-inorganic system comprising:
hierarchically-ordered fluorapatite crystalline structures, wherein the hierarchically-ordered fluorapatite crystalline structures comprise prism-shaped microstructures, and
a protein scaffold membrane capable of growing the hierarchically-ordered fluorapatite crystalline structures thereon or therein,
wherein the protein scaffold membrane comprises a polypeptide comprising an amino acid sequence of MESLLP-[(((VPGIG)$_2$VPGKG(VPGIG)$_2$)$_2$-DD-DEEKFLRRIGRFG-(VPGIG)$_2$VPGKG(VPGIG)$_2$)$_2$]$_3$-V,
wherein the protein scaffold membrane comprises an elastin-like polypeptide membrane having an aggregated macromolecular arrangement comprising random coil conformations and one or more of β-sheet or β-spiral conformations, wherein the aggregated macromolecular arrangement controls a formation of the hierarchically-ordered fluorapatite crystalline structures, and wherein at least a portion of the hierarchically-ordered fluorapatite crystalline structures comprise two or more of nanostructures, microstructures, or macrostructures assembled in a hierarchical order across multiple length-scales and exhibit a spherulitic radial geometry.

2. A dental enamel, dentine tissue, or bone graft comprising the hierarchically-ordered apatite crystalline structures of claim 1.

3. A hybrid organic-inorganic system comprising:
hierarchically-ordered crystalline structures, and
a protein scaffold membrane capable of growing the hierarchically-ordered crystalline structures thereon or therein,
wherein the protein scaffold membrane comprises an elastin-like polypeptide membrane having an aggregated macromolecular arrangement comprising disorder conformations and ordered conformations, wherein the aggregated macromolecular arrangement controls a formation of the hierarchically-ordered crystalline structures, and
wherein at least a portion of the hierarchically-ordered crystalline structures comprise one or more of nanostructures, microstructures, or macrostructures assembled in a hierarchal order across multiple length-scales, and wherein the levels of hierarchy comprise needle-shaped nanocrystals that are organized into prism-shaped microstructures, and the prism-shaped microstructures comprise circular or asymmetrical structures hundreds of microns in diameter and can fill macroscopic areas.

4. The hybrid organic-inorganic system of claim 3, wherein the disordered conformations comprise random coil conformations.

5. The hybrid organic-inorganic system of claim 3, wherein the ordered conformations comprise one or more of β-sheet or β-spiral conformations.

6. The hybrid organic-inorganic system of claim 3, wherein at least a portion of the hierarchically-ordered crystalline structures exhibit a spherulitic radial geometry.

7. A dental enamel, dentine tissue, or bone graft comprising the hierarchically-ordered crystalline structures of claim 3.

* * * * *